US010695328B2

(12) United States Patent
Turdi et al.

(10) Patent No.: US 10,695,328 B2
(45) Date of Patent: *Jun. 30, 2020

(54) ARYL DIHYDROPYRIDINONES AND PIPERIDINONE MGAT2 INHIBITORS

(71) Applicant: BRISTOL-MYERS SQUIBB COMPANY, Princeton, NJ (US)

(72) Inventors: Huji Turdi, Yardley, PA (US); Jon J. Hangeland, Morrisville, PA (US); R. Michael Lawrence, Yardley, PA (US); Saleem Ahmad, Wall, NJ (US); Wei Meng, Pennington, NJ (US); Robert Paul Brigance, Levittown, PA (US); Pratik Devasthale, Plainsboro, NJ (US); Guohua Zhao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/445,913

(22) Filed: Jun. 19, 2019

(65) Prior Publication Data

US 2019/0314346 A1 Oct. 17, 2019

Related U.S. Application Data

(63) Continuation of application No. 15/867,825, filed on Jan. 11, 2018, now Pat. No. 10,369,140, which is a (Continued)

(51) Int. Cl.

| | |
|---|---|
| *A61K 31/438* | (2006.01) |
| *A61K 31/675* | (2006.01) |
| *C07D 211/90* | (2006.01) |
| *A61K 31/4418* | (2006.01) |
| *C07D 401/04* | (2006.01) |
| *A61K 31/4439* | (2006.01) |
| *C07D 413/04* | (2006.01) |
| *C07D 221/20* | (2006.01) |
| *C07D 413/14* | (2006.01) |
| *A61K 31/5377* | (2006.01) |
| *C07D 401/14* | (2006.01) |
| *A61K 45/06* | (2006.01) |
| *C07F 9/59* | (2006.01) |
| *C07F 9/40* | (2006.01) |
| *C07D 401/10* | (2006.01) |
| *C07D 401/12* | (2006.01) |

(Continued)

(52) U.S. Cl.

CPC ........ *A61K 31/438* (2013.01); *A61K 31/4418* (2013.01); *A61K 31/4439* (2013.01); *A61K 31/5377* (2013.01); *A61K 31/675* (2013.01); *A61K 45/06* (2013.01); *C07D 211/86* (2013.01); *C07D 211/90* (2013.01); *C07D 221/20* (2013.01); *C07D 401/04* (2013.01); *C07D 401/10* (2013.01); *C07D 401/12* (2013.01); *C07D 401/14* (2013.01); *C07D 405/14* (2013.01); *C07D 407/14* (2013.01); *C07D 413/04* (2013.01); *C07D 413/12* (2013.01); *C07D 413/14* (2013.01); *C07D 417/04* (2013.01); *C07D 417/14* (2013.01); *C07F 9/4006* (2013.01); *C07F 9/5352* (2013.01); *C07F 9/59* (2013.01)

(58) Field of Classification Search

None

See application file for complete search history.

(56) References Cited

U.S. PATENT DOCUMENTS

| | | | |
|---|---|---|---|
| 3,073,838 | A | 1/1963 | Kühnis et al. |
| 8,071,603 | B2 | 12/2011 | Kamboj et al. |

(Continued)

FOREIGN PATENT DOCUMENTS

| | | | |
|---|---|---|---|
| WO | WO 2010/095767 | A1 | 8/2010 |
| WO | WO 2012/124744 | A1 | 9/2012 |

OTHER PUBLICATIONS

Attia, A. et al., "Synthesis of some 3-cyano-5,6-dihydropyridin-2-ones and their N-substituted derivatives", Egyptian Journal of Chemistry, vol. 26, No. 5, pp. 447-452 (1983) (English Abstract).

Carrié, R. et al., "Organic Chemistry. On the condensation of benzalacetophenone and dypnone with cyanoacetamide", Comptes Rendus Hebdomadaires des Séances de l'Académie des Sciences, vol. 257, No. 18, pp. 2849-2851 (1963) (English Translation).

Grudzinski, S. et al., "New amino-acid derivatives of isonicotinic, cyanoacetic, and sulfanilamidoacetic hydrazides with possible tuberculostatic activity", Acta Poloniae Pharmaceutica, vol. 19, No. 4, pp. 311-316 (1962) (CAS Abstract).

(Continued)

*Primary Examiner* — Zinna Northington Davis

(74) *Attorney, Agent, or Firm* — Jing G. Sun

(57) ABSTRACT

The present invention provides compounds of Formula (I):

(I)

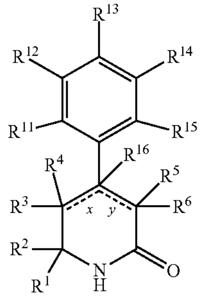

or a stereoisomer, or a pharmaceutically acceptable salt thereof, wherein all of the variables are as defined herein. These compounds are monoacylglycerol acyltransferase type 2 (MGAT2) inhibitors which may be used as medicaments.

40 Claims, No Drawings

Related U.S. Application Data continuation of application No. 15/488,642, filed on Apr. 17, 2017, now Pat. No. 9,901,572, which is a continuation of application No. 14/883,067, filed on Oct. 14, 2015, now Pat. No. 9,663,466, which is a continuation of application No. 14/305,098, filed on Jun. 16, 2014, now Pat. No. 9,187,424, which is a continuation of application No. 13/688,584, filed on Nov. 29, 2012, now Pat. No. 8,791,091.

(60) Provisional application No. 61/566,039, filed on Dec. 2, 2011.

(51) Int. Cl.

| | |
|---|---|
| *C07D 407/14* | (2006.01) |
| *C07D 413/12* | (2006.01) |
| *C07D 417/04* | (2006.01) |
| *C07D 417/14* | (2006.01) |
| *C07D 211/86* | (2006.01) |
| *C07F 9/535* | (2006.01) |
| *C07D 405/14* | (2006.01) |

(56) References Cited

U.S. PATENT DOCUMENTS

| | | | | |
|---|---|---|---|---|
| 8,232,282 | B2 | 7/2012 | Nakamura et al. | |
| 8,232,447 | B2 | 7/2012 | Aragane et al. | |
| 8,791,091 | B2 | 7/2014 | Turdi et al. | |
| 9,187,424 | B1 | 11/2015 | Turdi et al. | |
| 9,663,466 | B2 | 5/2017 | Turdi et al. | |
| 9,688,656 | B2 | 6/2017 | Ahmad et al. | |
| 9,701,672 | B2 | 7/2017 | Meng et al. | |
| 9,856,244 | B2 | 1/2018 | Meng et al. | |
| 9,896,431 | B2 | 2/2018 | Ahmad et al. | |
| 9,901,572 | B2 | 2/2018 | Turdi et al. | |
| 10,369,140 | B2 * | 8/2019 | Turdi ................ | A61K 31/4439 |
| 2011/0275647 | A1 | 11/2011 | Arakawa et al. | |

OTHER PUBLICATIONS

McElvain, S.M. et al., “Piperidine Derivatives. XXX. 1,4-Dialkyl-4-arylpiperidines”, Journal of the American Chemical Society, vol. 80, pp. 3915-3923 (1958).

Nagai, W., “Structure of the by-products of the Cope-Knoevenagel condensation of p-substituted acetophenones”, Nippon Kagaku Zasshi, vol. 89, No. 8, pp. 819-820 (1968) (English Abstract).

Okawa, M. et al., “Role of MGAT2 and DGAT1 in the release of gut peptides after triglyceride ingestion”, Biochemical and Biophysical Research Communications, vol. 390, pp. 377-381 (2009).

Sakurai, A. et al., “The Cyclization of Ethyl Cyanoacetate and Ketones by Ammonium Acetate”, Bulletin of the Chemical Society of Japan, vol. 40, pp. 1680-1684 (1967).

Sammour, A. et al., “Chalcones. Condensation with ethyl cyanoacetate and malononitrile in the presence of ammonium acetate”, United Arab Republic Journal of Chemistry, vol. 13, No. 4, pp. 421-437 (1971) (English Abstract).

Seethala, R. et al., “A simple homogeneous scintillation proximity assay for acyl-coenzyme A:diacylglycerol acyltransferase”, Analytical Biochemistry, vol. 383, pp. 144-150 (2008).

Yen, C.-L.E. et al., “Deficiency of the intestinal enzyme acyl CoA: monoacylglycerol acytransferase-2 protects mice from metabolic disorders induced by high-fat feeding”, Nature Medicine, vol. 15, No. 4, pp. 442-446 (2009).

Yen, C.-L.E. et al., “MGAT2, a Monoacylglycerol Acyltransferase Expressed in the Small Intestine”, The Journal of Biological Chemistry, vol. 278, No. 20, pp. 18532-18537 (2003).

* cited by examiner

ARYL DIHYDROPYRIDINONES AND PIPERIDINONE MGAT2 INHIBITORS

CROSS-REFERENCE TO RELATED APPLICATIONS

This application is a continuation of U.S. patent application Ser. No. 15/867,825, filed Jan. 11, 2018, which is a continuation of U.S. patent application Ser. No. 15/488,642, filed Apr. 17, 2017, now U.S. Pat. No. 9,901,572, which is a continuation of U.S. application Ser. No. 14/883,067, filed on Oct. 14, 2015, now U.S. Pat. No. 9,663,466, issued May 30, 2017, which is a continuation of U.S. application Ser. No. 14/305,098 filed on Jun. 16, 2014, now U.S. Pat. No. 9,187,424, issued Nov. 17, 2015, which is a continuation of U.S. application Ser. No. 13/688,584 filed on Nov. 29, 2012, now U.S. Pat. No. 8,791,091, issued Jul. 19, 2014, which claims the priority benefit of U.S. Provisional Application No. 61/566,039, filed Dec. 2, 2011; the contents of which are herein incorporated by reference in their entirety.

FIELD OF THE INVENTION

The present invention provides novel aryl dihydropyridinone and piperidinone compounds, and their analogues thereof, which are MGAT2 inhibitors, compositions containing them, and methods of using them, for example, for the treatment or prophylaxis of diabetes, obesity, dyslipidemia and related conditions.

BACKGROUND OF THE INVENTION

The prevalence of obesity and diabetes is increasing at an alarming rate. According to WHO, in 2008, 70% of the U.S. adult population was overweight, and among them 33% were obese. Parallel to the explosive number of people becoming overweight and obese, in 2008, it was estimated that 12.3% of the U.S. population had elevated blood glucose [http://www.who.int/diabetes/facts/en/]. The obesity/diabetes epidemic is not unique to the U.S. According to WHO (Fact Sheet No. 312, September 2012), 347 million people worldwide have diabetes. Treating obesity and improving glycemic control effectively and safely remain major challenges for modern medicine.

Monoacylglycerol acyltransferase 2 (MGAT2) has emerged as an attractive target for the treatment of obesity and type II diabetes [Yen, C. L. et al., *Nat. Med.,* 15(4):442-446 (2009)]. MGAT2 is highly and selectively expressed in the small intestine where it exerts a pivotal role in the monoacylglycerol-pathway for the absorption of dietary fat. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body. MGAT2 knockout mice exhibit a healthy metabolic phenotype and show resistance to high-fat diet induced obesity, improvement in insulin sensitivity and decreased fat accumulation in liver and adipose tissue. In addition, genetic deletion of MGAT2 produces mice with increased levels of GLP1 [Yen, C. L. et al., Nat. Med., 15(4):442-446 (2009)]. Taken together, these data show that MGAT2 inhibitors hold promise to treat metabolic disorders such as obesity, type II diabetes and dyslipidemia.

SUMMARY OF THE INVENTION

The present invention provides aryl dihydropyridinone and piperidinone compounds, and their analogues thereof, which are useful as MGAT2 inhibitors, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with MGAT2, such as diabetes, obesity, dyslipidemia and related conditions, such as microvascular and macrovascular complications associated with diabetes, cardiovascular diseases, Metabolic Syndrome and its component conditions, disorders of glucose and lipid metabolism and other maladies.

The compounds of the invention may be used in therapy.

The compounds of the invention may be used for the manufacture of a medicament for the treatment and/or prophylaxis of multiple diseases or disorders associated with MGAT2.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

(I)

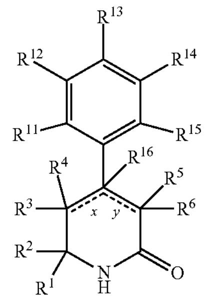

or a stereoisomer, a tautomer, a pharmaceutically acceptable salt, or a solvate thereof, wherein: ⎓ designates a single or double bond;

x and y can be both a single bond; when x is a double bond, then y is a single bond and $R^4$ and $R^{16}$ are absent; when y is a double bond, then x is a single bond and $R^5$ and $R^{16}$ are absent;

$R^1$ is independently selected from the group consisting of: —$CONH(C_{4-18}$ alkyl), —$CONHC_{2-8}$ haloalkyl, —$CONH(CH_2)_{1-8}Ph$, —$CONHCH_2COC_{2-8}$ alkyl, —$(CH_2)_m$—($C_{3-10}$ carbocycle substituted with 0-2 $R^b$ and 0-2 $R^g$), —$(CH_2)_m$-(5- to 6-membered heteroaryl comprising: carbon atoms and 1-4 heteroatoms selected from N, $NR^e$, O and S; wherein said heteroaryl is substituted with 0-1 $R^b$ and 0-2 $R^g$), and a $C_{1-12}$ hydrocarbon chain substituted with 0-3 $R^a$; wherein said hydrocarbon chain may be straight or branched, saturated or unsaturated;

$R^2$ is independently selected from the group consisting of: $C_{1-4}$ alkyl, $C_{3-4}$ cycloalkyl, and $C_{1-4}$ haloalkyl;

$R^3$ is independently selected from the group consisting of: H, F, Cl, $C_{1-4}$ alkyl and CN;

$R^4$ and $R^5$ are independently selected from the group consisting of: H, F, Cl, and $C_{1-4}$ alkyl;

when x is a single bond, $R^3$ and $R^4$ may be combined with the carbon atom to which they are attached to form a 3- to 6-membered carbocycle;

$R^6$ is independently selected from the group consisting of: H, halo, $C_{1-4}$ alkyl, CN, $NO_2$, $R^c$, —$(CH_2)_n$—$(X)_t$—$(CH_2)_mR^c$, $NH_2$, —$CONH(C_{1-6}$ alkyl), —$NHCOX_1SO_2R^j$, —$NHCOCH_2PO(OEt)_2$, —$NHCOCOR^j$, —$NHCOCH(OH)R^j$, —$NHCOCH_2COR^j$, —$NHCONHR^j$, and —$OCONR^fR^j$;

X is independently selected from the group consisting of: O, S, NH, CONH, and NHCO;

$X_1$ is independently $C_{1-4}$ hydrocarbon chain optionally substituted with $C_{1-4}$ alkyl or $C_{3-4}$ cycloalkyl;

when y is a single bond, $R^5$ and $R^6$ may be combined with the carbon atom to which they are attached to form a 3- to 6-membered carbocycle;

$R^{11}$, $R^{12}$, $R^{13}$, $R^{14}$ and $R^{15}$ are independently selected from the group consisting of: H, halo, $C_{1-4}$ alkyl substituted with 0-2 $R^j$, $C_{1-4}$ alkoxy, $C_{1-4}$ haloalkyl, $C_{1-4}$ haloalkoxy, —$(CH_2)_m$—$C_{3-6}$ cycloalkyl, CN, $NR^fR^j$, $OR^j$, $SR^j$, $NHCO_2(C_{1-4}$ alkyl), $NHSO_2(C_{1-4}$ alkyl), and a 4- to 6-membered heterocycle comprising: carbon atoms and 1-4 heteroatoms selected from N, $NR^e$, O, and S;

alternatively, $R^{11}$ and $R^{12}$, together with the carbon atoms to which they are attached, combine to form a 5 to 6-membered carbocyclic ring or a 5 to 6-membered heterocyclic ring comprising: carbon atoms and 1-3 heteroatoms selected from N, $NR^e$, O, and S;

alternatively, $R^{12}$ and $R^{13}$, together with the carbon atoms to which they are attached, combine to form a 5 to 6-membered carbocyclic ring or a 5 to 6-membered heterocyclic ring comprising: carbon atoms and 1-3 heteroatoms selected from N, $NR^e$, O, and S;

$R^{16}$ is independently selected from the group consisting of: H and $C_{1-4}$ alkyl;

$R^a$ is, at each occurrence, independently selected from the group consisting of: halo, OH, $C_{1-6}$ alkoxy, $C_{1-6}$ haloalkyl, $C_{1-6}$ haloalkoxy, $N(C_{1-4}$ alkyl$)_2$, —$(CH_2)_n$—$(X)_t$—$(CH_2)_mR^c$, and —$(CH_2)_n$—$(CH_2O)_m$—$(CH_2)_nR^f$;

$R^b$ is, at each occurrence, independently selected from the group consisting of: halo, OH, $C_{1-10}$ alkyl, $C_{1-10}$ alkoxy, $C_{1-10}$ haloalkyl, $C_{1-10}$ haloalkoxy, $C_{1-10}$ alkylthio, $C_{1-10}$ haloalkylthio, $N(C_{1-4}$ alkyl$)_2$, —$CONH(CH_2)_{4-20}H$, —$O(CH_2)_sO(C_{1-6}$ alkyl), $R^c$, —$(CH_2)_n$—$(X)_t$—$(CH_2)_mR^c$, and —$(CH_2)_n$—$(CH_2O)_m$—$CH_2)_nR^f$;

$R^c$ is, at each occurrence, independently selected from the group consisting of: $C_{3-6}$ cycloalkyl substituted with 0-2 $R^d$, $C_{3-6}$ cycloalkenyl substituted with 0-2 $R^d$, —$(CH_2)_m$-(phenyl substituted with 0-3 $R^d$), and a 5- to 6-membered heterocycle comprising: carbon atoms and 1-4 heteroatoms selected from N, $NR^e$, O, and S; wherein said heterocycle is substituted with 0-2 $R^d$;

$R^d$ is, at each occurrence, independently selected from the group consisting of: halo, OH, CN, $NO_2$, $C_{1-4}$ alkyl, $C_{1-4}$ alkoxy, $C_{1-4}$ haloalkyl, $C_{1-4}$ haloalkoxy, tetrazolyl, OBn and phenyl substituted with 0-2 $R^h$;

$R^e$ is, at each occurrence, independently selected from the group consisting of: H, $C_{1-8}$ alkyl, $C_{1-8}$ haloalkyl, benzyl optionally substituted with $C_{1-4}$ alkoxy, $CO(C_{1-4}$ alkyl) and COBn;

$R^f$ is, at each occurrence, independently selected from the group consisting of: H and $C_{1-4}$ alkyl;

$R^g$, $R^h$ and $R^i$ are, at each occurrence, independently selected from the group consisting of: halo, $C_{1-4}$ alkyl, $C_{1-4}$ alkoxy, $C_{1-4}$ haloalkyl, and $C_{1-4}$ haloalkoxy;

$R^j$ is, at each occurrence, independently selected from the group consisting of: $C_{1-4}$ alkyl, $C_{3-4}$ cycloalkyl and phenyl;

n, at each occurrence, is independently 0 or 1;

m, at each occurrence, is independently 0, 1, 2, 3, or 4;

s, at each occurrence, is independently 1, 2, or 3; and t, at each occurrence, is independently 0 or 1;

provided that the following compounds are excluded:

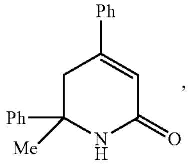
,
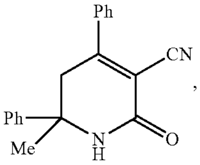
,
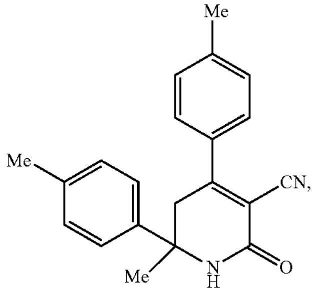
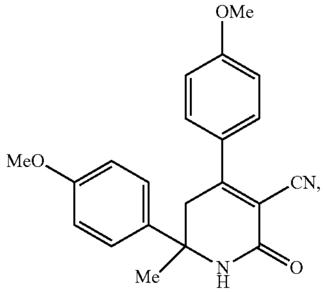
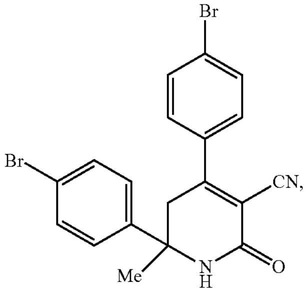

-continued

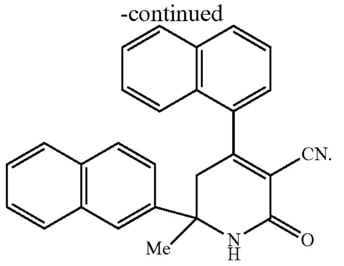

In a second aspect, the present invention includes a compound of Formula (I), or a stereoisomer, a tautomer, a pharmaceutically acceptable salt, or a solvate thereof, within the scope of the first aspect, wherein:

$R^1$ is independently selected from the group consisting of: —$CONHC_{4-18}$ alkyl, —$CONH(CH_2)_{1-8}$ Ph, $C_{1-12}$ alkyl substituted with 0-2 $R^a$, $C_{1-12}$ alkenyl substituted with 0-2 $R^a$, $C_{1-12}$ alkynyl substituted with 0-2 $R^a$, —$(CH_2)_m$-(phenyl substituted with 0-1 $R^b$ and 0-2 $R^g$), —$(CH_2)_m$—($C_{3-6}$ cycloalkyl substituted with 0-1 $R^b$), and —$(CH_2)_m$-(5- to 6-membered heteroaryl substituted with 0-1 $R^b$ and 0-2 $R^g$), wherein said heteroaryl is selected from: pyridyl, oxazolyl, thiazolyl and

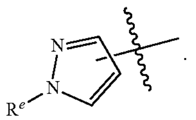

In a third aspect, the present invention includes a compound of Formula (I), or a stereoisomer, a tautomer, a pharmaceutically acceptable salt, or a solvate thereof, within the scope of the first or second aspect, wherein:

$R^{11}$ and $R^{15}$ are independently selected from the group consisting of: H, $C_{1-4}$ alkyl and halo;

$R^{12}$ and $R^{14}$ are independently selected from the group consisting of: H, halo, $C_{1-4}$ alkyl and $C_{1-4}$ alkoxy; and $R^{13}$ is independently selected from the group consisting of: H, halo, $C_{1-4}$ alkyl substituted with 0-1, $R^i$, $C_{1-4}$ alkoxy, $C_{1-4}$ haloalkyl, $C_{1-4}$ haloalkoxy, —$(CH_2)_m$—$C_{3-4}$ cycloalkyl, CN, $NR^fR^j$, $SR^j$, $NHCO_2(C_{1-4}$ alkyl), $NHSO_2(C_{1-4}$ alkyl), and a 4- to 6-membered heterocycle comprising: carbon atoms and 1-4 heteroatoms selected from N, $NR^e$, O, and S.

In a fourth aspect, the present invention provides a compound of Formula (II):

(II)

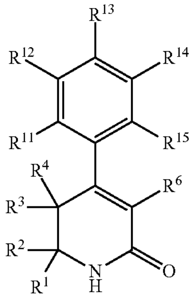

or a stereoisomer, a tautomer, a pharmaceutically acceptable salt, or a solvate thereof;

within the scope of any of the above aspects.

In a fifth aspect, the present invention includes a compound of Formula (I) or (II), or a stereoisomer, a tautomer, a pharmaceutically acceptable salt, or a solvate thereof, within the scope of any of the above aspects, wherein:

$R^1$ is independently selected from the group consisting of: $C_{1-6}$ alkyl, $C_{3-6}$ cycloalkyl, —$CONHC_{4-18}$ alkyl, —$CONHC_{2-8}$ haloalkyl, —$CONH(CH_2)_{1-8}$ Ph, —$(CH_2)_m$-(phenyl substituted with 1 $R^b$ and 0-2 $R^g$), and a 5- to 6-membered heteroaryl substituted with 0-1 $R^b$ and 0-2 $R^g$, wherein said heteroaryl is selected from: pyridyl, oxazolyl, thiazolyl and

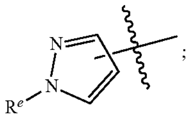

$R^2$ is independently selected from the group consisting of: $C_{1-4}$ alkyl and $C_{1-4}$ haloalkyl;

$R^3$ is independently selected from the group consisting of: H and F;

$R^4$ is independently selected from the group consisting of: H and F;

$R^6$ is independently selected from the group consisting of: CN, $NH_2$, —$CONH(C_{1-6}$ alkyl), $R^c$, —$(CH_2)_n$—$(X)_t$—$(CH_2)_mR^c$, —$NHCO(CH_2)SO_2(C_{1-4}$ alkyl), —$NHCOCH_2PO(OEt)_2$, —$NHCOCO(C_{1-4}$ alkyl), —$NHCOCH(OH)(C_{1-4}$ alkyl), —$NHCOCH_2CO(C_{1-4}$ alkyl), —$NHCONH(C_{1-4}$ alkyl), and —$OCONH(C_{1-4}$ alkyl);

$R^{11}$ and $R^{15}$ are independently selected from the group consisting of: H, $C_{1-4}$ alkyl and halo;

$R^{12}$ and $R^{14}$ are independently selected from the group consisting of: H, halo, $C_{1-4}$ alkyl and $C_{1-4}$ alkoxy;

$R^{13}$ is independently selected from the group consisting of: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, —$(CH_2)_m$—$C_{3-4}$ cycloalkyl, CN, $N(C_{1-4}$ alkyl$)_2$, $NHCO_2(C_{1-4}$ alkyl), $NHSO_2(C_{1-4}$ alkyl), pyrazolyl, and morpholinyl;

alternatively, $R^{12}$ and $R^{13}$, together with the carbon atoms to which they are attached, combine to form a 5 to 6-membered carbocyclic ring or a 5 to 6-membered heterocyclic ring comprising: carbon atoms and 1-3 heteroatoms selected from N, $NR^e$, O, and S;

$R^b$ is, at each occurrence, independently selected from the group consisting of: halo, OH, $C_{1-8}$ alkyl, $C_{1-8}$ alkoxy, $C_{1-8}$ haloalkyl, $C_{1-10}$ haloalkoxy, —$O(CH_2)_sO(C_{1-6}$ alkyl), $N(C_{1-4}$ alkyl$)_2$, —$CONH(CH_2)_{6-20}H$, —$(CH_2)_m$($C_{3-6}$ cycloalkyl), —$(CH_2)_m$($C_{4-6}$ cycloalkenyl), —$O(CH_2)_m$($C_{3-6}$ cycloalkyl), 4-$C_{1-4}$ alkoxy-Ph, —$O(CH_2)_{1n}$Ph, morpholinyl, pyridyl, 2-$C_{1-4}$ alkoxy-pyridin-5-yl, pyrimidinyl, pyrazinyl, and —O-pyrimidinyl;

$R^g$ is, at each occurrence, independently selected from the group consisting of: halo, $C_{1-4}$ alkyl, $C_{1-4}$ alkoxy, $C_{1-4}$ haloalkyl, and $C_{1-4}$ haloalkoxy;

m, at each occurrence, is independently 0, 1, 2 or 3; and s, at each occurrence, is independently 1, 2, or 3;

provided that the following compounds are excluded:

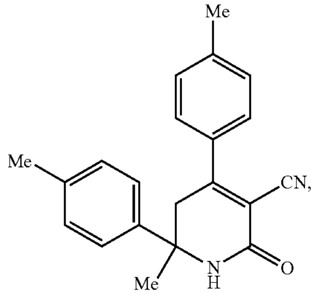
,

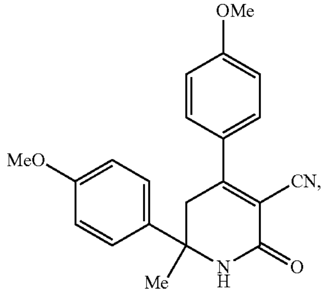
,

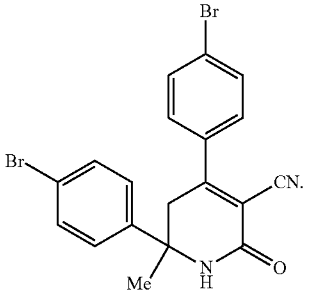
.

In a sixth aspect, the present invention includes a compound of Formula (I) or (II), or a stereoisomer, a tautomer, a pharmaceutically acceptable salt, or a solvate thereof, within the scope of any of the above aspects, wherein:

$R^1$ is independently selected from the group consisting of: $C_{1-6}$ alkyl, —$CONHC_{4-18}$ alkyl, —$CONH(CH_2)_{1-8}Ph$, and

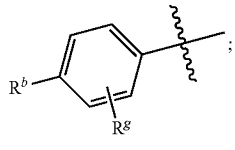
;

$R^6$ is independently selected from the group consisting of: CN, $NH_2$, —$CONH(C_{1-6}$ alkyl), —$NHCOCH_2PO(OEt)_2$, —$NHCO(CH_2)SO_2(C_{1-4}$ alkyl), $R^c$, $OR^c$, —$CONHR^c$, and —$NHCOR^c$;

$R^{12}$ is independently selected from the group consisting of: H, halo, $C_{1-4}$ alkyl and $C_{1-4}$ alkoxy;

$R^{13}$ is independently selected from the group consisting of: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, —$(CH_2)_m$—$C_{3-4}$ cycloalkyl, CN, $N(C_{1-4}$ alkyl$)_2$, $NHCO_2(C_{1-4}$ alkyl), $NHSO_2(C_{1-4}$ alkyl), pyrazolyl, and morpholinyl;

alternatively, $R^{12}$ and $R^{13}$, together with the carbon atoms to which they are attached, combine to form a 5 to 6-membered carbocyclic ring or a 5 to 6-membered saturated heterocyclic ring comprising: carbon atoms and 1-2 oxygen atoms;

$R^{14}$ is independently selected from the group consisting of: H and $C_{1-4}$ alkoxy;

$R^b$ is, at each occurrence, independently selected from the group consisting of: halo, $C_{1-6}$ alkyl, $C_{1-6}$ alkoxy, $C_{1-6}$ haloalkyl, $C_{1-10}$ haloalkoxy, —$O(CH_2)_sO(C_{1-6}$ alkyl), —$CONH(CH_2)_{6-20}H$, —$(CH_2)_m(C_{3-6}$ cycloalkyl), —$(CH_2)_m(C_{4-6}$ cycloalkenyl), —$O(CH_2)_m(C_{3-6}$ cycloalkyl), phenoxy, benzoxy, morpholinyl, 2-$C_{1-4}$ alkoxy-pyridin-5-yl, pyrimidin-5-yl, pyrazin-2-yl and —O-pyrimidinyl; and $R^c$ is, at each occurrence, independently selected from the group consisting of: $C_{3-6}$ cycloalkyl substituted with 0-2 $R^d$, —$(CH_2)_m$-(phenyl substituted with 0-3 $R^d$), and a heteroaryl selected from: oxazolyl, isoxazolyl, thiazolyl, pyrazolyl, imidazolyl, oxadiazolyl, triazolyl, tetrazolyl, pyridyl, and pyrazinyl; wherein said heteroaryl is substituted with 0-2 $R^d$; and provided that the following compounds are excluded:

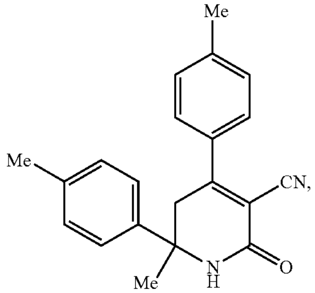
,

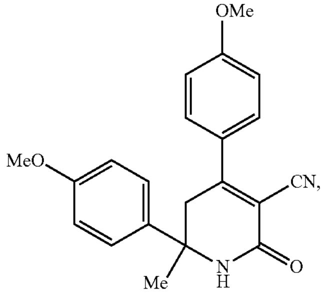
,

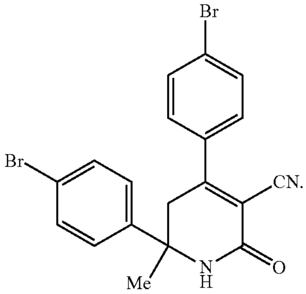
.

In a seventh aspect, the present invention includes a compound of Formula (I) or (II), or a stereoisomer, a tautomer, a pharmaceutically acceptable salt, or a solvate thereof, within the scope of any of the above aspects, wherein:

$R^1$ is

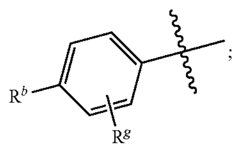

$R^6$ is independently selected from the group consisting of: $NH_2$, CN, —CONH($C_{1-4}$ alkyl), OPh, —CONH($C_{3-6}$ cycloalkyl), —CONHPh, —CONH-(2-halo-Ph), —CONH-(3-halo-Ph), —CONH-(4-halo-Ph), —CONH-(4-$C_{1-4}$ alkyl-Ph), —CONH(4-OH-Ph), —CONH-(3-$C_{1-4}$ alkoxy-Ph), —CONH-(4-$C_{1-4}$ alkoxy-Ph), —CONH-(4-$C_{1-4}$ haloalkyl-Ph), —CONH-(4-$C_{1-4}$ haloalkoxy-Ph), —CONH-(4-CN-Ph), —CONH-(4-tetrazolyl-Ph), —CONH-(3-halo-4-$C_{1-4}$ alkyl-Ph), —CONH-(3-halo-4-$C_{1-4}$ alkoxy-Ph), —CONH($CH_2$)$_2$Ph, —CONH(4-(4-$C_{1-4}$ alkoxy-Ph)-thiazol-2-yl), —CONH(1-$C_{1-4}$ alkyl-pyrazol-3-yl), —CONH(5-$C_{1-4}$ alkoxy-pyrid-2-yl), —CONH(6-$C_{1-4}$ alkoxy-pyrid-3-yl), —CONH(5-$C_{1-4}$ alkoxy-pyrazin-2-yl), —CONH(6-$C_{1-4}$ alkoxy-pyridazin-3-yl), —NHCO($CH_2$)$SO_2$($C_{1-4}$ alkyl), —NHCOPh, —NHCO(2-$C_{1-4}$ alkyl-Ph), —NHCO(3-$C_{1-4}$ alkyl-Ph), —NHCO(4-$C_{1-4}$ alkyl-Ph), —NHCO(2-halo-Ph), —NHCO(3-halo-Ph), —NHCO(2-$C_{1-4}$ haloalkyl-Ph), —NHCO(2-$C_{1-4}$ haloalkoxy-Ph), —NHCO(2-halo-4-halo-Ph), —NHCO(2-halo-5-halo-Ph), —NHCO(oxazolyl), —NHCO(isoxazolyl), —NHCO(3-$C_{1-4}$ alkyl-isoxazol-5-yl), —NHCO(4-$C_{1-4}$ alkyl-isoxazol-5-yl), —NHCO(3-$C_{1-4}$ alkoxy-isoxazol-5-yl), —NHCO(4-$C_{1-4}$ alkoxy-isoxazol-5-yl), —NHCO(3-halo-isoxazol-5-yl), —NHCO(3-OBn-isoxazol-5-yl), —NHCO(3-(2-halo-Ph)-isoxazol-5-yl), —NHCO(3-(3-halo-Ph)-isoxazol-5-yl), —NHCO(5-$C_{1-4}$ alkyl-1H-pyrazol-3-yl), imidazolyl, —NHCO(5-$C_{1-4}$ alkyl-1,3,4-oxadiazol-2-yl), —NHCO(1-$C_{1-4}$ alkyl-1,2,3-triazol-4-yl), —NHCO(6-$C_{1-4}$ alkoxy-pyrid-3-yl), —NHCO(pyrazinyl), —NHCO(6-halo-pyridazin-3-yl), 5-$C_{1-4}$ haloalkyl-1,3,4-oxadiazol-2-yl, 3-$NO_2$-1H-1,2,4-triazol-1-yl, tetrazolyl and 5-$C_{1-4}$ alkyl-tetrazol-1-yl;

$R^b$ is independently selected from the group consisting of: halo, $C_{1-6}$ alkyl, $C_{1-6}$ alkoxy, $C_{1-6}$ haloalkyl, $C_{1-8}$ haloalkoxy, —CONH($CH_2$)$_{6-20}$H, $C_{3-6}$ cycloalkyl, $C_{4-6}$ cycloalkenyl, —O($CH_2$)$_m$($C_{3-6}$ cycloalkyl), phenoxy, benzoxy, pyrimidinyl, pyrazinyl and —O-pyrimidinyl; and $R^g$ is independently selected from the group consisting of: halo and $C_{1-4}$ alkyl;

provided that the following compounds are excluded:

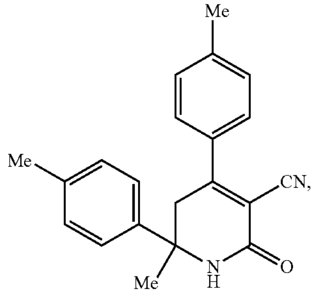

-continued

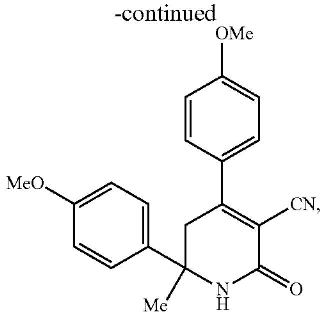

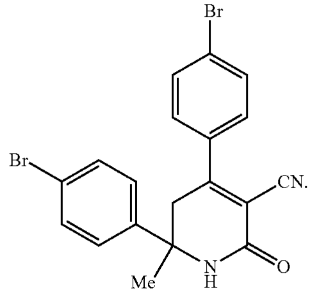

In an eighth aspect, the present invention includes a compound of Formula (I) or (II), or a stereoisomer, a tautomer, a pharmaceutically acceptable salt, or a solvate thereof, within the scope of any of the above aspects, wherein:

$R^2$ is independently selected from the group consisting of: $CF_3$ and Me;

$R^3$ is independently selected from the group consisting of: H and F;

$R^4$ is independently selected from the group consisting of: H and F;

$R^6$ is independently selected from the group consisting of: $NH_2$, CN, —CONHMe, OPh, —CONH(cyclopropyl), —CONH(cyclobutyl), —CONH(cyclopentyl), —CONH(cyclohexyl), —CONHPh, —CONH(4-F-Ph), —CONH(2-Cl-Ph), —CONH(4-Cl-Ph), —CONH(4-Me-Ph), —CONH(4-OH-Ph), —CONH(3-OMe-Ph), —CONH(4-OMe-Ph), —CONH(4-$CF_3$-Ph), —CONH(4-$OCF_3$-Ph), —CONH(1-Me-pyrazol-3-yl), —CONH(4-(1H-tetrazol-2-yl)-Ph), —CONH(4-(2H-tetrazol-5-yl)-Ph), —CONH(3-F-4-Me-Ph), —CONH(3-F-4-OMe-Ph), —CONH($CH_2$)$_2$Ph, —CONH(5-OMe-pyrid-2-yl), —CONH(6-OMe-pyrid-3-yl), —CONH(5-OMe-pyrazin-2-yl), —CONH(6-OMe-pyridazin-3-yl), —NHCO($CH_2$)$SO_2$Me, —NHCOPh, —NHCO(2-Me-Ph), —NHCO(3-Me-Ph), —NHCO(4-Me-Ph), —NHCO(2-Cl-Ph), —NHCO(3-Cl-Ph), —NHCO(2-$C_{1-4}$—F-Ph), —NHCO(2-$C_{1-5}$—F-Ph), —NHCO(isoxazol-5-yl), —NHCO(3-Me-isoxazol-5-yl), —NHCO(4-Me-isoxazol-5-yl), —NHCO(3-OMe-isoxazol-5-yl), —NHCO(3-Br-isoxazol-5-yl), —NHCO(3-(2-Cl-Ph)-isoxazol-5-yl), —NHCO(3-(3-F-Ph)-isoxazol-5-yl), —NHCO(3-OBn-isoxazol-5-yl), 1H-imidazol-1-yl, —NHCO(5-Me-1,3,4-oxadiazol-2-yl), —NHCO(1-Me-1,2,3-triazol-4-yl), —NHCO(6-OMe-pyrid-3-yl), —NHCO(6-Cl-pyridazin-3-yl), 5-$CF_3$-1,3,4-oxadiazol-2-yl, 1H-tetrazol-1-yl, 1H-tetrazol-3-yl, and 2H-tetrazol-5-yl;

$R^{11}$ and $R^{15}$ are independently selected from the group consisting of: H, Me, F, and Cl;

$R^{12}$ is independently selected from the group consisting of: H, F, Cl, Me and OMe;

$R^{13}$ is independently selected from the group consisting of: H, F, Cl, Br, Me, OMe, OEt, $CH_2OMe$, $CF_3$, $CH_2CF_3$, $OCHF_2$, $OCF_3$, CN, $N(Me)_2$, cyclopropyl and cyclopropylmethyl;

alternatively, $R^{12}$ and $R^{13}$, together with the carbon atoms to which they are attached, combine to form a 5 to 6-membered carbocyclic ring or a 5 to 6-membered saturated heterocyclic ring comprising: carbon atoms and 1-2 oxygen atoms;

$R^{14}$ is H;

$R^b$ is, at each occurrence, independently selected from the group consisting of: n-pentyl, methoxy, n-butoxy, i-butoxy, i-pentoxy, $—O(CH_2)_{1-6}CF_3$, $—O(CH_2)_{1-4}CF_2CF_3$, $—CONH(CH_2)_{6-20}H$, cyclopropyl, cyclopent-1-en-1-yl, cyclohex-1-en-1-yl, $—O(CH_2)_2$(cyclopentyl), phenoxy, benzoxy, pyrimidin-5-yl, pyrazin-2-yl and —O-pyrimidin-2-yl; and $R^g$ is F;

provided that the following compound is excluded:

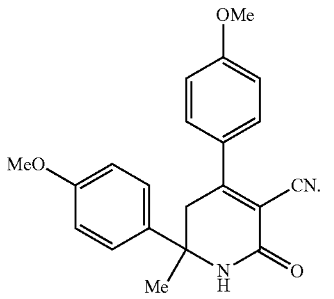 [SMILES: COc1ccc(C2=C(C#N)C(=O)NC(C)(c3ccc(OC)cc3)C2)cc1]

In a ninth aspect, the present invention includes a compound of Formula (I) or (II), or a stereoisomer, a tautomer, a pharmaceutically acceptable salt, or a solvate thereof, within the scope of any of the first, second, third, fourth, fifth and sixth aspects, wherein:

$R^1$ is

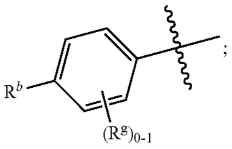

$R^2$ is independently selected from $CF_3$ and $CH_3$;

$R^6$ is independently selected from: CN, $R^c$, $—CONHR^c$, $—NHCOR^c$, and $—NHCOCH_2SO_2$ ($C_{1-4}$ alkyl);

$R^b$ is independently selected from: $—O(CH_2)_{1-6}CF_3$, $—O(CH_2)_{1-4}CF_2CF_3$, $—CONH(CH_2)_{6-20}H$, cyclopent-1-en-1-yl, cyclohex-1-en-1-yl, $—O(CH_2)_2$(cyclopentyl), phenoxy, benzoxy, pyrimidin-5-yl, pyrazin-2-yl and —O-pyrimidin-2-yl;

$R^c$ is, at each occurrence, independently selected from the group consisting of: $—(CH_2)_m$-(phenyl substituted with 0-3 $R^d$), and a heteroaryl selected from: oxazolyl, isoxazolyl, pyrazolyl, imidazolyl, oxadiazolyl, triazolyl, tetrazolyl, pyridyl, and pyrazinyl; wherein said heteroaryl is substituted with 0-2 $R^d$; and $R^d$ is, at each occurrence, independently selected from the group consisting of: halo, OH, CN, $C_{1-4}$ alkyl, $C_{1-4}$ alkoxy, $C_{1-4}$ haloalkyl, $C_{1-4}$ haloalkoxy, tetrazolyl and OBn.

In another aspect, the present invention includes a compound of Formula (I) or (II), or a stereoisomer, a tautomer, a pharmaceutically acceptable salt, or a solvate thereof, within the scope of any of the first, second, third, fourth, fifth, sixth and ninth aspects, wherein:

$R^1$ is

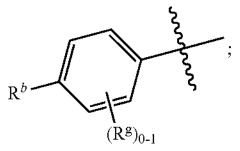

$R^2$ is independently selected from $CF_3$ and $CH_3$;

$R^6$ is independently selected from: CN, $R^c$, $—CONHR^c$, $—NHCOR^c$, and $—NHCOCH_2SO_2$ ($C_{1-zi}$ alkyl);

$R^{11}$, $R^{12}$, $R^{14}$ and $R^{15}$ are H;

$R^{13}$ is independently selected from the group consisting of: H, $C_{1-4}$ alkyl, $C_{1-4}$ haloalkyl, $C_{1-4}$ alkoxy, and $C_{1-4}$ haloalkoxy; and $R^b$ is independently selected from: $—O(CH_2)_{1-6}CF_3$ and $—O(CH_2)_{1-4}CF_2CF_3$.

In another aspect, the present invention includes a compound of Formula (II), or a stereoisomer, a tautomer, a pharmaceutically acceptable salt, or a solvate thereof, within the scope of the fourth or fifth aspect, wherein:

$R^1$ is

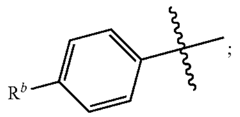

$R^2$ is independently selected from $CF_3$ and $CH_3$;

$R^3$ and $R^4$ are H;

$R^6$ is independently 5-membered nitrogen heteroaryl;

$R^{11}$, $R^{12}$, $R^{14}$ and $R^{15}$ are H;

$R^{13}$ is independently selected from the group consisting of: H, $C_{1-4}$ alkyl, $C_{1-4}$ haloalkyl, $C_{1-4}$ alkoxy, and $C_{1-4}$ haloalkoxy; and $R^b$ is independently selected from: $—O(CH_2)_{1-6}CF_3$ and $—O(CH_2)_{1-4}CF_2CF_3$.

In another aspect, the present invention includes a compound of Formula (II), or a stereoisomer, a tautomer, a pharmaceutically acceptable salt, or a solvate thereof, within the scope of the fourth or fifth aspect, wherein:

$R^1$ is

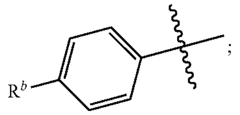

$R^2$ is independently selected from $CF_3$ and $CH_3$;

$R^3$ and $R^4$ are H;

$R^6$ is independently selected from: 1H-imidazol-1-yl, 1H-tetrazol-1-yl, 1H-tetrazol-3-yl, and 2H-tetrazol-5-yl;

$R^{11}$, $R^{12}$, $R^{14}$ and $R^{15}$ are H;

$R^{13}$ is independently selected from the group consisting of: H, Me, OMe, and $OCHF_2$; and $R^b$ is independently selected from: $—O(CH_2)_{1-6}CF_3$ and $—O(CH_2)_{1-4}CF_2CF_3$.

In a tenth aspect, the present invention provides, inter alia, a compound of Formula (I):

(I)

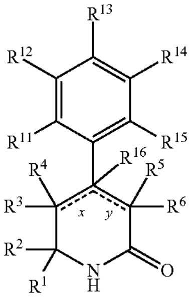

or a stereoisomer, a tautomer, a pharmaceutically acceptable salt, or a solvate thereof, wherein:

- $\overline{---}$ designates a single or double bond;
- x and y can be both a single bond; when x is a double bond, then y is a single bond and $R^4$ and $R^{16}$ are absent; when y is a double bond, then x is a single bond and $R^5$ and $R^{16}$ are absent;
- $R^1$ is independently selected from the group consisting of: $—(CH_2)_m—(C_{3-10}$ carbocycle substituted with 0-3 $R^b)$ or a $C_{1-12}$ hydrocarbon chain substituted with 0-3 $R^a$; wherein said hydrocarbon chain may be straight or branched, saturated or unsaturated;
- $R^2$ is independently selected from the group consisting of: $C_{1-4}$ alkyl and $C_{1-4}$ haloalkyl;
- $R^3$ is independently selected from the group consisting of: H, halo, $C_{1-4}$ alkyl and CN;
- $R^4$ and $R^5$ are independently selected from the group consisting of: H, halo and $C_{1-4}$ alkyl;
- when x is a single bond, $R^3$ and $R^4$ may be combined with the carbon atom to which they are attached to form a 3- to 6-membered carbocycle;
- $R^6$ is independently selected from the group consisting of: H, halo, $C_{1-4}$ alkyl, CN, $NO_2$, and $—(CH_2)_n—(X)_t—(CH_2)_mR^c$;
- X is independently selected from the group consisting of: O, S, NH, CONH and NHCO;
- when y is a single bond, $R^5$ and $R^6$ may be combined with the carbon atom to which they are attached to form a 3- to 6-membered carbocycle;
- $R^{11}$, $R^{12}$, $R^{13}$, $R^{14}$ and $R^{15}$ are independently selected from the group consisting of: H, halo, $C_{1-4}$ alkyl, $C_{1-4}$ alkoxy, $C_{1-4}$ haloalkyl, $C_{1-4}$ haloalkoxy, CN and a 5- to 6-membered heterocycle comprising: carbon atoms and 1-4 heteroatoms selected from N, $NR^e$, O, and S;
- $R^{16}$ is independently selected from the group consisting of: H and $C_{1-4}$ alkyl;
- $R^a$ is, at each occurrence, independently selected from the group consisting of: halo, OH, $C_{1-6}$ alkoxy, $C_{1-6}$ haloalkyl, $C_{1-6}$ haloalkoxy, $N(C_{1-4}\text{ alkyl})_2$, $—(CH_2)_n—(X)_t—(CH_2)_mR^c$, and $—(CH_2)_n—(CH_2O)_m—(CH_2)_nR^f$;
- $R^b$ is, at each occurrence, independently selected from the group consisting of: halo, OH, $C_{1-6}$ alkyl, $C_{1-6}$ alkoxy, $C_{1-6}$ haloalkyl, $C_{1-6}$ haloalkoxy, $—(CH_2)_n—(X)_t—(CH_2)_mR^c$, and $—(CH_2)_n—(CH_2O)_m—(CH_2)_nR^f$;
- $R^c$ is independently selected from the group consisting of: $C_{3-6}$ cycloalkyl substituted with 0-2 $R^d$, phenyl substituted with 0-3 $R^d$, and a 5- to 6-membered heterocycle comprising: carbon atoms and 1-4 heteroatoms selected from N, $NR^e$, 0, and S; wherein said heterocycle is substituted with 0-2 $R^d$;
- $R^d$ is, at each occurrence, independently selected from the group consisting of: halo, OH, CN, $C_{1-4}$ alkyl, $C_{1-4}$ alkoxy, $C_{1-4}$ haloalkyl, and $C_{1-4}$ haloalkoxy;
- $R^e$ is independently selected from the group consisting of: H, $C_{1-4}$ alkyl, benzyl, $CO(C_{1-4}$ alkyl) and COBn;
- $R^e$ is independently selected from the group consisting of: H and $C_{1-4}$ alkyl;
- n, at each occurrence, is independently 0 or 1;
- m, at each occurrence, is independently 0, 1, 2, 3 or 4; and
- t, at each occurrence, is independently 0 or 1;

provided that the following compounds are excluded:

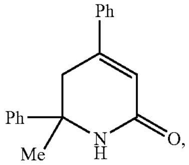
,
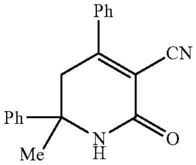
,
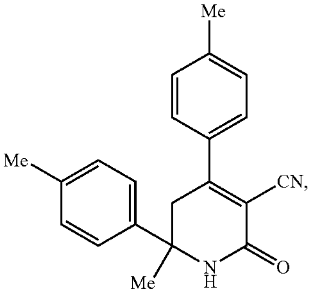
,
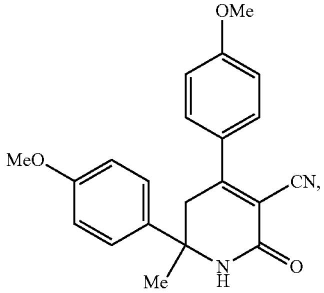
,
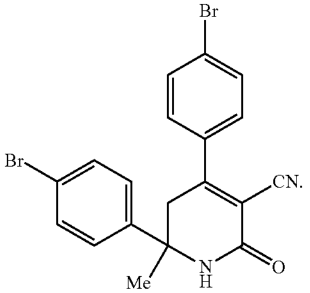
.

In an eleventh tenth aspect, the present invention includes a compound of Formula (I), or a stereoisomer, a tautomer, a pharmaceutically acceptable salt, or a solvate thereof, within the scope of the tenth aspect, wherein:

- $R^1$ is independently selected from the group consisting of: $C_{1-6}$ alkyl substituted with 0-2 $R^a$, $—(CH_2)_m$-(phenyl substituted with 0-3 $R^b$), and $—(CH_2)_m—(C_{3-6}$ cycloalkyl substituted with 0-2 $R^b$).

In a twelfth aspect, the present invention includes a compound of Formula (I), or a stereoisomer, a tautomer, a pharmaceutically acceptable salt, or a solvate thereof, within the scope of the tenth or eleventh aspect, wherein:

$R^{11}$ and $R^{15}$ are independently selected from the group consisting of: H and halo;

$R^{12}$ and $R^{14}$ are independently selected from the group consisting of: H, $C_{1-4}$ alkyl and $C_{1-4}$ alkoxy; and $R^{13}$ is independently selected from the group consisting of: H, halo, $C_{1-4}$ alkyl, $C_{1-4}$ alkoxy, $C_{1-4}$ haloalkyl, $C_{1-4}$ haloalkoxy, CN and morpholinyl.

In a thirteenth aspect, the present invention provides a compound of Formula (II):

(II)

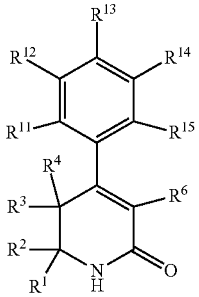

or a stereoisomer, a tautomer, a pharmaceutically acceptable salt, or a solvate thereof;
within the scope of any of the tenth, eleventh and twelfth aspects.

In a fourteenth aspect, the present invention includes a compound of Formula (I) or (II), or a stereoisomer, a tautomer, a pharmaceutically acceptable salt, or a solvate thereof, within the scope of any of the tenth, eleventh, twelfth and thirteenth aspects, wherein:

$R^1$ is independently selected from the group consisting of: $C_{1-6}$ alkyl, $C_{3-6}$ cycloalkyl, —$(CH_2)_m$Ph and

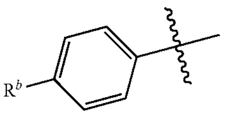

;

$R^2$ is independently selected from the group consisting of: $C_{1-4}$ alkyl and $C_{1-4}$ haloalkyl;

$R^3$ is H;

$R^4$ is H;

$R^6$ is independently selected from the group consisting of: CN, $NO_2$, —CONH($C_{1-6}$ alkyl), —CONHPh, —CONH-(3-halo-Ph), —CONH-(4-halo-Ph), —CONH-(4-$C_{1-4}$ alkyl -Ph), —CONH-(3-$C_{1-4}$ alkoxy-Ph), —CONH-(4-$C_{1-4}$ alkoxy-Ph), —CONH-(4-$C_{1-4}$ haloalkyl-Ph), —CONH-(4-$C_{1-4}$ haloalkoxy-Ph), —CONH-(3-halo-4-$C_{1-4}$ alkyl-Ph), —CONH-(3-halo-4-$C_{1-4}$ alkoxy-Ph), —CONH$(CH_2)_2$Ph, and 2H-tetrazol-5-yl;

$R^{11}$ and $R^{15}$ are independently selected from the group consisting of: H and halo;

$R^{12}$ and $R^{14}$ are independently selected from the group consisting of: H, $C_{1-4}$ alkyl and $C_{1-4}$ alkoxy;

$R^{13}$ is independently selected from the group consisting of: H, halo, $C_{1-4}$ alkyl, $C_{1-4}$ alkoxy, $C_{1-4}$ haloalkyl, $C_{1-4}$ haloalkoxy, CN and morpholinyl;

$R^b$ is independently selected from the group consisting of: halo, OH, $C_{1-6}$ alkyl, $C_{1-6}$ alkoxy, $C_{1-6}$ haloalkyl, $C_{1-6}$ haloalkoxy, —$O(CH_2)_mO$($C_{1-4}$ alkyl), N($C_{1-4}$ alkyl)$_2$, —$O(CH_2)_m$($C_{3-6}$ cycloalkyl), 4-$C_{1-4}$ alkoxy-Ph, —$O(CH_2)_m$Ph, pyridin-2-yl, 2-$C_{1-4}$ alkoxy-pyridin-5-yl, pyrimidin-5-yl, pyrazin-2-yl and —O-pyrimidin-2-yl; and m, at each occurrence, is independently 0, 1, 2 or 3.

In a fifteenth aspect, the present invention includes a compound of Formula (I) or (II), or a stereoisomer, a tautomer, a pharmaceutically acceptable salt, or a solvate thereof, within the scope of any of the tenth, eleventh, twelfth, thirteenth and fourteenth aspects, wherein:

$R^1$ is independently selected from the group consisting of: $C_{1-6}$ alkyl and

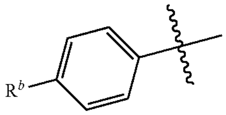

;

$R^6$ is independently selected from the group consisting of: CN, —CONH($C_{1-6}$ alkyl), —CONHPh, —CONH-(3-halo-Ph), —CONH-(4-halo-Ph), —CONH-(4-$C_{1-4}$ alkyl -Ph), —CONH-(3-$C_{1-4}$ alkoxy-Ph), —CONH-(4-$C_{1-4}$ alkoxy-Ph), —CONH-(4-$C_{1-4}$ haloalkyl-Ph), —CONH-(4-$C_{1-4}$ haloalkoxy-Ph), —CONH-(3-halo-4-$C_{1-4}$ alkoxy-Ph), —CONH$(CH_2)_2$Ph, and 2H-tetrazol-5-yl;

$R^{12}$ is independently selected from the group consisting of: H, $C_{1-4}$ alkyl and $C_{1-4}$ alkoxy;

$R^{14}$ is independently selected from the group consisting of: H and $C_{1-4}$ alkoxy;

$R^{13}$ is independently selected from the group consisting of: H, halo, $C_{1-4}$ alkyl, $C_{1-4}$ alkoxy, $C_{1-4}$ haloalkyl, $C_{1-4}$ haloalkoxy and CN;

$R^b$ is independently selected from the group consisting of: $C_{1-6}$ alkyl, $C_{1-6}$ alkoxy, $C_{1-6}$ haloalkyl, $C_{1-6}$ haloalkoxy, —$O(CH_2)_mO$($C_{1-4}$ alkyl), —$O(CH_2)_m$($C_{3-6}$ cycloalkyl), phenoxy, benzoxy, 2-$C_{1-4}$ alkoxy-pyridin-5-yl, pyrimidin-5-yl, pyrazin-2-yl and —O-pyrimidin-2-yl; and m, at each occurrence, is independently 0, 1, 2 or 3;

provided that the following compounds are excluded:

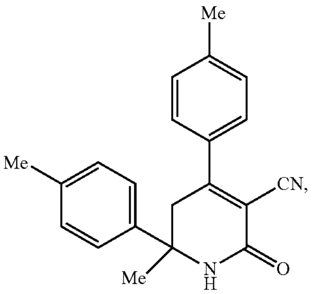

-continued

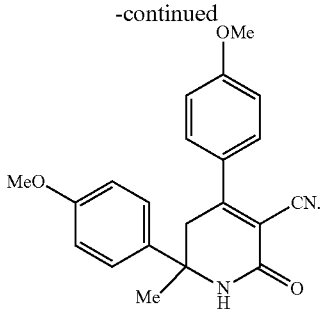

In a sixteenth aspect, the present invention includes a compound of Formula (I) or (II), or a stereoisomer, a tautomer, a pharmaceutically acceptable salt, or a solvate thereof, within the scope of any of the ninth, tenth, eleventh, twelfth, thirteenth, fourteenth and fifteenth aspects, wherein:

$R^1$ is

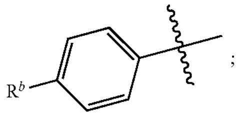

$R^6$ is independently selected from the group consisting of: CN, —CONHPh, —CONH-(4-halo-Ph), —CONH-(4-$C_{1-4}$ alkyl -Ph), —CONH-(3-$C_{1-4}$ alkoxy-Ph), —CONH-(4-$C_{1-4}$ alkoxy-Ph), —CONH-(4-$C_{1-4}$ haloalkyl-Ph), —CONH-(4-$C_{1-4}$ haloalkoxy-Ph), —CONH-(3-halo-4-$C_{1-4}$ alkoxy-Ph), —$CONH(CH_2)_2$ Ph, and 2H-tetrazol-5-yl; and $R^b$ is independently selected from the group consisting of: $C_{1-6}$ alkyl, $C_{1-6}$ alkoxy, $C_{1-6}$ haloalkyl, $C_{1-6}$ haloalkoxy, —$O(CH_2)_m(C_{3-6}$ cycloalkyl), phenoxy, benzoxy, pyrimidin-5-yl, pyrazin-2-yl and —O-pyrimidin-2-yl;

provided that the following compounds are excluded:

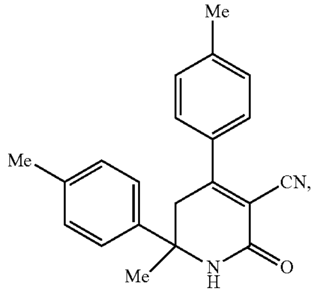

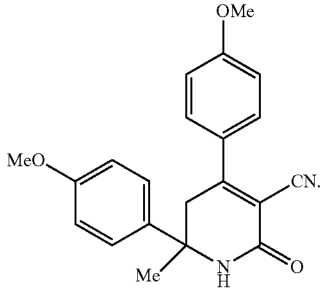 [SMILES: COc1ccc(C2=C(C#N)C(=O)NC(C)(c3ccc(OC)cc3)C2)cc1]

In a seventeenth aspect, the present invention includes a compound of Formula (I) or (II), or a stereoisomer, a tautomer, a pharmaceutically acceptable salt, or a solvate thereof, within the scope of any of the ninth, tenth, eleventh, twelfth, thirteenth, fourteenth, fifteenth and sixteenth aspects, wherein:

$R^2$ is independently selected from the group consisting of: $CF_3$ and Me;

$R^6$ is independently selected from the group consisting of: CN, —CONHPh, —CONH-(4-F-Ph), —CONH-(4-Cl-Ph), —CONH-(4-Me-Ph), —CONH-(3-OMe-Ph), —CONH-(4-OMe-Ph), —CONH-(4-$CF_3$-Ph), —CONH-(4-$OCF_3$-Ph), —CONH-(3-F-4-OMe-Ph), —$CONH(CH_2)_2Ph$, and 2H-tetrazol-5-yl;

$R^{11}$ and $R^{15}$ are independently selected from the group consisting of: H and F;

$R^{12}$ is independently selected from the group consisting of: H, Me and OMe;

$R^{13}$ is independently selected from the group consisting of: H, F, Cl, Me, OMe, OEt, $CF_3$, $OCHF_2$, $OCF_3$ and CN;

$R^{14}$ is H; and $R^b$ is independently selected from the group consisting of: n-pentyl, methoxy, n-butoxy, i-butoxy, —$O(CH_2)_{1-3}$ $CF_3$, —$O(CH_2)_2$(cyclopentyl), phenoxy, benzoxy, pyrimidin-5-yl, pyrazin-2-yl and —O-pyrimidin-2-yl;

provided that the following compounds are excluded:

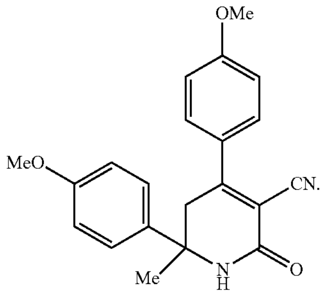

In an eighteenth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds or a single compound from the exemplified examples within the scope of any of the above aspects.

In another aspect, the present disclosure provides a compound selected from:

(S)-3-(1H-tetrazol-5-yl)-4-(p-tolyl)-6-(4-(4,4,4-trifluorobutoxy)phenyl)-6-(trifluoromethyl)-5,6-dihydropyridin-2(1H)-one, (S)—N-(4-methoxyphenyl)-2-oxo-4-(p-tolyl)-6-(4-(4,4,4-trifluorobutoxy)phenyl)-6-(trifluoromethyl)-1,2,5,6-tetrahydropyridine-3-carboxamide, (S)-3-(2H-tetrazol-5-yl)-4-(p-tolyl)-6-(4-((6,6,6-trifluorohexyl)oxy)phenyl)-6-(trifluoromethyl)-5,6-dihydropyridin-2(1H)-one, (S)-2-oxo-4-(p-tolyl)-6-(4-(4,4,4-trifluorobutoxy)phenyl)-6-(trifluoromethyl)-1,2,5,6-tetrahydropyridine-3-carbonitrile, (S)-2-oxo-4-(p-tolyl)-6-(4-(4,4,4-trifluorobutoxy)phenyl)-N-(4-(trifluoromethoxy)phenyl)-6-(trifluoromethyl)-1,2,5,6-tetrahydropyridine-3-carboxamide, (S)—N-(6-methoxypyridin-3-yl)-2-oxo-4-(p-tolyl)-6-(4-(4,4,4-trifluorobutoxy)phenyl)-6-(trifluoromethyl)-1,2,5,6-tetrahydropyridine-3-carboxamide, (S)—N-cyclopropyl-2-oxo-4-(p-tolyl)-6-(4-(4,4,4-trifluorobutoxy)phenyl)-6-(trifluoromethyl)-1,2,5,6-tetrahydropyridine-3-carboxamide, (S)—N-(4-hydroxyphenyl)-2-oxo-4-(p-tolyl)-6-(4-(4,4,4-trifluorobutoxy)phenyl)-6-(trifluoromethyl)-1,2,5,6-tetrahydropyridine-3-carboxamide, (S)-4-(4-(difluoromethoxy)phenyl)-2-oxo-6-(4-(4,4,4-trifluorobutoxy)phenyl)-6-(trifluoromethyl)-1,2,5,6-tetrahydropyridine-3-carbonitrile, (S)-2-oxo-4-(p-tolyl)-6-(trifluoromethyl)-6-(4-(3,3,3-trifluoropropoxy)phenyl)-1,2,5,6-tetrahydropyridine-3-carbonitrile, (S)-4-(4-(difluoromethoxy)phenyl)-3-(1H-tetrazol-1-yl)-6-(4-(4,4,4-trifluorobutoxy)phenyl)-6-(trifluoromethyl)-5,6-dihydropyridin-2(1R)-one, (S)-3-methyl-N-(2-oxo-4-(p-tolyl)-6-(4-(4,4,4-trifluorobutoxy)phenyl)-6-(trifluoromethyl)-1,2,5,6-tetrahydropyridin-3-yl)isoxazole-5-carboxamide, (S)-5-methyl-N-(2-oxo-4-(p-tolyl)-6-(4-(4,4,4-trifluorobutoxy)phenyl)-6-(trifluoromethyl)-1,2,5,6-tetrahydropyridin-3-yl)-1,3,4-oxadiazole-2-carboxamide, $N^2$-heptyl-$N^5$-(4-methoxyphenyl)-2-methyl-6-oxo-4-(p-tolyl)-1,2,3,6-tetrahydropyridine-2,5-dicarboxamide, (S)-3-(1H-tetrazol-1-yl)-4-(p-tolyl)-6-(4-((6,6,6-trifluorohexyl)oxy)phenyl)-6-(trifluoromethyl)-5,6-dihydropyridin-2(1H)-one, (S)-2-oxo-4-(p-tolyl)-6-(4-((6,6,6-trifluorohexyl)oxy)phenyl)-6-(trifluoromethyl)-1,2,5,6-tetrahydropyridine-3-carbonitrile, (S)-4-(5,6,7,8-tetrahydronaphthalen-2-yl)-3-(1H-tetrazol-5-yl)-6-(4-(4,4,4-trifluorobutoxy)phenyl)-6-(trifluoromethyl)-5,6-dihydropyridin-2(1H)-one, (S)-2-(methylsulfonyl)-N-(2-oxo-4-(p-tolyl)-6-(4-(4,4,4-trifluorobutoxy)phenyl)-6-(trifluoromethyl)-1,2,5,6-tetrahydropyridin-3-yl)acetamide, (S)-3-(1H-tetrazol-5-yl)-6-(4-(4,4,4-trifluorobutoxy)phenyl)-4-(4-(2,2,2-trifluoroethyl)phenyl)-6-(trifluoromethyl)-5,6-dihydropyridin-2(1H)-one, and (S)—N-(5-methoxypyrazin-2-yl)-2-oxo-4-(p-tolyl)-6-(4-(4,4,4-trifluorobutoxy)phenyl)-6-(trifluoromethyl)-1,2,5,6-tetrahydropyridine-3-carboxamide;

or a pharmaceutically acceptable salt thereof.

In another embodiment, $R^1$ is independently —CONH($C_{4-18}$ alkyl), —CONH$C_{2-8}$ haloalkyl, or —CONH$(CH_2)_{1-8}$ Ph.

In another embodiment, $R^1$ is —$(CH_2)_m$—($C_{3-10}$ carbocycle substituted with 0-2 $R^b$ and 0-2 $R^g$), or —$(CH_2)_m$-(5- to 6-membered heteroaryl comprising: carbon atoms and 1-4 heteroatoms selected from N, $NR^e$, O and S; wherein said heteroaryl is substituted with 0-1 $R^b$ and 0-2 $R^g$).

In another embodiment, $R^1$ is —$(CH_2)_m$—($C_{3-10}$ carbocycle substituted with 0-2 $R^b$ and 0-2 $R^g$).

In another embodiment, $R^1$ is —$(CH_2)_m$-(phenyl substituted with 0-2 $R^b$ and 0-2 $R^g$).

In another embodiment, $R^1$ is —$(CH_2)_m$-(5- to 6-membered heteroaryl comprising: carbon atoms and 1-4 heteroatoms selected from N, $NR^e$, O and S; wherein said heteroaryl is substituted with 0-1 $R^b$ and 0-2 $R^g$).

In another embodiment, $R^1$ is a $C_{1-12}$ hydrocarbon chain substituted with 0-3 $R^a$; wherein said hydrocarbon chain may be straight or branched, saturated or unsaturated.

In another embodiment, $R^1$ is independently: $C_{1-6}$ alkyl, $C_{3-6}$ cycloalkyl, —CONH$C_{4-18}$ alkyl, —CONH$C_{2-8}$ haloalkyl, —CONH$(CH_2)_{1-8}$ Ph, —$(CH_2)_m$-(phenyl substituted with 1 $R^b$ and 0-2 $R^g$), or a 5- to 6-membered heteroaryl substituted with 0-1 $R^b$ and 0-2 $R^g$, wherein said heteroaryl is selected from: pyridyl, oxazolyl, thiazolyl and

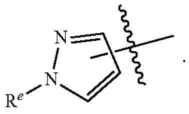

In another embodiment, $R^1$ is independently: $C_{1-6}$ alkyl, —CONH$C_{4-18}$ alkyl, —CONH$(CH_2)_{1-8}$Ph, or

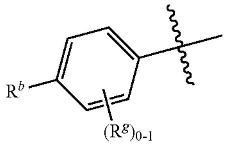

In another embodiment, $R^1$ is

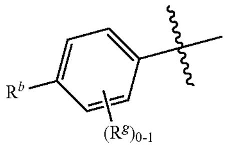

In another embodiment, $R^1$ is independently

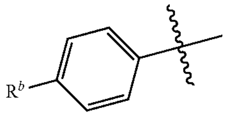

In another embodiment, $R^2$ is independently $C_{1-4}$ alkyl or $C_{1-4}$ haloalkyl.

In another embodiment, $R^2$ is $C_{1-4}$ alkyl.

In another embodiment, $R^2$ is $C_{1-4}$ haloalkyl.

In another embodiment, $R^2$ is independently $CF_3$ or Me.

In another embodiment, $R^2$ is $CF_3$.

In another embodiment, $R^2$ is Me.

In another embodiment, $R^3$ is independently H or F.

In another embodiment, $R^3$ is H.

In another embodiment, $R^3$ is F.

In another embodiment, $R^4$ is independently H or F.

In another embodiment, $R^4$ is H.

In another embodiment, $R^4$ is F.

In another embodiment, $R^5$ is independently H or F.

In another embodiment, $R^5$ is H.

In another embodiment, $R^5$ is F.

In another embodiment, $R^6$ is independently $C_{1-4}$ alkyl, CN, $R^c$, or —$(CH_2)_n$—$(X)_t$—$(CH_2)_m R^c$.

In another embodiment, $R^6$ is independently —CONH($C_{1-6}$ alkyl), —NHCO$X_1SO_2R^j$, —NHCOCO$R^j$, —NHCOCH(OH)$R^j$, —NHCO$CH_2$CO$R^j$, —NHCONH$R^j$, or —OCON$R^fR^j$.

In another embodiment, $R^6$ is independently CN, $NH_2$, —CONH($C_{1-6}$ alkyl), $R^c$, —$(CH_2)_n$—$(X)_t$—$(CH_2)_m R^c$, —NHCO$(CH_2)SO_2$($C_{1-4}$ alkyl), —NHCOCO($C_{1-4}$ alkyl), —NHCOCH(OH)($C_{1-4}$ alkyl), —NHCO$CH_2$CO($C_{1-4}$ alkyl), —NHCONH($C_{1-4}$ alkyl), or —OCONH($C_{1-4}$ alkyl).

In another embodiment, $R^6$ is independently CN, $NH_2$, —CONH($C_{1-6}$ alkyl), —NHCO$(CH_2)SO_2$($C_{1-4}$ alkyl), $R^c$, O$R^c$, —CONH$R^c$, or —NHCO$R^c$.

In another embodiment, $R^6$ is independently CN, $NH_2$, —CONH($C_{1-6}$ alkyl), —NHCO($CH_2$)$SO_2$($C_{1-4}$ alkyl), $R^c$, $OR^c$, —$CONHR^c$, or —$NHCOR^c$.

In another embodiment, $R^6$ is independently CN, $R^c$, —$CONHR^c$, —$NHCOR^c$, or —$NHCOCH_2SO_2$ ($C_{1-4}$ alkyl).

In another embodiment, $R^6$ is independently 5-membered nitrogen heteroaryl.

In another embodiment, $R^6$ is independently: 1H-imidazol-1-yl, 1H-tetrazol-1-yl, 1H-tetrazol-3-yl, or 2H-tetrazol-5-yl.

In another embodiment, $R^{11}$ is independently H, $C_{1-4}$ alkyl or halo.

In another embodiment, $R^{11}$ is independently H, Me, F, or Cl.

In another embodiment, $R^{11}$ is H.

In another embodiment, $R^{11}$ is $C_{1-4}$ alkyl.

In another embodiment, $R^{11}$ is Me.

In another embodiment, $R^{11}$ is halo.

In another embodiment, $R^{11}$ is independently F or Cl.

In another embodiment, $R^{12}$ is independently H, halo, $C_{1-4}$ alkyl or $C_{1-4}$ alkoxy.

In another embodiment, $R^{12}$ is independently H, F, Cl, Me and OMe.

In another embodiment, $R^{12}$ is H.

In another embodiment, $R^{12}$ is $C_{1-4}$ alkyl.

In another embodiment, $R^{12}$ is Me.

In another embodiment, $R^{12}$ is $C_{1-4}$ alkoxy.

In another embodiment, $R^{12}$ is OMe.

In another embodiment, $R^{12}$ is halo.

In another embodiment, $R^{12}$ is independently F or Cl.

In another embodiment, $R^{13}$ is independently: H, halo, $C_{1-4}$ alkyl substituted with 0-1 $R^i$, $C_{1-4}$ alkoxy, $C_{1-4}$ haloalkyl, $C_{1-4}$ haloalkoxy, $C_{3-4}$ cycloalkyl, CN, $NR^fR^j$, $SR^j$, $NHCO_2$($C_{1-4}$ alkyl), $NHSO_2$($C_{1-4}$ alkyl), or a 4- to 6-membered heterocycle comprising: carbon atoms and 1-4 heteroatoms selected from N, $NR^e$, O, and S.

In another embodiment, $R^{13}$ is independently: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, CN, $C_{3-4}$ cycloalkyl, N($C_{1-4}$ alkyl)$_2$, $NHCO_2$($C_{1-4}$ alkyl), $NHSO_2$($C_{1-4}$ alkyl), pyrazolyl, or morpholinyl.

In another embodiment, $R^{13}$ is independently: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, CN or $C_{3-4}$ cycloalkyl.

In another embodiment, $R^{13}$ is independently: $NR^fR^j$, $NHCO_2$($C_{1-4}$ alkyl), $NHSO_2$($C_{1-4}$ alkyl), or a 4- to 6-membered heterocycle comprising: carbon atoms and 1-4 heteroatoms selected from N, $NR^e$, O, and S.

In another embodiment, $R^{14}$ is independently H, halo, $C_{1-4}$ alkyl or $C_{1-4}$ alkoxy.

In another embodiment, $R^{14}$ is independently H, F, Cl, Me and OMe.

In another embodiment, $R^{14}$ is H.

In another embodiment, $R^{14}$ is $C_{1-4}$ alkyl.

In another embodiment, $R^{14}$ is Me.

In another embodiment, $R^{14}$ is $C_{1-4}$ alkoxy.

In another embodiment, $R^{14}$ is OMe.

In another embodiment, $R^{14}$ is halo.

In another embodiment, $R^{14}$ is independently F or Cl.

In another embodiment, $R^{15}$ is independently H, $C_{1-4}$ alkyl or halo.

In another embodiment, $R^{15}$ is independently H, Me, F, or Cl.

In another embodiment, $R^{15}$ is H.

In another embodiment, $R^{15}$ is $C_{1-4}$ alkyl.

In another embodiment, $R^{15}$ is Me.

In another embodiment, $R^{15}$ is halo.

In another embodiment, $R^{15}$ is independently F or Cl.

In another embodiment, $R^{16}$ is H.

In another embodiment, $R^{16}$ is $C_{1-4}$ alkyl.

In another embodiment, X is independently O, S, or NH.

In another embodiment, X is independently O or S.

In another embodiment, X is O.

In another embodiment, X is independently CONH or NHCO.

In another embodiment, X is CONH.

In another embodiment, X is NHCO.

In another embodiment, $R^b$ is, at each occurrence, independently: $C_{1-10}$ alkyl, $C_{1-10}$ alkoxy, $C_{1-10}$ haloalkyl, $C_{1-10}$ haloalkoxy, $C_{1-10}$ alkylthio, $C_{1-10}$ haloalkylthio, —CONH($CH_2$)$_{4-20}$H, —O($CH_2$)$_s$O($C_{1-6}$ alkyl), $R^c$, —($CH_2$)$_n$—(X)$_t$—($CH_2$)$_m$$R^c$, or —($CH_2$)$_n$—($CH_2$O)$_m$—($CH_2$)$_n$$R^f$.

In another embodiment, $R^b$ is, at each occurrence, independently: halo, OH, $C_{1-8}$ alkyl, $C_{1-8}$ alkoxy, $C_{1-8}$ haloalkyl, $C_{1-10}$ haloalkoxy, —O($CH_2$)$_s$O($C_{1-6}$ alkyl), N($C_{1-4}$ alkyl)$_2$, —CONH($CH_2$)$_{6-20}$H, —($CH_2$)$_m$($C_{3-6}$ cycloalkyl), —($CH_2$)$_m$ ($C_{4-6}$ cycloalkenyl), —O($CH_2$)$_m$($C_{3-6}$ cycloalkyl), 4-$C_{1-4}$ alkoxy-Ph, —O($CH_2$)$_m$Ph, morpholinyl, pyridyl, 2-$C_{1-4}$ alkoxy-pyridin-5-yl, pyrimidinyl, pyrazinyl, or —O-pyrimidinyl.

In another embodiment, $R^b$ is, at each occurrence, independently: halo, $C_{1-6}$ alkyl, $C_{1-6}$ alkoxy, $C_{1-6}$ haloalkyl, $C_{1-10}$ haloalkoxy, —O($CH_2$)$_s$O($C_{1-6}$ alkyl), —CONH($CH_2$)$_{6-20}$H, —($CH_2$)$_m$($C_{3-6}$ cycloalkyl), —($CH_2$)$_m$($C_{4-6}$ cycloalkenyl), —O($CH_2$)$_m$($C_{3-6}$ cycloalkyl), phenoxy, benzoxy, morpholinyl, 2-$C_{1-4}$ alkoxy-pyridin-5-yl, pyrimidin-5-yl, pyrazin-2-yl or —O-pyrimidinyl.

In another embodiment, $R^b$ is, at each occurrence, independently: halo, $C_{1-6}$ alkyl, $C_{1-6}$ alkoxy, $C_{1-6}$ haloalkyl, $C_{1-8}$ haloalkoxy, —CONH($CH_2$)$_{6-20}$H, $C_{3-6}$ cycloalkyl, $C_{4-6}$ cycloalkenyl, —O($CH_2$)$_m$($C_{3-6}$ cycloalkyl), phenoxy, benzoxy, pyrimidinyl, pyrazinyl and —O-pyrimidinyl.

In another embodiment, $R^b$ is, at each occurrence, independently: —O($CH_2$)$_{1-6}$$CF_3$ and —O($CH_2$)$_{1-4}$$CF_2CF_3$.

In another embodiment, $R^c$ is, at each occurrence, independently: $C_{3-6}$ cycloalkyl substituted with 0-2 $R^d$, $C_{3-6}$ cycloalkenyl substituted with 0-2 $R^d$, or —($CH_2$)$_m$-(phenyl substituted with 0-3 $R^d$).

In another embodiment, $R^c$ is, at each occurrence, independently: $C_{3-6}$ cycloalkyl substituted with 0-2 $R^d$ or $C_{3-6}$ cycloalkenyl substituted with 0-2 $R^d$.

In another embodiment, $R^c$ is, at each occurrence, independently —($CH_2$)$_m$-(phenyl substituted with 0-3 $R^d$).

In another embodiment, $R^c$ is, at each occurrence, independently $C_{3-6}$ cycloalkyl substituted with 0-2 $R^d$.

In another embodiment, $R^c$ is, at each occurrence, independently $C_{3-6}$ cycloalkenyl substituted with 0-2 $R^d$.

In another embodiment, $R^c$ is, at each occurrence, independently a 5- to 6-membered heterocycle comprising: carbon atoms and 1-4 heteroatoms selected from N, $NR^e$, O, and S; wherein said heterocycle is substituted with 0-2 $R^d$.

In another embodiment, $R^c$ is, at each occurrence, independently —($CH_2$)$_m$-(phenyl substituted with 0-3 $R^d$), or a heteroaryl selected from: oxazolyl, isoxazolyl, pyrazolyl, imidazolyl, oxadiazolyl, triazolyl, tetrazolyl, pyridyl, and pyrazinyl; wherein said heteroaryl is substituted with 0-2 $R^d$.

In another embodiment, $R^c$ is, at each occurrence, independently a heteroaryl selected from: oxazolyl, isoxazolyl, pyrazolyl, imidazolyl, oxadiazolyl, triazolyl, tetrazolyl, pyridyl, and pyrazinyl; wherein said heteroaryl is substituted with 0-2 $R^d$.

In another embodiment, the compounds of the present invention have hMGAT2 $IC_{50}$ values ≤10 μM, using the MGAT2 SPA assay.

In another embodiment, the compounds of the present invention have hMGAT2 $IC_{50}$ values ≤5 μM, using the MGAT2 SPA assay.

In another embodiment, the compounds of the present invention have hMGAT2 $IC_{50}$ values ≤1 μM, using the MGAT2 SPA assay.

In another embodiment, the compounds of the present invention have hMGAT2 $IC_{50}$ values ≤0.5 μM, using the MGAT2 SPA assay.

In another embodiment, the compounds of the present invention have hMGAT2 $IC_{50}$ values ≤10 μM, using the MGAT2 LCMS assay.

In another embodiment, the compounds of the present invention have hMGAT2 $IC_{50}$ values ≤5 μM, using the MGAT2 LCMS assay.

In another embodiment, the compounds of the present invention have hMGAT2 $IC_{50}$ values ≤2.5 μM, using the MGAT2 LCMS assay.

In another embodiment, the compounds of the present invention have hMGAT2 $IC_{50}$ values ≤1 μM, using the MGAT2 LCMS assay.

In another embodiment, the compounds of the present invention have hMGAT2 $IC_{50}$ values ≤0.5 μM, using the MGAT2 LCMS assay.

In another embodiment, the compounds of the present invention have hMGAT2 $IC_{50}$ values ≤0.1 μM, using the MGAT2 LCMS assay.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an inte mediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment and/or prophylaxis of multiple diseases or disorders associated with MGAT2, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the MGAT2 that can be prevented, modulated, or treated according to the present invention include, but are not limited to, diabetes, hyperglycemia, impaired glucose tolerance, gestational diabetes, insulin resistance, hyperinsulinemia, nonalcoholic fatty liver disease (NAFLD) including nonalcoholic steatohepatitis (NASH), retinopathy, neuropathy, nephropathy, delayed wound healing, atherosclerosis and its sequelae, abnormal heart function, myocardial ischemia, stroke, Metabolic Syndrome, hypertension, obesity, dyslipidemia, dyslipidemia, hyperlipidemia, hypertriglyceridemia, hypercholesterolemia, low high-density lipoprotein (HDL), high low-density lipoprotein (LDL), non-cardiac ischemia, lipid disorders, and glaucoma.

In another embodiment, the present invention provides a method for the treatment and/or prophylaxis of diabetes, hyperglycemia, gestational diabetes, obesity, dyslipidemia, and hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with MGAT2.

In another embodiment, the present invention also provides the use of a compound of the present invention for the manufacture of a medicament for the treatment and/or prophylaxis of multiple diseases or disorders associated with MGAT2.

In another embodiment, the present invention provides a method for the treatment and/or prophylaxis of multiple diseases or disorders associated with MGAT2, comprising: administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with MGAT2.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the MGAT2 inhibitor of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the MGAT2 inhibitor of the present invention include, but are not limited to, insulin secretagogues or insulin sensitizers, other MGAT2 inhibitors, or other antidiabetic agents. These agents include, but are not limited to, dipeptidyl peptidase IV (DP4) inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR40 receptor modulators (e.g. TAK-875), GPR119 receptor modulators (for example, MBX-2952, PSN821, and APD597), sodium-glucose transporter-2 (SGLT2) inhibitors (for example, dapagliflozin, canagliflozin and remagliflozin), 11b-HSD-1 inhibitors (for example MK-0736, BI35585, BMS-823778, and LY2523199), amylin analogs such as pramlintide, and/or insulin.

The MGAT2 inhibitor of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compounds of the present invention may also be employed in combination with an agonist of the glucagon-like peptide-1 receptor (GLP-1 R), such as exenatide, liraglutide, GPR-1(1-36) amide, GLP-1 (7-36) amide, GLP-1(7-37), which may be administered via injection, intranasal, or by transdermal or buccal devices.

The MGAT2 inhibitor of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs that increase HDL such as CETP inhibitors.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic fonds. Optically active forms may be prepared by resolution of racemic forms or by synthesis from optically active starting materials. All processes used to prepare compounds of the present invention and inteiniediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free foini and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in *Hawley's Condensed Chemical Dictionary* ($15^{th}$ ed.), R. J. Lewis, ed., J. Wiley & Sons, Inc., New York, 2007. "$C_{6-10}$ aryl" refers to phenyl and naphthyl.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O) and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and Spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology, Vol.* 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are forming between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base foinis of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: The Science and Practice of Pharmacy, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Pro drugs*, Elsevier (1985), and Widder, K. et al., eds., *Methods in Enzymology,* 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.,* 8:1-38 (1992);
d) Bundgaard, H. et al., *J. Pharm. Sci.,* 77:285 (1988);
e) Kakeya, N. et al., *Chem. Pharm. Bull.,* 32:692 (1984); and f) Rautio, J (Editor). *Prodrugs and Targeted Delivery* (*Methods and Principles in Medicinal Chemistry*), Vol 47, Wiley-VCH, 2011.

Compounds containing a carboxy group can faun physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Hex | hexanes |
| MeOH | methanol |
| EtOH | ethanol |
| i-PrOH or IPA | isopropanol |
| AcOH or HOAc | acetic acid |
| $Ag_2CO_3$ | silver carbonate |
| AgOAc | silver acetate |
| $CDCl_3$ | deutero-chloroform |
| $CHCl_3$ | chloroform |
| cDNA | complimentary DNA |
| DCC | N,N'-dicyclohexylcarbodiimide |
| DIAD | diisopropyl azodicarboxylate |
| DMA | dimethylamine |
| DME | dimethylether |
| DMF | dimethyl formamide |
| DMSO | dimethyl sulfoxide |
| DMAP | 4-dimethylaminopyridine |
| EDTA | ethylenediaminetetraacetic acid |
| EtOAc | ethyl acetate |
| $Et_2O$ | diethyl ether |
| $AlCl_3$ | aluminum chloride |
| Boc | tert-butyloxycarbonyl |
| $CH_2Cl_2$ | dichloromethane |
| $CH_3CN$ or ACN | acetonitrile |
| $Cs_2CO_3$ | cesium carbonate |
| HCl | hydrochloric acid |
| $H_2SO_4$ | sulfuric acid |
| $K_2CO_3$ | potassium carbonate |
| KCN | potassium cyanide |
| mCPBA or m-CPBA | meta-chloroperbenzoic acid |
| Pd/C | palladium on carbon |
| $PhSO_2Cl$ | benzenesulfonyl chloride |
| $i\text{-}Pr_2NEt$ | diisopropylethylamine |
| PS | polystyrene |
| SFC | Supercritical Fluid Chromatography |
| $SiO_2$ | silica oxide |
| $SnCl_2$ | tin(II) chloride |
| TBAT | tetrabutylammonium triphenydifluorosilicate |
| TEA | triethylamine |
| TFA | trifluoroacetic acid |
| THF | tetrahydrofuran |
| KOAc | potassium acetate |
| $MgSO_4$ | magnesium sulfate |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |
| $NH_3$ | ammonia |
| $NH_4Cl$ | ammonium chloride |
| $NH_4OH$ | ammonium hydroxide |

-continued

| | |
|---|---|
| LG | leaving group |
| $Pd_2dba_3$ | tris(dibenzylideneacetone)dipalladium(0) |
| selectFluor | N-fluoro-N'-methyl-triethylenediamine bis(tetrafluoroborate) |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transfottnations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. and Greene, T. W. *Protecting Groups in Organic Synthesis,* 4th Edition, Wiley (2007)). General methods of organic synthesis and functional group transformations are found in: Trost, B. M. and Fleming, I., eds., *Comprehensive Organic Synthesis: Selectivity, Strategy & Efficiency in Modern Organic Chemistry*, Pergamon Press, New York, N.Y. (1991); Smith, M. B. and March, J., *March's Advanced Organic Chemistry: Reactions, Mechanisms, and Structure.* 6th Edition, Wiley & Sons, New York, N.Y. (2007); Katritzky, A. R. and Taylor, R. J. K., eds., *Comprehensive Organic Functional Groups Transformations II,* 2nd Edition, Elsevier Science Inc., Tarrytown, N.Y. (2004); Larock, R. C., *Comprehensive Organic Transformations*, VCH Publishers, Inc., New York, N.Y. (1999), and references therein.

For example, compounds of Formula (II), where $R^3$=$R^4$=H and $R^6$=CN, can be made according to Scheme 1. Ketones 1 and 2 and 2-cyanoethyl acetate (3) are heated to between 80° C. and 110° C. with ammonium acetate in a solvent such as DMF or DMSO. Ketones 1 and 2 may be different or the same.

Scheme 1

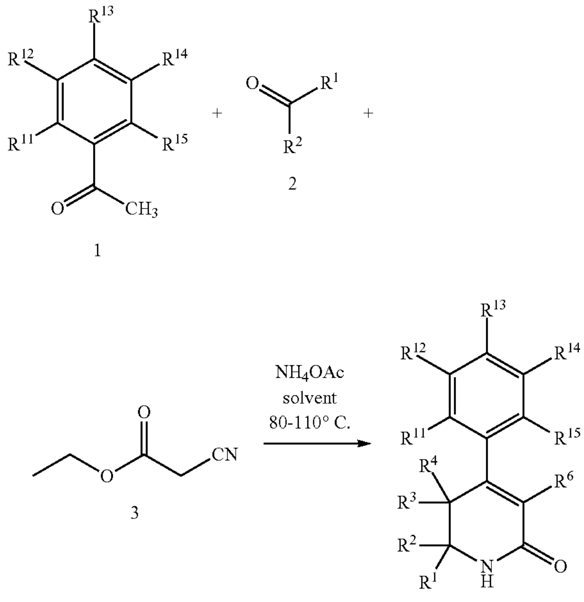

1 2 3 (II)

Alternatively, compounds of Formula (II), where $R^3$=$R^4$=H, may be made according to Scheme 2. α-Bromoketone 4 is combined with triphenylphosphine in a solvent such as THF, $CH_2Cl_2$ or 1,4-dioxane at temperatures between room temperature and reflux. The intermediate triphenylphosphonium bromide is treated with base, such as NaOH, in a solvent such as methanol and water to form the phosphorous ylide 5. The phosphorous ylide 5 is heated to 80° C. with ketone 2 in a suitable solvent such as THF or DMSO to give α,β-unsat'd ketone 6, which may exist as a mixture of E/Z isomers. Microwave irradiation may be employed to shorten the reaction time. α,β-Unsat'd ketone 6 is treated with concentrated aq $NH_4OH$ in a solvent such as DMSO in a sealed vessel to provide amine 7. Alternatively, alkene 6 may be treated with $NH_3$ in a solvent such as DMSO or DMSO and methanol in a sealed vessel to provide amine 7. Amine 7 is couple with carboxylic acid 8 using a variety of amide bond forming reactions. For example, carboxylic acid 8 may be converted to the corresponding acid chloride using oxalyl chloride in a solvent such as $CH_2Cl_2$ and catalytic DMF. Alternatively, when $R^6$ is an amide or a heterocycle, the carboxylic acid 8 may be activated using triphenylphosphine and trichloroacetonitrile in a suitable solvent such as $CH_2Cl_2$. The acid chlorides thus formed are combined with amine 7 in a suitable solvent such as $CH_2Cl_2$ or $CH_2Cl_2$ and DMF in the presence of a base, preferably pyridine. When $R^2$ is $CF_3$, cyclization of amide 9 to a compound of Formula (I) typically occurs during the work-up procedure for amide 9; for example, when an EtOAc solution of amide 9 is washed with sat'd aq $NaHCO_3$. When cyclization does not occur under these conditions, cyclization may be affected by stirring amide 9 in the presence of a weak base such as piperidine in a suitable solvent such as EtOH at a temperature between room temperature and reflux.

Scheme 2

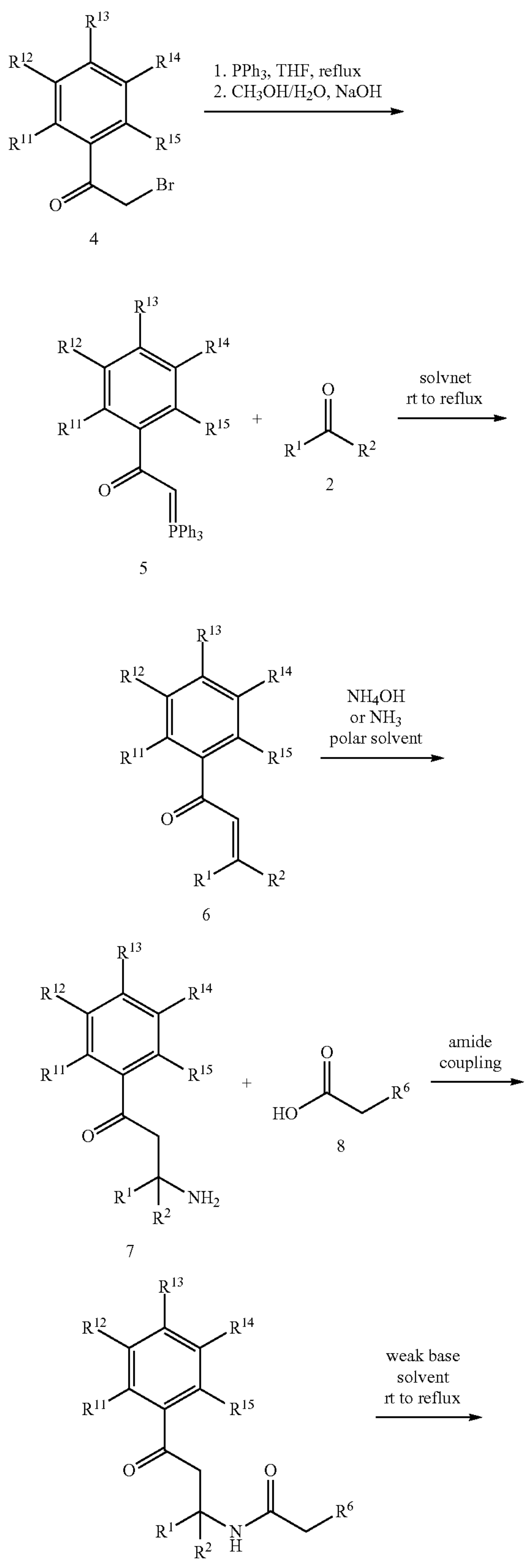

4 5 2 6 7 8 9

-continued

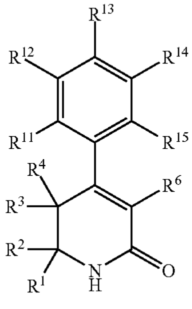

(II)

An alternate synthesis to α,β-unsaturated ketone 6, where $R^1$ is —$(CH_2)_m$— (phenyl substituted with 0-3 $R^b$) and m=0, is shown in Scheme 3. Aryl bromide 10 and α,β-unsat'd ester 11 are coupled using palladium (II) acetate, tetrabutylammonium chloride and dicyclohexylamine in DMA at 110° C. α,β-Unsat'd ester 12 is combined with O,N-dimethylhydroxyl-amine 13 in the presence of a strong base such as iso-propylmagnesium bromide in an aprotic solvent such as THF. α,β-Unsat'd amide 14 is combined with aryl magnesium halide 15 to provide α,β-unsat'd ketone 6. The identity of the halide in the aryl magnesium halide is dependent upon availability of the aryl halide used to make the Grignard reagent; typically the halide is chloride or bromide.

Scheme 3

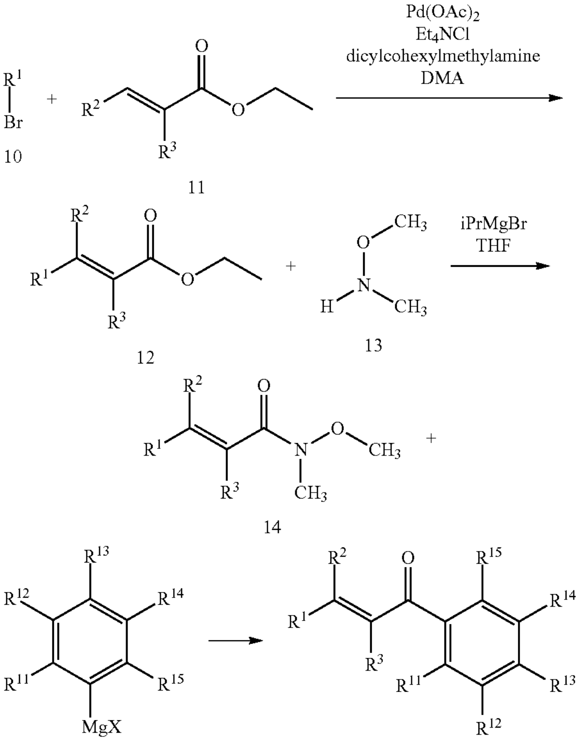

10 11 12 13 14 15 6

Non-commercial α,α□,α-trifluoroketones 2, where $R^2$=$CF_3$, may be made from the corresponding aldehyde 16 as shown in Scheme 4. Aldehyde 16 is reacted with trimethyl-(trifluoromethyl)silane in the presence of a fluoride source, for example cesium fluoride, using a suitable solvent such dimethoxyethane at room temperature. Other fluoride sources, such as potassium hydrogen fluoride or tetrabutylammonium difluorotriphenylsilicate, and other solvents, such as THF or acetonitrile and methanol, may also be employed. Trifluoromethyl alcohol 17 is oxidized using, for example, Dess-Martin periodinane in a suitable solvent such as $CH_2Cl_2$.

Scheme 4

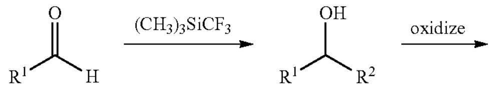

16

17: $R^2 = CF_3$

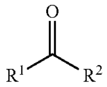

2: $R^2 = CF_3$

Ketones of formula 2 may be made according to Scheme 5. For example, aryl halide 18, where X=bromine and the aryl group is a suitable chemical moiety to form a Grignard reagent, is combined with magnesium metal in the presence of an initiator such as iodine in a suitable solvent such as THF. Other alkyl halides having a chemical moiety suitable for formation of Grignard reagents, other halides such as chlorine or iodine, other solvents such as diethyl ether or 1,4-dioxane, and other initiators such as 1,2-dibromoethene, may be employed as determined by one skilled in the art. Grignard reagent 19 is combined with amide 20 in a suitable solvent such as THF to provide ketone 2. Other solvents such as 1,4-dioxane or diethyl ether may be employed as determined by one skilled in the art.

Scheme 5

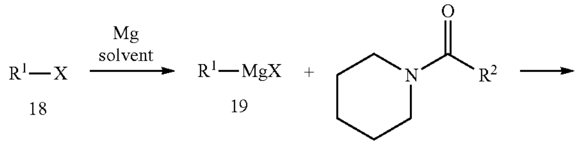

18

19

20

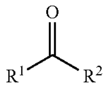

2

Compounds of Formula 23 having $R^3$=$R^4$=H, $R^1$=—$(CH_2)_m$-(phenyl substituted with 0-3 $R^b$) where m=0, and at least one $R^b$=—$(CH_2)_n$—$(X)_t(CH_2)_m$—$R^c$ where n=m=t=0, or n=m=0 and t=1 when X=0 or NH, and $R^c$ is a suitable chemical moiety to participate in palladium cross coupling reactions, may be made according to Scheme 6. Compound 21 is heated with boronic acid 22, where R=H, in the presence of a palladium catalyst and base using a suitable solvent such as 1,4-dioxane, toluene, DMF with or without water. Boronic acid 22 may be substituted with alternative boronic acid analogs such as boronate esters, trifluoroborates, and others known to those skilled in the art. Palladium catalyst commonly employed include, but are not restricted to, $Pd(PPh_3)_4$ and $PdCl_2(dppf)$. Other palladium catalyst known to those skilled in the art may be employed. Bases commonly employed include, but are not restricted to, $K_3PO_4$ and $K_2CO_3$. Other bases known to those skilled in the art may also be employed. When n=m=0 and t=1 when X=0 or NH, biarylethers or biarylamines such as 23 can be obtained from 21 when G=OH. Alternatively, biaryl ethers and amines can also be obtained from 21, when G=boronic acid or equivalent, via metal-catalyzed coupling with suitable phenols or amines Scheme 6

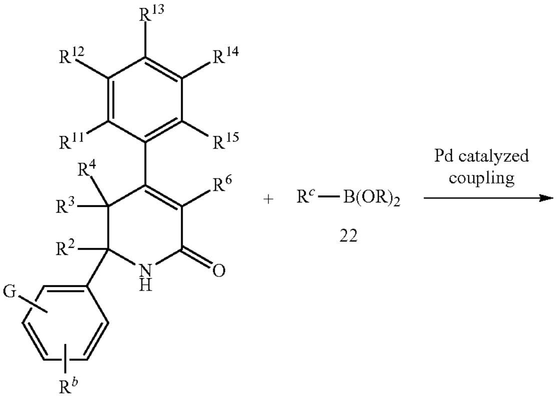

21

22

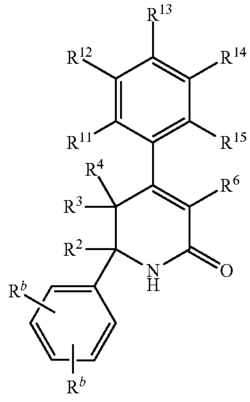

23

G = Cl, Br, I, OMs, OTs, OTf, OH, $NH_2$

Compounds of Formula 27 having $R^3$=$R^4$=H, $R^1$=—$(CH_2)_m$-(phenyl substituted with 0-3 $R^b$) where m=0, and at least one $R^b$=—$(CH_2)_n$—$(X)_t$—$(CH_2)_m$—$R^c$ where n=0, t=1, m=1-4 and X=0, may be made according to Scheme 7. Bromide 24 is treated with tris(dibenzylideneacetone)palladium (0) in the presence of bis(1,1-dimethylethyl)[2',4',6'-tris(1-methylethyl)[1,1'-biphenyl]-2-yl]-phosphine (t-butyl-Xphos) using 1,4-dioxane and water as solvent and KOH as base. Phenol 25 and alcohol 26 were stirred in the presence of triphenylphosphine and DIAD in a suitable solvent such as $CH_2Cl_2$.

Scheme 7

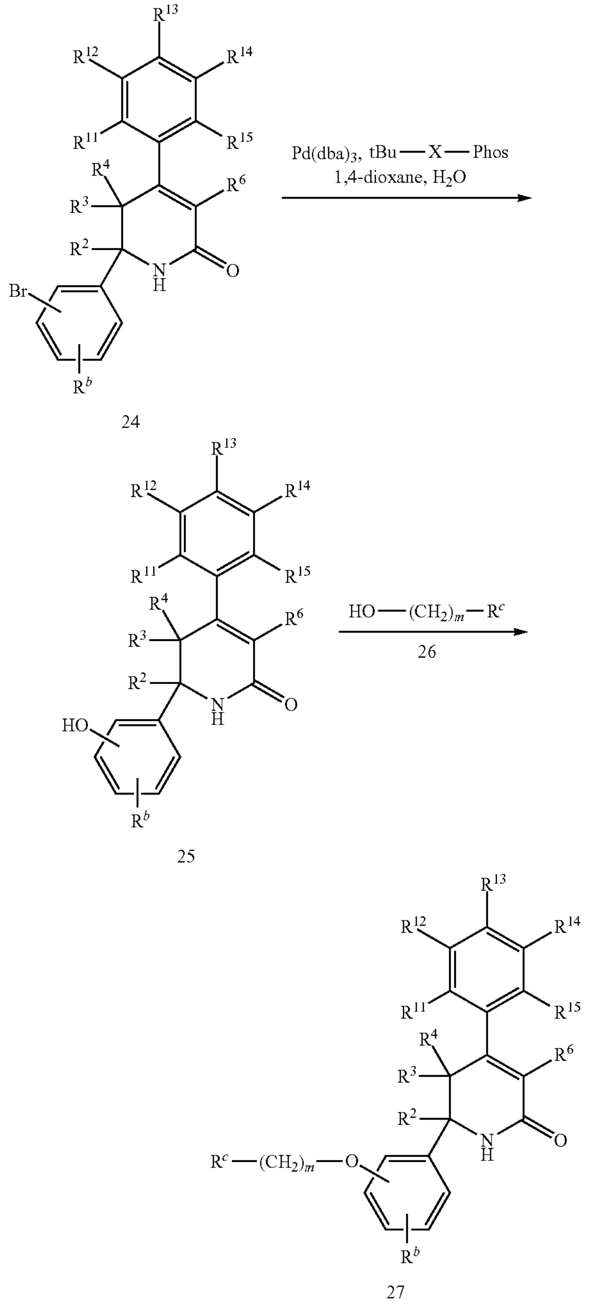

Carboxylic acid 8, where $R^6$=CONHR$^c$, may be made according to Scheme 8. The mono-ester of malonic acid 28, where PG=benzyl group, and amine 29 are coupled together using standard amide bond forming conditions. For example, treatment of carboxylic acid 28 with oxalyl chloride in $CH_2Cl_2$ and DMF provides the acid chloride. The acid chloride is then combined with amine 29 in the presence of pyridine in a suitable solvent such as $CH_2Cl_2$. Other amide bond forming reaction known to those skilled in the art may be employed. The benzyl group is removed using a combination of hydrogen gas and 10% palladium on carbon in a suitable solvent such as methanol or methanol and EtOAc. Other PG moieties and methods for their removal known to those skilled in the art may be employed.

Scheme 8

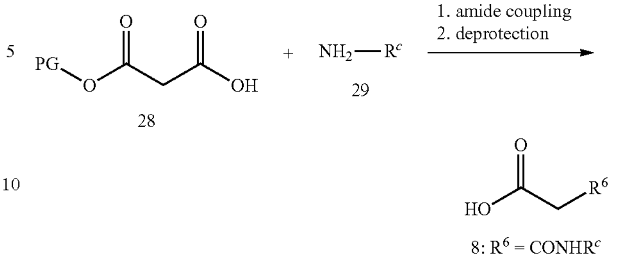

Compounds of Formula (I), where $R^3$ and $R^4$ are combined with the carbon atom to which they are attached to form a 3-6 membered carbocycle, or $R^3$=$R^4$=F, may be made according to Scheme 9. For example, to synthesize compounds for Formula (I) where $R^3$ and $R^4$ are combined with the carbon atom to which they are attached to form a 3-membered ring (i.e., cyclopropyl), β-ketoester 30 is stirred at room temperature with 1,2-dibromoethane in the presence of a base, for example $K_2CO_3$, in a suitable solvent such as DMF to provide the cyclopropyl β-ketoester 31. Cyclopropyl β-ketoester 31 is stirred with a suitable amine, such as benzyl amine, in the presence of a suitable Lewis acid, such as $TiCl_4$, in a solvent such as $CH_2Cl_2$ starting at 0° C. then warming to room temperature. Other amines, Lewis acids, solvents and temperatures may be used as determined by those skilled in the art. The use of benzylamine provides imine 32, where PG=benzyl Imine 32 is alkylated with, for example, trimethyl(trifluoromethyl)silane in the presence of a fluoride source such as potassium hydrogen fluoride and TFA, using acetonitrile and DMF. Other fluoride sources, such as tetrabutylammonium difluorotriphenylsilicate or cesium fluoride, other acids such as HOAc or HCl, and other solvents may be employed as determined by those skilled in the art. Use of trimethyl(trifluoromethyl)silane provides amino ester 33, where $R^2$=$CF_3$. Ester hydrolysis of amino ester 33 was done in the presence of lithium iodide in refluxing pyridine to provide amino acid 34. Use of other hydrolysis conditions known to those skilled in the art may be employed. Cyclization of amino acid 34 to β-lactam 35 was affected by activating the carboxylic acid of amino acid 34 with oxalyl chloride in a suitable solvent such as $CH_2Cl_2$ containing catalytic DMF. The cyclization occurred spontaneously at room temperature to provide β-lactam 35. Other methods for activating the carboxylic acid may be employed as determined by those skilled in the art. β-Lactam 35 is arylated using an organometallic reagent. Organometallic reagents may include, for example, Grignard reagents or organolithium reagents, formed from a suitably substituted phenyl ring containing a halide atom able to react with either elemental magnesium to form a Grignard reagent or with an alkyl lithium reagent to form an phenyl lithium reagent via transmetallation. Exact conditions required to form these phenyl organometallic species must determined by those skilled in the art. A suitable aprotic solvent is used, for example, THF. Other suitable solvents may be employed as determined by those skilled in the art. The reaction is carried out between room temperature and reflux depending upon the identity of the organometallic reagent employed and the substitution pattern on β-lactam 35. The β-amino ketone 37 thus formed is deprotected using hydrogen gas and 10% palladium on carbon in a suitable solvent such as methanol containing 4.4% formic acid to provide β-amino ketone 38. Other conditions to remove the benzyl group may be employed as determined by those skilled in the art. β-Amino ketone 38 is acylated with carboxylic acid 8 using conditions described in Scheme 2 to give the β-keto amide 39. Stirring β-keto amide 39 with a base such as sodium ethoxide in a suitable solvent such as ethanol at room temperature provides compounds having Formula (I).

Scheme 9

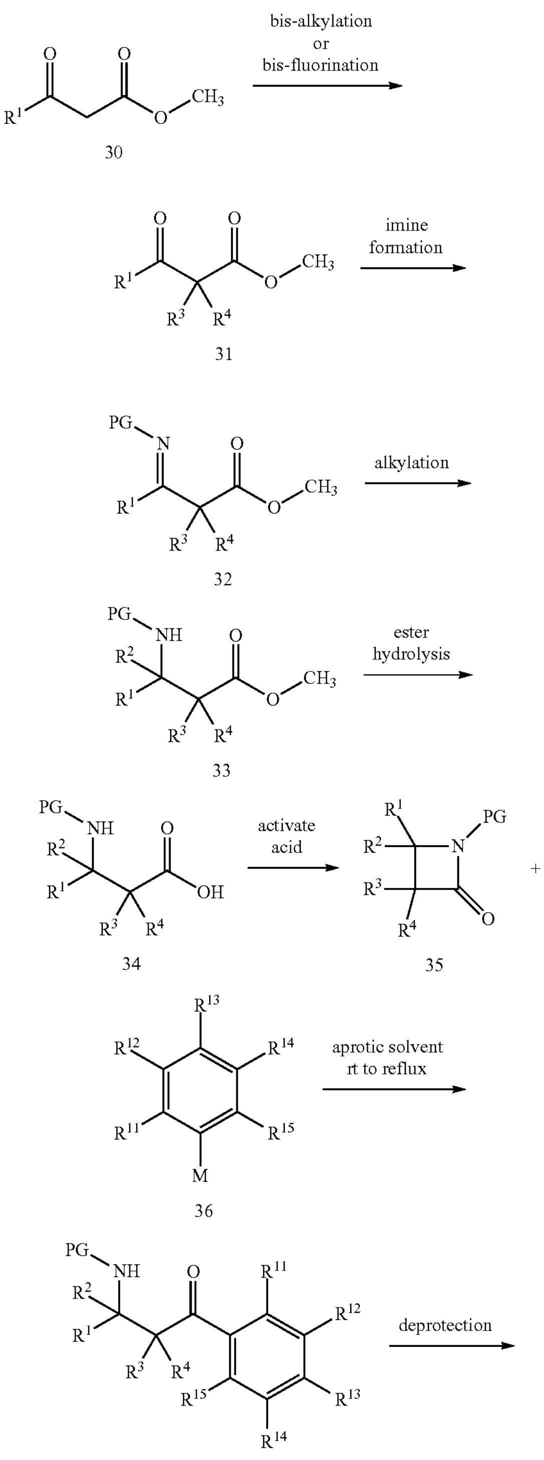

30 31 32 33 34 35 36 37

-continued

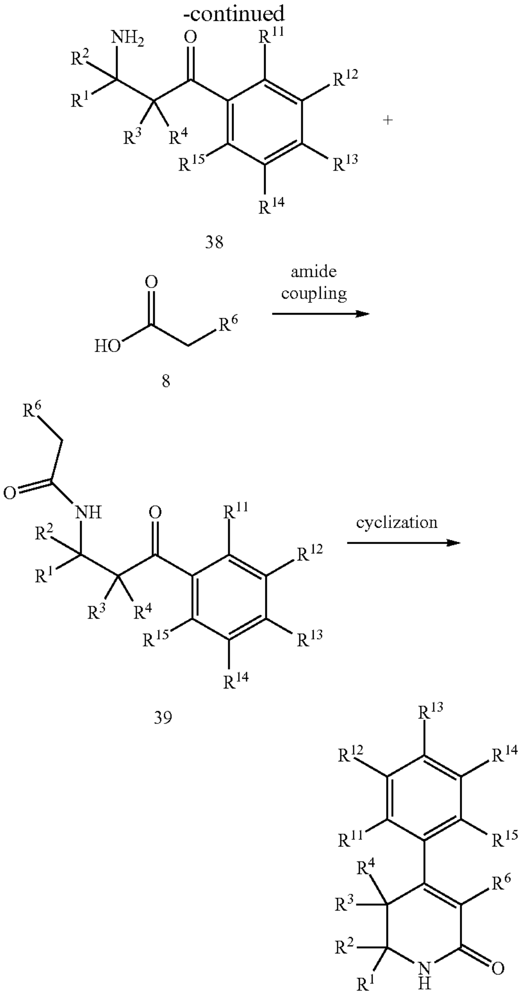

38 8 39 (I)

Compounds of Formula (I), where y is a single bond and $R^5$=F may be made according to Scheme 10. This synthesis is exemplified for a compound of Formula (I) where $R^6$=CN. Thus, a compound of Formula (I), where x is a single bond and $R^6$=CN, was heated to 80° C. in the presence of a fluorinating reagent, 1-fluoro-4-hydroxy-1,4-diazoniabicyclo[2,2,2]octane bis(tetrafluoroborate), in a suitable solvent such as DMF in the presence of a base such as $Na_2CO_3$ to provide compounds of Formula (I), where y is a single bond, $R^5$=F and $R^6$=CN. Other fluorinating reagents, solvents and bases may be employed as determined by one skilled in the art.

Scheme 10

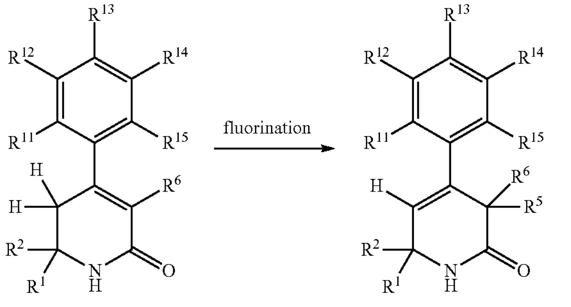

(I): x = single bond (I): y = single bond $R^6$ = F

Compounds of Formula (I), where x and y are both single bonds and $R^5$=H, can be made according to Scheme 11. Reduction of compounds of Formula (I), where x equals a single bond and y equals a double bond, is carried out using a suitable catalyst such as palladium on carbon under an atmosphere of hydrogen gas at suitable pressure, such as 50 psi, to effect reduction of the double bond y to a single bond. Suitable solvents include, but are not restricted to, methanol.

Scheme 11

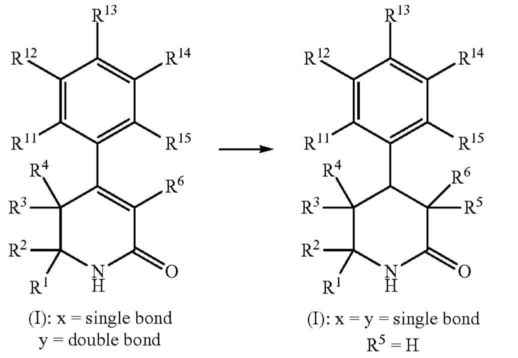

Compounds of Formula (II), single enantiomer, where $R^3$=$R^4$=H, can be made according to Scheme 12. Ketone 2 was stirred with 2-methylpropane-2-sulfinamide in the presence of a suitable Lewis acid, such as $Ti(OEt)_4$, in a solvent such as THF at refluxed temperature provides imine 40. Other Lewis acids, solvents and temperatures may be used as determined by those skilled in the art Imine 40 is alkylated with ketone 1 in the presence of a base, such as LiHMDS, KHMDS, NaHMDS, or LDA in an aprotic solvent such as THF or ether at a temperature ranging from −78° C. to ambient to provide β-amino ketone 41 as a mixture of two diastereomers, which can be separated by silica gel chromatography to give the desired isomer 42. Other metal enolates (such as titanium enolate), solvents, and temperatures may be used as determined by those skilled in the art (T. P. Tang, J. A Ellman, J. Org. Chem. 1999, 64, 12-13, J. Org. Chem. 2002, 67, 7819-7832). Preferably, chiral S- or R-2-methylpropane-2-sulfinamide can be optionally used to generate each of the optically pure enantiomers of imine 40 that can allow for chiral induction to prepare diastereomerically enriched ketone 42. In these cases, the product mixture can be further purified by silica gel chromatography to obtain desired products with diasteromeric excess of >97%. β-amino ketone 42 thus formed is deprotected using HCl in a suitable solvent such as MeOH to provide β-amino ketone 43. Other conditions to remove the t-butylsulfinyl group may be employed as determined by those skilled in the art. β-Amino ketone 43 is acylated with carboxylic acid 8 using conditions described in Scheme 2 to give the β-keto amide 44. Stirring β-keto amide 44 with a base such as sodium ethoxide in a suitable solvent such as ethanol at room temperature provides compounds having Formula (II).

Scheme 12

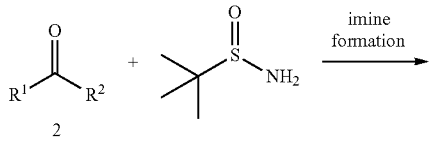

2

-continued

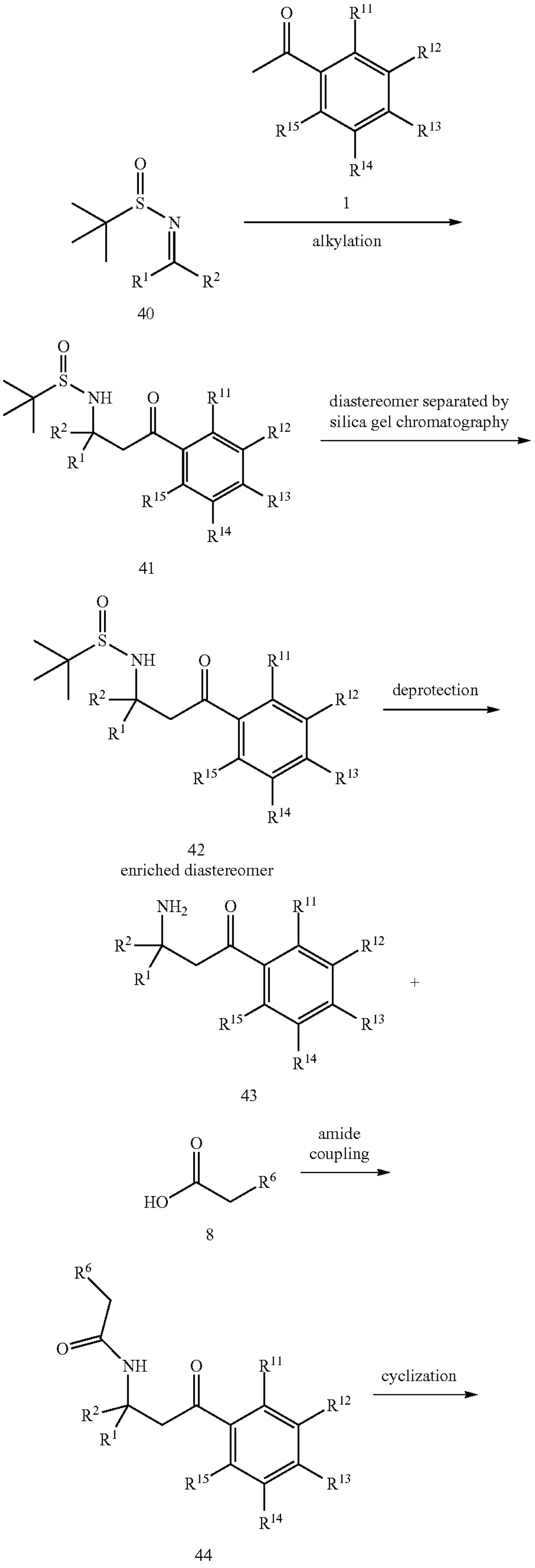

-continued

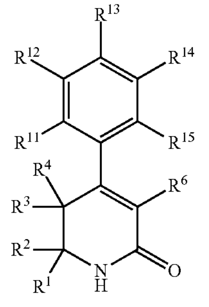

(I): $R^3 = R^4 = H$

Alternatively, compounds of Formula (II), where $R^3$=$R^4$=H, may be made according to Scheme 13. Ketone 2 can be reacted with 2-methylpropane-2-sulfinamide in the presence of a suitable Lewis acid, such as $Ti(OEt)_4$, in a solvent such as THF at a temperature ranging from ambient to reflux to provide imine 45. Other Lewis acids, solvents and temperatures may be used as determined by those skilled in the art. Imine 45 is alkylated with the enolate of an ester in a suitable aprotic solvent such as THF or ether starting at −78° C. then warming to 0° C. or room temperature to provide protected β-amino ketone 46 as a mixture of two diastereomers, which can be separated by silica gel chromatography to give each individual chiral compound. The generation of the ester enolate is achieved by treating the ester, such as methyl acetate, with a suitable base such as LHMDS, KHMDS, NaHMDS, or LDA in an aprotic solvent such as THF or ether at a temperature ranging from −78° C. to ambient. Other metal enolates (such as titanium enolate), solvents, and temperatures may be used as determined by those skilled in the art (T. P. Tang, J. A Ellman, J. Org. Chem. 1999, 64, 12-13, J. Org. Chem. 2002, 67, 7819-7832). Preferably, chiral S- or R-2-methylpropane-2-sulfinamide can be optionally used to generate each of the optically pure enantiomers of imine 45 that can allow for chiral induction to prepare diastereomerically enriched ester 46. In these cases, the product mixture can be further purified by silica gel chromatography to obtain desired products with diaseteromeric excess of >97%. The tert-butyl sulfinyl group of 46 is removed using acids such as HCl and TFA in a suitable solvent such as MeOH or dioxane to generate amino ester 47. Other conditions to remove the t-butylsulfinyl group may be employed as determined by those skilled in the art. β-Amino ketone 47 is acylated with carboxylic acid 8 using conditions described in Scheme 2 to give the β-keto amide 48. Stirring β-keto amide 48 with a base such as sodium ethoxide in a suitable solvent such as ethanol at room temperature to 80° C. provides cyclic enol 49. Other conditions can also by used to effect the cyclization as determined by those skilled in the art. Compound 49, when treated with stoichiometric amount of a chlorinating agent, such as $POCl_3$, at elevated temperature in an inert solvent such as toluene, is converted to mono-chloride 50. Chloride 50 can then react with various boronic reagents through a Suzuki-type of cross coupling reaction to generate compounds of Formula (II). The choices of boronic reagents, catalysts, ligands, bases, solvents and temperatures are well documented in the literature and can be selected appropriately by those skilled in the art.

Scheme 13

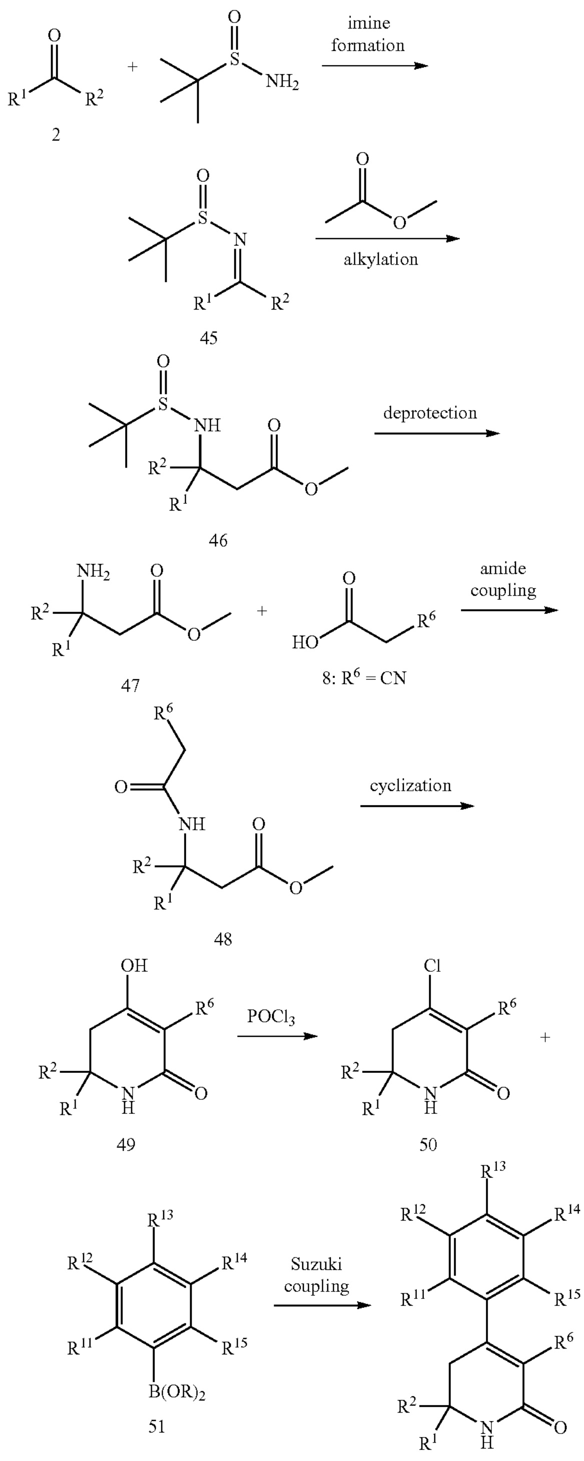

(II): $R^3 = R^4 = H$

Compounds of Formula (II), where $R^3$=$R^4$=H and $R^1$=$CONHC_{4-18}$ alkyl or $CONH(CH_2)_{1-8}Ph$ can be made according to Scheme 14. The phosphorous ylide 5 is heated, using microwave irradiation, to 150° C. with α-ketoester 52 in a suitable solvent such as THF or DMSO to give α,β-unsat'd ketone 53. α,β-Unsat'd ketone 53 is treated with concentrated aq $NH_4OH$ in a solvent such as DMSO in a sealed vessel to provide amine 54. Alternatively, alkene 53 may be treated with $NH_3$ in a solvent such as DMSO or DMSO and methanol in a sealed vessel to provide amine 54. Amine 54 is couple with carboxylic acid 8 using a variety of amide bond forming reactions. For example, carboxylic acid 8 may be converted to the corresponding acid chloride using oxalyl chloride in a solvent such as $CH_2Cl_2$ and catalytic DMF. Alternatively, the carboxylic acid 8 may be activated using 1-chloro-N,N,2-trimethylprop-en-1-amine in a suitable solvent such as $CH_2Cl_2$. The acid chlorides thus formed are combined with amine 54 in a suitable solvent such as $CH_2Cl_2$ or $CH_2Cl_2$ and DMF in the presence of a base, preferably pyridine. Other amide bond forming reaction known to those skilled in the art may be employed. Cyclization of amide 55 and subsequent hydrolysis to a the carboxylic acid 56 typically occurs by stirring amide 55 in the presence of a weak base such as piperidine in a suitable solvent such as EtOH at a temperature between room temperature and reflux or a base such as lithium hydroxide in a suitable solvent such as THF and water at room temperature. Alternatively, when $R^6$ is a nitrile, cyclization of amide 55 typically occurs by stirring amide 55 in the presence of a base such as lithium hydroxide in a suitable solvent such as THF and water at room temperature. Hydrolysis is then carried out under acidic conditions using a strong acid such as HCl in a suitable solvent such as acetic acid at temperatures between room temperature and 50° C. Carboxylic acid 56 and an amine are coupled together using standard amide bond forming conditions. For example, treatment of carboxylic acid 56 and an amine with HOBt, EDC and DIEA in the presence of pyridine in a suitable solvent such as DCM at room temperature provides compounds having Formula (II). Other amide bond forming reaction known to those skilled in the art may be employed.

Scheme 14

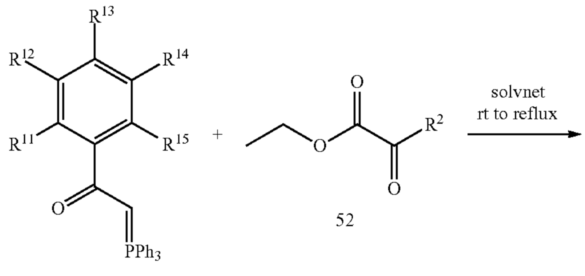

5

52

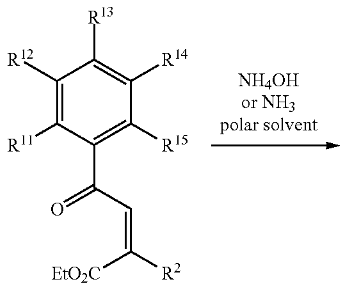

53

-continued

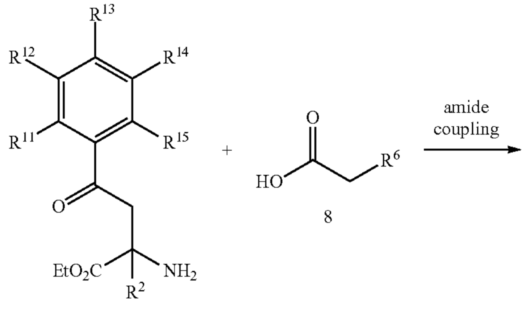

54

8

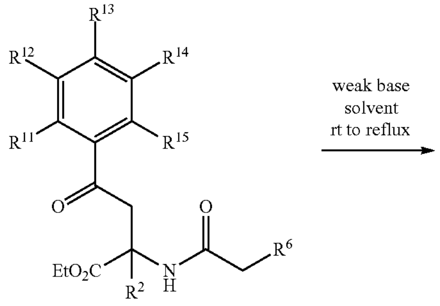

55

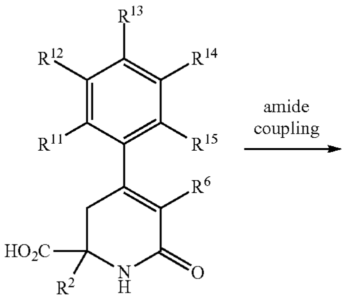

56

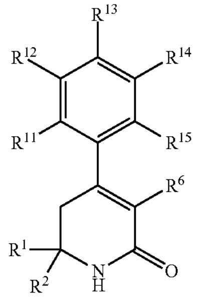

(II): $R^1$ = $CONHC_{4\text{-}18}$ alkyl, $CONH(CH_2)_{2\text{-}8}Ph$ $R^3 = R^4 = H$ Compounds of formula 60 having $R^e$=alkyl and $R^6$=cyano can be synthesized by coupling acid 56 with N, O-dimethylhydroxylamine using typical amide bond forming reactions. For example, carboxylic acid 56 is coupled to N, O-dimethylhydroxylamine using EDC in the presence of base, preferably N-methylmopholine, in a suitable solvent, such as $CH_2Cl_2$, to provide the Weinreb amide 57. Other amide forming reactions known to those skilled in the art may also be employed. The intermediate Weinreb amide 57 is reacted with ethynylmagnesium bromide in an aprotic solvent such as THF at 0-35° C. to provide the acylacetylide intermediate 58. Compounds of formula 60 are obtained when acylacetylide intermediate 58 is reacted with hydrazine 59 in the presence of a base such as TEA in a suitable solvent such as EtOH.

Scheme 15

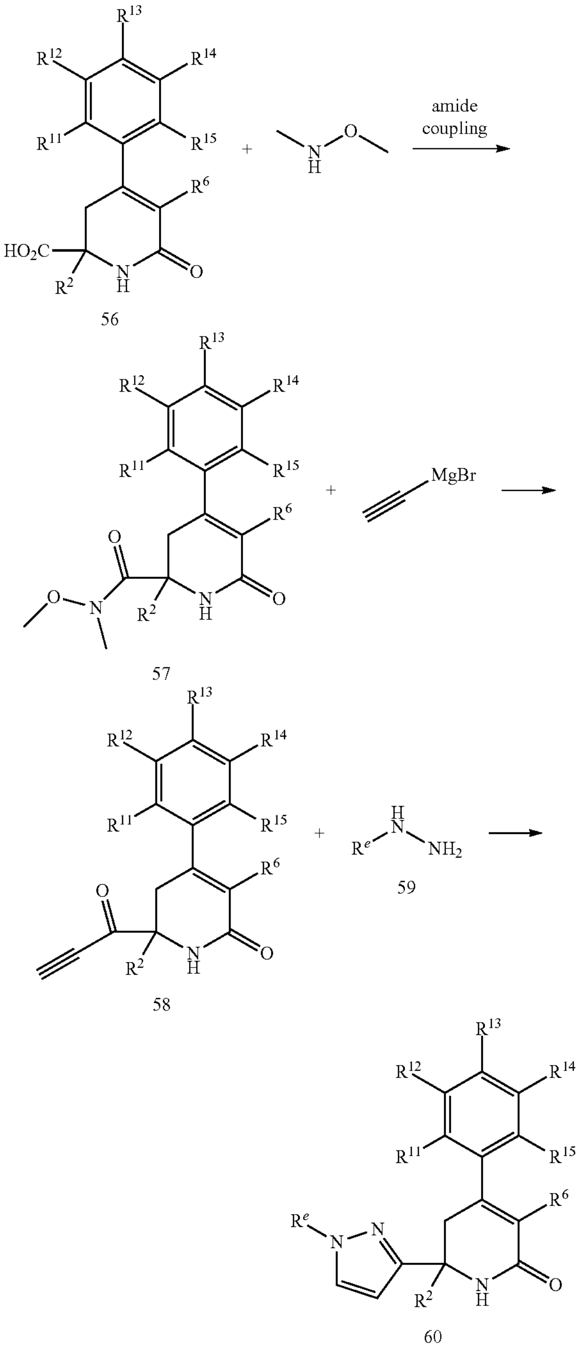

56
57
58
59
60

$R^e$ = alkyl $R^6$ = cyano

Compounds of formula 63 having $R^b$=alkyl and $R^6$=cyano can be synthesized by first coupling acid 56 with β-ketoamine 61 using typical amide bond forming reactions. For example, carboxylic acid 56 is coupled to α-ketoamine 61 using EDC and HOBt in the presence of base, preferably DIEA, in a suitable solvent, such as $CH_2Cl_2$, to provide β-ketoamide 62. Other amide forming reactions known to those skilled in the art may also be employed. 5-Alkyl substituted oxazole 63 is then obtained via the dehydrative cyclization of β-ketoamide 62 using a dehydrating agent, preferably $POCl_3$, in the presence of a suitable base, such as DIEA, in a suitable solvent such as dichloroethane at a temperature of 80-120° C.

Scheme 16

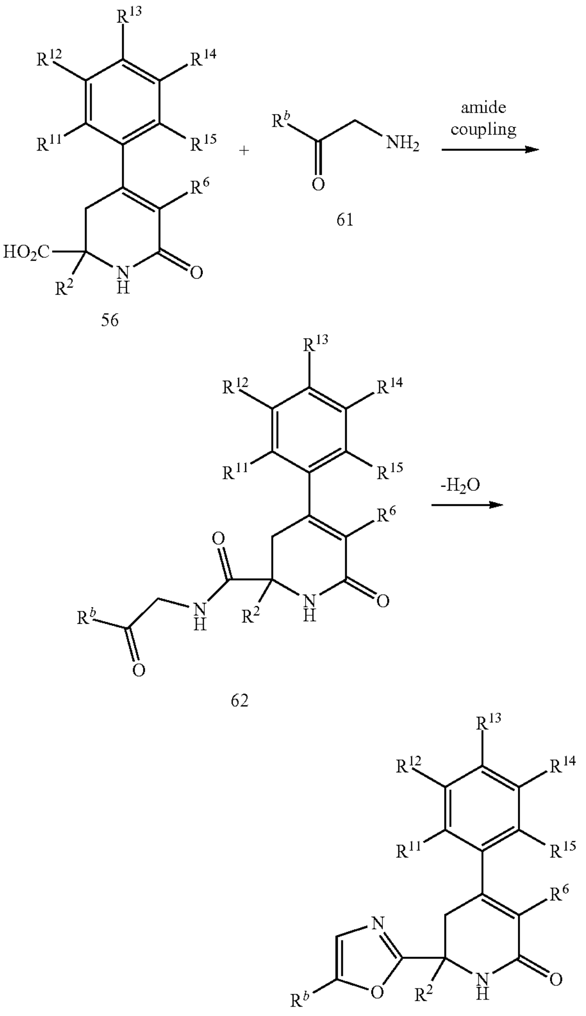

56
61
62
63

$R^b$ = alkyl $R^6$ = cyano

IV. Biology

In mammals, there are two triglyceride synthesis pathways: glycerol-3-phosphate pathway and monoacylglycerol pathway. The former is mainly responsible for energy storage in the peripheral tissues such as fat, liver, skeletal muscle; the latter is essential for the dietary fat absorption which takes place in the small intestine. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body.

Monoacylglycerol acyltransferase 2 (MGAT2) is a membrane bound acyltransferase that belongs to diacylglycerol acyltransferase 2 (DGAT2) gene family. It is highly and selectively expressed in the small intestine. Genetic deletion of MGAT2 in mice decreased the rate of absorption for the orally ingested triglycerides, indicating that MGAT2 plays an important role for the intestinal MGAT/DGAT pathway [Yen, C. L. et al, Nat. Med., 15(4):442-446 (2009); Okawa, M. et al., *Biochem. Biophys. Res. Commun.,* 390(3):377-381 (2009)]. When chronically challenged with a high fat diet, in contrast to wild type mice that became obese, MGAT2 knockout mice resisted the impact of high-fat feeding and demonstrated with a lower body weight, less adiposity, and less hepatic fat accumulation. In contrast to hyperinsulinemic wild type mice after high-fat challenge, MGAT2 deletion normalizes the insulin level and decreased fasting glucose. In the glucose tolerance test, they also had an improved glucose excursion. Consistent with their improved glycemic profile, MGAT2 knockout mice also had an increased level of GLP1, an incretin gut hormone that profoundly impacts glucose metabolism[Yen, C. L. et al., *Nat. Med.,* 15(4):442-446 (2009)]. Taken together, it is expected that inhibition of MGAT2 through pharmacological intervention would provide the same benefit as demonstrated in the knock-out mice, e.g., resistance to weight gain, or conversely, reduction in fat body mass. In addition, MGAT2 inhibition would lead to an improved insulin sensitivity and glucose metabolism which either leads to a decrease in the incidence of Type II diabetes, or a treatment of diabetic condition.

It is also desirable and preferable to find compounds with advantageous and improved characteristics compared with known anti-diabetic agents, in one or more of the following categories that are given as examples, and are not intended to be limiting: (a) phainiacokinetic properties, including oral bioavailability, half life, and clearance; (b) phainiaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a MGAT2 inhibitor. Exemplary subjects include human beings of any age with risk factors for metabolic disease. Common risk factors include, but are not limited to, age, sex, weight, family history, or signs of insulin resistance such as acanthosis *nigricans*, hypertension, dyslipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit MGAT2 and/or to prevent or treat the disorders listed herein. When applied to a combination, the term refers to combined amounts of the active ingredients that result in the preventive or therapeutic effect, whether administered in combination, serially, or simultaneously.

A. Assay Methods

MGAT SPA Assay

MGAT2 enzyme was assayed using membranes isolated from Sf9 cells expressing the recombinant human MGAT2 cDNA with 2-monooleoylglycerol and [$^3$H]-oleoyl-CoA as substrates as described by Seethala et al. [*Anal. Biochem.,* 383(2):144-150 (Dec. 15, 2008)]. Briefly, the assays were conducted in 384-well plates in a total volume of 30 μL at 25° C. In each assay, 200 ng of recombinant human MGAT2 membrane was incubated with 10 μM of 2-monooleoylglycerol and 15 μM of [$^3$H]-oleoyl-CoA in 100 mM potassium phosphate (pH 7.4) for 20 min with various concentrations of compounds delivered in DMSO. The assay was terminated by the addition of 20 μl of Stopping Solution (7.5 mg/ml Yittrium Oxide Polylysine beads, 3.3 mg/ml Fraction V BSA and 200 μM Mercuric chloride in 50 mM HEPES, pH 7.4). The signal was measured 1 h after quenching the reaction using LEADSEEKER$^{SM}$ for 5 minutes. To calculate the degree of inhibition, the zero level of enzyme activity (blank) was defined by the above assay procedure using membrane form Sf9 cell uninfected with baculovirus (Naive) and the 100% level of MGAT2 enzyme activity was defined by human MGAT2 assay with the vehicle DMSO. The $IC_{50}$s of inhibitors were determined by logistic 4 parameter equation in XL-fit.

MGAT LCMS Assay

The MGAT enzyme reactions were performed in CORNING Falcon 96-well Polypropylene plates, in a total volume of 60 μL of 50 mM Potassium Phosphate buffer pH 7.4, containing a final concentration of 100 μM 2-oleoylglycerol, 15 μM oleoyl-Coenzyme A and 0.0013 μg/μL Human or Mouse MGAT-2 or 0.0026 μg/μL Rat recombinant MGAT-2 membranes expressed in Sf9 cells. Assay plates were run through a fully automated robotics system and shaken for 5 seconds every minute for a total 10 minutes. The reactions were then quenched with 120 μL of ice cold methanol containing 1 μg/mL 1,2-distearoyl-rac-glycerol as the internal standard. Plates were shaken for 2 minutes and spun down to remove protein precipitation. After the spin, samples were transferred to LC/MS compatible PCR plates. For LC/MS analysis, a ThermoFisher Surveyor pump, utilizing a Waters Symmetry C8, 50×2.1 mm column, was used for the chromatography of enzyme products. The buffer system consists of 0.1% formic acid in water with a mobile phase consisting 0.1% formic acid in methanol. The shallow gradient is 90-100% mobile phase in 0.2 min with a total run time of 2.3 min. The first 0.5 minutes of each injection was diverted to waste to eliminate the presence of Phosphate buffer in the enzymatic reaction. The column was run at 0.6 mL/min and a temperature of 65° C. Mass spectrometry analysis of the samples was performed on a ThermoFisher Quantum Triple quad utilizing APCI (+) as the mode of ionization. Data was acquired in Single Ion Monitoring (SIM) mode analyzing Diolein=m/z 603.6 (PRODUCT) and 1,2-distearoyl-rac-glycerol (IS)=m/z 607.6. The ratio of Diolein to internal standard (Peak Area Ratio) is utilized to calculate $IC_{50}$ values.

The exemplified Examples disclosed below were tested in the MGAT2 in vitro assays described above and were found having MGAT2 inhibitory activity. Table 1 below lists human MGAT2 $IC_{50}$ values measured for the following examples. “NT” denotes “Not tested”.

TABLE 1

| Example | h-MGAT2 $IC_{50}$ (nM) | |
|---|---|---|
| No. | SPA Assay | LCMS Assay |
| 1 | 651 | 2049 |
| 2 | 85 | 5 |
| 2-1 | 35 | 8 |
| 2-2 | 1400 | 261 |
| 3 | 1804 | NT |
| 4 | 5871 | NT |
| 5 | 309 | 21 |
| 6 | 15 | 7 |
| 6-1 | 1435 | NT |
| 6-2 | 14 | 2 |
| 7 | 818 | NT |
| 8 | NT | 7 |
| 9 | 33330 | 121 |
| 10 | 2716 | 138 |
| 11 | 48 | 13 |
| 12 | NT | 374 |
| 13 | 3333 | 35 |
| 14 | NT | 2050 |
| 15-1 | 3306 | 12 |
| 15-2 | 33330 | 431 |
| 15-3 | 33330 | 756 |
| 15-4 | 33330 | 2049 |
| 16-1 | 25 | 7 |
| 16-2 | 8430 | 416 |
| 17 | 1931 | NT |
| 18 | 5762 | NT |
| 19 | 2905 | NT |
| 20 | 3456 | NT |
| 21 | 913 | NT |
| 22 | 801 | NT |
| 23 | 1292 | NT |
| 24 | 1731 | NT |
| 25 | 4569 | NT |
| 26 | 6428 | NT |
| 27 | 2519 | NT |
| 28 | 564 | NT |
| 29 | 7602 | NT |
| 30 | 774 | NT |
| 31 | 1510 | NT |
| 32 | 9956 | NT |
| 33 | 167 | 12 |
| 34 | 656 | 126 |
| 35 | 5199 | 13 |
| 36 | 396 | 57 |
| 37 | 263 | 15 |
| 38 | 2143 | NT |
| 39 | 401 | 20 |
| 40 | 2546 | 164 |
| 41 | 170 | 15 |
| 42 | 403 | 77 |
| 43 | 5387 | 60 |
| 44 | 1458 | NT |
| 45 | 569 | NT |
| 46 | 871 | NT |
| 47 | 756 | NT |
| 48 | 226 | 7 |

TABLE 1-continued

| Example | h-MGAT2 $IC_{50}$ (nM) | |
|---|---|---|
| No. | SPA Assay | LCMS Assay |
| 49 | 127 | 64 |
| 50 | 242 | 95 |
| 51 | 63 | 13 |
| 52 | 477 | 99 |
| 53 | 111 | 3 |
| 54 | 258 | 20 |
| 55 | 846 | 20 |
| 56 | 6550 | NA |
| 57 | 412 | 16 |
| 58 | 275 | 29 |
| 59 | 53 | 4 |
| 60 | 441 | 12 |
| 61 | 709 | NT |
| 62 | 156 | 24 |
| 63 | 116 | 28 |
| 64 | 761 | 280 |
| 65 | 96 | 3 |
| 66 | 731 | 265 |
| 67 | 1935 | 253 |
| 68 | 7523 | 1282 |
| 69 | 9230 | 983 |
| 70 | 3404 | NA |
| 71 | 2931 | 1917 |
| 72 | 3519 | 214 |
| 73 | 684 | 15 |
| 74 | 2476 | 697 |
| 75 | 873 | 209 |
| 76 | 5073 | 370 |
| 77 | 89 | 27 |
| 78 | 151 | 4 |
| 79 | 1856 | 45 |
| 80 | 310 | 5 |
| 81 | 55 | 4 |
| 82 | 133 | 2 |
| 83 | 89 | 1 |
| 84 | 115 | 2 |
| 85 | 1465 | 7 |
| 86 | 201 | 1 |
| 87 | NT | 1215 |
| 88 | 28 | 5 |
| 89 | 731 | 20 |
| 90 | 815 | 18 |
| 91 | 916 | 2 |
| 92 | NT | 136 |
| 93 | 37 | 30 |
| 94 | 32 | 4 |
| 95 | 95 | 43 |
| 96 | NT | 1431 |
| 97 | NT | 1199 |
| 98 | 154 | 69 |
| 99 | NT | 795 |
| 100 | NT | 1575 |
| 101 | 379 | 108 |
| 102 | NT | 1088 |
| 103 | NT | 645 |
| 104 | NT | 103 |
| 105 | 672 | 24 |
| 106 | NT | 552 |
| 107 | NT | 93 |
| 108 | NT | 189 |
| 109 | NT | 39 |
| 110 | 11 | 5 |
| 111 | 9 | 7 |
| 112 | 1297 | 204 |
| 113 | 158 | 8 |
| 114 | NT | 704 |
| 115 | NT | 40 |
| 116 | 48 | 4 |
| 117 | 22 | 18 |
| 118 | 32 | 4 |
| 119 | 94 | 21 |
| 120 | 58 | 6 |
| 121 | 231 | 20 |
| 122 | 14 | 1 |
| 123 | 743 | 5 |
| 124 | 4264 | 55 |

TABLE 1-continued

| Example | h-MGAT2 IC$_{50}$ (nM) | |
|---|---|---|
| No. | SPA Assay | LCMS Assay |
| 125 | NT | 282 |
| 126 | 1874 | 33 |
| 127 | 655 | 10 |
| 128 | NT | 328 |
| 129 | NT | 222 |
| 130 | 20 | 1 |
| 131 | NT | 1050 |
| 132 | NT | 163 |
| 133 | 1518 | 127 |
| 134 | NT | 168 |
| 135 | NT | 778 |
| 136 | NT | 328 |
| 137 | NT | 252 |
| 138 | NT | 5799 |
| 140 | NT | 356 |
| 141 | NT | 459 |
| 142 | 93 | 10 |
| 143 | 156 | 4 |
| 144 | 175 | 16 |
| 145 | 130 | 25 |
| 146 | 397 | 25 |
| 147 | 91 | 14 |
| 148 | 102 | 9 |
| 149 | 53 | 6 |
| 150 | 11 | 3 |
| 151 | NT | 5115 |
| 152 | NT | 252 |
| 153 | NT | 247 |
| 154 | 34 | 8 |
| 155 | NT | 484 |
| 156 | NT | 254 |
| 157 | 168 | 84 |
| 158 | 302 | 75 |
| 159 | NT | 16710 |
| 160 | NT | 5401 |
| 161 | NT | 1261 |
| 162 | NT | 214 |
| 163 | 1176 | 47 |
| 164 | NT | 162 |
| 165 | 60 | 8 |
| 166 | 237 | 102 |
| 167 | 8 | 2 |
| 168 | NT | 113 |
| 169 | NT | 421 |
| 170 | NT | 210 |
| 171 | 724 | 57 |
| 172 | 16 | 3 |
| 173 | 43 | 63 |
| 174 | 237 | 60 |
| 175 | NT | 264 |
| 176 | NT | 3 |
| 177 | NT | 399 |
| 178 | 47 | 78 |
| 179 | 24 | 2 |
| 180 | 36 | 30 |
| 181 | NT | 2049 |
| 182 | NT | 2049 |
| 183 | NT | 50 |
| 184 | NT | 76 |
| 185 | NT | 121 |
| 186 | NT | 229 |
| 187 | NT | 4 |
| 188 | NT | 1524 |
| 189 | NT | 1159 |
| 190 | NT | 155 |
| 191 | NT | 797 |
| 192 | NT | 433 |
| 193 | NT | 46 |
| 194 | NT | 6 |
| 195 | NT | 33 |
| 196 | NT | 826 |
| 197 | NT | 178 |
| 198 | NT | 16 |
| 199 | NT | 16 |
| 200 | NT | 37 |
| 201 | NT | 24 |

TABLE 1-continued

| Example | h-MGAT2 IC$_{50}$ (nM) | |
|---|---|---|
| No. | SPA Assay | LCMS Assay |
| 202 | NT | 89 |
| 203 | NT | 59 |
| 204 | NT | 41 |
| 205 | NT | 13 |
| 206 | NT | 78 |
| 207 | NT | 11 |
| 208 | NT | 30 |
| 209 | NT | 37 |
| 210 | NT | 2 |
| 211 | NT | 97 |
| 212 | NT | 416 |
| 213 | NT | 1096 |
| 214 | NT | 12 |
| 215 | NT | 11 |
| 216 | NT | 440 |
| 217 | NT | 118 |
| 218 | NT | 166 |
| 219 | NT | 172 |
| 220 | NT | 13 |
| 221 | NT | 152 |
| 222 | NT | 733 |
| 223 | NT | 112 |
| 224 | NT | 414 |
| 225 | NT | 889 |
| 226 | NT | 206 |
| 227 | NT | 63 |
| 228 | NT | 7 |
| 229 | NT | 25 |
| 230 | NT | 1532 |
| 231 | NT | 34 |
| 232 | NT | 6 |
| 233 | NT | 639 |
| 234 | NT | 40 |
| 235 | NT | 22 |
| 236 | NT | 489 |
| 237 | NT | 130 |
| 238 | NT | 7 |
| 239 | NT | 15 |
| 240 | NT | 7 |
| 242 | NT | 44 |
| 243 | NT | 14 |
| 244 | NT | 61 |
| 245 | NT | 46 |
| 246 | NT | 36 |
| 247 | NT | 51 |
| 248 | NT | 8 |
| 249 | NT | 185 |
| 250 | NT | 243 |
| 251 | NT | 3 |
| 252 | NT | 7 |
| 253 | NT | 411 |
| 254 | NT | 170 |
| 255 | NT | 702 |
| 256 | NT | 22 |
| 257 | NT | 421 |
| 258 | NT | 1147 |
| 259 | NT | 15 |
| 260 | NT | 56 |
| 261 | NT | 1222 |
| 262 | NT | 96 |
| 263 | NT | 103 |
| 264 | NT | 46 |
| 265 | NT | 40 |
| 266 | NT | 10 |
| 267 | NT | 796 |
| 268 | NT | 8 |
| 269 | NT | 171 |
| 270 | NT | 407 |
| 271 | NT | 12 |
| 272 | NT | 112 |
| 273 | 21 | 10 |
| 274 | NT | 1 |
| 275 | NT | 2 |
| 276 | NT | 2 |
| 277 | NT | 2 |
| 278 | NT | 2 |

TABLE 1-continued

| Example | h-MGAT2 $IC_{50}$ (nM) | |
|---|---|---|
| No. | SPA Assay | LCMS Assay |
| 279 | NT | 2 |
| 280 | NT | 2 |
| 281 | NT | 3 |
| 282 | NT | 3 |
| 283 | NT | 3 |
| 284 | NT | 4 |
| 285 | NT | 4 |
| 286 | NT | 4 |
| 287 | NT | 13 |
| 288 | NT | 19 |
| 289 | NT | 19 |
| 290 | NT | 56 |
| 291 | NT | 178 |
| 292 | NT | 304 |
| 293 | NT | 7 |
| 294 | NT | 84 |
| 295 | NT | 183 |
| 296 | NT | 2 |
| 297 | NT | 639 |
| 298 | NT | 2 |
| 299 | NT | 11 |
| 300 | NT | 11 |
| 301 | NT | 19 |
| 302 | NT | 105 |
| 303 | NT | 28 |
| 304 | NT | 6 |
| 305 | NT | 94 |
| 306 | NT | 3 |
| 307 | NT | 3 |
| 308 | NT | 61 |
| 309 | NT | 1 |
| 310 | NT | 4 |
| 311 | NT | 3 |
| 312 | NT | 21 |
| 313 | NT | 4 |
| 314 | NT | 109 |

The compounds of the present invention possess activity as inhibitors of MGAT2, and, therefore, may be used in the treatment of diseases associated with MGAT2 activity. Via modulation of MGAT2, the compounds of the present invention may preferably be employed to modulate, either enhance or decrease the production/secretion of insulin and/or gut hormones, such as GLP1, GIP, CCK, PYY, PP, Amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, lipid disorders, PCOS, and glaucoma.

Metabolic Syndrome or "Syndrome X" is described in Ford et al., *J. Am. Med. Assoc.,* 287:356-359 (2002) and Arbeeny et al., *Curr. Med. Chem.—Imm., Endoc. & Metab. Agents,* 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other MGAT2 inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the MGAT2 inhibitor of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other MGAT2 inhibitors, or other antidiabetic agents. These agents include, but are not limited to, dipeptidyl peptidase IV (DP4) inhibitors (for example, sitagliptin, saxagliptin, alogliptin, vildagliptin and the like), biguanides (for example, metformin, phenfoimin and the like), sulfonyl ureas (for example, glyburide, glimepiride, glipizide and the like), glucosidase inhibitors (for example, acarbose, miglitol, and the like), PPARγ agonists such as thiazolidinediones (for example, rosiglitazone, pioglitazone, and the like), PPAR α/γ dual agonists (for example, muraglitazar, tesaglitazar, aleglitazar, and the like), glucokinase activators (as described in Fyfe, M. C. T. et al., *Drugs of the Future,* 34(8):641-653 (2009) and incorporated herein by reference), GPR40 receptor modulators, GPR119 receptor modulators (MBX-2952, PSN821, APD597 and the like), SGLT2 inhibitors (dapagliflozin, canagliflozin, remagliflozin and the like), amylin analogs such as pramlintide, and/or insulin. Reviews of current and emerging therapies for the treatment of diabetes can be found in: Mohler, M. L. et al., *Medicinal Research Reviews,* 29(1):125-195 (2009), and Mizuno, C. S. et al., *Current Medicinal Chemistry,* 15:61-74 (2008).

The compounds of the present invention may also be optionally employed in combination with agents for treating complication of diabetes. These agents include PKC inhibitors and/or AGE inhibitors.

The compounds of the present invention may also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, *D., Nature Reviews: Drug Discovery,* 8:833-834 (2009); *Obici, S., Endocrinology,* 150(6):2512-2517 (2009); and Elangbam, C. S., *Vet. Pathol.,* 46(1):10-24 (2009).

The compounds of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs increase HDL such as CETP inhibitors.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate form's but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the MGAT2 enzyme. Such compounds may be provided in a commercial kit, for example, for use in pharmaceutical research involving MGAT2 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving MGAT2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of multiple diseases or disorders associated with MGAT2 (as defined previously). In another embodiment, the package insert states that the pharmaceutical composition can be used in combination (as defined previously) with a second therapeutic agent for the treatment and/or prophylaxis of multiple diseases or disorders associated with MGAT2. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS, Preparatory/Analytical HPLC, and Chiral Separation Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following methods:

Linear Gradient of 0% to 100% solvent B over 2 min, with 1 minute hold at 100% B, or Linear Gradient of 0% to 100% solvent B over 4 min, with 1 minute hold at 100% B;

UV visualization at 220 nm;

Column: PHENOMENEX® Luna C18 (2) 30 mm×4.6 mm; 5μ particle (heated to Temp. 40° C.);

Flow rate: 1.0 mL/min (2 min gradient) or 0.8 ml/min (4 min gradient);

Solvent A: 10% ACN, 90% water, 0.1% TFA; or, 10% MeOH, 90% water, 0.1% TFA and

Solvent B: 90% ACN, 10% water, 0.1% TFA; or, 90% MeOH, 10% water, 0.1% TFA.

Preparatory HPLC (unless otherwise noted) was performed on a Shimadzu SCL-10A liquid chromatograph with a linear gradient of 20-100% Solvent B over 10 to 30 min, with either a 2 to 5 min hold at 100% Solvent B as determined by on skilled in the art;

UV visualization at 220 nm;

Column: PHENOMENEX® Luna Axia 5μ, C18 30×100 mm;

Flow rate: 20 mL/min;

Solvent A: 10% ACN, 90% water, 0.1% TFA; or 10% MeOH, 90% water, 0.1% TFA; and

Solvent B: 90% ACN, 10% water, 0.1% TFA; or 90% MeOH, 10% water, 0.1% TFA.

Preparatory chiral SFC chromatography (unless otherwise noted) was performed on a Berger Multigram II SFC chromatograph using one of the following methods:

Preparative chiral SFC method A:

Column: CHIRALCEL® OD-H, 30×250 mm ID, 5μ

Flow rate: 90 mL/min, 100 bar BP, 40° C.

Mobile Phase: 15% Methanol/85% $CO_2$

Detector Wavelength: 254 nm

Injection Vol and Sample Solution: 0.5 mL of 4.65 g in 35 mL Methanol (133 mg/mL)

Preparative chiral SFC method B:

Instrument: Berger SFC MGII (HPW-2501)

Column: CHIRALPAK® IA 25×3 cm ID, 5 μm

Flow rate: 85.0 mL/min

Mobile Phase: 85/15/0.1, $CO_2$/IPA/DEA, 150 bar

Detector Wavelength: 225 nm (Lamda max)

Sample Prep and Inj. Volume: 300 μL of ~13 mg/0.5 mL IPA (~26 mg/mL)

Preparative chiral SFC method C

Column: CHIRALPAK® IA 25×3 cm ID, 5 μm

Flow rate: 90 mL/min

Mobile Phase: 85/15/0.1, $CO_2$/MeOH/DEA, 150 bar

Detector Wavelength: 270 nm (Lambda max)

Sample Prep and Inj. Volume: 300 μL of ~90 mg/2 mL MeOH (~45 mg/mL)

Preparative chiral SFC method D

Flow rate: 40 mL/min, 100 Bar, 35° C.

Mobile Phase: 20% Methanol/80% $CO_2$

Detector Wavelength: 224 nm (Lambda max)

Injection Volume: 300 μL

Sample Preparation: 10 mg dissolved in 0.5 mL MeCN (20 mg/mL);

17 mg dissolved in 0.5 mL MeCN (34 mg/mL)

Analytical chiral SFC chromatography (unless otherwise noted) was performed on an Aurora Analytical SFC or Berger Analytical SFC using one of the following methods:

Analytical chiral SFC method A:

Column: CHIRALCEL it OD-H, 4.6×250 mm ID, 5 μm

Flow rate: 3.0 mL/min, 100 bar BP, 35° C.

Mobile Phase: 15% Methanol/85% $CO_2$

Detector Wavelength: 220 nm

Sample Solution: 1 mg/mL in methanol (concentrated/reconstituted)

Injection Volume: 10 μL

Analytical chiral SFC method B:

Column: CHIRALPAK® IA 250×4 6 mm ID, 5 μm

Flow rate: 2.0 mL/min

Mobile Phase: 85/15/0.1, $CO_2$/IPA/DEA, 150 bar

Detector Wavelength: 225 nm (Lamda max)

Injection Volume: 10 μL

Analytical chiral SFC method C:

Column: CHIRALPAK® IA 250×4 6 mm ID, 5 μm

Flow rate: 3.0 mL/min

Mobile Phase: 65/35/0.1, $CO_2$/MeOH/DEA, 150 bar

Detector Wavelength: 270 nm (Lambda max)

Injection Volume: 10 μL

Analytical chiral SFC method D:

Column: CHIRALCEL® OD, 250×4.6 mm ID, 10 μm

Flow rate: 2.0 mL/min, 100 bar, 35° C.

Mobile Phase: 20% Methanol/80% $CO_2$

Detector Wavelength: 223 nm

Injection Volume: 10 μL

NMR Employed in Characterization of Examples $^1$H NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Microwave instrumentation employed in heating reactions.

BIOTAGE® Initiator 2.5, maximum power 400 W, reaction volume range 0.2-10 mL. Reactions are run in sealed pressure vessels specially manufactured for this instrument.

Example 1. 6-Methyl-2-oxo-6-phenyl-4-p-tolyl-1,2,5,6-tetrahydropyridine-3-carbonitrile

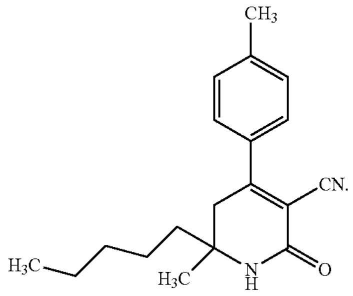 [SMILES: CCCCCC1(C)CC(c2ccc(C)cc2)=C(C#N)C(=O)N1]

A solution of heptan-2-one (51 mg, 0.45 mmol), 1-p-tolylethanone (60 mg, 0.45 mmol), ethyl-2-cyanoacetate (51 mg, 0.45 mmol) and ammonium acetate (42 mg, 0.55 mmol) in anhydrous DMF (0.6 mL) was heated with stirring at 100° C. for 16 h. The reaction was diluted with EtOAc and washed with water. The solvent was removed in vacuo and the product was purified by preparative HPLC (MeOH/$H_2O$/TFA) to provide the desired product (8 mg, 6%) as a white solid. LCMS Anal. Called for $C_{19}H_{24}N_2O$ 297.41, found [M+H] 297.2. $^1H$ NMR (500 MHz, $CDCl_3$) δ 0.89 (t, J=6.87 Hz, 3H), 1.24-1.40 (m, 9H), 1.51-1.71 (m, 2H) 2.42 (s, 3H), 2.73-2.97 (m, 2H), 6.09 (s, 1H), 7.30 (d, J=7.70 Hz, 2H), 7.52 (d, J=7.70 Hz, 2H).

Example 2. 3-(1H-Tetrazol-5-yl)-4-p-tolyl-6-(4-(4,4,4-trifluorobutoxy)phenyl)-6-(trifluoromethyl)-5,6-dihydropyridin-2(1H)-one

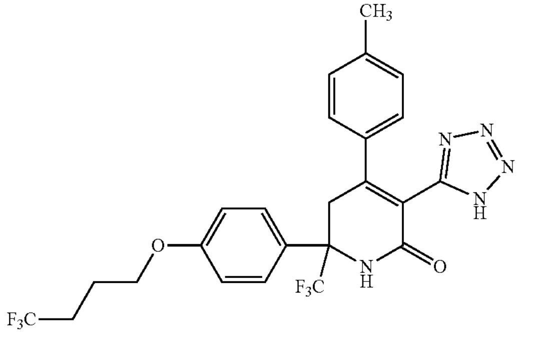 [SMILES: Cc1ccc(C2=C(c3nnn[nH]3)C(=O)NC(c3ccc(OCCCC(F)(F)F)cc3)(C(F)(F)F)C2)cc1]

Intermediate 2A. 4-(4,4,4-Trifluorobutoxy)benzaldehyde

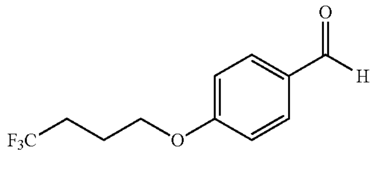

To a solution of 4-hydroxybenzaldehyde (20 g, 164 mmol) and 4,4,4-trifluorobutan-1-ol (25 g, 195 mmol) in anhydrous $CH_2Cl_2$ (500 mL) at 0° C. under Ar was added a solution of $PPh_3$ (51.5 g, 196 mmol) in $CH_2Cl_2$ (200 mL) over 15 min, and then DIAD (36.4 g, 180 mmol) in anhydrous $CH_2Cl_2$ (150 mL) was added dropwise. The mixture was stirred at 0° C. for 0.5 h. The reaction was warmed to rt and stirred for another 3 h. The solvent was removed in vacuo and the residue was triturated with $CH_2Cl_2$ three times to remove insoluble solids. The combined $CH_2Cl_2$ washings were concentrated and the residue was purified by silica gel chromatography (330 g silica gel, eluted with EtOAc in hexanes) to provide Intermediate 2A (27 g, 71%) as a light brown oil. LCMS Anal. Calc'd for $C_{11}H_{11}F_3O_2$ 232.20, found [M+H] 233.0.

Intermediate 2B. 2,2,2-Trifluoro-1-(4-(4,4,4-trifluorobutoxy)phenyl)ethanol

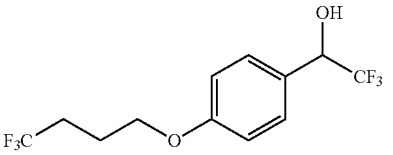 [SMILES: OC(c1ccc(OCCCC(F)(F)F)cc1)C(F)(F)F]

To the solution of Intermediate 2A (26.7 g, 114 mmol) and trimethyl(trifluoromethyl)silane (16.9 g, 119 mmol) in anhydrous DME (112 mL) was added CsF (500 mg, 3.29 mmol). The reaction was stirred at rt for 16 h. To the mixture was added 4 N aq HCl (114 mL) and the reaction was stirred at rt for 2.5 h. The reaction was diluted with EtOAc (300 mL) and washed with water, sat'd aq $NaHCO_3$, sat'd aq NaCl, dried over anhydrous $MgSO_4$, filtered and concentrated to provide Intermediate 2B (42.5 g, 122%) as an oil. The crude product was used without further purification. LCMS Anal. Calc'd for $C_{12}H_{12}F_6O_2$ 302.21, found [M−H] 301.2.

Intermediate 2C. 2,2,2-Trifluoro-1-(4-(4,4,4-trifluorobutoxy)phenyl)ethanone

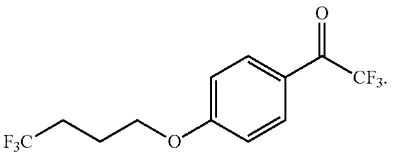 [SMILES: O=C(c1ccc(OCCCC(F)(F)F)cc1)C(F)(F)F]

To a solution of Intermediate 2B (115 mmol) in anhydrous $CH_2Cl_2$ (320 mL) was added Dess-Martin periodinane (50.2 g, 118 mmol) portionwise at 0° C. The reaction was stirred at 0° C. for 0.5 h then at rt for 3 h. To the reaction was added 100 mL of sat'd aq $Na_2CO_3$ and 250 mL of EtOAc. The reaction was stirred for another 2 h. The insoluble material was removed by filtration. The layers were separated. The organic layer was washed with sat'd aq $Na_2CO_3$. Additional solids that formed upon standing overnight were removed. The organic solution was washed with sat'd aq NaCl, dried over anhydrous $MgSO_4$, filtered and concentrated to provide a dark brown liquid, which was purified by silica gel chromatography (220 g silica gel, elute with EtOAc in hexanes to provide Intermediate 2C (26 g, 76%) as a colorless oil.

Intermediate 2D. Triphenylphosphoniump-tolylcarbonylylide

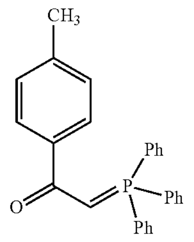 [SMILES: Cc1ccc(C(=O)C=P(c2ccccc2)(c2ccccc2)c2ccccc2)cc1]

To a refluxing solution of $PPh_3$ (6.15 g, 23.47 mmol) in anhydrous THF (220 mL) under argon was added dropwise a solution of 2-bromo-1-p-tolylethanone (5 g, 23.47 mmol) in THF (60 mL). The reaction was refluxed for 2.5 h and then cooled to rt. The precipitate was collected by filtration and rinsed with diethyl ether. The solids were suspended in 1:1 MeOH and $H_2O$ (500 mL), and then 2 N aq NaOH (55 mL) was added. The reaction was stirred at rt for 16 h. MeOH was removed in vacuo and the aq solution was extracted with $CHCl_3$. The combined organic extracts were washed with sat'd aq NaCl, dried over anhydrous $Na_2SO_4$, filtered and concentrated to provide Intermediate 2D (9 g, 97%) as a white solid. LCMS Anal. Calc'd for $C_{27}H_{230}P$ 394.44, found [M+H] 395.2.

Intermediate 2E. (Z)-4,4,4-Trifluoro-1-p-tolyl-3-(4-(4,4,4-trifluorobutoxy)phenyl)but-2-en-1-one

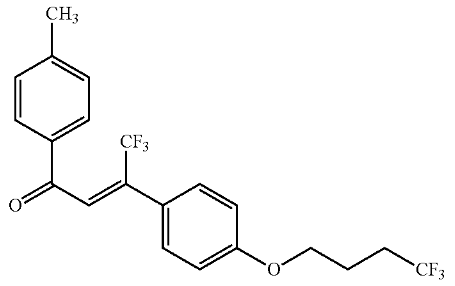 [SMILES: Cc1ccc(C(=O)/C=C(/c2ccc(OCCCC(F)(F)F)cc2)C(F)(F)F)cc1]

Intermediate 2D (5.13 g, 13 mmol) and Intermediate 2C (3.90 g, 13 mmol) were suspended in DMSO (15 mL). The reaction was heated to 160° C. for 1000 s under microwave conditions. The reaction was cooled to rt and diluted with EtOAc (60 mL). The mixture was washed with water and sat'd aq NaCl, dried over anhydrous $MgSO_4$, filtered and concentrated. The crude product was purified by silica gel chromatography (120 g silica gel, elute with EtOAc in hexanes to provide Intermediate 2E (5.9 g, 98%) as a light brown oil.

Intermediate 2F, isomer 1. (R)-3-Amino-4,4,4-trifluoro-1-p-tolyl-3-(4-(4,4,4-trifluorobutoxy)phenyl)-butan-1-one

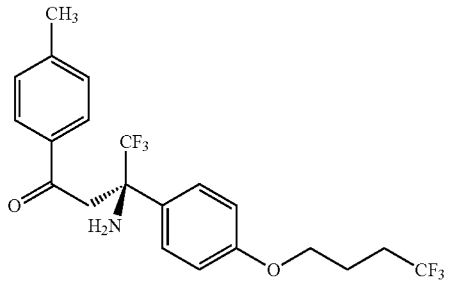 [SMILES: Cc1ccc(C(=O)C[C@@](N)(c2ccc(OCCCC(F)(F)F)cc2)C(F)(F)F)cc1]

Intermediate 2F, isomer 2. (S)-3-Amino-4,4,4-trifluoro-1-p-tolyl-3-(4-(4,4,4-trifluorobutoxy)phenyl)-butan-1-one

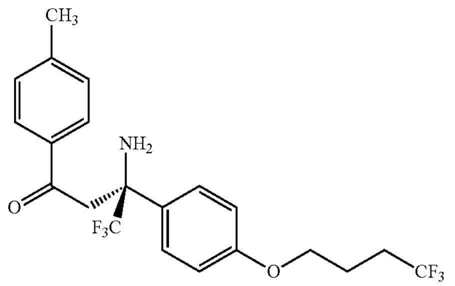 [SMILES: Cc1ccc(C(=O)C[C@](N)(c2ccc(OCCCC(F)(F)F)cc2)C(F)(F)F)cc1]

To a solution of Intermediate 2E (2.1 g, 5.04 mmol) in DMSO (50 mL) was added 15 N aq $NH_4OH$ (25 mL). The mixture was stirred in sealed pressure vessel for 2 days. The reaction was diluted with EtOAc (60 mL), washed with water and sat'd aq NaCl, dried over anhydrous $MgSO_4$, filtered and concentrated. The residue was purified by silica gel chromatography column (eluted with EtOAc in hexanes to provide racemic Intermediate 2F (2.2 g, 101%) as a white solid. LCMS Anal. Calc'd for $C_{21}H_{21}F_6NO_2$ 433.39, found [M+H] 434.2. Separation of the individual enantiomers of Intermediate 2F was carried out using preparative chiral SFC method A: Racemic Intermediate 2F (2200 mg) provided Intermediate 2F, isomer 1 (817 mg) and Intermediate 2F, isomer 2 (790 mg). Enantiomeric purity determination of Intermediate 2F, isomer 1 and 2 was carried out using analytical SFC method A. Intermediate 2F, isomer 1: RT=2.2 min, 99% ee. Intermediate 2F, isomer 2: RT=2.8 min, 99% ee. X-ray crystal data collected for the camphorsulfonic acid salt of Intermediate 2F, isomer 1 showed the chiral center to have the R-configuration; therefore, the chiral center for Intermediate 2F, isomer 2 has the S-configuration.

Intermediate 2G. 2-(1H-Tetrazol-5-yl)-N-(1,1,1-trifluoro-4-oxo-4-p-tolyl-2-(4-(4,4,4-trifluorobutoxy)-phenyl)butan-2-yl)acetamide

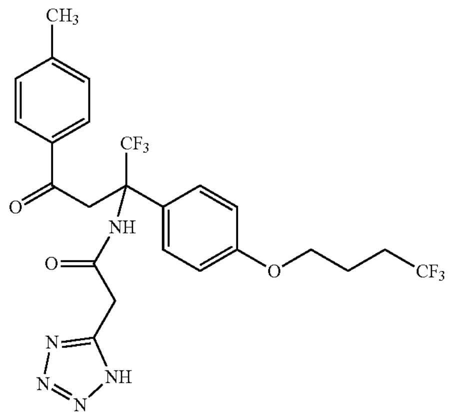 [SMILES: Cc1ccc(C(=O)CC(NC(=O)Cc2nnn[nH]2)(c2ccc(OCCCC(F)(F)F)cc2)C(F)(F)F)cc1]

To a solution of Intermediate 2F (789 mg, 1.82 mmol) in anhydrous THF (9 ml) at 0° C. was added DCC (1.13 g, 5.46 mmol). 2-Tetrazole acetic acid (700 mg, 5.46 mmol) was added dropwise as a suspension in anhydrous THF (8 mL). The reaction was stirred at 0° C. for 1 h and then at rt overnight. The reaction was filtered and solids were rinsed with THF. The filtrate was diluted with EtOAc (40 mL), washed with sat'd $Na_2CO_3$ and sat'd aq NaCl, dried over anhydrous $MgSO_4$, filtered and concentrated to provide Intermediate 2G (1.5 g, 152%) as a reddish brown solid. Intermediate 2G was used in the next step without further purification. LCMS Anal. Calc'd for $C_{24}H_{23}F_6N_5O_3$ 543.46, found [M+H] 543.9.

Example 2

To a solution of Intermediate 2G (1.5 g) in EtOH (11 mL) was added piperidine (0.33 mL). The reaction was heated to 78° C. for 16 h in a sealed vial. The reaction was cooled to rt and the solvent was removed in vacuo. The residue was purified by preparative HPLC ($MeOH/H_2O/TFA$). Fractions containing the product were dried in vacuo and the product was re-dissolved in MeOH and concentrated again. The oily brown product was re-dissolved in $CH_2Cl_2$ (5 mL) and concentrated in vacuo to provide Example 2 (552 mg, 57% over 2 steps) as a reddish foam. LCMS Anal. Calc'd for $C_{24}H_{21}F_6N_5O_2$ 525.45, found [M+H] 526.2. $^1H$ NMR (500 MHz, $CD_3OD$) δ 7.61 (d, J=9.1 Hz, 2H), 7.11 (d, J=8.0 Hz, 2H), 7.07-7.01 (m, 2H), 6.90 (d, J=8.3 Hz, 2H), 4.10 (t, J=6.1 Hz, 2H), 3.84-3.64 (m, 2H), 2.48-2.35 (m, 2H), 2.30 (s, 3H), 2.14-2.00 (m, 2H).

Example 2-1. (S)-3-(1H-Tetrazol-5-yl)-4-p-tolyl-6-(4-(4,4,4-trifluorobutoxy)phenyl)-6-(trifluoromethyl)-5,6-dihydropyridin-2(1H)-one

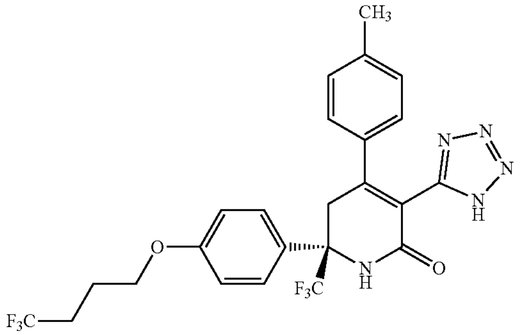 [SMILES: Cc1ccc(C2=C(c3nnn[nH]3)C(=O)N[C@@](c3ccc(OCCCC(F)(F)F)cc3)(C(F)(F)F)C2)cc1]

Separation of the individual enantiomers of Example 2 was carried out using preparative chiral SFC method C: Racemic Example 2 (89 mg) provided Example 2-1 (21 mg). Enantiomeric purity determination of Example 2-1 was carried out using analytical SFC method C. RT=6.0 min, 99% ee.

Example 2-1 can be alternatively obtained from Intermediate 2F, isomer 2 using a sequence similar to one used for the conversion of Intermediate 2F to Example 2.

Example 2-2. (R)-3-(1H-Tetrazol-5-yl)-4-p-tolyl-6-(4-(4,4,4-trifluorobutoxy)phenyl)-6-(trifluoromethyl)-5,6-dihydropyridin-2(1H)-one

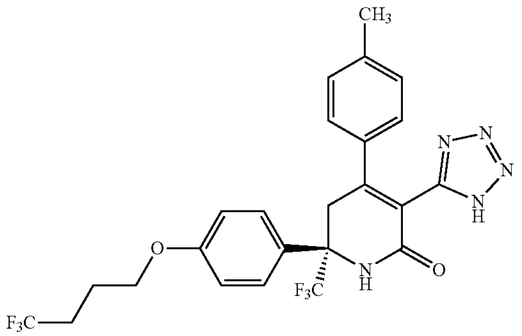 [SMILES: Cc1ccc(C2=C(c3nnn[nH]3)C(=O)N[C@](c3ccc(OCCCC(F)(F)F)cc3)(C(F)(F)F)C2)cc1]

Separation of the individual enantiomers of Example 2 was carried out using preparative chiral SFC method C: Racemic Example 2 (89 mg) provided Example 2-2 (22 mg). Enantiomeric purity determination of Example 2-2 was carried out using analytical SFC method C. RT=15.1 min, 99% ee.

Example 2-2 can be alternatively obtained from Intermediate 2F, isomer 1 using a sequence similar to one used for the conversion of Intermediate 2F to Example 2.

Example 3. 6-(4-Bromophenyl)-2-oxo-4-p-tolyl-6-(trifluoromethyl)-1,2,5,6-tetrahydropyridine-3-carbonitrile

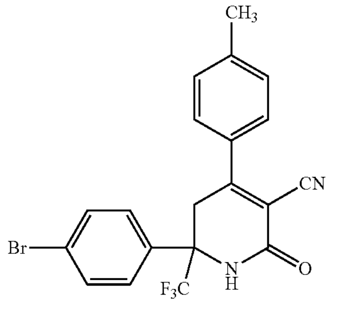 [SMILES: Cc1ccc(C2=C(C#N)C(=O)NC(c3ccc(Br)cc3)(C(F)(F)F)C2)cc1]

Intermediate 3A. (Z)-3-(4-Bromophenyl)-4,4,4-trifluoro-1-p-tolylbut-2-en-1-one

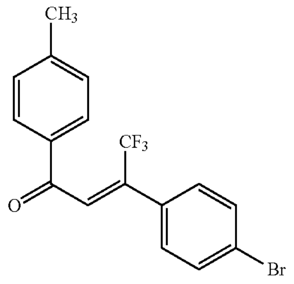 [SMILES: Cc1ccc(C(=O)/C=C(/c2ccc(Br)cc2)C(F)(F)F)cc1]

Intermediate 2D (1.84 g, 4.74 mmol) and 1-(4-bromophenyl)-2,2,2-trifluoroethanone (1.2 g, 4.74 mmol) were dissolved in THF (8 mL) and heated to 150° C. for 1000 s under microwave conditions. The reaction was cooled to rt and the solvent was removed in vacuo. The residue was purified by silica gel chromatography (24 g silica gel, elute with EtOAc in hexanes) to yield Intermediate 3A (1.51 g, 86%) as a light brown solid. LCMS Anal. Calc'd for $C_{17}H_{12}BrF_3O$ 369.18, found [M+H] 371.0.

Intermediate 3B. 3-Amino-3-(4-bromophenyl)-4,4,4-trifluoro-1-p-tolylbutan-1-one

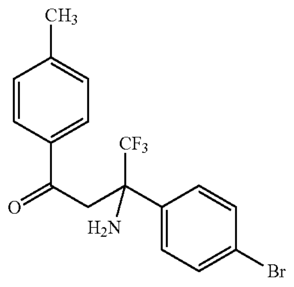 [SMILES: Cc1ccc(C(=O)CC(N)(c2ccc(Br)cc2)C(F)(F)F)cc1]

To a solution of Intermediate 3A (1.53 g, 4.14 mmol) in DMSO (23 mL) was added 15 N aq $NH_4OH$ (10 mL). The reaction vessel was sealed and the reaction was stirred at rt for 16 h. Additional DMSO (3 mL) and 15 N aq $NH_4OH$ (1 mL) were added and the reaction was stirred at rt for 16 h. Addition of DMSO (4 mL) was repeated and the reaction was stirred for another 16 h. The solution was concentrated in vacuo followed by lyophilization to provide Intermediate 3B (1.8 g, 100%) as a brown oil. LCMS Anal. Calc'd for $C_{17}H_{15}BrF_3NO$ 386.21, found [M+H] 388.1.

Intermediate 3C. 2-Cyanoacetyl Chloride

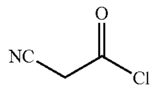

To a mixture of 2-cyanoacetic acid (893 mg, 10.5 mmol) and DMF (16A) in anhydrous $CH_2Cl_2$ (20 mL) at 0 C was added dropwise a 2 M solution of oxalyl chloride (6 mL, 12 mmol) in $CH_2Cl_2$. The reaction was stirred at 0° C. for 20 min, and then warmed to rt and stirred for 2 h. The solvent was removed in vacuo to provide Intermediate 3C, which was used in the next reaction without purification.

Example 3

To a solution of Intermediate 3B (1.6 g, 4.1 mmol) in anhydrous $CH_2Cl_2$ (15 mL) at 0° C. was added a solution of Intermediate 3C (1.1 g, 10.5 mmol), pyridine (0.85 mL), and DMAP (20 mg) in anhydrous $CH_2Cl_2$ (5 mL). The reaction was stirred at 0° C. for 20 min, then at rt for 2.5 h. The solvent was removed in vacuo. The crude product was dissolved in EtOAc (30 mL), washed with sat'd aq $Na_2CO_3$ and sat'd aq NaCl, dried over anhydrous $Na_2SO_4$, filtered and concentrated to yield a brown solid. The solid was triturated with $CH_2Cl_2$/diethyl ether to provide Example 3 (1.27 g) as an off white solid. The supernatant was evaporated and the residue was purified by silica gel chromatography (eluted with EtOAc in hexanes) to provide a second batch of Example 3 (0.22 g). The combined yield was 1.49 g (80%). LCMS Anal. Calc'd for $C_{20}H_{14}BrF_3N_2O$ 435.24, found [M+H] 437.0. $^1H$ NMR (500 MHz, $CDCl_3$) δ 2.42 (s, 3H), 3.45-3.67 (m, 2H), 7.30 (d, J=7.70 Hz, 2H), 7.39 (d, J=8.25 Hz, 2H), 7.45 (d, J=7.70 Hz, 2H), 7.60 (d, J=8.80 Hz, 2H).

Example 4. 6-(4-Hydroxyphenyl)-2-oxo-4-p-tolyl-6-(trifluoromethyl)-1,2,5,6-tetrahydro-pyridine-3-carbonitrile

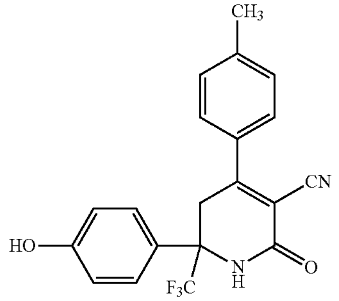 [SMILES: Cc1ccc(C2=C(C#N)C(=O)NC(c3ccc(O)cc3)(C(F)(F)F)C2)cc1]

Example 3 (1.49 g, 3.42 mmol), $Pd_2dba_3$ (78 mg, 0.086 mmol), KOH (403 mg, 7.2 mmol) and bis(1,1-dimethylethyl)[2',4',6'-tris(1-methylethyl)[1,1'-biphenyl]-2-yl]-phosphine (73 mg, 0.17 mmol) were placed in a microwave vial. The vial was evacuated and back filled with Ar. 1,4-Dioxane (23 mL) and water (13 mL) were added to the vial and the reaction mixture was heated to 140° C. for 15 min under microwave conditions. The reaction was cooled to rt, neutralized with 1 N HCl, diluted with water, and extracted with EtOAc. The combined organic extracts were washed with water and sat'd aq NaCl, dried over anhydrous $Na_2SO_4$, filtered and concentrated. The residue was purified by silica gel chromatography to provide Example 4 (1.14 g, 85%) as a light brown solid. LCMS Anal. Calc'd for $C_{20}H_{15}F_3N_2O_2$ 372.34, found [M+H] 373.2. $^1H$ NMR (500 MHz, DMSO-$d_6$) δ 2.30 (s, 3H), 3.65 (q, J=18.15 Hz, 2H), 6.73 (d, J=8.25 Hz, 2H), 7.28 (d, J=8.25 Hz, 2H), 7.38 (d, J=8.80 Hz, 2H), 7.47 (d, J=8.25 Hz, 2H), 9.63 (s, 1H), 9.70 (s, 1H).

Example 5. 6-(4-Butoxyphenyl)-2-oxo-4-p-tolyl-6-(trifluoromethyl)-1,2,5,6-tetrahydropyridine-3-carbonitrile

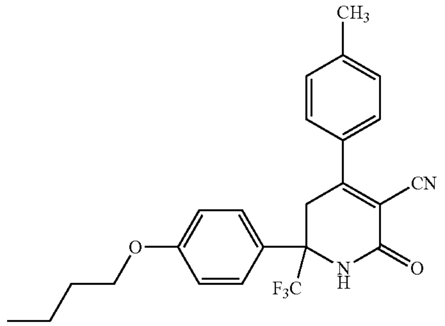 [SMILES: CCCCOc1ccc(C2(C(F)(F)F)CC(c3ccc(C)cc3)=C(C#N)C(=O)N2)cc1]

To a solution of Example 4 (20 mg, 0.054 mmol) and n-butanol (6 mg, 0.081 mmol) in anhydrous $CH_2Cl_2$ (0.3 mL) under Ar was added sequentially triphenylphosphine (21 mg, 0.081 mmol) in $CH_2Cl_2$ (0.3 mL) and DEAD (14 mg, 0.081 mmol) in $CH_2Cl_2$ (0.3 mL). The reaction mixture was stirred at 0° C. under argon for 20 min, then at rt for 2 h. The solvent was evaporated in vacuo and the product was purified by preparative HPLC ($CH_3CN/H_2O$/TFA) to provide Example 5 (5.6 mg, 24%). LCMS Anal. Calc'd for $C_{24}H_{23}F_3N_2O_2$ 428.45, found [M+H] 429.3. $^1H$ NMR (500 MHz, $CDCl_3$) δ 0.98 (t, J=7.42 Hz, 3H), 1.41-1.56 (m, 2H), 1.73-1.84 (m, 2H), 2.41 (s, 3H), 3.56 (q, J=18.15 Hz, 2H), 3.92-4.03 (m, 2H), 6.94 (d, J=8.25 Hz, 3H), 7.29 (d, J=8.25 Hz, 2H), 7.37 (d, J=8.80 Hz, 2H), 7.45 (d, J=7.70 Hz, 2H).

Example 6. N-(4-Methoxyphenyl)-2-oxo-4-p-tolyl-6-(4-(4,4,4-trifluorobutoxy)phenyl)-6-(trifluoromethyl)-1,2,5,6-tetrahydropyridine-3-carboxamide

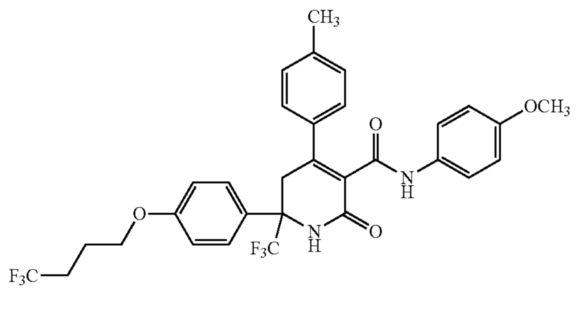

Intermediate 6A. Benzyl 3-(4-(methylamino)phenylamino)-3-oxopropanoate

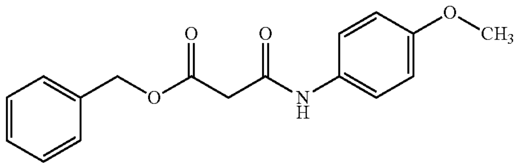 [SMILES: COc1ccc(NC(=O)CC(=O)OCc2ccccc2)cc1]

To a solution of monobenzyl malonate (12.2 g, 63.1 mmol) and DMF (90 μL) in anhydrous $CH_2Cl_2$ (100 mL) at 0° C. was added 2 M oxalyl chloride (35 mL, 70 mmol) in $CH_2Cl_2$. The reaction was stirred at 0° C. for 30 min, then at rt for 2.5 h. The solvent was removed in vacuo to provide freshly prepared acid chloride. This was dissolved in anhydrous $CH_2Cl_2$ (50 mL) and added dropwise to a solution of 4-methoxyaniline (7.76 g, 63 mmol) in anhydrous $CH_2Cl_2$ (50 mL) at 0° C. followed by the addition of pyridine (5.35 mL, 66.2 mmol). The reaction was stirred at 0° C. for 0.5 h, then at rt overnight. The reaction was washed with water and sat'd aq NaCl, dried over anhydrous $MgSO_4$, filtered and concentrated. The residue was triturated with EtOAc/$CH_2Cl_2$ to yield the first batch of Intermediate 6A as a light brown solid (6.95 g). The supernatant was evaporated and the residue was purified by silica gel chromatography (eluted with EtOAc in hexanes) to provide a second batch of Intermediate 6A as a light brown solid (7.4 g). The combined yield was 14.4 g (76%). LCMS Anal. Calc'd for $C_{17}H_{18}N_2O_3$ 298.34, found [M+H] 300.2.

Intermediate 6B. 3-(4-Methoxyphenylamino)-3-oxopropanoic acid

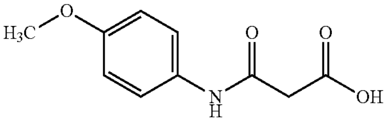

To a solution of Intermediate 6A (14.4 g, 4.8 mmol) in 10:1 EtOAc/MeOH (220 mL) was added 10% Pd/C (250 mg). The reaction mixture was stirred vigorously under an atmosphere of hydrogen (40 psi) for 2 h. More 10% Pd/C (250 mg) was added and the reaction was stirred under 50 psi hydrogen for another 1 h. Additional 10% Pd/C (500 mg) was added and the reaction was stirred under 50 psi hydrogen for an additional 1 h. The reaction was filtered through a pad of Celite® and the filtrate was concentrated in vacuo to yield Intermediate 6B (11.1 g, 96%) as an off-white solid. LCMS Anal. Calc'd for $C_{10}H_{11}NO_4$ 209.20, found [M+H] 210.1.

Intermediate 6C. $N^1$-(4-Methoxyphenyl)-$N^3$-(1,1,1-trifluoro-4-oxo-4-p-tolyl-2-(4-(4,4,4-trifluoro-butoxy)phenyl)-butan-2-yl)malonamide

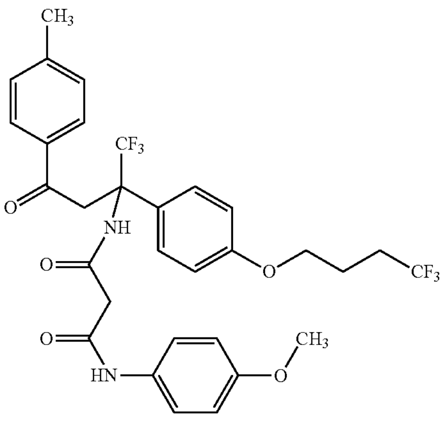 [SMILES: COc1ccc(NC(=O)CC(=O)NC(CC(=O)c2ccc(C)cc2)(c2ccc(OCCCC(F)(F)F)cc2)C(F)(F)F)cc1]

To triphenylphosphine (8.42 g, 32.1 mmol) in anhydrous $CH_2Cl_2$ (70 mL) was added Intermediate 6B (2.24 g, 10.7 mmol) in anhydrous $CH_2Cl_2$ (30 mL) followed by trichloroacetonitrile (1.86 g, 12.8 mmol). The mixture was stirred at rt for 3 h. The freshly prepared acid chloride was added to a solution of Intermediate 2F (1.13 g, 2.61 mmol) in anhydrous $CH_2Cl_2$ (20 mL), followed by the addition of pyridine (1.04 mL, 1.02 g, 12.85 mmol). The reaction was stirred at rt under argon overnight. The reaction was cooled to 0° C. and MeOH (40 mL) was added. The reaction was stirred at 0° C. for 10 min, then at rt for 30 min. The solvent was removed in vacuo and the crude product was purified by silica gel chromatography (120 g silica gel, eluted with EtOAc in hexanes). Product and triphenylphosphine oxide co-eluted. Fractions containing both were combined and evaporated to dryness. The solids were triturated with hexanes/EtOAc to remove most of the triphenylphosphine oxide. The product was again purified by silica gel chromatography (40 g silica gel, eluted with EtOAc in hexanes) to provide Intermediate 6C (1.03 g, 63%) as a brown oil. LCMS Anal. Calc'd for $C_{31}H_{30}F_6N_2O_5$ 624.57, found [M+H] 625.3.

Example 6

To a solution of Intermediate 6C (1.03 g, 1.65 mmol) in MeOH (10 mL) was added piperidine (100 μL, 1.01 mmol). The reaction was stirred at 75° C. for 1 h. The solvent was removed in vacuo and the crude product was purified by silica gel chromatography (120 g silica gel, eluted with EtOAc in hexanes). Mixed fractions from the first column were purified again by silica gel chromatography (40 g silica gel, eluted with EtOAc in hexanes) to provide Example 6 (546 mg, 55%) as a off-white solid. LCMS Anal. Calc'd for $C_{31}H_{28}F_6N_2O_4$ 606.56, found [M+H] 607.3. $^1H$ NMR (500 MHz, $CD_3OD$) δ 1.97-2.08 (m, 2H), 2.30 (s, 3H), 2.32-2.44 (m, 2H), 3.45-3.67 (m, 2H), 3.72 (s, 3H), 4.06 (t, J=6.05 Hz, 2H), 6.77 (d, J=9.35 Hz, 2H), 6.97 (d, J=8.80 Hz, 2H), 7.13-7.24 (m, 4H), 7.28 (d, J=8.25 Hz, 2H), 7.52 (d, J=8.80 Hz, 2H).

Example 6-1. (R)—N-(4-Methoxyphenyl)-2-oxo-4-p-tolyl-6-(4-(4,4,4-trifluorobutoxy)phenyl)-6-(trifluoro-methyl)-1,2,5,6-tetrahydropyridine-3-carboxamide

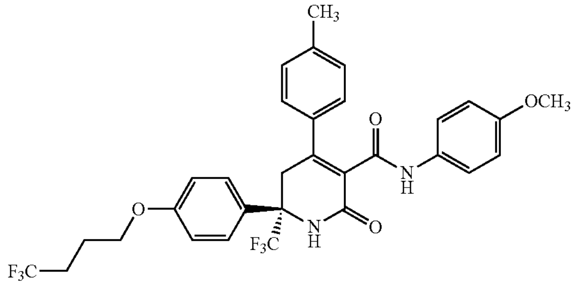 [SMILES: COc1ccc(NC(=O)C2=C(c3ccc(C)cc3)C[C@@](c3ccc(OCCCC(F)(F)F)cc3)(C(F)(F)F)NC2=O)cc1]

Example 6-1 was prepared using a procedure analogous to Example 6 by replacing Intermediate 2F with Intermediate 2F, isomer 1.

Example 6-2. (S)—N-(4-Methoxyphenyl)-2-oxo-4-p-tolyl-6-(4-(4,4,4-trifluorobutoxy)phenyl)-6-(trifluoro-methyl)-1,2,5,6-tetrahydropyridine-3-carboxamide

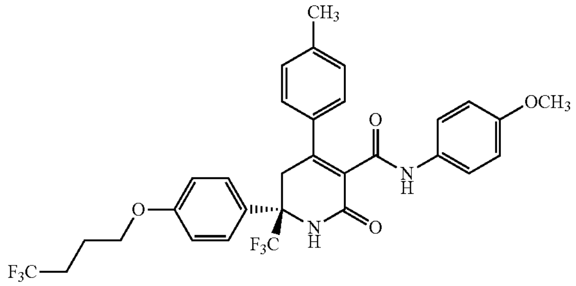 [SMILES: COc1ccc(NC(=O)C2=C(c3ccc(C)cc3)C[C@](c3ccc(OCCCC(F)(F)F)cc3)(C(F)(F)F)NC2=O)cc1]

Example 6-2 was prepared using a procedure analogous to Example 6 by replacing Intermediate 2F with Intermediate 2F, isomer 2.

Example 7. 6-(4-(6-Ethoxypyridin-3-yl)phenyl)-2-oxo-4-p-tolyl-6-(trifluoromethyl)-1,2,5,6-tetrahydro-pyridine-3-carbonitrile

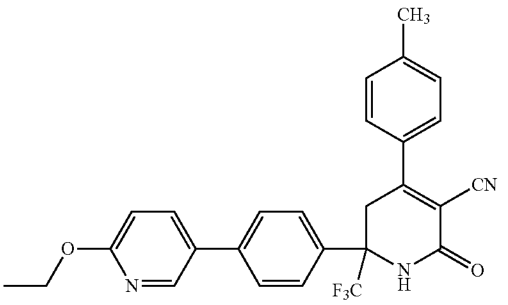 [SMILES: CCOc1ccc(-c2ccc(C3(C(F)(F)F)CC(c4ccc(C)cc4)=C(C#N)C(=O)N3)cc2)cn1]

To a solution of Example 3 (20 mg, 0.046 mmol), 6-ethoxypyridin-3-yl boronic acid (11 mg, 0.07 mmol) and tetrakis(triphenylphosphine) palladium(0) (5 mg, 10 mol %) in DMF (0.6 mL) sparged with Ar was added 2 N aq $K_2CO_3$ (46 μL, 0.096 mmol). The vessel was sealed and the reaction heated to 80° C. for 22 h. The reaction was cooled to rt and the product was purified twice by preparative HPLC ($CH_3CN/H_2O$/TFA and $CH_3OH/H_2O$/TFA sequentially) to provide Example 7 (10 mg, 45%) as a light brown solid. LCMS Anal. Calc'd for $C_{27}H_{22}F_3N_3O_2$ 477.48, found [M+H] 478.3. $^1H$ NMR (500 MHz, $CD_3OD$) δ 1.40 (t, J=6.87 Hz, 3H), 2.40 (s, 3H), 3.71-3.88 (m, 2H), 4.37 (q, J=7.15 Hz, 2H), 6.94 (d, J=8.25 Hz, 1H), 7.33 (d, J=7.70 Hz, 2H), 7.54 (d, J=8.25 Hz, 2H), 7.66-7.78 (m, 4H), 8.05 (dd, J=8.80, 2.20 Hz, 1H), 8.42 (d, J=2.20 Hz, 1H).

Example 8. (S)-3-(2H-Tetrazol-5-yl)-4-p-tolyl-6-(4-(6,6,6-trifluorohexyloxy)phenyl)-6-(trifluoromethyl)-5,6-dihydropyridin-2(1H)-one

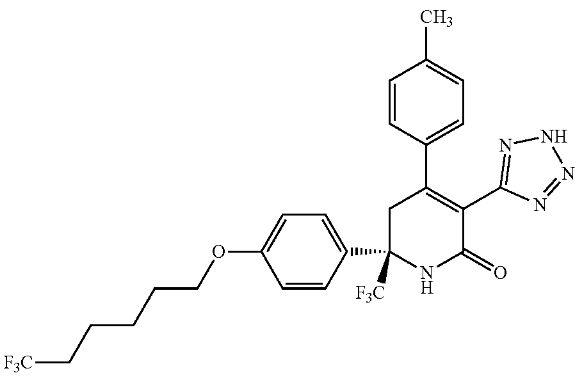 [SMILES: Cc1ccc(C2=C(c3nn[nH]n3)C(=O)N[C@@](c3ccc(OCCCCCC(F)(F)F)cc3)(C(F)(F)F)C2)cc1]

Intermediate 8A. 4-(6,6,6-Trifluorohexyloxy)benzaldehyde

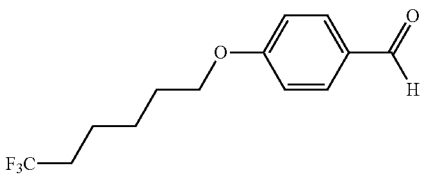 [SMILES: O=Cc1ccc(OCCCCCC(F)(F)F)cc1]

To a suspension of 4-hydroxybenzaldehyde (488 mg, 4 mmol) and 6-bromo-1,1,1-trifluorohexane (657 mg, 3 mmol) in MeCN (10 mL) was added $K_2CO_3$ (829 mg, 6.00 mmol). The resulting mixture was reflux overnight. Insoluble material was filtered off and rinsed with MeCN. The combined filtrate was concentrated to afford a white solid. This white solid was partitioned between EtOAc and 1 N NaOH solution. The organic layer was separated, washed with sat'd $NH_4Cl$, dried over $MgSO_4$, filtered and concentrated to afford Intermediate 8A as a clear liquid. LCMS Anal. Calc'd for $C_{13}H_{15}F_3O_2$ 260.10, found [M+H] 261.0.

Intermediate 8B. 2,2,2-Trifluoro-1-(4-(6,6,6-trifluorohexyloxy)phenyl)ethanone

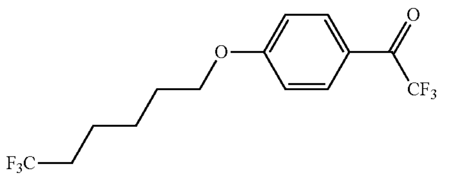

Intermediate 8B was prepared using a procedure analogous to Intermediate 2C except that Intermediate 2A was replaced with Intermediate 8A. $^1H$ NMR (500 MHz, $CDCl_3$) δ 8.06-8.02 (m, 2H), 6.99-6.97 (m, 1H), 4.08 (t, J=6.2 Hz, 2H), 2.19-2.06 (m, 2H), 1.92-1.82 (m, 2H), 1.71-1.55 (m, 4H).

Intermediate 8C. (S,E)-2-Methyl-N-(2,2,2-trifluoro-1-(4-(6,6,6-trifluorohexyloxy)phenyl)ethylidene)propane-2-sulfinamide

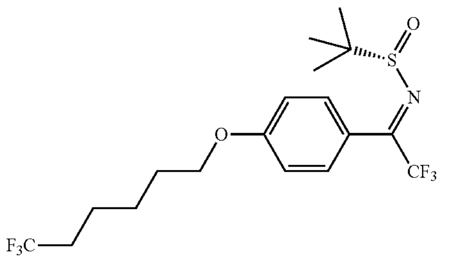 [SMILES: CC(C)(C)[S@](=O)/N=C(\c1ccc(OCCCCCC(F)(F)F)cc1)C(F)(F)F]

To a solution of Intermediate 8B (717 mg, 2.184 mmol) and (S)-2-methylpropane-2-sulfinamide (529 mg, 4.37 mmol) in THF (10 mL) was added tetraethoxytitanium (1993 mg, 8.74 mmol) in THF (20 mL). The resulting mixture was reflux for 5 h. TLC (20% EtOAc in hexane) indicated the starting ketone was completely consumed. The solvent was evaporated to afford a yellow oil. This yellow oil was dissolved in EtOAc and then washed with saturated $NaHCO_3$ (25 mL) and a large amount of white precipitation formed which was removed by filtering through a bed of Celite®. The white precipitation was rinsed with EtOAc. The combined EtOAc solution was washed again with saturated $NaHCO_3$, dried ($MgSO_4$) and concentrated. The crude product was purified by silica gel chromatography (40 g silica gel, eluted with EtOAc in hexanes) to afford Intermediate 8C (620 mg, 66%).

Intermediate 8D. (S)-2-Methyl-N—((S)-1,1,1-trifluoro-4-oxo-4-p-tolyl-2-(4-(6,6,6-trifluorohexyloxy)phenyl)butan-2-yl)propane-2-sulfinamide

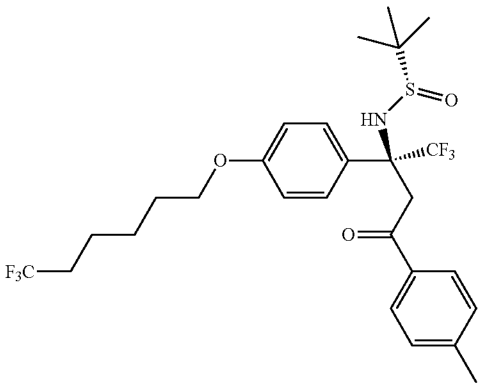 [SMILES: Cc1ccc(C(=O)C[C@](N[S@@](=O)C(C)(C)C)(c2ccc(OCCCCCC(F)(F)F)cc2)C(F)(F)F)cc1]

To a solution of 1-(p-tolyl)ethanone (609 mg, 4.31 mmol) in THF (10 mL) was cooled to −78° C. and to this solution was added lithium bis(trimethylsilyl)amide (4.31 mL, 4.31 mmol). The resulting mixture was stirred at −78° C. for 20 min and then Intermediate 8C (620 mg, 1.437 mmol) in THF (3 mL) was added dropwise. The resulting mixture was stirred at −78° C. for 1.5 h and then at 0° C. for 1.5 h. The reaction was quenched with $NH_4Cl$ and concentrated. The crude product was purified by silica gel chromatography (80 g silica gel, eluted with EtOAc in hexanes) to afford Intermediate 8D (482 mg, 59%) as the slower eluting diastereomer on silica gel column. LCMS Anal. Calc'd for $C_{27}H_{33}F_6NO_3S$ 565.21, found [M+H] 566.0.

Intermediate 8E. (S)-3-Amino-4,4,4-trifluoro-1-p-tolyl-3-(4-(6,6,6-trifluorohexyloxy)phenyl)butan-1-one

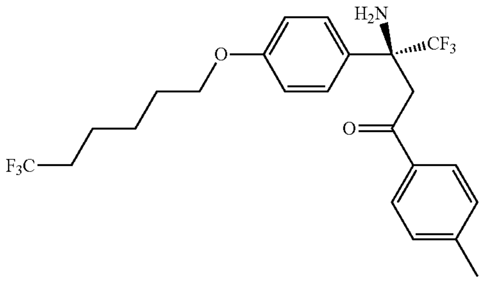 [SMILES: Cc1ccc(C(=O)C[C@](N)(c2ccc(OCCCCCC(F)(F)F)cc2)C(F)(F)F)cc1]

To a solution of Intermediate 8D (482 mg, 0.852 mmol) in MeOH (4 mL) was added 4 M HCl (1 mL, 4.00 mmol) in dioxane. The resulting mixture was stirred at rt for 2 h and then concentrated. The residue was taken up in EtOAc, washed with saturated $NaHCO_3$ and brine, dried ($MgSO_4$), filtered and concentrated to afford Intermediate (386 mg, 58%) as a colorless oil, which was used for the subsequent reaction without further purification. LCMS Anal. Calc'd for $C_{23}H_{25}F_6NO_2$ 461.18, found [M+H] 461.9.

Example 8

To a solution of Intermediate 8E (140 mg, 0.303 mmol) and 2-(2H-tetrazol-5-yl)acetic acid (117 mg, 0.910 mmol) in THF (3 mL) at 0° C. was added DCC (188 mg, 0.910 mmol). The resulting mixture was stirred overnight. The solvent was evaporated and the crude mixture was taken up in EtOAc. The organic solution was washed with saturated $NaHCO_3$, 1 N HCl and brine, dried ($MgSO_4$), filtered and concentrated to afford a brown oil. This oil was dissolved in EtOH (3 mL) and added piperidine (300 μL, 3.03 mmol). The resulting mixture was stirred at 80° C. overnight. The reaction mixture was diluted with MeOH and purified by preparative HPLC ($MeCN/H_2O$/TFA) to yield Example 8 (86 mg, 51%) as a solid. LCMS Anal. Calc'd for $C_{26}H_{25}F_6N_5O_2$ 553.19, found [M+H] 554.0. $^1H$ NMR (500 MHz, $CDCl_3$) δ 7.46 (d, J=8.8 Hz, 2H), 7.19 (d, J=8.0 Hz, 3H), 7.02-6.93 (m, 4H), 3.99 (t, J=6.3 Hz, 2H), 3.68-3.56 (m, 2H), 2.39 (s, 3H), 2.19-2.07 (m, 2H), 1.89-1.79 (m, 2H), 1.71-1.63 (m, 2H), 1.62-1.53 (m, 2H).

Example 9. 3-(2-Ethyl-2H-tetrazol-5-yl)-4-p-tolyl-6-(4-(4,4,4-trifluorobutoxy)phenyl)-6-(trifluoromethyl)-5,6-dihydropyridin-2(1H)-one

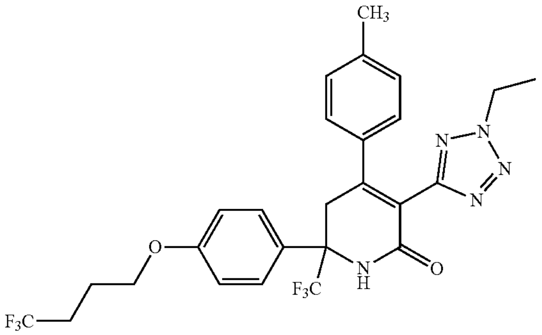 [SMILES: CCn1nnc(C2=C(c3ccc(C)cc3)CC(c3ccc(OCCCC(F)(F)F)cc3)(C(F)(F)F)NC2=O)n1]

To Example 2 (30 mg, 0.057 mmol) in anhydrous $CH_2Cl_2$ (0.6 mL) was added iodoethane (9 mg, 0.057 mmol) and triethylamine (24 μL, 0.17 mmol). The reaction was heated to 120° C. for 10 min under microwave conditions. The solvent was evaporated in vacuo and the residue was purified by preparative HPLC ($CH_3CN/H_2O$/TFA) to provide Example 9 (2.3 mg, 7%) as a light brown solid. LCMS Anal. Calc'd for $C_{26}H_{25}F_6N_5O_2$ 553.50, found [M+H] 554.3. $^1H$ NMR (500 MHz, $CDCl_3$) δ 1.51 (t, J=7.42 Hz, 2H), 1.98-2.13 (m, 2H), 2.21-2.39 (m, 5H), 3.51 (d, J=17.60 Hz, 1H), 3.72 (d, J=17.60 Hz, 1H), 4.04 (t, J=6.05 Hz, 2H), 4.56 (q, J=7.52 Hz, 2H) 6.87 (d, J=8.25 Hz, 2H), 6.95 (d, J=8.80 Hz, 2H), 7.02 (d, J=8.25 Hz, 2H), 7.46 (d, J=8.80 Hz, 2H), 7.93 (s, 1H).

Example 10. 4-p-Tolyl-6-(4-(4,4,4-trifluorobutoxy)phenyl)-6-(trifluoromethyl)-3-(5-(trifluoromethyl)-1,3,4-oxadiazol-2-yl)-5,6-dihydropyridin-2(1H)-one

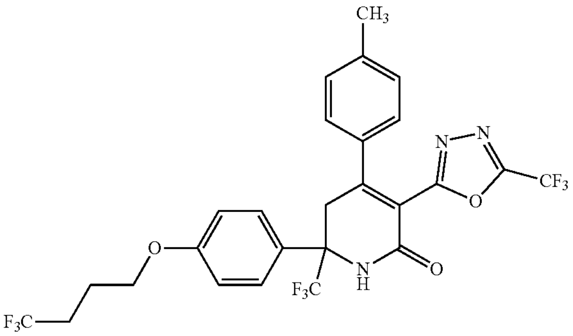 [SMILES: Cc1ccc(C2=C(c3nnc(C(F)(F)F)o3)C(=O)NC(c3ccc(OCCCC(F)(F)F)cc3)(C(F)(F)F)C2)cc1]

To Example 2 (29 mg, 0.055 mmol) in anhydrous $CH_2Cl_2$ (0.3 mL) was added a solution of trifluoroacetic anhydride (23.2 mg, 0.11 mmol) in anhydrous $CH_2Cl_2$ (0.2 mL) dropwise. The mixture was stirred at rt for 4 h and then concentrated. The residue was purified by preparative HPLC to provide Example 10 (19 mg, 58%) as a white solid. LCMS Anal. Calc'd for $C_{26}H_{20}F_9N_3O_3$ 593.44, found [M+H] 594.2. $^1H$ NMR (500 MHz, $CD_3OD$) δ 1.97-2.11 (m, 2H), 2.31 (s, 3H), 2.34-2.44 (m, 2H), 3.64-3.88 (m, 2H), 4.08 (t, J=6.05 Hz, 2H), 6.98 (d, J=8.25 Hz, 2H), 7.03 (d, J=8.80 Hz, 2H), 7.16 (d, J=8.25 Hz, 2H), 7.57 (d, J=8.80 Hz, 2H).

Example 11. 6-Methyl-2-oxo-4-p-tolyl-6-(4-(4,4,4-trifluorobutoxy)phenyl)-N-(4-(trifluoromethoxy)-phenyl)-1,2,5,6-tetrahydropyridine-3-carboxamide

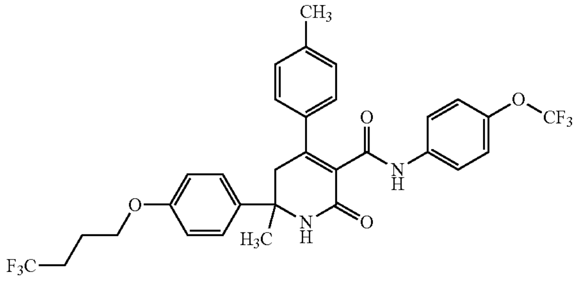 [SMILES: Cc1ccc(C2=C(C(=O)Nc3ccc(OC(F)(F)F)cc3)C(=O)NC(C)(c3ccc(OCCCC(F)(F)F)cc3)C2)cc1]

Intermediate 11A. 1-Bromo-4-(4,4,4-trifluorobutoxy)benzene

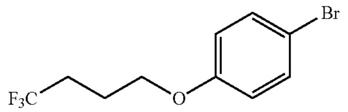 [SMILES: FC(F)(F)CCCOc1ccc(Br)cc1]

To a solution of 4-bromophenol (2.2 g, 12.7 mmol) and 4-bromo-1,1,1-trifluorobutane (2.4 g, 12.7 mmol) in anhydrous DMF (15 mL) was added $K_2CO_3$ (3.5 g, 25.4 mmol). The mixture was stirred at rt overnight. The mixture was diluted with EtOAc (120 mL) and the solids were removed by filtration. The filtrate was washed with water and sat'd aq NaCl, dried over anhydrous $MgSO_4$, filtered and concentrated. The residue was purified by silica gel chromatography (40 g silica gel, eluted with EtOAc in hexanes) to provide Intermediate 11A (3.05 g, 85%) as a colorless oil.

Intermediate 11B. (E)-Ethyl 3-(4-(4,4,4-trifluorobutoxy)phenyl)but-2-enoate

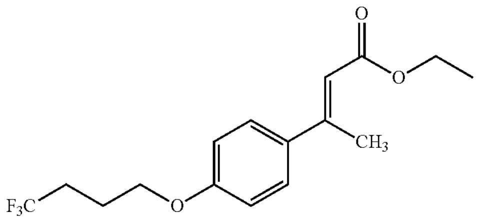 [SMILES: CCOC(=O)/C=C(\C)c1ccc(OCCCC(F)(F)F)cc1]

Intermediate 11A (2.81 g, 9.93 mmol), (E)-ethyl but-2-enoate (1.25 g, 10.9 mmol), palladium(II) acetate (0.11 g, 0.5 mmol), tetraethylammonium chloride (1.65 g, 9.9 mmol), N-cyclohexyl-N-methylcyclohexanamine (2.91 g, 14.9 mmol) and dimethylacetamide (30 ml) were placed in a oven-dried vial and sparged with argon for 5 min. The vial was sealed and the reaction heated to 110° C. for 6 h. The reaction was cooled to rt, diluted with EtOAc (75 mL), washed with water and sat'd aq NaCl, dried over anhydrous $MgSO_4$, filtered and concentrated. The residue was purified by silica gel chromatography eluting with EtOAc in hexanes to provide Intermediate 11B (1.81 g, 49%) as a colorless oil. LCMS Anal. Calc'd for $C_{16}H_{19}F_3O_3$ 316.32, found [M+H] 317.2.

Intermediate 11C. (E)-N-Methoxy-N-methyl-3-(4-(4,4,4-trifluorobutoxy)phenyl)but-2-enamide

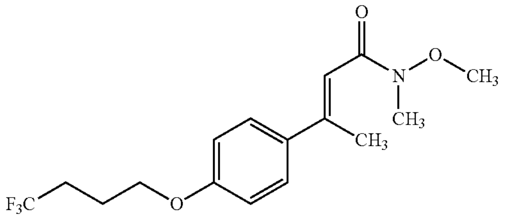 [SMILES: CON(C)C(=O)/C=C(\C)c1ccc(OCCCC(F)(F)F)cc1]

A solution of Intermediate 11B (2.67 g, 8.44 mmol) and N,O-dimethylhydroxylamine hydrochloride (1.65 g, 16.9 mmol) in anhydrous THF (35 mL) was cooled to −61° C. ($CHCl_3$/dry ice) under an atmosphere of Ar. To this solution was added 0.5 M isopropylmagnesium chloride (16.9 mL, 33.8 mmol) in THF slowly via a syringe. The reaction was stirred at −61° C. for 1.5 h, warmed to −20° C. (sat'd aq NaCl/ice) and stirred for 40 min, then warmed to 0° C. and stirred for 20 min. The reaction was poured into 10 mL of sat'd aq $NH_4Cl$ and 12 mL of water, and then extracted with EtOAc. The organic layer was washed with sat'd aq NaCl, dried over anhydrous $MgSO_4$, filtered and concentrated. The residue was purified by silica gel chromatography eluting with EtOAc in hexanes to provide Intermediate 11C (1.62 g, 58%) as a light brown oil. LCMS Anal. Calc'd for $C_{16}H_{20}F_3NO_3$ 331.33, found [M+H] 332.2.

Intermediate 11D. (E)-1-p-Tolyl-3-(4-(4,4,4-trifluorobutoxy)phenyl)but-2-en-1-one

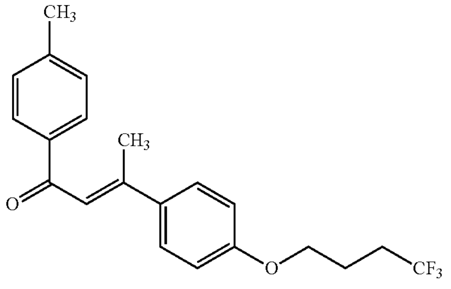

To a solution of Intermediate 11C (1.62 g, 4.89 mmol) in anhydrous THF (25 mL) at −78° C. was added dropwise 0.5 Mp-tolylmagnesium bromide in ether (25 mL, 12.5 mmol). The reaction was stirred at −78° C. for 40 min, then gradually warmed to rt. The reaction was poured into 1:1 sat'd aq $NH_4Cl$ and water (60 mL). The mixture was extracted with EtOAc. The organic layer was washed with sat'd aq NaCl, dried over $MgSO_4$, filtered and concentrated. The residue was purified by silica gel chromatography (eluted with EtOAc in hexanes) to provide Intermediate 11D (1.34 g, 76%) as a light brown solid. LCMS Anal. Calc'd for $C_{21}H_{21}F_3O_2$ 362.39, found [M+H] 363.2. $^1H$ NMR (500 MHz, $CDCl_3$) δ 2.01-2.11 (m, 2H), 2.29-2.37 (m, 2H), 2.42 (s, 3H), 2.58 (s, 3H), 4.07 (t, J=6.05 Hz, 2H), 6.92 (d, J=8.80 Hz, 2H), 7.14 (s, 1H), 7.23-7.34 (m, J=8.25 Hz, 2H), 7.55 (d, J=8.80 Hz, 2H), 7.90 (d, J=8.25 Hz, 2H).

Intermediate 11E. 3-Amino-1-p-tolyl-3-(4-(4,4,4-trifluorobutoxy)phenyl)butan-1-one

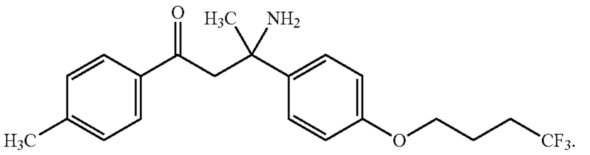 [SMILES: Cc1ccc(C(=O)CC(C)(N)c2ccc(OCCCC(F)(F)F)cc2)cc1]

Ammonia was bubble into a solution of Intermediate 11D (1.34 mg, 0.64 mmol) in EtOH (20 mL) and DMSO (12 mL) for 10 min at 0° C. The reaction was stirred at rt overnight in a sealed pressure vessel. Analytical HPLC showed reaction to have progressed only ca. 10%. The mixture was cooled to −15° C., then ammonia was bubbled through for 7 min. The vessel was sealed and the reaction was stirred at rt overnight. Analytical HPLC showed the reaction to be ca. 25-30% complete. The mixture was diluted with EtOAc (75 mL), washed with water and sat'd aq NaCl, dried over anhydrous $MgSO_4$, filtered and concentrated in vacuo. The residue was purified by silica gel chromatography to provide Intermediate 11E (281 mg, 20%) as a light brown oil. LCMS Anal. Calc'd for $C_{21}H_{24}F_3NO_2$ 379.42, found [M+H] 380.3.

Intermediate 11F. 3-Oxo-3-(4-(trifluoromethoxy)phenylamino)propanoic acid

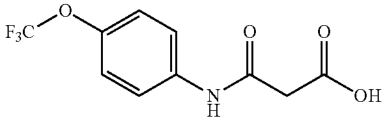 [SMILES: O=C(O)CC(=O)Nc1ccc(OC(F)(F)F)cc1]

By sequential application of the procedures for Intermediates 6A and 6B, 4-trifluoromethoxyaniline (2.3 g, 13 mmol) was converted to Intermediate 11F (2.8 g, 11 mmol), which was isolated as a white solid. LCMS Anal. Calc'd for $C_{10}H_8F_3NO_4$ 263.17, found [M+H] 264.1.

Intermediate 11G. $N^1$-(4-Oxo-4-p-tolyl-2-(4-(4,4,4-trifluorobutoxy)phenyl)butan-2-yl)-$N^3$-(4-(trifluoromethoxy)-phenyl)malonamide

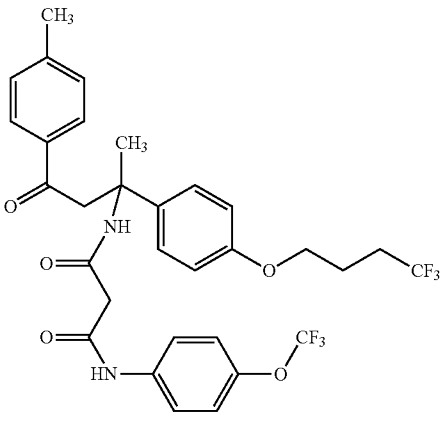 [SMILES: Cc1ccc(C(=O)CC(C)(NC(=O)CC(=O)Nc2ccc(OC(F)(F)F)cc2)c2ccc(OCCCC(F)(F)F)cc2)cc1]

To a solution of Intermediate 11F (41.6 mg, 0.158 mmol) in anhydrous $CH_2Cl_2$ (0.6 mL) was added $PPh_3$ (124 mg, 0.474 mmol) followed by dropwise addition of trichloroacetonitrile (27.4 mg, 0.19 mmol). The reaction was stirred at rt for 3 h. To the freshly prepared acid chloride was added a solution of Intermediate 11E (20 mg, 0.053 mmol) in anhydrous $CH_2Cl_2$ (0.3 mL) followed by pyridine (19.4, 0.237 mmol). The mixture was stirred at rt overnight. The solvent was removed in vacuo. The product was purified by preparative HPLC (MeOH/$H_2O$/TFA) to yield Intermediate 11G (11 mg, 33%) as a brown solid. LCMS Anal. Calc'd for $C_{31}H_{30}F_6N_2O_5$ 624.57, found [M+H] 625.4.

Example 11

To a solution of Intermediate 11G (11 mg, 0.018 mmol) in MeOH (0.8 ml) was added piperidine (15.4). The reaction was stirred at 75° C. for 1.5 h. The product was isolated by preparative HPLC ($CH_3CN/H_2O$/TFA) to provide Example 11 (5.2 mg, 44%) as a brown solid. LCMS Anal. Calc'd for $C_{31}H_{28}F_6N_2O_4$ 606.56, found [M+H] 607.4. $^1H$ NMR (500 MHz, $CD_3OD$) δ 1.68 (s, 3H), 1.95-2.07 (m, 2H), 2.27 (s, 3H), 2.30-2.41 (m, 2H), 3.11-3.26 (m, 2H), 4.03 (t, J=6.05 Hz, 2H), 6.91 (d, J=8.80 Hz, 2H), 7.08-7.18 (m, 4H), 7.22 (d, J=8.25 Hz, 2H), 7.38 (d, J=8.80 Hz, 2H), 7.45 (d, J=8.80 Hz, 2H).

Example 12. 3-(2H-Tetrazol-5-yl)-4-p-tolyl-6-(trifluoromethyl)-6-(1-(5,5,5-trifluoropentyl)-1H-pyrazol-4-yl)-5,6-dihydropyridin-2(1H)-one

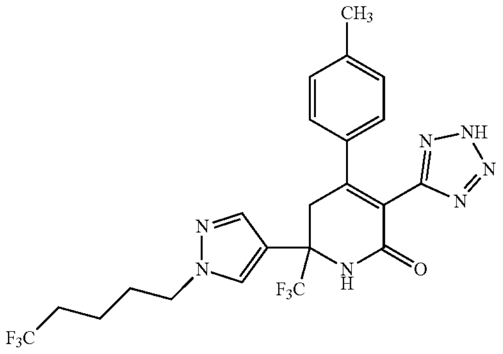 [SMILES: Cc1ccc(C2=C(c3nn[nH]n3)C(=O)NC(c3cnn(CCCCC(F)(F)F)c3)(C(F)(F)F)C2)cc1]

Intermediate 12A. 4-Iodo-1-(5,5,5-trifluoropentyl)-1H-pyrazole

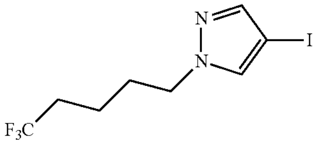 [SMILES: FC(F)(F)CCCCn1cc(I)cn1]

To a stirred solution of 4-iodo-1H-pyrazole (337 mg, 1.737 mmol) in DMF (10 mL) was added sodium hydride (104 mg, 2.61 mmol). After 30 min, 5-bromo-1,1,1-trifluoropentane (427 mg, 2.085 mmol) was added. The reaction was stirred at rt for 2 h. 3:1 hexane:ether and water were added. The organic layer was washed with $H_2O$, dried over $MgSO_4$, filtered and concentrated in vacuo. The crude product was purified by silica gel chromatography (24 g silica gel, eluted with 0-60% EtOAc in hexanes) to give the desired product (460 mg, 83%) as clear oil. LCMS Anal. Calc'd for $C_8H_{10}F_{31}N_2$ 318.0, found [M+H] 319.0. $^1$H NMR (400 MHz, $CDCl_3$) δ 7.49 (s, 1H), 7.40 (s, 1H), 4.12 (t, J=6.9 Hz, 2H), 2.00-2.15 (m, 2H), 1.85-1.96 (m, 2H), 1.47-1.61 (m, 2H).

Intermediate 12B. 2,2,2-Trifluoro-1-(1-(5,5,5-trifluoropentyl)-1H-pyrazol-4-yl)ethanone

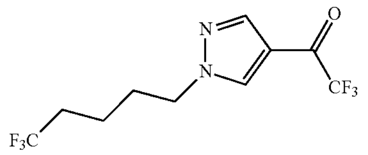 [SMILES: O=C(c1cnn(CCCCC(F)(F)F)c1)C(F)(F)F]

To a stirred solution of Intermediate 12A (460 mg, 1.446 mmol) in tetrahydrofuran (5 mL) at 0° C. was added isopropylmagnesium chloride (0.795 mL, 1.591 mmol) quickly. After 30 min, additional 0.25 eq of iPrMgCl was added and after 30 min, the mixture was cooled to −78° C. 2,2,2-Trifluoro-1-(piperidin-1-yl)ethanone (288 mg, 1.591 mmol) was added quickly and the reaction was warmed to rt and stirred for 3 h. The reaction was quenched with sat'd aq $NH_4Cl$ and diluted with EtOAc. The organic layer was washed with sat'd aq $NH_4Cl$, dried over $MgSO_4$, filtered and concentrated in vacuo. The crude product was purified by silica gel chromatography (40 g silica gel, eluted with 0-100% EtOAc in hexanes) to give the desired product (265 mg, 64%) as clear oil. $^1$H NMR (500 MHz, $CDCl_3$) δ 8.08 (s, 2H), 4.22 (t, J=7.0 Hz, 2H), 2.07-2.20 (m, 2H), 1.98-2.05 (m, 2H), 1.55-1.65 (m, 2H).

Example 12

Example 12 was prepared using a procedure analogous to Example 2 by replacing Intermediate 2C with Intermediate 12B. LCMS Anal. Calc'd for $C_{22}H_{21}F_6N_7O$ 513.2, found [M+H] 514.3. $^1$H NMR (500 MHz, $CDCl_3$) δ 7.75 (s, 1H), 7.63 (s, 1H), 7.54-7.59 (m, 1H), 7.06 (d, J=8.0 Hz, 2H), 6.88 (d, J=8.0 Hz, 2H), 4.16 (t, J=7.0 Hz, 2H), 3.58 (d, J=18.2 Hz, 1H), 3.39 (d, J=17.9 Hz, 1H), 2.28 (s, 3H), 2.02-2.17 (m, 2H), 1.93 (quin, J=7.4 Hz, 2H), 1.46-1.55 (m, 2H).

Example 13. 3-Nitro-4-p-tolyl-6-(4-(4,4,4-trifluorobutoxy)phenyl)-6-(trifluoromethyl)-5,6-dihydropyridin-2(1H)-one

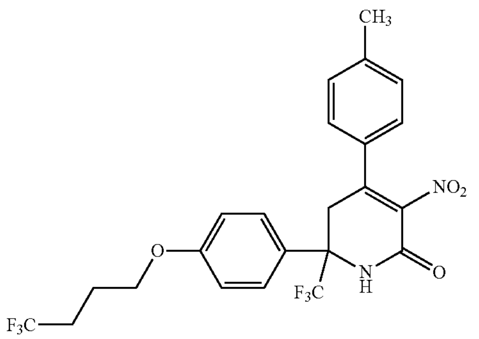 [SMILES: Cc1ccc(C2=C([N+](=O)[O-])C(=O)NC(c3ccc(OCCCC(F)(F)F)cc3)(C(F)(F)F)C2)cc1]

Intermediate 13A. 2-Nitro-N-(1,1,1-trifluoro-4-oxo-4-p-tolyl-2-(4-(4,4,4-trifluorobutoxy)phenyl)butan-2-yl)-acetamide

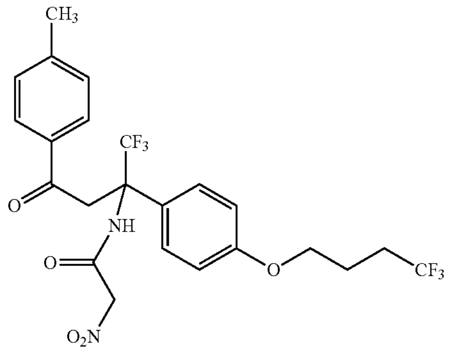 [SMILES: Cc1ccc(C(=O)CC(NC(=O)C[N+](=O)[O-])(c2ccc(OCCCC(F)(F)F)cc2)C(F)(F)F)cc1]

To a solution of Intermediate 2F (130 mg, 0.3 mmol) in anhydrous THF (1 mL) at 0° C. was added DCC (204 mg, 0.99 mmol) followed by a solution of 2-nitroacetic acid (104 mg, 0.99 mmol) in anhydrous THF (0.5 mL) dropwise. The reaction was stirred at 0° C. for 1 h then at rt overnight. The reaction was heated to 70° C. for 4 h. The reaction was cooled to rt and diluted with EtOAc (3 mL). The solids were filtered off and the filtrate was concentrated in vacuo. The residue was purified by silica gel chromatography (eluted with EtOAc in hexanes) to provide Intermediate 13A (129 mg, 83%) as a brown oil. LCMS Anal. Calc'd for $C_{23}H_{22}F_6N_2O_5$ 520.42, found [M+H] 521.1.

Example 13

To a solution of Intermediate 13A (126 mg, 0.24 mmol) in MeOH (2 mL) was added piperidine (35 μL). The reaction mixture was heated at 75° C. for 1.5 h. The product was isolated by preparative HPLC (MeOH/$H_2O$/TFA) to provide Example 13 (21 mg, 17%) as a off-white solid. LCMS Anal. Calc'd for $C_{23}H_{20}F_3N_2O_4$ 502.41, found [M+H] 503.1. $^1$H NMR (500 MHz, $CD_3OD$) δ 1.98-2.08 (m, 2H), 2.28-2.45 (m, 5H), 3.58 (d, J=17.60 Hz, 1H), 3.76 (d, J=17.60 Hz, 1H), 4.08 (t, J=6.05 Hz, 2H), 7.02 (d, J=8.80 Hz, 2H), 7.12-7.19 (m, 2H), 7.22-7.30 (m, 2H), 7.53 (d, J=8.80 Hz, 2H).

Example 14. 8-(4-Methoxyphenyl)-6-oxo-4-(4-(4,4,4-trifluorobutoxy)phenyl)-4-(trifluoro-methyl)-5-azaspiro[2.5]oct-7-ene-7-carbonitrile

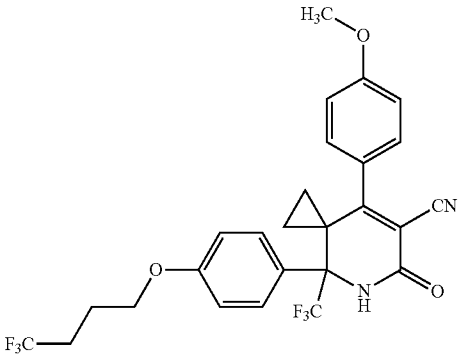 [SMILES: COc1ccc(C2=C(C#N)C(=O)NC(c3ccc(OCCCC(F)(F)F)cc3)(C(F)(F)F)C23CC3)cc1]

Intermediate 14A. Methyl 3-oxo-3-(4-(4,4,4-trifluorobutoxy)phenyl)propanoate

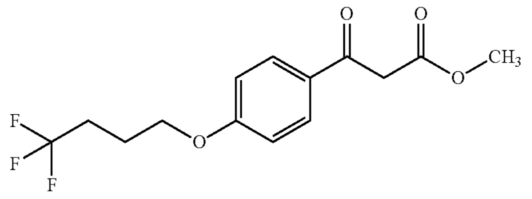 [SMILES: COC(=O)CC(=O)c1ccc(OCCCC(F)(F)F)cc1]

To a solution of methyl 3-(4-hydroxyphenyl)-3-oxopropanoate (7.8 g, 40.2 mmol) and 4,4,4-trifluorobutan-1-ol (5.15 g, 40.2 mmol) in $CH_2Cl_2$ (201 mL) at 0° C. was added triphenylphosphine (12.6 g, 48.2 mmol). The mixture was stirred for a few min, and then DIAD (9.37 mL, 48.2 mmol) was added. The reaction was stirred at 0° C. for 30 min, then warmed to rt and stirred for 3 days. The reaction was loaded directly onto a 300 g silica gel column and eluted with EtOAc in hexanes. Fractions containing the product were combined and concentrated to provide Intermediate 14A (9.9 g, 80%) as a colorless solid. $^1$H NMR (500 MHz, $CDCl_3$) δ 2.03-2.13 (m, 2H), 2.26-2.39 (m, 2H), 3.75 (s, 3H), 3.96 (s, 2H), 4.09 (t, J=6.05 Hz, 2H), 6.92-6.96 (m, 2H), 7.86-7.97 (m, 2H).

Intermediate 14B. Methyl 1-(4-(4,4,4-trifluorobutoxy)benzoyl)cyclopropanecarboxylate

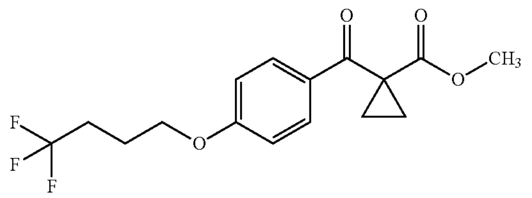 [SMILES: COC(=O)C1(C(=O)c2ccc(OCCCC(F)(F)F)cc2)CC1]

To a solution of Intermediate 14A (6.0 g, 19.7 mmol) in DMF (197 mL) was added $K_2CO_3$ (8.18 g, 59.2 mmol) followed by 1,2-dibromoethane (2.6 mL, 30 mmol). The reaction mixture was stirred at rt for 2 days. The reaction was reduced in volume in vacuo, then diluted with EtOAc, washed with a 1:1 solution of sat'd aq NaCl and water, dried over anhydrous $MgSO_4$, filtered and concentrated. The product was isolated by silica gel chromatography (220 g silica gel, eluted with EtOAc in hexanes) to provide Intermediate 14B (4.2 g, 61%) as a colorless oil. $^1$H NMR (500 MHz, $CDCl_3$) δ 1.45-1.49 (m, 2H), 1.56-1.61 (m, 2H), 2.03-2.14 (m, 2H), 2.26-2.39 (m, 2H), 3.60 (s, 3H), 4.09 (t, J=6.05 Hz, 2H), 6.90-6.94 (m, 2H), 7.86-7.93 (m, 2H).

Intermediate 14C. Methyl 1-((benzylimino)(4-(4,4,4-trifluorobutoxy)phenyl)methyl)cyclopropane carboxylate

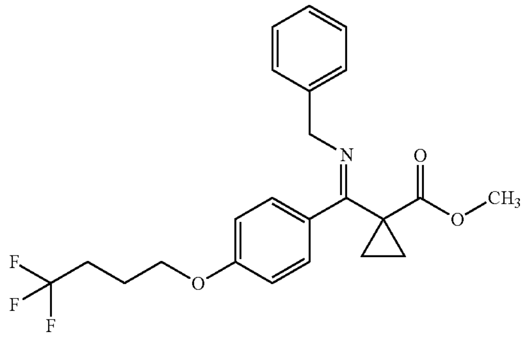 [SMILES: COC(=O)C1(/C(=N/Cc2ccccc2)c2ccc(OCCCC(F)(F)F)cc2)CC1]

To a solution of Intermediate 14B (4.2 g, 13 mmol) and benzylamine (5.5 mL, 50 mmol) in diethyl ether (63 mL) at 0° C. was added 1.0 M $TiCl_4$ in $CH_2Cl_2$ (7.6 mL, 7.5 mmol). The reaction was stirred at 0° C. for a few minutes, then warmed to rt and stirred for 16 h. Celite® was added to the reaction and the solids were removed by filtering through a bed of Celite®. The filtrate was concentrated and purified by silica gel chromatography (120 g silica gel, eluted with EtOAc in hexanes) to provide Intermediate 14C (4.6 g, 83%) as a colorless oil. $^1$H NMR (500 MHz, $CDCl_3$) δ 7.82 (d, J=8.8 Hz, 2H), 7.42-7.38 (m, 2H), 7.34 (t, J=7.7 Hz, 2H), 7.27-7.24 (m, 1H), 6.87 (d, J=8.8 Hz, 2H), 4.90 (s, 2H), 4.04 (t, J=6.0 Hz, 2H), 3.69 (s, 3H), 2.39-2.26 (m, 2H), 2.11-2.02 (m, 2H), 1.78-1.72 (m, 2H), 1.11 (d, J=3.3 Hz, 2H).

Intermediate 14D. Methyl 1-(1-(benzylamino)-2,2,2-trifluoro-1-(4-(4,4,4-trifluorobutoxy)phenyl)ethyl)-cyclopropane carboxylate

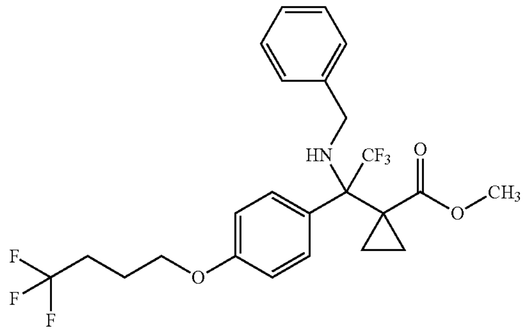 [SMILES: COC(=O)C1(C(NCc2ccccc2)(c2ccc(OCCCC(F)(F)F)cc2)C(F)(F)F)CC1]

To a solution of Intermediate 14C (4.6 g, 11 mmol) in acetonitrile (22 mL) and DMF (2.6 mL, 33 mmol) at 0° C. was added neat TFA (1.1 mL, 13.7 mmol) followed by potassium hydrogen fluoride (0.64 g, 8.2 mmol). The reaction was stirred for ca. 5 min, then trimethyl(trifluoromethyl)silane (2.4 mL, 16.4 mmol) was added and the reaction was warmed to rt and stirred for 16 h. Sat'd aqueous $NaHCO_3$ was added to the reaction and the mixture was extracted with EtOAc. The combined organic extracts were washed with sat'd aq NaCl, dried over $Na_2SO_4$, filtered and concentrated. The residue was purified by silica gel chromatography (220 g silica gel, eluted with EtOAc in hexanes) to provide Intermediate 14D (1.8 g, 31%) as an oil. LCMS Anal. Calc'd for $C_{24}H_{25}F_6NO_3$ 489.45, found [M+H] 490.1.

Intermediate 14E. 1-(1-(Benzylamino)-2,2,2-trifluoro-1-(4-(4,4,4-trifluorobutoxy)phenyl)ethyl)-cyclopropane carboxylic acid

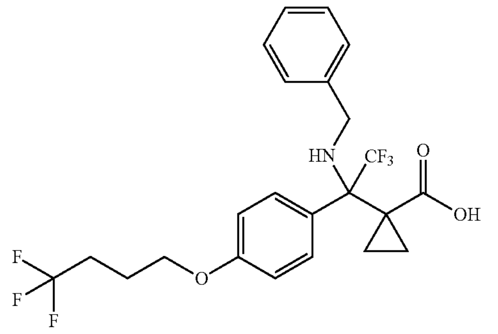 [SMILES: O=C(O)C1(C(NCc2ccccc2)(c2ccc(OCCCC(F)(F)F)cc2)C(F)(F)F)CC1]

To a solution Intermediate 14D (558 mg, 1.140 mmol) in pyridine (5.7 mL) was added lithium iodide (1.53 g, 11.4 mmol). The reaction was heated to reflux overnight. The reaction was cooled to rt and diluted with water and EtOAc. The aqueous layer was made acidic with 1 N HCl and the layers were separated. The organic layer was washed with sat'd aq NaCl, dried over $MgSO_4$, filtered and concentrated to provide Intermediate 14E (506 mg, 84%) which was used in the next step without further purification. LCMS Anal. Calc'd for $C_{23}H_{23}F_6NO_3$ 475.42, found [M+H] 476.2.

Intermediate 14F. 5-Benzyl-6-(4-(4,4,4-trifluorobutoxy)phenyl)-6-(trifluoromethyl)-5-azaspiro[2.3]-hexan-4-one

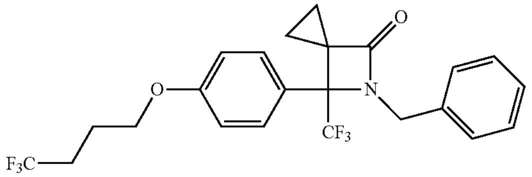 [SMILES: O=C1N(Cc2ccccc2)C(c2ccc(OCCCC(F)(F)F)cc2)(C(F)(F)F)C12CC2]

To a solution of Intermediate 14E (506 mg, 1.1 mmol) in $CH_2Cl_2$ (11 mL) was added oxalyl chloride (0.12 mL, 2.2 mmol) followed by several drops of DMF. The reaction was stirred at rt for 16 h. The solvent was removed in vacuo and the residue was purified by silica gel chromatography (24 g silica gel, eluted with EtOAc in hexanes) to provide Intermediate 14F (389 mg, 72%) as a yellow oil. LCMS Anal. Calc'd for $C_{23}H_{21}F_6NO_2$ 457.41, found [M+H] 458.2.

Intermediate 14G. (1-(1-(Benzylamino)-2,2,2-trifluoro-1-(4-(4,4,4-trifluorobutoxy)phenyl)ethyl)-cyclopropyl)-(4-methoxyphenyl)methanone

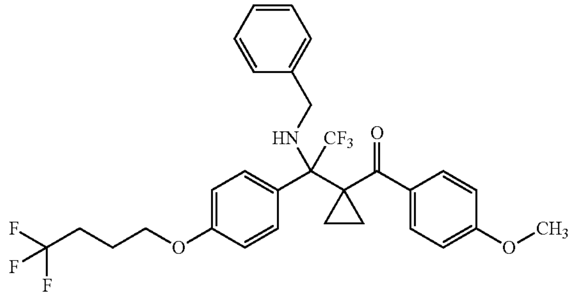 [SMILES: COc1ccc(C(=O)C2(C(NCc3ccccc3)(c3ccc(OCCCC(F)(F)F)cc3)C(F)(F)F)CC2)cc1]

Magnesium turnings (130 mg, 5.4 mmol) were suspended in anhydrous THF (13 mL). 4-Bromoanisole (1 g, 670 μL, 5.4 mmol) was added followed by a few drops of 1,2-dibromoethane. The reaction mixture was stirred at rt for 1.5 h after which most of the magnesium had dissolved. The reaction was warmed to 50° C. for 30 min, then cooled to rt. Final concentration of the Grignard reagent was 0.4 M assuming complete conversion. To a cold solution (−40° C.) of Intermediate 14F (200 mg, 0.44 mmol) in THF (4.4 mL) was added the freshly prepared Grignard reagent. The reaction was warmed from −40° C. to rt, then heated to reflux overnight. The reaction was cooled to room temperature and quenched with sat'd aq $NH_4Cl$. The layers were separated and the aqueous layer was extracted with EtOAc. The combined organic extracts were washed with sat'd aq NaCl, dried over $MgSO_4$, filtered and concentrated. The product was isolated using preparative HPLC ($MeOH/H_2O$/TFA). Fractions containing the product were combined and reduced in volume in vacuo. The resulting aqueous solution was made basic with sat'd aq $NaHCO_3$ and extracted with EtOAc. The combined organic extracts were washed with sat'd aq NaCl, dried over $Na_2SO_4$, filtered and concentrated to provide Intermediate 14G (6.1 mg, 2.5%). LCMS Anal. Calc'd for $C_{30}H_{29}F_6NO_3$ 565.55, found [M+H] 566.3.

Intermediate 14H. (1-(1-Amino-2,2,2-trifluoro-1-(4-(4,4,4-trifluorobutoxy)phenyl)ethyl)cyclopropyl)(4-methoxy-phenyl)methanone

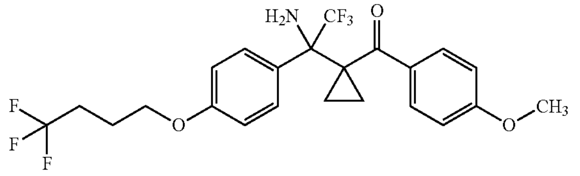 [SMILES: COc1ccc(C(=O)C2(C(N)(c3ccc(OCCCC(F)(F)F)cc3)C(F)(F)F)CC2)cc1]

To a solution of Intermediate 14G (6 mg, 10.6 μmol) in MeOH (1 mL) containing 4.4% formic acid was added 10% palladium on carbon (2 mg, 2 μmol). The reaction was stirred at rt overnight. The reaction was filtered through Celite®. The filtrate was made basic with sat'd aq $NaHCO_3$, and then evaporated to remove MeOH. The aqueous residue was diluted with sat'd aq NaCl and extracted with EtOAc. The combined organic extracts were washed with sat'd aq NaCl, dried over $Na_2SO_4$, filtered and concentrated to provide Intermediate 14H (4 mg, 71%) as a tan glass. LCMS Anal. Calc'd for $C_{23}H_{23}F_6NO_3$ 475.42, found [M+H] 476.2.

Intermediate 14I. 2-Cyano-N-(2,2,2-trifluoro-1-(1-(4-methoxybenzoyl)cyclopropyl)-1-(4-(4,4,4-trifluorobutoxy)-phenyl)ethyl)acetamide

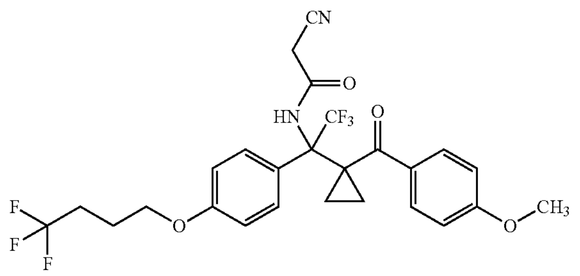 [SMILES: COc1ccc(C(=O)C2(C(NC(=O)CC#N)(c3ccc(OCCCC(F)(F)F)cc3)C(F)(F)F)CC2)cc1]

To a solution of 2-cyanoacetic acid (320 mg, 3.8 mmol) in $CH_2Cl_2$ (9.1 mL) was added oxalyl chloride (523 mg, 360 μL, 4.1 mmol) followed by a few drops of DMF. The reaction was stirred at rt for 1 h. Final concentration of 2-cyanoacetyl chloride was 0.4 M assuming complete conversion. To a solution of Intermediate 14H (4 mg, 8.4 μmol) and pyridine (2.0 μL, 0.025 mmol) in $CH_2Cl_2$ (100 μL) at 0° C. was added the freshly prepared 0.4 M 2-cyanoacetyl chloride in $CH_2Cl_2$ (0.032 mL, 0.013 mmol). The reaction was warmed to rt and stirred for 16 h. The reaction was quenched with one drop of MeOH, diluted with EtOAc and washed with 1:1 sat'd aq NaCl and water, dried over $MgSO_4$, filtered and concentrated to provide Intermediate 14I (7 mg, 153%), which was used in the next step without further purification. LCMS Anal. Calc'd for $C_{26}H_{24}F_6N_2O_4$ 542.47, found [M+H] 543.3.

Example 14

To a solution of Intermediate 14I (7 mg, 0.013 mmol) in EtOH (2 mL) was added 25% w/w sodium methoxide (0.015 mL, 0.065 mmol). The reaction was stirred at rt for 1.5 h. The reaction was made acidic with a few drops of 1 N aqueous HCl and then concentrated. The product was isolated by preparative HPLC (MeOH/$H_2$OTFA). The fraction containing the product was reduced in volume in vacuo, made basic with sat'd aq $NaHCO_3$ and extracted with EtOAc. The combined organic extracts were washed with sat'd aq NaCl, dried over $MgSO_4$, filtered and concentrated to provide Example 14 (2.9 mg, 42%). LCMS Anal. Calc'd for $C_{26}H_{22}F_6N_2O_3$ 524.46, found [M+H] 525.2. $^1$H NMR (500 MHz, $CD_3OD$) δ 0.65 (t, J=8.80 Hz, 2H), 1.18-1.25 (m, 2H), 1.99-2.08 (m, 2H), 2.31-2.43 (m, 2H), 3.85 (s, 3H), 4.09 (t, J=6.05 Hz, 2H), 7.03 (d, J=8.80 Hz, 2H), 7.06 (br. s., 2H), 7.23 (br. s., 2H), 7.58 (d, J=9.35 Hz, 2H).

Examples 15-1 and Example 15-2. 3-Fluoro-4-(4-methoxyphenyl)-2-oxo-6-(4-(4,4,4-trifluorobutoxy)phenyl)-6-(trifluoromethyl)-1,2,3,6-tetrahydropyridine-3-carbonitrile

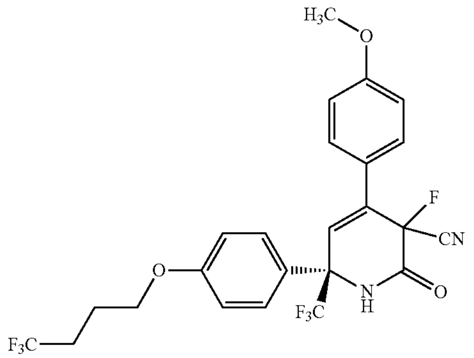 [SMILES: COc1ccc(C2=C[C@](c3ccc(OCCCC(F)(F)F)cc3)(C(F)(F)F)NC(=O)C2(F)C#N)cc1]

To a solution of the Example 77 (70 mg, 0.140 mmol) in DMF (1.4 mL) was added $Na_2CO_3$ (30 mg, 0.28 mmol) followed by 1-fluoro-4-hydroxy-1,4-diazoniabicyclo[2,2,2]octane-bis-(tetrafluoroborate) (196 mg, 0.28 mmol). The reaction was heated to 80° C. overnight. The reaction was cooled to rt and diluted with EtOAc and water. The layers were separated and the aqueous layer was extracted with EtOAc. The combined organic layers were washed with sat'd aq NaCl, dried over $MgSO_4$, filtered and concentrated in vacuo. The residue was purified by preparative HPLC (MeOH/$H_2$OTFA) to yield the product (44 mg, 61%) as a mixture of two diastereoisomers. The two diastereoisomers were separated by preparative chiral SFC method B to provide Example 15-1 (14.6 mg, 20%) and Example 15-2 (17.2 mg, 23%). Data for Example 15-1: LCMS Anal. Calc'd for $C_{24}H_{19}F_7N_2O_3$ 516.41, found [M+H] 517.2. $^1$H NMR (500 MHz, $CD_3OD$) δ 2.00-2.08 (m, 2H), 2.32-2.44 (m, 2H), 3.85 (s, 3H), 4.10 (t, J=6.05 Hz, 2H), 6.92 (d, J=1.10 Hz, 1H), 7.02 (d, J=8.80 Hz, 2H), 7.07 (d, J=9.35 Hz, 2H), 7.50 (d, J=8.25 Hz, 2H), 7.57 (d, J=8.80 Hz, 2H). Analytical chiral HPLC method B: RT=3.23 min, 99% ee. Data for Example 15-2: LCMS Anal. Calc'd for $C_{24}H_{19}F_7N_2O_3$ 516.41, found [M+H] 517.2. $^1$H NMR (500 MHz, $CD_3OD$) δ 2.00-2.08 (m, 2H), 2.32-2.44 (m, 2H), 3.85 (s, 3H), 4.10 (t, J=6.05 Hz, 2H), 6.92 (d, J=1.10 Hz, 1H), 7.02 (d, J=8.80 Hz, 2H), 7.07 (d, J=9.35 Hz, 2H), 7.50 (d, J=8.25 Hz, 2H), 7.57 (d, J=8.80 Hz, 2H). Analytical chiral HPLC method B: RT=4.84 min, 99% ee.

Examples 15-3 and Example 15-4. 3-Fluoro-4-(4-methoxyphenyl)-2-oxo-6-(4-(4,4,4-trifluorobutoxy)phenyl)-6-(trifluoromethyl)-1,2,3,6-tetrahydropyridine-3-carbonitrile

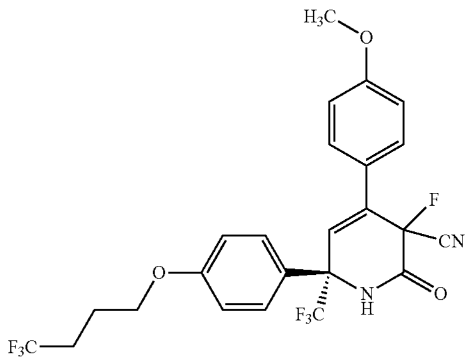 [SMILES: COc1ccc(C2=C[C@@](c3ccc(OCCCC(F)(F)F)cc3)(C(F)(F)F)NC(=O)C2(F)C#N)cc1]

Application of the method described for Example 15-1 and Example 15-2 provided Example 15-3 (4.6 mg, 43%) and Example 15-4 (4.6 mg, 43%) from the R-isomer of Example 65 (10 mg, 0.02 mmol). Data for Example 15-3: LCMS Anal. Calc'd for $C_{24}H_{19}F_7N_2O_3$ 516.41, found [M+H] 517.1. $^1$H NMR (500 MHz, $CD_3OD$) δ 2.00-2.08 (m, 2H) 2.31-2.44 (m, 2H) 3.85 (s, 3H) 4.10 (t, J=6.05 Hz, 2H) 6.92 (d, J=1.65 Hz, 1H) 7.02 (d, J=8.80 Hz, 2H) 7.07 (d, J=8.80 Hz, 2H) 7.50 (d, J=8.25 Hz, 2H) 7.57 (d, J=8.80 Hz, 2H). Analytical chiral HPLC method B: RT=5.13 min, 99% ee. Data for Example 15-4: LCMS Anal. Calc'd for $C_{24}H_{19}F_7N_2O_3$ 516.41, found [M+H] 517.1. $^1$H NMR (500 MHz, $CD_3OD$) δ 1.99-2.07 (m, 2H) 2.30-2.43 (m, 2H) 3.84 (s, 3H) 4.09 (t, J=6.05 Hz, 2H) 6.78 (s, 1H) 7.02 (d, J=8.80 Hz, 2H) 7.05 (d, J=9.35 Hz, 2H) 7.54 (dd, J=8.25, 4.95 Hz, 4H). Analytical chiral HPLC method B: RT=5.13 min, 99% ee.

Example 16-1 and Example 16-2. N-(4-Methoxy-phenyl)-2-oxo-4-p-tolyl-6-(4-(4,4,4-trifluorobutoxy)phenyl)-6-(trifluoromethyl)piperidine-3-carboxamide

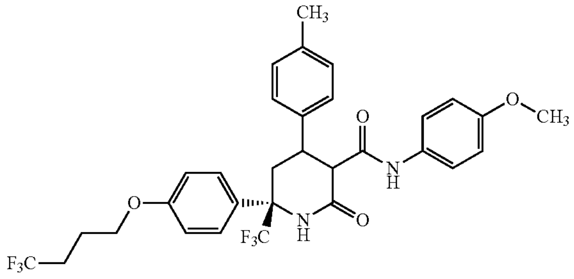 [SMILES: COc1ccc(NC(=O)C2C(=O)N[C@@](c3ccc(OCCCC(F)(F)F)cc3)(C(F)(F)F)CC2c2ccc(C)cc2)cc1]

To a solution of Example 6-2 (90 mg, 0.15 mol) in MeOH (2 mL) was added 10% palladium on carbon (5 mg). The mixture was stirred under hydrogen (50 psi) overnight. Additional palladium on carbon (5 mg) was added and the reaction was stirred under hydrogen (50 psi) for an additional 1 h. The catalyst was removed by filtration through a pad of Celite® and the solution was concentrated in vacuo. The products were partly separated by preparative HPLC ($CH_3CN/H_2O$/TFA). Fractions containing the two products were combined and separated by chiral HPLC method D to provide Example 16-1 and Example 16-2. Data for Example 16-1: LCMS Anal. Calc'd for $C_{31}H_{30}F_6N_2O_4$ 608.57, found [M+H] 609.2. $^1$H NMR (400 MHz, $CD_3OD$) δ 1.97-2.14 (m, 2H), 2.25 (s, 3H), 2.32-2.46 (m, 2H), 2.54-2.69 (m, 2H), 3.17 (td, J=11.82, 3.85 Hz, 1H), 3.60 (d, J=11.54 Hz, 1H), 3.71 (s, 3H), 4.10 (t, J=6.05 Hz, 2H), 6.76 (d, J=8.79 Hz, 2H), 6.99-7.12 (m, 6H), 7.13-7.23 (m, 2H), 7.55 (d, J=8.79 Hz, 2H). Analytical chiral HPLC method D RT=6.75 min, 99% ee. Data for Example 16-2: LCMS Anal. Calc'd for $C_{31}H_{30}F_6N_2O_4$ 608.57, found [M+H] 609.2. $^1$H NMR (400 MHz, $CD_3OD$) δ 7.52 (d, J=8.8 Hz, 2H), 7.25-7.20 (m, 2H), 7.19-7.15 (m, 2H), 7.14-7.10 (m, 2H), 7.02-6.97 (m, 2H), 6.81-6.75 (m, 2H), 4.07 (t, J=6.0 Hz, 2H), 3.94-3.84 (m, 1H), 3.73 (s, 3H), 3.60 (d, J=12.1 Hz, 1H), 2.90 (dd, J=14.8, 3.3 Hz, 1H), 2.45-2.32 (m, 2H), 2.31 (dd, 1H, overlaps with peak at δ□ 2.27), 2.27 (s, 3H), 2.08-1.98 (m, 2H). Preparative chiral HPLC method D: RT=10.9 min, 99% ee.

Examples 17-101 expressed by Formula (IIa), unless noted in the table, may be made by one skilled in the art by appropriate application of the procedures described for Examples 1-16. $R^{11}$ to $R^{15}$ are hydrogen, unless noted in the table.

TABLE 2
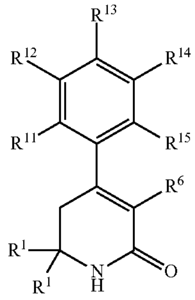
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 17 Rac | 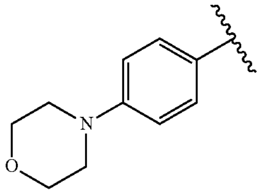 [SMILES: *c1ccc(N2CCOCC2)cc1] | $CH_3$ | CN | $R^{13}$ = morpholine | 459.2* | |
| 18 Rac | 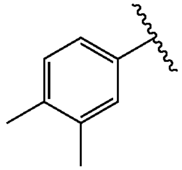 [SMILES: *c1ccc(C)c(C)c1] | $CH_3$ | CN | $R^{12} = CH_3$<br>$R^{13} = CH_3$ | 345.1* | |
| 19 Rac | 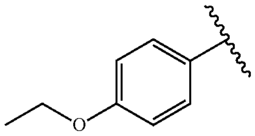 [SMILES: *c1ccc(OCC)cc1] | $CH_3$ | CN | $R^{13} = OCH_2CH_3$ | 377.2* | |

TABLE 2-continued
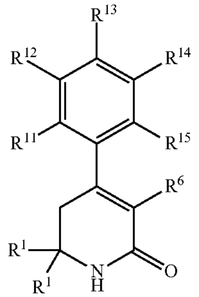
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 20 Rac | 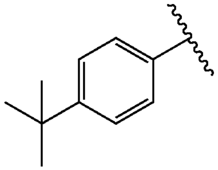 [SMILES: *c1ccc(C(C)(C)C)cc1] | $CH_3$ | CN | $R^{13}$ = t-Bu | 401.2* | |
| 21 Rac | 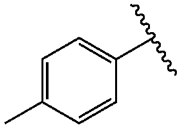 [SMILES: *c1ccc(C)cc1] | $CH_3$ | 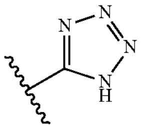 [SMILES: *c1nnn[nH]1] | $R^{13}$ = $CH_3$ | 360.2 | |
| 22 Rac | 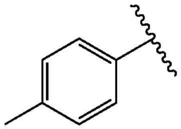 [SMILES: *c1ccc(C)cc1] | $CF_3$ | CN | $R^{13}$ = $CH_3$ | 371.2 | |
| 23 Rac | 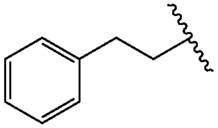 [SMILES: *CCc1ccccc1] | $CH_3$ | CN | $R^{13}$ = $CH_3$ | 331.3 | |

TABLE 2-continued
(IIa)
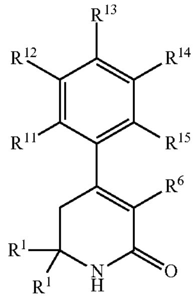
| Example | $R^1$ | $R^2$ | $R^6$ | $R^{11}$-$R^{15}$ | [M + H] | $^1$HNMR (400 MHz, MeOD) |
|---|---|---|---|---|---|---|
| 24 Rac | 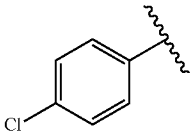 [SMILES: *c1ccc(Cl)cc1] | $CF_3$ | CN | $R^{13} = CH_3$ | 391.1 | |
| 25 Rac | 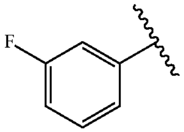 [SMILES: *c1cccc(F)c1] | $CF_3$ | CN | $R^{13} = CH_3$ | 375.2 | |
| 26 Rac | 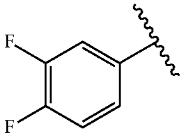 [SMILES: *c1ccc(F)c(F)c1] | $CF_3$ | CN | $R^{13} = CH_3$ | 393.2 | |
| 27 Rac | 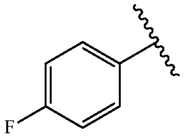 [SMILES: *c1ccc(F)cc1] | $CF_3$ | CN | $R^{13} = CH_3$ | 375.2 | |

TABLE 2-continued
(IIa)
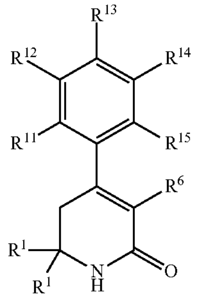
| Example | $R^1$ | $R^2$ | $R^6$ | $R^{11}$-$R^{15}$ | [M + H] | $^1$HNMR (400 MHz, MeOD) |
|---|---|---|---|---|---|---|
| 28<br>Rac | 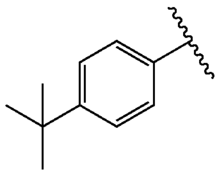 [SMILES: *c1ccc(C(C)(C)C)cc1] | $CF_3$ | CN | $R^{13} = CH_3$ | 413.3 | |
| 29<br>Rac | 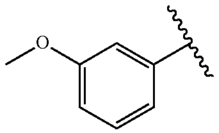 [SMILES: *c1cccc(OC)c1] | $CF_3$ | CN | $R^{12} = CH_3$ | 387.2 | |
| 30<br>Rac | 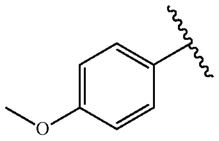 [SMILES: *c1ccc(OC)cc1] | $CF_3$ | CN | $R^{13} = CH_3$ | 387.2 | |
| 31<br>Rac | 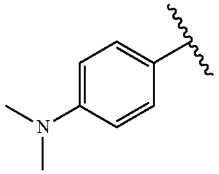 [SMILES: *c1ccc(N(C)C)cc1] | $CF_3$ | CN | $R^{13} = CH_3$ | 400.2 | |

TABLE 2-continued
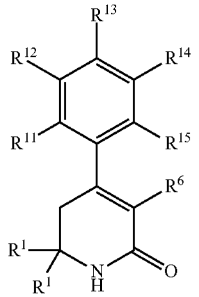
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 32 Rac | 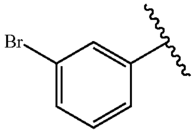 | $CF_3$ | CN | $R^{13} = CH_3$ | 435.2 | |
| 33 Rac | 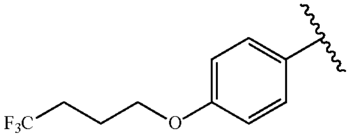 | $CF_3$ | CN | $R^{13} = CH_3$ | 483.3 | 2.03-2.12 (m, 2 H) 2.25-2.36 (m, 2 H) 2.42 (s, 3 H) 3.51-3.68 (m, 2 H) 4.04 (t, J = 5.50 Hz, 2 H) 6.94 (d, J = 8.80 Hz, 2 H) 7.31 (d, J = 7.70 Hz, 2 H) 7.40 (d, J = 8.80 Hz, 2 H) 7.47 (d, J = 7.70 Hz, 2 H) 7.64 (br. s., 1 H). |
| 34 Rac | 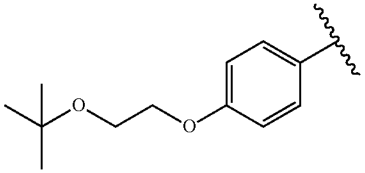 [SMILES: *c1ccc(OCCOC(C)(C)C)cc1] | $CF_3$ | CN | $R^{13} = CH_3$ | 471.4 [M − H]− | |

TABLE 2-continued
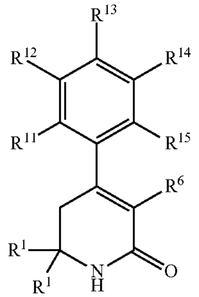
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 35 Rac | 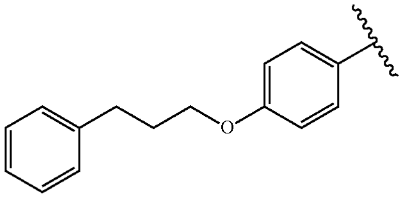 [SMILES: *c1ccc(OCCCc2ccccc2)cc1] | $CF_3$ | CN | $R^{13} = CH_3$ | 491.3 | 2.06-2.18 (m, 2 H) 2.41 (s, 3 H) 2.81 (t, J = 7.70 Hz, 2 H) 3.45-3.68 (m, 2 H) 3.97 (t, J = 6.32 Hz, 2 H) 6.55 (s, 1 H) 6.93 (d, J = 8.80 Hz, 2 H) 7.21 (d, J = 7.15 Hz, 3 H) 7.25-7.31 (m, 4 H) 7.37 (d, J = 8.25 Hz, 2 H) 7.45 (d, J = 8.25 Hz, 2 H). |
| 36 Rac | 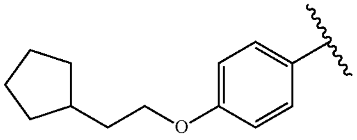 [SMILES: *c1ccc(OCCC2CCCC2)cc1] | $CF_3$ | CN | $R^{13} = CH_3$ | 469.3 | 1.16 (dd, J = 12.10, 8.25 Hz, 2 H) 1.54 (dd, J = 7.42, 4.67 Hz, 2 H) 1.60-1.70 (m, 2 H) 1.81 (q, J = 6.60 Hz, 4 H) 1.96 (m, J = 7.70 Hz, 1 H) 2.41 (s, 3 H) 3.45-3.64 (m, 2 H) 3.98 (t, J = 6.60 Hz, 2 H) 6.50 (s, 1 H) 6.94 (d, J = 9.35 Hz, 2 H) 7.23-7.32 (m, 2 H) 7.37 (d, J = 8.80 Hz, 2 H) 7.44 (d, J = 8.25 Hz, 2 H). |
| 37 Rac | 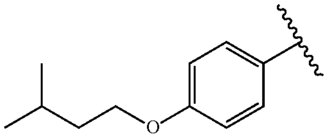 [SMILES: *c1ccc(OCCC(C)C)cc1] | $CF_3$ | CN | $R^{13} = CH_3$ | 443.3 | |

TABLE 2-continued
(IIa)
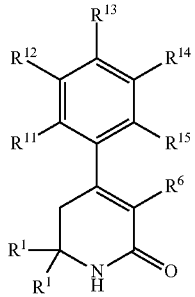
| Example | $R^1$ | $R^2$ | $R^6$ | $R^{11}$-$R^{15}$ | [M + H] | $^1$HNMR (400 MHz, MeOD) |
|---|---|---|---|---|---|---|
| 38 Rac | 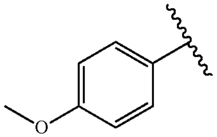 [SMILES: *c1ccc(OC)cc1] | $CF_3$ | 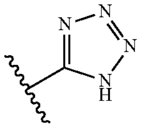 [SMILES: *c1nnn[nH]1] | $R^{13} = CH_3$ | 430.1 | |
| 39 S-isomer | 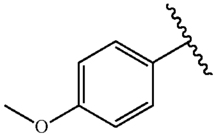 [SMILES: *c1ccc(OC)cc1] | $CF_3$ | CN | $R^{13} = CH_3$ | 387.2 | |
| 40 Rac | 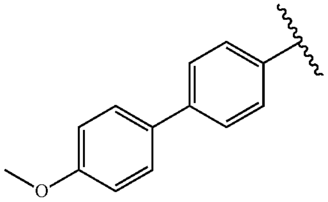 [SMILES: *c1ccc(-c2ccc(OC)cc2)cc1] | $CF_3$ | CN | $R^{13} = CH_3$ | 463.2 | |
| 41 Rac | 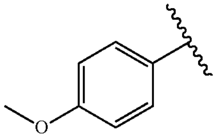 [SMILES: *c1ccc(OC)cc1] | $CF_3$ | 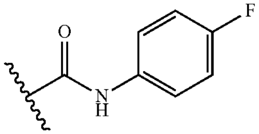 [SMILES: *C(=O)Nc1ccc(F)cc1] | $R^{13} = CH_3$ | 499.2 | |

TABLE 2-continued
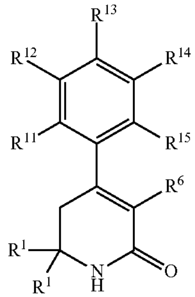
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 42 Rac | 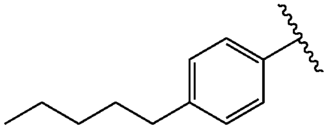 [SMILES: *c1ccc(CCCCC)cc1] | $CF_3$ | CN | $R^{13} = CH_3$ | 427.4 | 0.85-0.96 (m, 3 H) 1.33 (d, J = 2.75 Hz, 4 H) 1.47-1.69 (m, 4 H) 2.41 (s, 3 H) 2.56-2.67 (m, 2 H) 3.45-3.66 (m, 2 H) 6.46 (br. s., 1 H) 7.20-7.31 (m, 4 H) 7.37 (d, J = 7.15 Hz, 2 H) 7.45 (d, J = 6.60 Hz, 2 H). |
| 43 Rac | 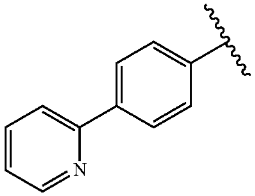 [SMILES: *c1ccc(-c2ccccn2)cc1] | $CF_3$ | CN | $R^{13} = CH_3$ | 434.3 | |
| 44 Rac | 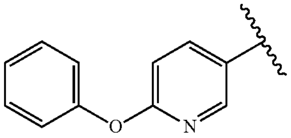 [SMILES: *c1ccc(Oc2ccccc2)nc1] | $CF_3$ | CN | $R^{13} = CH_3$ | 450.3 | |
| 45 Rac | 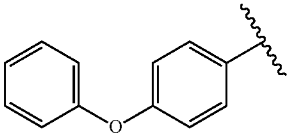 [SMILES: *c1ccc(Oc2ccccc2)cc1] | $CF_3$ | CN | $R^{13} = CH_3$ | 449.3 | |

TABLE 2-continued
(IIa)
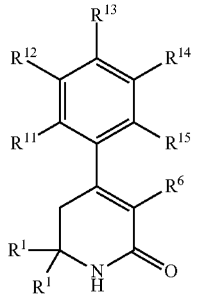
| Example | $R^1$ | $R^2$ | $R^6$ | $R^{11}$-$R^{15}$ | [M + H] | $^1$HNMR (400 MHz, MeOD) |
|---|---|---|---|---|---|---|
| 46 Rac | 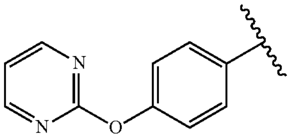 [SMILES: *c1ccc(Oc2ncccn2)cc1] | $CF_3$ | CN | $R^{13} = CH_3$ | 451.3 | |
| 47 Rac | 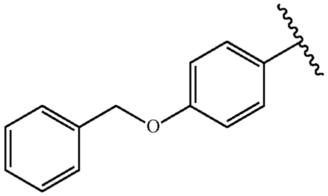 [SMILES: *c1ccc(OCc2ccccc2)cc1] | $CF_3$ | CN | $R^{13} = CH_3$ | 463.3 | |
| 48 Rac | 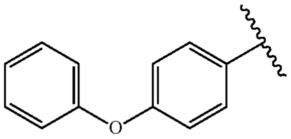 [SMILES: *c1ccc(Oc2ccccc2)cc1] | $CF_3$ | 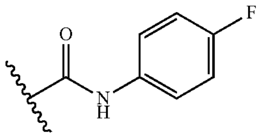 [SMILES: *C(=O)Nc1ccc(F)cc1] | $R^{13} = CH_3$ | 561.4 | 2.36 (s, 3 H) 3.40-3.59 (m, 2 H) 6.82 (s, 1 H) 6.93 (t, J = 8.79 Hz, 2 H) 7.01-7.13 (m, 5 H) 7.15-7.20 (m, 3 H) 7.34-7.45 (m, 4 H) 7.48 (d, J= 8.79 Hz, 2 H) 9.86 (s, 1 H). |

TABLE 2-continued
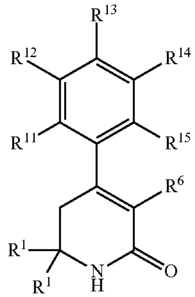
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 49 Rac | 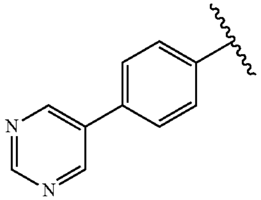 [SMILES: *c1ccc(-c2cncnc2)cc1] | $CF_3$ | 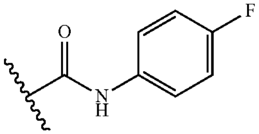 [SMILES: *C(=O)Nc1ccc(F)cc1] | $R^{13} = CH_3$ | 547.4 | 2.30 (s, 3 H) 3.57-3.81 (m, 2 H) 6.96 (t, J = 8.79 Hz, 2 H) 7.17 (d, J = 7.70 Hz, 2 H) 7.27-7.38 (m, 4 H) 7.83 (m, 4 H) 9.11 (s, 2 H) 9.16 (s, 1 H) |
| 50 Rac | 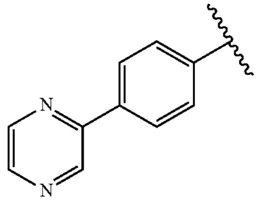 [SMILES: *c1ccc(-c2cnccn2)cc1] | $CF_3$ | 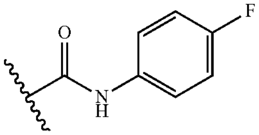 [SMILES: *C(=O)Nc1ccc(F)cc1] | $R^{13} = CH_3$ | 547.4 | |
| 51 Rac | 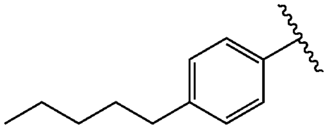 [SMILES: *c1ccc(CCCCC)cc1] | $CF_3$ | 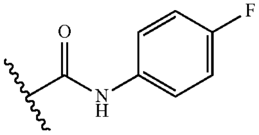 [SMILES: *C(=O)Nc1ccc(F)cc1] | $R^{13} = CH_3$ | 539.5 | 0.90 (t, J = 6.87 Hz, 3 H) 1.28-1.40 (m, 4 H) 1.58-1.71 (m, 2 H) 2.35 (s, 3 H) 2.55-2.71 (m, 2 H) 3.30-3.60 (m, 2 H) 6.63 (s, 1 H) 6.92 (t, J = 8.52 Hz, 2 H) 7.05-7.12 (m, 2 H) 7.14-7.20 (m, 2 H) 7.22-7.31 (m, 2 H) 7.37-7.49 (m, 4 H) 9.94 (s, 1 H). |

TABLE 2-continued
(IIa)
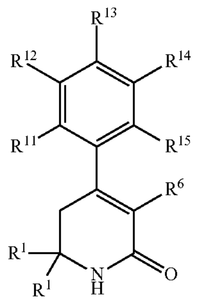
| Example | $R^1$ | $R^2$ | $R^6$ | $R^{11}$-$R^{15}$ | [M + H] | $^1$HNMR (400 MHz, MeOD) |
|---|---|---|---|---|---|---|
| 52 Rac | 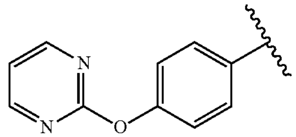 | $CF_3$ | 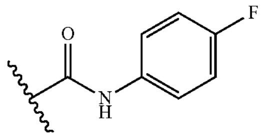 [SMILES: *C(=O)Nc1ccc(F)cc1] | $R^{13} = CH_3$ | 563.4 | |
| 53 S-isomer | 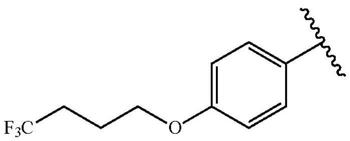 | $CF_3$ | CN | $R^{13} = CH_3$ | 483.2 | 1.93-2.09 (m, 2 H) 2.27-2.38 (m, 2 H) 2.40 (s, 3 H) 3.62-3.78 (m, 2 H) 4.06 (t, J = 6.05 Hz, 2 H) 7.00 (d, J = 8.80 Hz, 2 H) 7.33 (d, J = 7.70 Hz, 2 H) 7.44-7.58 (m, 4 H). |
| 54 Rac | 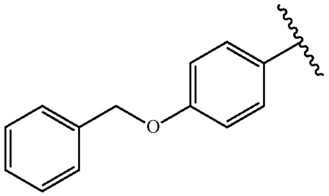 [SMILES: *c1ccc(OCc2ccccc2)cc1] | $CF_3$ | 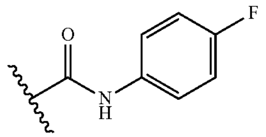 [SMILES: *C(=O)Nc1ccc(F)cc1] | $R^{13} = CH_3$ | 575.3 | |
| 55 Rac | 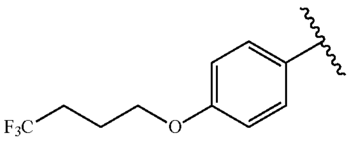 | $CF_3$ | 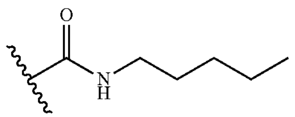 [SMILES: *C(=O)NCCCCC] | $R^{13} = CH_3$ | 571.4 | |

TABLE 2-continued
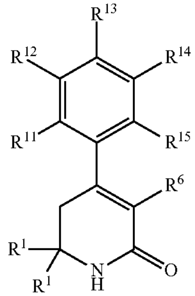
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 56 Rac | 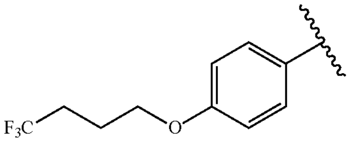 [SMILES: *c1ccc(OCCCC(F)(F)F)cc1] | $CF_3$ | 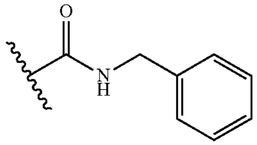 [SMILES: *C(=O)NCc1ccccc1] | $R^{13} = CH_3$ | 591.3 | |
| 57 Rac | 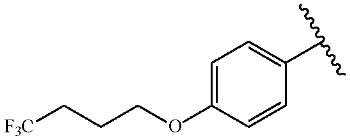 | $CF_3$ | 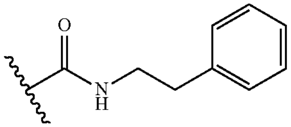 [SMILES: *C(=O)NCCc1ccccc1] | $R^{13} = CH_3$ | 605.4 | 2.02 (dd, J = 9.90, 6.05 Hz, 2 H) 2.28-2.40 (m, 5 H) 2.45-2.58 (m, 2 H) 3.12-3.35 (m, 2 H) 3.37-3.60 (m, 2 H) 4.05 (t, J = 6.05 Hz, 2 H) 6.91-7.01 (m, 4 H) 7.09-7.20 (m, 5 H) 7.21-7.26 (m, 2 H) 7.50 (d, J = 8.80 Hz, 2 H). |
| 58 Rac | 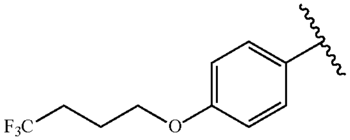 | $CF_3$ | 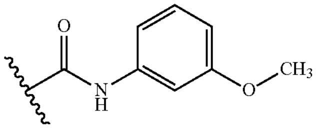 [SMILES: *C(=O)Nc1cccc(OC)c1] | $R^{13} = CH_3$ | 607.3 | 1.96-2.07 (m, 2 H) 2.26-2.32 (m, 3 H) 2.32-2.42 (m, 2H) 3.45-3.67 (m, 2 H) 4.06 (t, J = 6.05 Hz, 2 H) 6.61 (dd, J = 8.25, 2.20 Hz, 1 H) 6.83 (d, J = 8.25 Hz, 1 H) 6.98 (d, J = 8.80 Hz, 2 H) 7.03 (s, 1 H) 7.09 (t, J = 8.25 Hz, 1 H) 7.16 (d, J = 8.25 Hz, 2 H) 7.28 (d, J = 8.25 Hz, 2 H) 7.52 (d, J = 8.80 Hz, 2 H). |

TABLE 2-continued
(IIa)
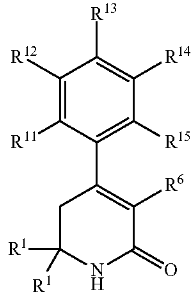
| Example | $R^1$ | $R^2$ | $R^6$ | $R^{11}$-$R^{15}$ | [M + H] | $^1$HNMR (400 MHz, MeOD) |
|---|---|---|---|---|---|---|
| 59<br>Rac | 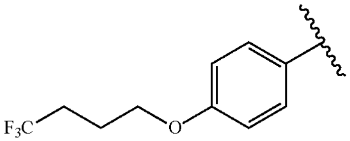 [SMILES: *c1ccc(OCCCC(F)(F)F)cc1] | $CF_3$ | 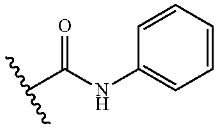 [SMILES: *C(=O)Nc1ccccc1] | $R^{13} = CH_3$ | 577.3 | 1.95-2.08 (m, 2 H) 2.28 (s, 3 H) 2.32-2.42 (m, 2 H) 3.42-3.70 (m, 2 H) 4.05 (t, J = 6.05 Hz, 2 H) 6.97 (d, J= 8.80 Hz, 2 H) 7.00-7.06 (m, 1 H) 7.15 (d, J= 8.25 Hz, 2 H) 7.20 (t, J = 7.97 Hz, 2H) 7.30 (dd, J = 16.77, 7.97 Hz, 4 H) 7.52 (d, J = 8.80 Hz, 2 H). |
| 60<br>Rac | 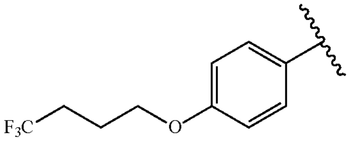 [SMILES: *c1ccc(OCCCC(F)(F)F)cc1] | $CF_3$ | 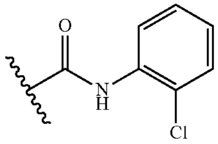 [SMILES: *C(=O)Nc1ccccc1Cl] | $R^{13} = CH_3$ | 611.3 | |
| 61<br>Rac | 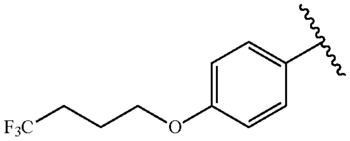 | $CF_3$ | 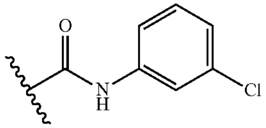 [SMILES: *C(=O)Nc1cccc(Cl)c1] | $R^{13} = CH_3$ | 611.3 | |
| 62<br>Rac | 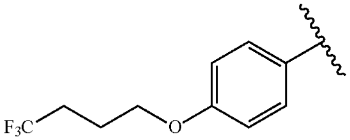 | $CF_3$ | 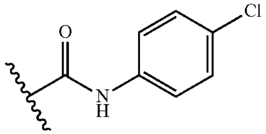 [SMILES: *C(=O)Nc1ccc(Cl)cc1] | $R^{13} = CH_3$ | 611.3 | |

TABLE 2-continued
(IIa)
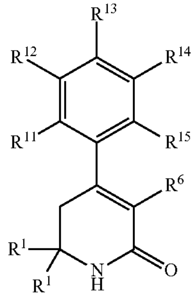
| Example | $R^1$ | $R^2$ | $R^6$ | $R^{11}$-$R^{15}$ | [M + H] | $^1$HNMR (400 MHz, MeOD) |
|---|---|---|---|---|---|---|
| 63 Rac | 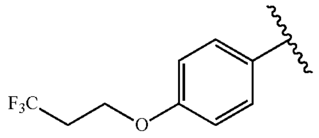 [SMILES: *c1ccc(OCCC(F)(F)F)cc1] | $CF_3$ | CN | $R^{13} = CH_3$ | 469.1 | 2.40 (s, 3 H) 2.63-2.75 (m, 2 H) 3.65-3.77 (m, 2 H) 4.24 (t, J = 6.05 Hz, 2 H) 7.01 (d, J = 9.35 Hz, 2H) 7.33 (d, J = 7.70 Hz, 2 H) 7.50 (d, J = 8.25 Hz, 2 H) 7.54 (d, J = 8.80 Hz, 2 H). |
| 64 Rac | 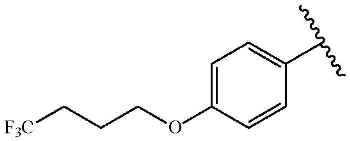 | $CF_3$ | CN | $R^{12} = OCH_3$ | 499.2 | |
| 65 Rac | 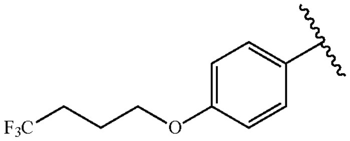 | $CF_3$ | CN | $R^{13} = OCH_3$ | 499.2 | 1.95-2.07 (m, 2 H) 2.29-2.43 (m, 2 H) 3.88 (s, 3 H) 3.92 (d, J = 16.51 Hz, 1 H) 4.06 (t, J = 6.05 Hz, 2 H) 4.55 (d, J = 16.23 Hz, 1 H) 6.96 (d, J = 9.08 Hz, 2 H) 7.01 (d, J = 8.80 Hz, 2 H) 7.52 (d, J = 9.08 Hz, 2 H) 7.97 (d, J = 9.08 Hz, 2 H) |
| 66 Rac | 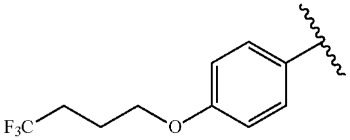 | $CF_3$ | CN | $R^{13} = CN$ | 494.2 | |

TABLE 2-continued
(IIa)
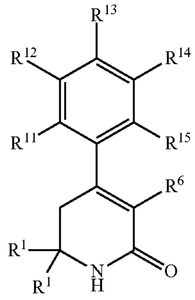
| Example | $R^1$ | $R^2$ | $R^6$ | $R^{11}$-$R^{15}$ | [M + H] | $^1$HNMR (400 MHz, MeOD) |
|---|---|---|---|---|---|---|
| 67<br>Rac | 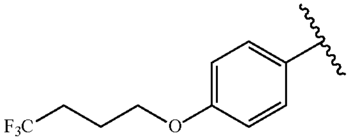 | $CF_3$ | CN | $R^{11}$ = F | 487.2 | |
| 68<br>Rac | 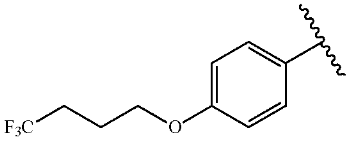 | $CF_3$ | CN | $R^{12}$ = Cl | 503.2 | |
| 69<br>Rac | 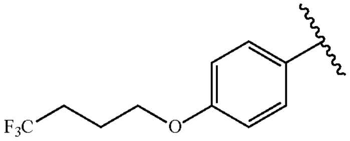 | $CF_3$ | CN | $R^{12}$ = CN | 494.2 | |
| 70<br>Rac | 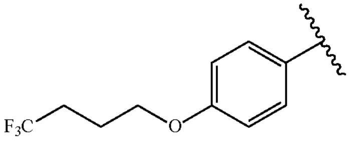 | $CF_3$ | H | $R^{13}$ = $CH_3$ | 458.2 | |

TABLE 2-continued
(IIa)
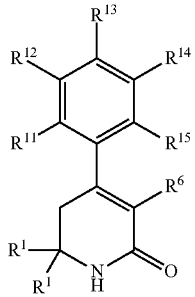
| Example | $R^1$ | $R^2$ | $R^6$ | $R^{11}$-$R^{15}$ | [M + H] | $^1$HNMR (400 MHz, MeOD) |
|---|---|---|---|---|---|---|
| 71 Rac | 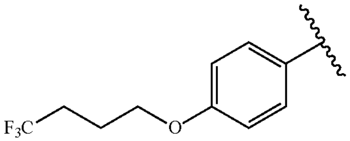 [SMILES: *c1ccc(OCCCC(F)(F)F)cc1] | $CF_3$ | CN | all H | 469.2 | |
| 72 Rac | 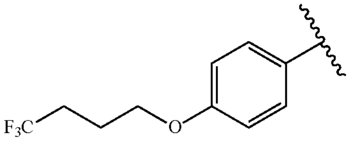 | $CF_3$ | CN | $R^{13}$ = Cl | 503.1 | |
| 73 Rac | 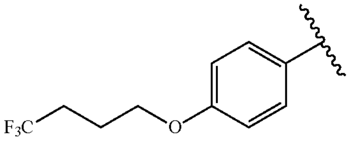 | $CF_3$ | CN | $R^{12}$ and $R^{13}$ 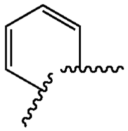 | 519.2 | 8.15 (d, J = 1.7 Hz, 1 H), 8.01-7.95 (m, 2 H), 7.92 (d, J= 8.0 Hz, 1H), 7.65-7.55 (m, 5H), 7.05-7.00 (m, 2H), 4.07 (t, J= 6.1 Hz, 2H), 3.85 (ABq, J = 18.1 Hz, 2H), 2.42-2.29 (m, 2H), 2.06-1.98 (m, 2H) |
| 74 Rac | 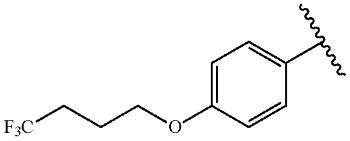 | $CF_3$ | CN | $R^{13}$ = F | 487.2 | |

TABLE 2-continued
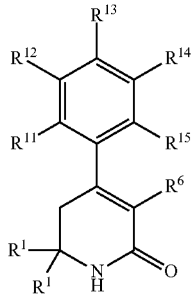
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 75 Rac | 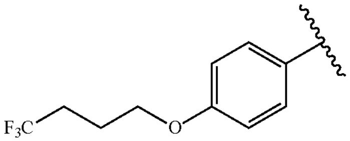 [SMILES: *c1ccc(OCCCC(F)(F)F)cc1] | $CF_3$ | CN | $R^{13} = CF_3$ | 537.2 | |
| 76 Rac | 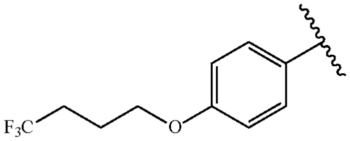 | $CF_3$ | CN | $R^{12} = CH_3$ | 483.2 | |
| 77 S-isomer | 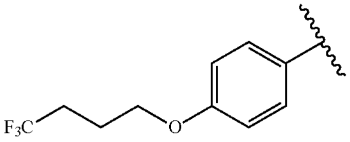 | $CF_3$ | CN | $R^{13} = OCH_3$ | 499.2 | 1.97-2.06 (m, 2 H) 2.27-2.42 (m, 2 H) 3.66 (d, J = 17.90 Hz, 1 H) 3.75 (d, J = 17.90 Hz, 1 H) 3.87 (s, 3 H) 4.06 (t, J = 6.05 Hz, 2 H) 6.96-7.02 (m, 1 H) 7.03-7.08 (m, 2 H) 7.52 (d, J = 8.80 Hz, 2 H) 7.61-7.68 (m, 2 H) |
| 78 Rac | 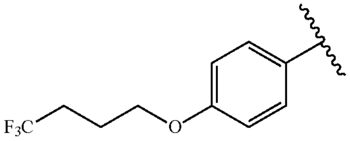 | $CF_3$ | CN | $R^{13} = OCHF_2$ | 535.1 | 7.69-7.63 (m, 2H), 7.54 (d, J = 9.1 Hz, 2H), 7.31-7.25 (m, 2H), 7.01 (m, 2H), 6.96 (t, J = 73.5 Hz, 1 H), 4.07 (t, J = 6.1 Hz, 2H), 3.78-3.67 (m, 2H), 2.44-2.30 (m, 2H), 2.07-1.97 (m, 2H) |

TABLE 2-continued
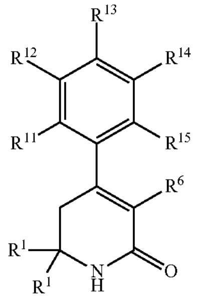
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 79 Rac | 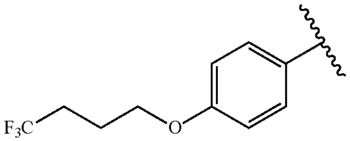 [SMILES: *c1ccc(OCCCC(F)(F)F)cc1] | $CF_3$ | CN | $R^{13}$ = $OCF_3$ | 553.1 | |
| 80 Rac | 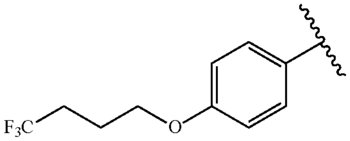 | $CF_3$ | CN | $R^{13}$ = $OCH_2CH_3$ | 513.2 | |
| 81 Rac | 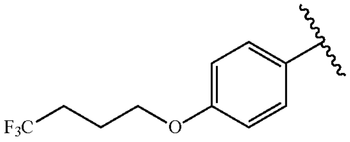 | $CF_3$ | CN | $R_{11}$ = F<br>$R^{13}$= $OCH_3$ | 517.2 | 7.51 (d, J= 9.1 Hz, 2H), 7.36-(t, J = 8.8 Hz, 1H), 7.04-6.97 (m, 2H), 6.91-6.83 (m, 2H), 4.08 (t, J = 6.1 Hz, 2H), 3.87 (s, 3H), 3.65 (s, 2 H), 2.46-2.29 (m, 2H), 2.08-1.98 (m, 2H) |
| 82 Rac | 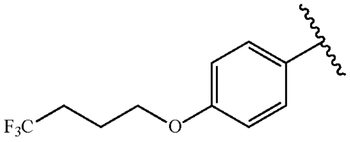 [SMILES: *c1ccc(OCCCC(F)(F)F)cc1] | $CF_3$ | 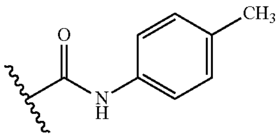 [SMILES: *C(=O)Nc1ccc(C)cc1] | $R^{13}$ = $CH_3$ | 591.2 | 7.52 (d, J= 8.8 Hz, 2H), 7.28 (d, J = 8.2 Hz, 2H), 7.15 (d, J= 7.7 Hz, 2H), 7.19 (d, J= 8.8 Hz, 2H), 7.02 (d, J = 8.2 Hz, 2H), 6.98 (d, J= 7.7 Hz, 2H), 4.06 (t, J = 6.0 Hz, 2H), 3.64 (d, J = 17.0 Hz, 1H), 3.48 (d, J= 17.0 Hz, 1H), 2.39-2.32 (m, 2H), 2.29 (s, 3H), 2.24 (s, 3H), 2.06-1.98 |

TABLE 2-continued
(IIa)
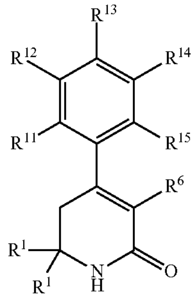
| Example | $R^1$ | $R^2$ | $R^6$ | $R^{11}$-$R^{15}$ | [M + H] | $^1$HNMR (400 MHz, MeOD) |
|---|---|---|---|---|---|---|
| | | | | | | (m, 2H). |
| 83 Rac | 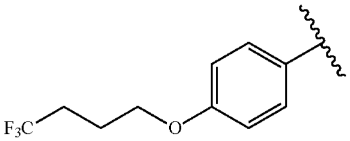 | $CF_3$ | 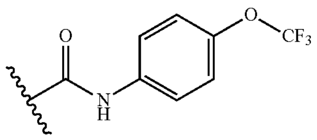 [SMILES: *C(=O)Nc1ccc(OC(F)(F)F)cc1] | $R^{13} = CH_3$ | 661.2 | 7.53 (d, J = 8.8 Hz, 2H), 7.46-7.41 (m, 2H), 7.31-7.24 (m, J = 8.2 Hz, 2H), 7.13 (d, J = 8.8 Hz, 2H), 7.17 (d, J = 7.7 Hz, 2H), 7.01-6.96 (m, 2H), 4.07 (t, J = 6.0 Hz, 2H), 3.65 (d, J = 17.0 Hz, 1H), 3.50 (d, J = 17.0 Hz, 1H), 2.43-2.33 (m, 2H), 2.30 (s, 3H), 2.07-1.99 (m, 2H). |
| 84 Rac | 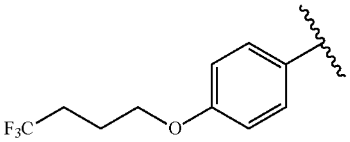 | $CF_3$ | 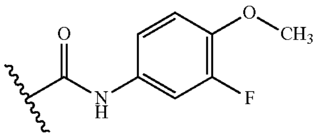 [SMILES: *C(=O)Nc1ccc(OC)c(F)c1] | $R^{13} = CH_3$ | 625.2 | 7.52 (d, J= 8.8 Hz, 2H), 7.30-7.24 (m, 3H), 7.17 (d, J = 7.7 Hz, 2H), 7.01-6.90 (m, 4H), 4.06 (t, J = 6.0 Hz, 2H), 3.82-3.77 (s, 3H), 3.64 (d, J = 17.0 Hz, 1H), 3.49 (d, J = 17.0 Hz, 1H), 2.42-2.33 (m, 2H), 2.30 (s, 3H), 2.08-1.96 (m, 2H). |
| 85 Rac | 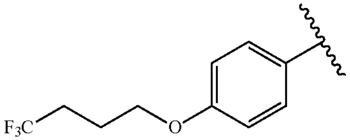 | $CF_3$ | 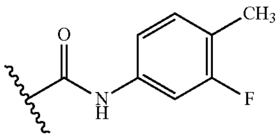 [SMILES: *C(=O)Nc1ccc(C)c(F)c1] | $R^{13} = CH_3$ | 609.2 | 7.56-7.50 (ab quartet, J = 9.3 Hz, 2H), 7.30-7.20 (m, 3H), 7.16 (d, J = 8.2 Hz, 2H), 7.05 (t, J = 8.2 Hz, 1H), 7.01-6.95 (m, J = 8.8 Hz, 2H), 6.91 (dd, J = 8.2, 1.6 Hz, 1H), 4.07 (t, J = 6.0 Hz, 2H), 3.64 (d, J= 17.6 Hz, 1H), 3.49 (d, J = 17.0 Hz, 1H), 2.43-2.32 (m, 2H), 2.30 (s, 3H), 2.16 (s, 3H), 2.08-1.97 |

TABLE 2-continued
(IIa)
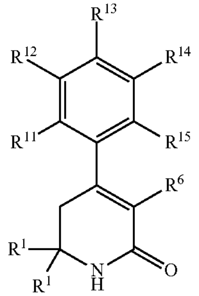
| Example | $R^1$ | $R^2$ | $R^6$ | $R^{11}$-$R^{15}$ | [M + H] | $^1$HNMR (400 MHz, MeOD) |
|---|---|---|---|---|---|---|
| | | | | | | (m, 2H). |
| 86<br>Rac | 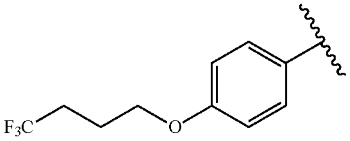 | $CF_3$ | 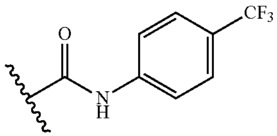 [SMILES: *C(=O)Nc1ccc(C(F)(F)F)cc1] | $R^{13} = CH_3$ | 645.2 | 7.58-7.48 (m, 6H), 7.27 (d, J = 8.2 Hz, 2H), 7.15 (d, J = 8.2 Hz, 2H), 7.00-6.95 (m, 2H), 4.06 (t, J = 6.0 Hz, 2H), 3.65 (d, J = 17.6 Hz, 1H), 3.50 (d, J = 17.0 Hz, 1H), 2.43-2.31 (m, 2H), 2.28 (s, 3H), 2.09-1.95 (m, 2H). |
| 87<br>Rac<br>S-isomer | 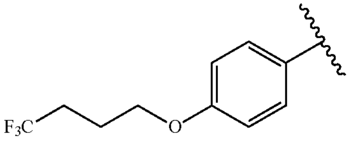 | $CF_3$ | 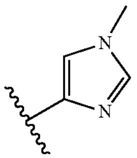 [SMILES: *c1cn(C)cn1] | $R^{13} = CH_3$ | 538.2 | |
| 88<br>Rac | 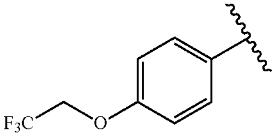 | $CF_3$ | 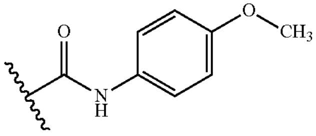 [SMILES: *C(=O)Nc1ccc(OC)cc1] | $R^{13} = CH_3$ | 579.2 | 2.31 (s, 3 H) 3.45-3.69 (m, 2 H) 3.70-3.76 (s, 3 H) 4.56 (q, J = 8.25 Hz, 2 H) 6.78 (d, J = 9.35 Hz, 2 H) 7.07 (d, J = 9.35 Hz, 2 H) 7.13-7.22 (m, 4 H) 7.29 (d, J = 8.25 Hz, 2 H) 7.59 (d, J = 8.80 Hz, 2 H). |
| 89<br>Rac | 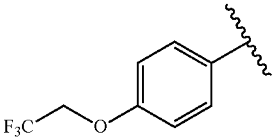 | $CF_3$ | CN | $R^{13} = CH_3$ | 455.1 | |

TABLE 2-continued
(IIa)
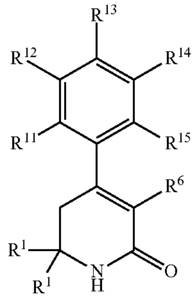
| Example | $R^1$ | $R^2$ | $R^6$ | $R^{11}$-$R^{15}$ | [M + H] | $^1$HNMR (400 MHz, MeOD) |
|---|---|---|---|---|---|---|
| 90 Rac | 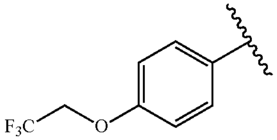 | $CF_3$ | 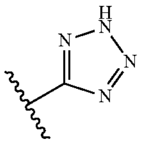 [SMILES: *c1nn[nH]n1] | $R^{13} = CH_3$ | 498.1 | 2.28 (s, 3 H) 3.63-3.82 (m, 2 H) 4.58 (q, J = 8.61 Hz, 2 H) 6.88 (d, J= 8.25 Hz, 2 H) 7.10 (dd, J = 12.65, 8.80 Hz, 4 H) 7.65 (d, J = 8.80 Hz, 2 H). |
| 91 S-isomer | 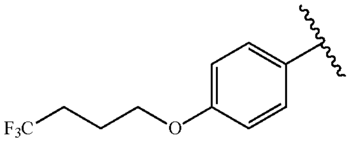 | $CF_3$ | CN | $R_{11} = F$<br>$R^{13} = OCH_3$ | 517.2 | 7.51 (d, J = 9.1 Hz, 2H), 7.36 (t, J = 8.8 Hz, 1H), 7.03-6.99 (m, 2H), 6.90-6.84 (m, 2H), 5.49 (s, 1H), 4.08 (t, J = 6.1 Hz, 2H), 3.87 (s, 3H), 3.65 (s, 2H), 2.46-2.28 (m, 2H), 2.10-1.97 (m, 2H) |
| 92 Rac | 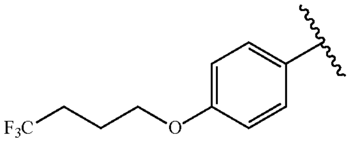 | $CF_3$ | 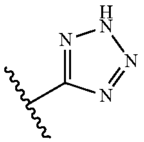 [SMILES: *c1nn[nH]n1] | $R^{13} = OCH_2CH_3$ | 556.3 | 1.34 (t, J = 6.87 Hz, 3 H) 1.96-2.09 (m, 2 H) 2.26-2.43 (m, 2 H) 3.70 (s, 2 H) 3.98 (q, J = 6.78 Hz, 2 H) 4.06 (t, J = 6.05 Hz, 2 H) 6.78 (d, J = 8.80 Hz, 2 H) 6.92 (d, J = 8.80 Hz, 2 H) 7.01 (d, J = 8.80 Hz, 2 H) 7.58 (d, J = 8.80 Hz, 2 H). |
| 93 Rac | 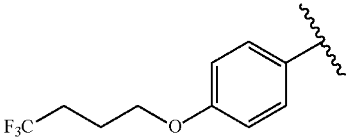 | $CF_3$ | 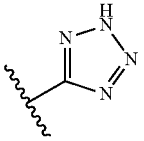 [SMILES: *c1nn[nH]n1] | $R^{13} = OCHF_2$ | 578.3 | 1.96-2.12 (m, 2 H) 2.28-2.45 (m, 2 H) 3.63-3.85 (m, 2 H) 4.07 (t, J = 6.05 Hz, 2 H) 6.95-7.08 (m, 7 H) 7.59 (d, J = 8.80 Hz, 2 H). |

TABLE 2-continued
(IIa)
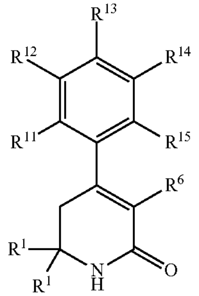
| Example | $R^1$ | $R^2$ | $R^6$ | $R^{11}$-$R^{15}$ | [M + H] | $^1$HNMR (400 MHz, MeOD) |
|---|---|---|---|---|---|---|
| 94 S-isomer | 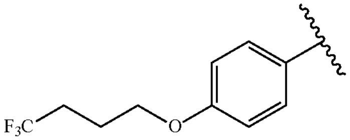 | $CF_3$ | 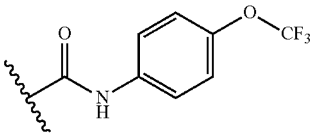 [SMILES: *C(=O)Nc1ccc(OC(F)(F)F)cc1] | $R^{13} = CH_3$ | 661.3 | 1.97-2.08 (m, 2 H) 2.29 (s, 3 H) 2.32-2.40 (m, 2 H) 3.50 (d, J = 17.05 Hz, 1 H) 3.65 (d, J = 17.60 Hz, 1 H) 4.06 (t, J = 6.05 Hz, 2 H) 6.98 (d, J = 8.80 Hz, 2 H) 7.14 (dd, J = 16.77, 8.52 Hz, 4 H) 7.28 (d, J = 8.25 Hz, 2 H) 7.43 (d, J = 9.35 Hz, 2 H) 7.52 (d, J = 8.80 Hz, 2 H). |
| 95 S-isomer | 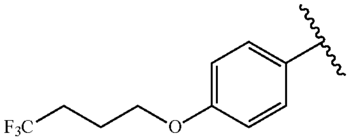 | $CF_3$ | 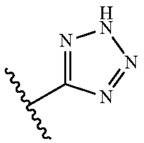 [SMILES: *c1nn[nH]n1] | $R^{11} = F$ $R^{13} = OCH_3$ | 560.3 | 1.95-2.08 (m, 2 H) 2.28-2.42 (m, 2 H) 3.58-3.71 (m, 2 H) 3.76 (s, 3 H) 4.06 (t, J = 6.05 Hz, 2 H) 6.59 (dd, J = 12.92, 2.47 Hz, 1 H) 6.69 (dd, J = 8.80, 2.75 Hz, 1 H) 6.91-6.96 (m, 1 H) 7.00 (d, J = 8.80 Hz, 2 H) 7.57 (d, J = 8.80 Hz, 2 H). |
| 96 Rac | 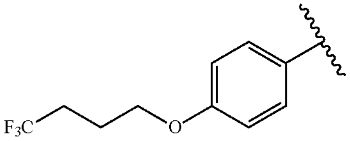 | $CF_3$ | 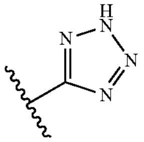 [SMILES: *c1nn[nH]n1] | $R^{12} = CH_3$ | 526.3 | |

TABLE 2-continued
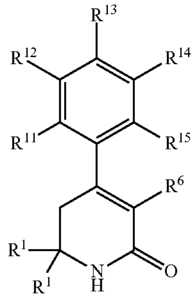
(IIa)
| Example | $R^1$ | $R^2$ | $R^6$ | $R^{11}$-$R^{15}$ | [M + H] | $^1$HNMR (400 MHz, MeOD) |
|---|---|---|---|---|---|---|
| 97 Rac | 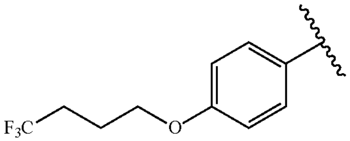 [SMILES: *c1ccc(OCCCC(F)(F)F)cc1] | $CF_3$ | 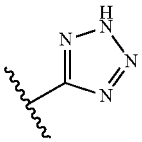 [SMILES: *c1nn[nH]n1] | All H | 512.2 | |
| 98 Rac | 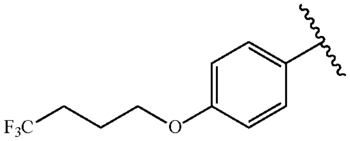 | $CF_3$ | 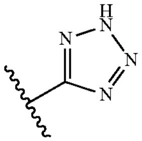 [SMILES: *c1nn[nH]n1] | $R^{13} = CF_3$ | 580.3 | 7.60 (t, J = 8.2 Hz, 4H), 7.18 (d, J = 8.2 Hz, 2H), 7.03 (d, J = 8.8 Hz, 2H), 4.08 (t, J = 6.0 Hz, 2H), 3.80 (d, J = 18.1 Hz, 1H), 3.69 (d, J = 18.1 Hz, 1H), 2.45-2.31 (m, 2H), 2.11-1.93 (m, 2H). |
| 99 Rac | 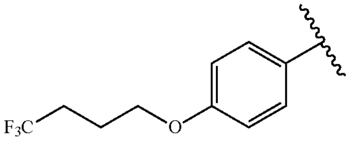 | $CF_3$ | 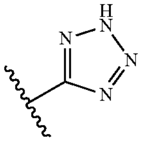 [SMILES: *c1nn[nH]n1] | $R^{12} = Cl$ | 546.2 | |
| 100 Rac | 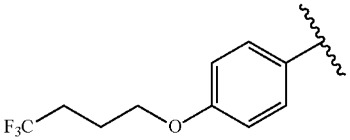 [SMILES: *c1ccc(OCCCC(F)(F)F)cc1] | $CF_3$ | 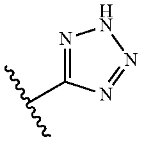 [SMILES: *c1nn[nH]n1] | $R^{12} = OCH_3$ | 542.3 | |

TABLE 2-continued
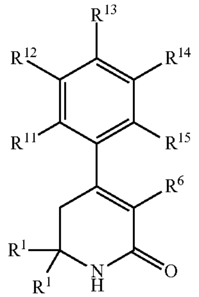
(IIa)
| Example | $R^1$ | $R^2$ | $R^6$ | $R^{11}$-$R^{15}$ | [M + H] | $^1$HNMR (400 MHz, MeOD) |
| --- | --- | --- | --- | --- | --- | --- |
| 101 Rac | 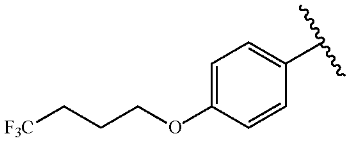 [SMILES: *c1ccc(OCCCC(F)(F)F)cc1] | $CF_3$ | 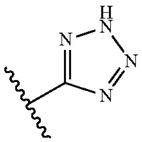 [SMILES: *c1nn[nH]n1] | $R^{13}$ = Cl | 546.2 | |
*Data reported as molecular weight of compound based on electrospray mass spec results Example 102. $N^5$-(4-Methoxyphenyl)-2-methyl-6-oxo-4-p-tolyl-$N^2$-(4,4,4-trifluorobutyl)-1,2,3,6-tetrahydropyridine-2,5-dicarboxamide

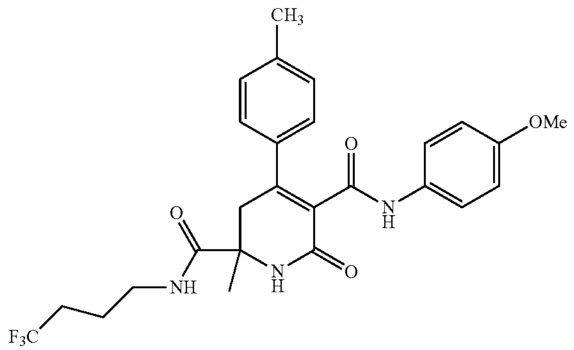 [SMILES: COc1ccc(NC(=O)C2=C(c3ccc(C)cc3)CC(C)(C(=O)NCCCC(F)(F)F)NC2=O)cc1]

Intermediate 102A. (E)-Ethyl 2-methyl-4-oxo-4-p-tolylbut-2-enoate

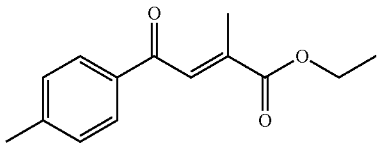 [SMILES: CCOC(=O)/C(C)=C/C(=O)c1ccc(C)cc1]

A solution of Intermediate 2D (3.02 g, 7.65 mmol) and ethyl 2-oxopropanoate (0.74 g, 6.37 mmol) in THF (12 mL) in a 5 mL microwave vial equipped with a magnetic stirrer was heated at 150° C. under microwave conditions for 20 min. The solvent was removed under vacuum and the residue was purified by silica gel chromatography (80 g silica gel, eluted with EtOAc in hexanes) to provide the desired product (1.067 g, 72%) as a yellow oil. LCMS Anal. Calc'd for $C_{14}H_{16}O_3$ 232.11, found [M+H] 233.1. $^1H$ NMR (500 MHz, $CDCl_3$) δ ppm 7.87 (d, J=8.25 Hz, 2H), 7.69 (q, J=1.56 Hz, 1H), 7.28 (d, J=7.98 Hz, 2H), 4.30 (q, J=7.15 Hz, 2H), 2.42 (s, 3H), 2.16 (d, J=1.38 Hz, 3H), 1.36 (t, J=7.02 Hz, 3H).

Intermediate 102B. Ethyl 2-amino-2-methyl-4-oxo-4-p-tolylbutanoate

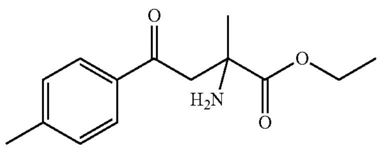 [SMILES: CCOC(=O)C(C)(N)CC(=O)c1ccc(C)cc1]

To a solution of Intermediate 102A (1.067 g, 4.59 mmol) in DMSO (20 mL) under argon was added $NH_4OH$ (18.04 mL, 271 mmol) and the reaction mixture was stirred at rt overnight. The reaction mixture was diluted with EtOAc (75 mL) and washed sequentially with water (40 mL) and brine (20 mL). The organic phase was dried over $MgSO_4$ and concentrated in vacuo to give a yellow oil. The oil was purified by silica gel chromatography (120 g silica gel) to provide the desired product (0.632 g, 55%) as a clear oil. LCMS Anal. Calc'd for $C_{14}H_{19}NO_3$ 249.14, found [M+H] 250.1. $^1H$ NMR (500 MHz, $CDCl_3$) δ 7.83 (d, J=8.25 Hz, 2H), 7.24 (d, J=7.98 Hz, 2H), 4.14 (dd, J=7.15, 2.75 Hz, 2H), 3.65 (d, J=17.61 Hz, 1H), 3.20 (d, J=17.61 Hz, 1H), 2.40 (s, 3H), 2.18-2.27 (m, 2H), 1.39 (s, 3H), 1.19 (t, J=7.01 Hz, 3H).

Intermediate 102C. Ethyl 2-(3-(4-methoxyphenylamino)-3-oxopropanamido)-2-methyl-4-oxo-4-p-tolylbutanoate

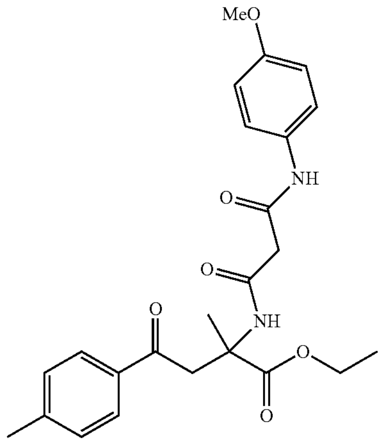 [SMILES: CCOC(=O)C(C)(CC(=O)c1ccc(C)cc1)NC(=O)CC(=O)Nc1ccc(OC)cc1]

To a solution of Intermediate 6B (0.388 g, 1.855 mmol) in DCM (10 mL) under argon was added 1-chloro-N,N,2-trimethylprop-1-en-1-amine (0.293 g, 2.192 mmol) and the reaction mixtrue was stirred at rt for 20 min A solution of Intermediate 102B (0.4204 g, 1.686 mmol) in DCM (1.000 mL) followed by pyridine (0.409 mL, 5.06 mmol) were added and the reaction mixture was stirred at rt for 2.5 h. The reaction mixture was concentrated to give a dark oil which was dissolved in EtOAc (15 mL) and washed with water (5 mL). The organic phase was dried over $MgSO_4$, filtered, and concentrated. The residue was purified by silica gel chromatography (80 g silica gel) to provide the desired product (0.650 g, 88%) as an orange oil. LCMS Anal. Calc'd for $C_{24}H_{28}N_2O_6$ 440.19, found [M+H] 441.2. $^1H$ NMR (500 MHz, $CDCl_3$) δ 7.83 (d, J=8.25 Hz, 2H), 7.24 (d, J=7.98 Hz, 2H), 4.14 (dd, J=7.15, 2.75 Hz, 2H), 3.65 (d, J=17.61 Hz, 1H), 3.20 (d, J=17.61 Hz, 1H), 2.40 (s, 3H), 2.18-2.27 (m, 2H), 1.39 (s, 3H), 1.19 (t, J=7.01 Hz, 3H).

Intermediate 102D, 5-(4-Methoxyphenylcarbamoyl)-2-methyl-6-oxo-4-p-tolyl-1,2,3,6-tetrahydropyridine-2-carboxylic acid

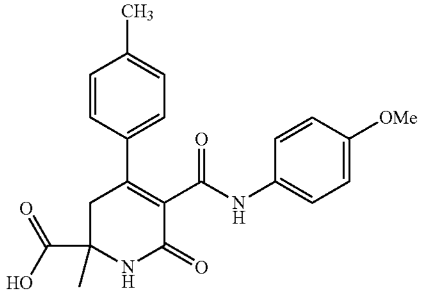 [SMILES: COc1ccc(NC(=O)C2=C(c3ccc(C)cc3)CC(C)(C(=O)O)NC2=O)cc1]

To a solution of Intermediate 102C (0.033 g, 0.075 mmol) in THF (8 mL) and water (1.600 mL) was added lithium hydroxide monohydrate (3.77 mg, 0.090 mmol) and the reaction mixture was stirred at rt for 1 h. The reaction mixture was acidified with AcOH (5 drops) and diluted with EtOAc (10 mL) and water (3 mL). The phases were separated and the aqueous phase was extracted with EtOAc (10 mL). The organic phases were combined and dried over $MgSO_4$, filtered, and concentrated in vacuo to give the desired product (0.0213 g, 72%) as a white solid. LCMS Anal. Calc'd for $C_{22}H_{22}N_2O_5$ 394.15, found [M+H] 395.0.

Example 102

To a solution of Intermediate 102D (0.0213 g, 0.054 mmol) in DCM (2 mL) under argon was added EDC (0.014 g, 0.076 mmol), HOBT (9.92 mg, 0.065 mmol), 4,4,4-trifluorobutan-1-amine (8.24 mg, 0.065 mmol), and DIEA (0.019 mL, 0.108 mmol). The reaction mixture was stirred at rt for 3 days. The reaction mixture was diluted with EtOAc (5 mL) and the solution was washed with water (2 mL) and brine (2 mL). The organic phase was dried over $MgSO_4$, filtered, and concentrated in vacuo to give an orange solid which was purified by preparative HPLC ($ACN/H_2O/TFA$) to afford the desired product (4.6 mg, 15%) as a pale yellow solid. LCMS Anal. Calc'd for $C_{26}H_{28}F_3N_3O_4$ 503.2, found [M+H] 504.1. $^1H$ NMR (500 MHz, $CDCl_3$) δ 8.46 (br. s., 1H), 7.61 (br. s., 1H), 7.24-7.32 (m, 4H), 7.16 (d, J=7.83 Hz, 2H), 6.79 (d, J=8.84 Hz, 2H), 3.75 (s, 3H), 3.56 (d, J=17.18 Hz, 1H), 3.22-3.37 (m, 2H), 3.14 (br. s., 1H), 2.73 (d, J=17.18 Hz, 1H), 2.34 (s, 3H), 2.00-2.15 (m, 2H), 1.70-1.80 (m, 2H), 1.54 (s, 3H).

Example 103. N-(4-Cyanophenyl)-5,5-difluoro-2-oxo-4-p-tolyl-6-(4-(4,4,4-trifluorobutoxy)phenyl)-6-(trifluoromethyl)-1,2,5,6-tetrahydropyridine-3-carboxamide

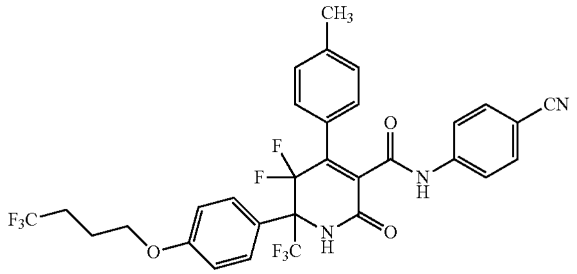 [SMILES: Cc1ccc(C2=C(C(=O)Nc3ccc(C#N)cc3)C(=O)NC(c3ccc(OCCCC(F)(F)F)cc3)(C(F)(F)F)C2(F)F)cc1]

Intermediate 103A. Methyl 2,2-difluoro-3-oxo-3-(4-(4,4,4-trifluorobutoxy)phenyl)propanoate

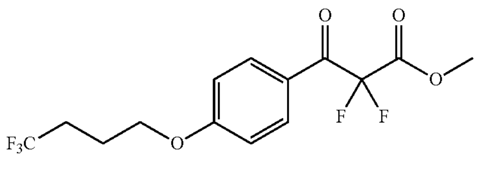 [SMILES: COC(=O)C(F)(F)C(=O)c1ccc(OCCCC(F)(F)F)cc1]

To a solution of Intermediate 14A (3 g, 9.86 mmol) and selectFluor (10.48 g, 29.6 mmol) in acetonitrile (10 mL) was added 1 M methanolic tetrabutylammonium hydroxide (19.72 mL, 19.72 mmol). The reaction mixture was heated to 82° C. for 10 min under microwave conditions. The reaction was diluted with 1:1 ACN and MeOH and filtered rinsing with 1:1 ACN in MeOH (50 mL). The filtrate was evaporated to dryness and the crude product was purified by silica gel chromatography (80 g silica gel, elute with EtOAc in hexanes) to yield the desired product (2.34 g, 69%) as a clear, colorless oil. $^1H$ NMR (500 MHz, $CDCl_3$) δ 8.08 (d, J=9.08 Hz, 2H), 6.98 (d, J=9.08 Hz, 2H), 4.13 (t, J=6.05 Hz, 2H), 3.93 (s, 3H), 2.27-2.39 (m, 2H), 2.07-2.15 (m, 2H).

Intermediate 103B. 2,2-Difluoro-1-(piperidin-1-yl)-3-(4-(4,4,4-trifluorobutoxy)phenyl)propane-1,3-dione

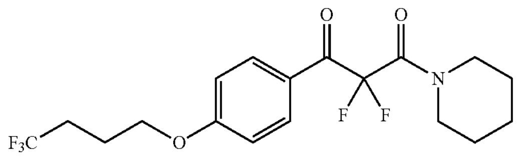 [SMILES: O=C(c1ccc(OCCCC(F)(F)F)cc1)C(F)(F)C(=O)N1CCCCC1]

Piperidine (175 μL, 1.763 mmol) was slowly added to Intermediate 103A (500 mg, 1.470 mmol) at rt. The reaction was stirred at rt for 3 h. The reaction was diluted with $CH_2Cl_2$, loaded onto a 12 g $SiO_2$ column and eluted with EtOAc in hexanes. Fractions containing the product were combined and evaporated to dryness to provide the product (520 mg, 81%) as a clear oil. LCMS Anal. Calc'd for $C_{18}H_{20}F_5NO_3$ 393.14, found [M+H] 394.2. $^1H$ NMR (500 MHz, $CDCl_3$) δ 8.10 (d, J=9.1 Hz, 2H), 6.98-6.91 (m, 2H), 4.10 (t, J=5.9 Hz, 2H), 3.61-3.56 (m, 2H), 3.54-3.50 (m, 2H), 2.39-2.26 (m, 2H), 2.14-2.05 (m, 2H), 1.69-1.61 (m, 2H), 1.60-1.51 (m, 4H).

Intermediate 103C. N-(2,2-Difluoro-3-oxo-3-(piperidin-1-yl)-1-(4-(4,4,4-trifluorobutoxy)phenyl)propylidene)-2-methylpropane-2-sulfinamide

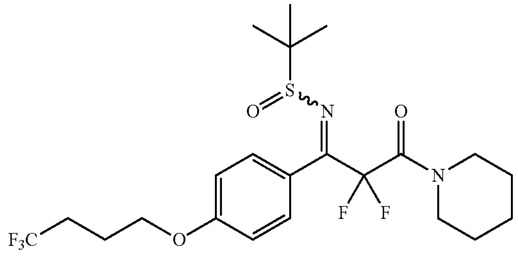 [SMILES: CC(C)(C)S(=O)N=C(c1ccc(OCCCC(F)(F)F)cc1)C(F)(F)C(=O)N1CCCCC1]

To a solution of Intermediate 103B (1.97 g, 5.01 mmol) and 2-methylpropane-2-sulfinamide (1.821 g, 15.02 mmol) in anhydrous THF (25.04 mL) was added $Ti(OEt)_4$ (5.19 mL, 25.04 mmol). The reaction was heated at refluxed temperature overnight. The reaction was cooled to rt, poured into brine, diluted with EtOAc, and stirred for 30 min. The titanium oxide was removed by filtering through a plug of Celite®. The filtrate layers were separated and the organic layer was washed with brine, dried over $Na_2SO_4$, filtered, and concentrated. The residue was purified by silica gel chromatography (80 g silica gel, eluted with EtOAc in hexanes to yield the desired product (1.62 g, 59%) as a yellow oil. $^1$H NMR (500 MHz, $CDCl_3$) δ 7.56 (d, J=8.80 Hz, 2H), 6.95 (d, J=9.08 Hz, 2H), 4.07 (t, J=6.05 Hz, 2H), 3.62-3.69 (m, 1H), 3.52-3.58 (m, 1H), 3.39 (t, J=5.09 Hz, 2H), 2.26-2.37 (m, 2H), 2.05-2.11 (m, 2H), 1.53-1.70 (m, 7H), 1.25 (s, 9H).

Intermediate 103D. 2-Methyl-N-(1,1,1,3,3-pentafluoro-4-oxo-4-(piperidin-1-yl)-2-(4-(4,4,4-trifluorobutoxy)phenyl)butan-2-yl)propane-2-sulfinamide

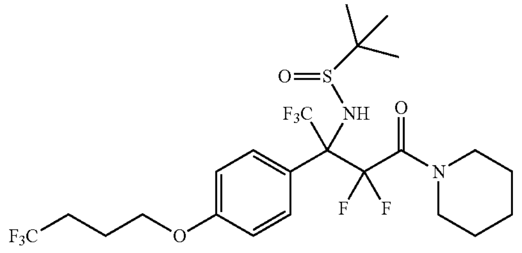 [SMILES: CC(C)(C)S(=O)NC(c1ccc(OCCCC(F)(F)F)cc1)(C(F)(F)F)C(F)(F)C(=O)N1CCCCC1]

To a solution of TBAT (3.43 g, 6.36 mmol) in DMF (5.89 mL) was added a solution of Intermediate 103C (1.17 g, 2.356 mmol) in THF (5.89 mL). The solution was cooled to 0° C., and then 2 M $TMSCF_3$ (3.53 mL, 7.07 mmol) in THF was added dropwise. The reaction was stirred at 0° C. for 1 h, and then quenched with brine (20 mL) at 0° C. The mixture was warmed to rt and diluted with water and EtOAc. The layers were separated. The aqueous layer was washed with EtOAc. The combined organic layers were washed with brine, dried over $Na_2SO_4$, filtered and concentrated. The residue was purified by silica gel chromatography (80 g silica gel, eluted with EtOAc in hexanes) to afford the desired product (773 mg, 58%) as a yellow gum. LCMS Anal. Calc'd for $C_{23}H_{30}F_8N_2O_3S$ 566.18, found [M+H] 567.1. $^1$H NMR (500 MHz, $CD_3OD$) δ 7.69 (d, J=8.53 Hz, 2H), 6.91 (d, J=9.08 Hz, 2H), 4.03 (t, J=5.91 Hz, 2H), 3.50-3.62 (m, 2H), 3.34-3.45 (m, 2H), 2.23-2.35 (m, 2H), 1.98-2.07 (m, 2H), 1.48-1.69 (m, 6H), 1.26 (s, 9H).

Intermediate 103E. N-Benzyl-2-methyl-N-(1,1,1,3,3-pentafluoro-4-oxo-4-(piperidin-1-yl)-2-(4-(4,4,4-trifluorobutoxy)phenyl)butan-2-yl)propane-2-sulfinamide

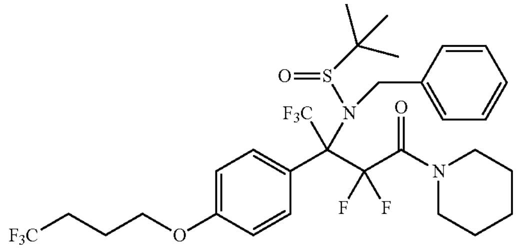 [SMILES: CC(C)(C)S(=O)N(Cc1ccccc1)C(c1ccc(OCCCC(F)(F)F)cc1)(C(F)(F)F)C(F)(F)C(=O)N1CCCCC1]

A solution of Intermediate 103D (461 mg, 0.814 mmol) in anhydrous DMF (0.5 mL) was added to a suspension of NaH (65 mg, 1.627 mmol) (60% in mineral oil) at 0° C. After stirring for 5 min, BnBr (0.484 mL, 4.07 mmol) was added. The reaction mixture was warmed to rt and stirred for 1 h. The reaction was diluted with EtOAc, washed with brine, dried over $Na_2SO_4$, filtered and concentrated. The residue was purified by silica gel chromatography (4 g silica gel, eluted with EtOAc in hexanes) to yield the desired product (260 mg, 44%) as a yellow gum. $^1$H NMR (500 MHz, $CDCl_3$) δ 7.75 (d, J=8.5 Hz, 2H), 7.33-7.27 (m, 3H), 7.14 (dd, J=7.3, 2.1 Hz, 2H), 6.80 (d, J=9.1 Hz, 2H), 4.46-4.38 (m, 2H), 4.00-3.95 (m, 2H), 3.72 (br. s., 1H), 3.51 (br. s., 1H), 3.35-3.10 (m, 2H), 2.37-2.25 (m, 2H), 2.09-1.99 (m, 2H), 1.70-1.39 (m, 6H), 1.34-1.29 (m, 9H).

Intermediate 103F. 2-Methyl-N-(1,1,1,3,3-pentafluoro-4-oxo-4-p-tolyl-2-(4-(4,4,4-trifluorobutoxy)phenyl)butan-2-yl)propane-2-sulfinamide

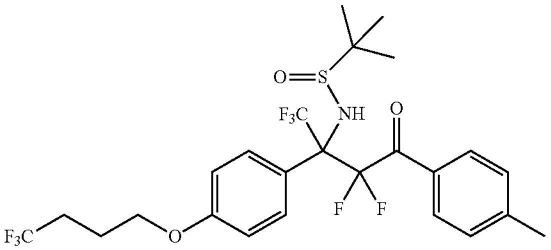 [SMILES: Cc1ccc(C(=O)C(F)(F)C(NS(=O)C(C)(C)C)(c2ccc(OCCCC(F)(F)F)cc2)C(F)(F)F)cc1]

Mg turnings were suspended in 0.1 N aq HCl for a few minutes, rinsed with water, MeOH and dried under vacuum. A flame dried flask equipped with a stir bar was charged with Mg turnings (0.243 g, 10 mmol), anhydrous THF (4.4 mL) and 4-bromotoluene (1.71 g, 10 mmol) in anhydrous THF (4.4 mL) followed by several drops of 1,2-dibromoethane. The reaction initiated in a few minutes and the mixture became warm. The approximate concentration of the Grignard reagent is 1 M. The mixture was diluted with 10 mL anhydrous THF to produce a clear solution of p-tolylmagnesium bromide (~0.5 M). To a solution of Intermediate 103E (260 mg, 0.396 mmol) in THF (3959 μL) at 0° C. was added the freshly prepared p-tolylmagnesium bromide (3959 μL, 1.980 mmol). The reaction was warmed to rt, concentrated to half of the original volume, and stirred for 3 h. The reaction was cooled to 0° C., quenched with sat'd aq $NH_4Cl$, and then diluted with EtOAc. The layers were separated and the organic layer was washed with brine, dried over $MgSO_4$, filtered and concentrated. The residue was purified by silica gel chromatography (24 g silica gel, eluted with EtOAc in hexanes) to afford the desired product (60 mg, 24%) as a yellow gum. $^1$H NMR (500 MHz, $CDCl_3$) δ 7.73 (d, J=8.0 Hz, 2H), 7.55 (d, J=8.5 Hz, 2H), 7.19 (d, J=8.0 Hz, 2H), 6.83 (d, J=8.8 Hz, 2H), 4.19 (s, 1H), 4.01 (br. s., 2H), 2.40 (s, 3H), 2.31 (dd, J=16.2, 10.2 Hz, 2H), 2.10-1.99 (m, 2H), 1.25 (s, 9H).

Intermediate 103G. 3-Amino-2,2,4,4,4-pentafluoro-1-p-tolyl-3-(4-(4,4,4-trifluorobutoxy)phenyl)butan-1-one, HCl

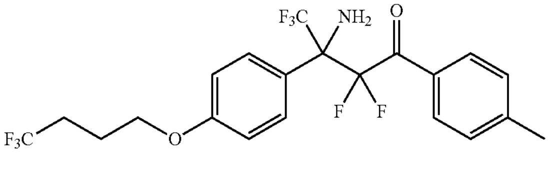 [SMILES: Cc1ccc(C(=O)C(F)(F)C(N)(c2ccc(OCCCC(F)(F)F)cc2)C(F)(F)F)cc1]

To a solution of Intermediate 103F (30 mg, 0.052 mmol) in MeOH (0.5 mL) was added 4.0 M HCl (0.026 mL, 0.105 mmol) in dioxane. The reaction was stirred at rt for 1 h. The reaction was concentrated and the crude product was used in the next step without further purification. LCMS Anal. Calc'd for $C_{21}H_{19}F_8NO_2$ 469.13, found [M+H] 470.1.

Intermediate 103H. Ethyl 5,5-difluoro-2-oxo-4-p-tolyl-6-(4-(4,4,4-trifluorobutoxy)phenyl)-6-(trifluoromethyl)-1,2,5,6-tetrahydropyridine-3-carboxylate

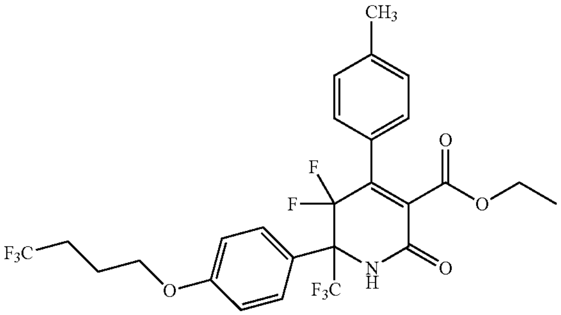 [SMILES: CCOC(=O)C1=C(c2ccc(C)cc2)C(F)(F)C(c2ccc(OCCCC(F)(F)F)cc2)(C(F)(F)F)NC1=O]

Intermediate 103G (268 mg, 0.530 mmol) was dissolved in MeOH and then passed through $NaHCO_3$ resin (500 mg; 0.9 mmol). The solution was concentrated to yield the free base (230 mg). The free base was dissolved in 9:1 $CH_2Cl_2$/pyridine (3 mL) added ethyl 3-chloro-3-oxopropanoate (160 mg, 1.060 mmol). The resulting mixture was stirred at rt for 24 h and then concentrated. The residue was taken up with EtOH (1 mL) and treated with piperidine (20 uL). The resulting mixture was stirred at 65° C. for 24 h and then concentrated. The residue was purified by preparative HPLC ($MeOH/H_2O$/TFA) to yield the desired product (100 mg, 33%) as a foam. LCMS Anal. Calc'd for $C_{26}H_{23}F_8NO_4$ 565.15, found [M+H] 566.1.

Intermediate 1031. 5,5-Difluoro-2-oxo-4-p-tolyl-6-(4-(4,4,4-trifluorobutoxy)phenyl)-6-(trifluoromethyl)-1,2,5,6-tetrahydropyridine-3-carboxylic acid

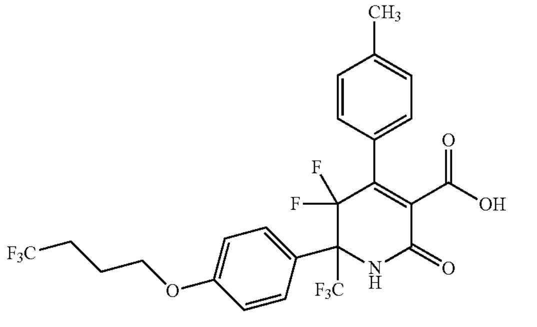 [SMILES: Cc1ccc(C2=C(C(=O)O)C(=O)NC(c3ccc(OCCCC(F)(F)F)cc3)(C(F)(F)F)C2(F)F)cc1]

To a solution of Intermediate 103H (100 mg, 0.177 mmol) in MeOH (2 mL) was added 2 M LiOH (0.4 mL, 0.800 mmol). The resulting mixture was stirred at 100° C. for 15 min. LC-MS indicated the product to be the major component along with a trace amount of SM and 14% of the corresponding methyl ester. 2 M LiOH (100 uL) was then added and the reaction was stirred at 100° C. for an additional 15 min. The reaction was concentrated, acidified with 1 N HCl, and extracted with EtOAc. The organic layer was washed with brine, dried over $MgSO_4$, filtered and concentrated to yield the desired product (75 mg, 78%) as a solid. LCMS Anal. Calc'd for $C_{24}H_{19}F_8NO_4$ 537.12, found [M+H] 537.9.

Example 103

To a solution of Intermediate 1031 (20 mg, 0.037 mmol) in MeCN (1 mL) was added 3H-[1,2,3]triazolo[4,5-b]pyridin-3-ol (7.60 mg, 0.056 mmol), 4-aminobenzonitrile (6.59 mg, 0.056 mmol), and EDC (10.70 mg, 0.056 mmol). The resulting mixture was stirred at rt overnight. The reaction mixture was diluted with MeCN and purified by preparative HPLC ($MeCN/H_2O$/TFA) to yield the desired product (11 mg, 46%) as a solid. LCMS Anal. Calc'd for $C_{31}H_{23}F_8N_3O_3$ 637.16, found [M+H] 637.9. $^1H$ NMR (500 MHz, $CD_3OD$) δ 7.67 (d, J=9.08 Hz, 2H), 7.56-7.63 (m, 4H), 7.22-7.26 (m, 2H), 7.15-7.20 (m, 2H), 7.04-7.09 (m, 2H), 4.12 (t, J 6.05 Hz, 2H), 2.33-2.44 (m, 2H), 2.30 (s, 3H), 2.02-2.09 (m, 2H).

Example 104. (S)-3-Amino-4-p-tolyl-6-(4-(4,4,4-trifluorobutoxy)phenyl)-6-(trifluoromethyl)-5,6-dihydropyridin-2(1H)-one

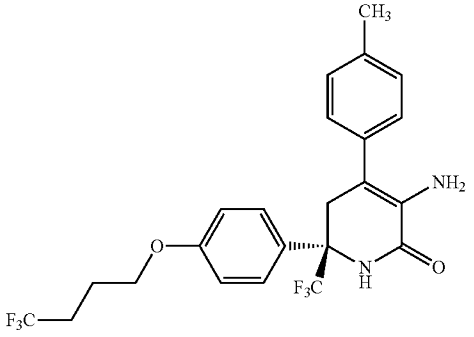 [SMILES: Cc1ccc(C2=C(N)C(=O)N[C@@](c3ccc(OCCCC(F)(F)F)cc3)(C(F)(F)F)C2)cc1]

Intermediate 104A. (S)-2-(1,3-Dioxoisoindolin-2-yl)-N-(1,1,1-trifluoro-4-oxo-4-p-tolyl-2-(4-(4,4,4-trifluorobutoxy)phenyl)butan-2-yl)acetamide

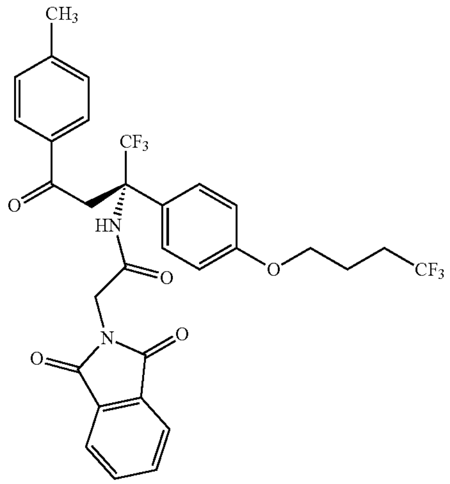 [SMILES: Cc1ccc(C(=O)C[C@](NC(=O)CN2C(=O)c3ccccc3C2=O)(c2ccc(OCCCC(F)(F)F)cc2)C(F)(F)F)cc1]

To a solution of 2-(1,3-dioxoisoindolin-2-yl)acetic acid (592 mg, 2.88 mmol) in dry DCM (10 mL) was added $PPh_3$ (2269 mg, 8.65 mmol) fairy rapidly, and then $CCl_3CN$ (500 mg, 3.46 mmol) was added dropwise. The mixture was stirred at rt for 3 h and a solution of Intermediate 2F, isomer 2 (500 mg, 1.15 mmol) in dry DCM (3 mL), followed by pyridine (0.3 mL) were added. The mixture was stirred at rt overnight. The mixture was diluted with DCM (10 mL) and washed with sat'd $NaHCO_3$ (2×8 mL). The organic layer was dried over anhydrous $MgSO_4$, filtered and concentrated. The residue was purified by silica gel chromatography to yield the desired product (620 mg, 87%). LCMS Anal. Calc'd for $C_{31}H_{26}F_6N_2O_5$ 620.17, found [M+H] 621.3.

Intermediate 104B. (S)-2-(2-Oxo-4-p-tolyl-6-(4-(4,4,4-trifluorobutoxy)phenyl)-6-(trifluoromethyl)-1,2,5,6-tetrahydropyridin-3-yl)isoindoline-1,3-dione

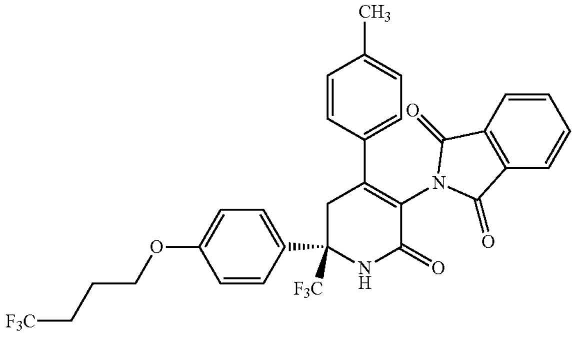 [SMILES: Cc1ccc(C2=C(N3C(=O)c4ccccc4C3=O)C(=O)N[C@@](c3ccc(OCCCC(F)(F)F)cc3)(C(F)(F)F)C2)cc1]

Intermediate 104A (145 mg, 0.234 mmol) was dissolved in MeOH (2.2 mL) and then 1 N NaOH (0.2 mL) was added. The mixture was stirred at 69° C. for 45 min and added another 0.2 mL of 1 N NaOH. The reaction was heated at 130° C. under microwave conditions for 10 min. The mixture was neutralized with 1 N HCl and then concentrated. The residue was purified by silica gel chromatography (12 g silica gel, eluted with EtOAc in hexanes) to yield the desired product (80 mg, 57%). LCMS Anal. Calc'd for $C_{31}H_{24}F_6N_2O_4$ 602.16, found [M+H] 603.3.

Example 104

To a solution of Intermediate 104B (80 mg, 0.133 mmol) in 1 mL of EtOH was added 1 mL of 2 N $MeNH_2$ in MeOH. The mixture was stirred at 67° C. for 24 h. The solvent was removed in vacuo and the crude product was purified by silica gel chromatography (4 g silics gel, eluted with EtOAc in hexanes) to yield the desired product (32.3 mg, 52%) as a light brown solid. LCMS Anal. Calc'd for $C_{23}H_{22}F_6N_2O_2$ 472.16, found [M+H] 473.2. $^1$H NMR (500 MHz, $CD_3OD$) δ 7.49 (d, J=8.8 Hz, 2H), 7.31-7.17 (m, 4H), 7.04-6.92 (m, 2H), 4.08 (s, 2H), 3.46 (d, J=16.2 Hz, 1H), 3.21 (d, J=16.2 Hz, 1H), 2.44-2.30 (m, 5H), 2.09-1.99 (m, 2H).

Example 105. (S)-2-Methyl-N-(2-oxo-4-p-tolyl-6-(4-(4,4,4-trifluorobutoxy)phenyl)-6-(trifluoromethyl)-1,2,5,6-tetrahydropyridin-3-yl)benzamide

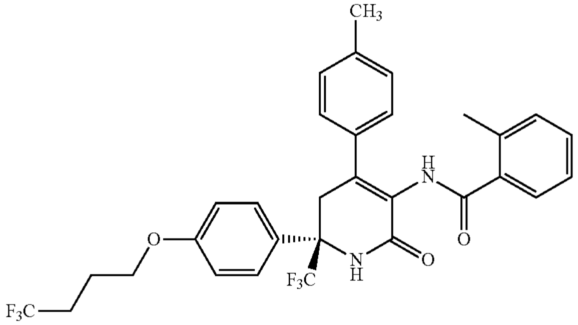 [SMILES: Cc1ccc(C2=C(NC(=O)c3ccccc3C)C(=O)N[C@@](c3ccc(OCCCC(F)(F)F)cc3)(C(F)(F)F)C2)cc1]

To a solution of 104 (15 mg, 0.032 mmol) in dry DCM (0.5 mL) was added 2-methylbenzoyl chloride (5.4 mg, 0.035 mmol) and pyridine (2.8 μL, 0.035 mmol). The mixture was stirred at rt for 2 h and then concentrated. The residue was purified by preparative HPLC ($MeCN/H_2O$/TFA) to yield the desired product. LCMS Anal. Calc'd for $C_{31}H_{28}F_6N_2O_3$ 590.20, found [M+H] 591.3. $^1$H NMR (500 MHz, $CD_3OD$) δ 7.56 (d, J=8.80 Hz, 2H), 7.11-7.29 (m, 8H), 6.98 (d, J=9.08 Hz, 2H), 4.06 (t, J=6.05 Hz, 2H), 3.73 (d, J=17.06 Hz, 1H), 3.46 (d, J=16.78 Hz, 1H), 2.33 (s, 3H), 2.30-2.42 (m, 2H), 2.22 (s, 3H), 1.98-2.06 (m, 2H).

Example 106. (S)-3-Phenoxy-4-p-tolyl-6-(4-(4,4,4-trifluorobutoxy)phenyl)-6-(trifluoromethyl)-5,6-dihydropyridin-2(1H)-one

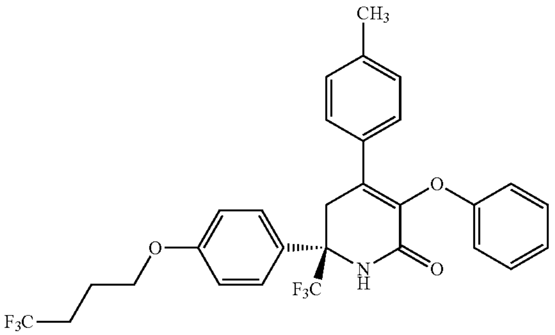 [SMILES: Cc1ccc(C2=C(Oc3ccccc3)C(=O)N[C@@](c3ccc(OCCCC(F)(F)F)cc3)(C(F)(F)F)C2)cc1]

Intermediate 106A. (S)-2-Phenoxy-N-(1,1,1-trifluoro-4-oxo-4-p-tolyl-2-(4-(4,4,4-trifluorobutoxy)phenyl)butan-2-yl)acetamide

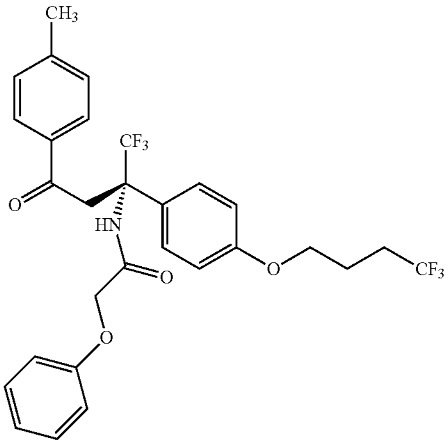 [SMILES: Cc1ccc(C(=O)C[C@](NC(=O)COc2ccccc2)(c2ccc(OCCCC(F)(F)F)cc2)C(F)(F)F)cc1]

To a mixture of triphenylphosphine (138 mg, 0.318 mmol) in dry DCM (0.8 mL) was added 2-phenoxyacetic acid (26 mg, 0.173 mmol), followed by trichloroacetonitrile (30 mg, 0.208 mmol). The mixture was stirred at rt for 2.5 h. To the mixture was added a solution of Intermediate 2F, isomer 2 (30 mg, 0.069 mmol) in dry DCM (0.5 mL) followed by pyridine (17 μL, 0.208 mmol). The reaction was stirred at rt overnight. The mixture was concentrated and purified by preparative HPLC (MeOH/$H_2O$/TFA) to yield the desired product (27 mg, 69%) as a brown oil. LCMS Anal. Calc'd for $C_{29}H_{27}F_6NO_4$ 567.18, found [M+H] 568.3.

Example 106

To a solution of Intermediate 106A (26 mg, 0.046 mmol) in MeOH (0.5 mL) was added 1 N NaOH (60 μL). The mixture was heated at 130° C. under microwave conditions for 10 min. The mixture was neutralized with 1 N HCl and concentrated. The residue was purified by preparative HPLC (MeCN/$H_2O$/TFA) to yield the desired product (1.5 mg, 6%) as a light brown oil. LCMS Anal. Calc'd for $C_{29}H_{25}F_6NO_3$ 549.17, found [M+H] 550.3. $^1H$ NMR (500 MHz, $CD_3OD$) δ 7.59 (d, J=8.80 Hz, 2H), 7.33 (d, J=8.25 Hz, 2H), 7.13 (d, J=8.25 Hz, 2H), 7.01-7.08 (m, 4H), 6.85-6.90 (m, 1H), 6.38 (dd, J=8.67, 0.96 Hz, 2H), 4.10-4.15 (m, 2H), 3.71-3.76 (m, 1H), 3.61-3.67 (m, 1H), 2.34-2.45 (m, 2H), 2.30 (s, 3H), 2.02-2.11 (m, 2H).

Example 107. 6-(4-Butoxyphenyl)-6-methyl-2-oxo-4-p-tolyl-1,2,5,6-tetrahydropyridine-3-carbonitrile

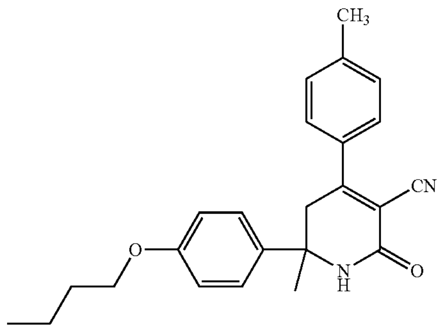 [SMILES: CCCCOc1ccc(C2(C)CC(c3ccc(C)cc3)=C(C#N)C(=O)N2)cc1]

Intermediate 107A. (Z)—N-(1-(4-Butoxyphenyl) ethylidene)-2-methylpropane-2-sulfinamide

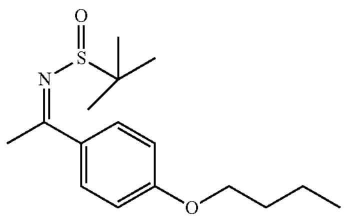 [SMILES: CCCCOc1ccc(/C(C)=N\S(=O)C(C)(C)C)cc1]

To a stirred solution of 1-(4-butoxyphenyl)ethanone (3 g, 15.60 mmol) and 2-methylpropane-2-sulfinamide (2.84 g, 23.41 mmol) in THF (50 mL) was added tetraethoxytitanium (8.90 g, 39.0 mmol). The reaction was heated to 70° C. for 3 d. Cold water was added and the reaction was stirred vigorously for 20 min. The mixture was filtered through Celite® and the filtrated was diluted with EtOAc. The organic solution was washed with $H_2O$, brine, dried over $MgSO_4$, filtered and concentrated. The crude product was by silica gel chromatography (220 g silica gel, eluted with EtOAc in hexanes) to yield the desired product (4 g, 87%) as a yellow oil. $^1H$ NMR (500 MHz, $CDCl_3$) δ 7.88 (d, J=8.80 Hz, 2H), 6.91 (d, J=8.80 Hz, 2H), 4.02 (t, J=6.46 Hz, 2 H), 2.73 (s, 3H), 1.75-1.83 (m, 2H), 1.46-1.56 (m, 2H), 1.32 (s, 9H), 0.99 (t, J=7.43 Hz, 3H).

Intermediate 107B. Methyl 3-(4-butoxyphenyl)-3-(1,1-dimethylethylsulfinamido)butanoate

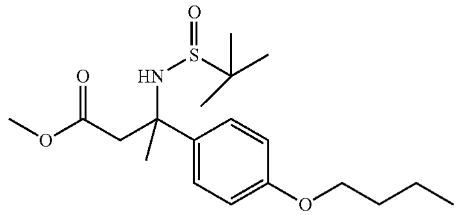 [SMILES: CCCCOc1ccc(C(C)(CC(=O)OC)NS(=O)C(C)(C)C)cc1]

To a stirred solution of diisopropylamine (3.86 mL, 27.1 mmol) in THF (40 mL) at −78° C. was added n-butyllithium (22.57 mL, 27.1 mmol) dropwise. The reaction was slowly warmed up to −20° C. and stirred for 45 min. The reaction was cooled to −78° C. and methyl acetate (2.006 g, 27.1 mmol) was added dropwise. After 30 min, chlorotitanium triisopropoxide (8.09 mL, 33.8 mmol) in THF (40 mL) was added dropwise. The reaction was stirred at −78° C. for 1 h. Intermediate 107A (4 g, 13.54 mmol) in THF (15 mL) was added dropwise and the reaction was stirred at −78° C. for 2 h. The reaction was quenched by addition of sat'd $NH_4Cl$ solution and stirred vigorously while warmed to rt. The mixture was filtered through Celite® and washed with EtOAc. The filtrate was washed with $H_2O$, brine, dried over $MgSO_4$, filtered and concentrated. The crude product was purified by silica gel chromatography (220 g silica gel, eluted with EtOAc in hexanes) to yield the desired product (4.33 g, 87%) as a light yellow oil. LCMS Anal. Calc'd for $C_{19}H_{31}NO_4S$ 369.20, found [M+H] 370.2. $^1H$ NMR (500 MHz, $CDCl_3$) δ 7.31 (d, J=8.80 Hz, 2H), 6.85 (d, J=8.80 Hz, 2H), 3.95 (t, J=6.46 Hz, 2H), 3.62 (s, 3H), 2.05 (s, 2H), 1.74-1.80 (m, 2H), 1.74 (s, 3H), 1.44-1.54 (m, 2H), 1.29 (s, 9H), 0.98 (t, J=7.43 Hz, 3H).

Intermediate 107C. Methyl 3-amino-3-(4-butoxyphenyl)butanoate

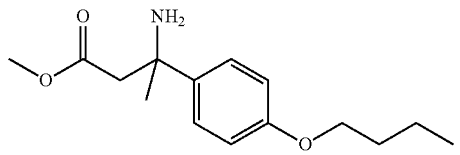 [SMILES: CCCCOc1ccc(C(C)(N)CC(=O)OC)cc1]

To a stirred solution of Intermediate 107B (1 g, 2.71 mmol) in MeOH (6 mL) was added 4 N HCl (3.38 mL, 13.53 mmol). The reaction was stirred at rt for 4 h. The reaction mixture was concentrated in vacuo and diluted with EtOAc. The organic layer was washed with saturated $NaHCO_3$, dried over $MgSO_4$, filtered and concentrated to yield the desired product (700 mg, 97%) as a yellow oil. $^1H$ NMR (500 MHz, $CDCl_3$) δ 7.38 (d, J=8.80 Hz, 2H), 6.86 (d, J=8.80 Hz, 2H), 3.95 (t, J 6.46 Hz, 2H), 3.59 (s, 3H), 1.73-1.80 (m, 2H), 1.53 (s, 2H), 1.45-1.52 (m, 2H), 1.19 (s, 3H), 0.98 (t, J 7.29 Hz, 3H).

Intermediate 107D. Methyl 3-(4-butoxyphenyl)-3-(2-cyanoacetamido)butanoate

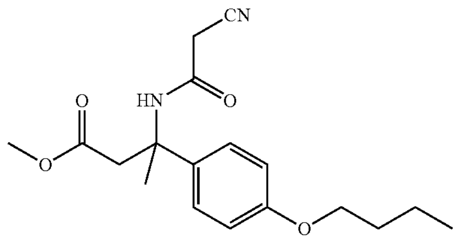 [SMILES: CCCCOc1ccc(C(C)(CC(=O)OC)NC(=O)CC#N)cc1]

To a stirred solution of 2-cyanoacetic acid (128 mg, 1.507 mmol) in $CH_2Cl_2$ (5 mL) was added oxalyl chloride (0.754 mL, 1.507 mmol) and 1 drop of DMF. The reaction was stirred at rt for 1 h and then concentrated. The resulting acid chloride was dissolved in $CH_2Cl_2$ (1 mL) and was then added to Intermediate 107C (200 mg, 0.754 mmol) and pyridine (0.183 mL, 2.261 mmol) in $CH_2Cl_2$ (5 mL). The reaction was stirred at rt for 5 h. The reaction mixture was concentrated and the residue was diluted with EtOAc. The organic layer was washed with saturated $NH_4Cl$, dried over $MgSO_4$, filtered and concentrated. The crude product was purified by silica gel chromatography (24 g silica gel, eluted with EtOAc in hexanes) to yield the desired product (218 mg, 87%) as a clear oil. $^1H$ NMR (500 MHz, $CDCl_3$) δ 7.22 (d, J=8.80 Hz, 2H), 6.85 (d, J=8.80 Hz, 2H), 3.94 (t, J=6.46 Hz, 2H), 3.65 (s, 3H), 3.30 (s, 2H), 3.03 (d, J 15.13 Hz, 1H), 2.85 (d, J=15.13 Hz, 1H), 1.80 (s, 3H), 1.71-1.78 (m, 2H), 1.44-1.53 (m, 2H), 0.97 (t, J=7.29 Hz, 3H).

Intermediate 107E. 6-(4-Butoxyphenyl)-4-hydroxy-6-methyl-2-oxo-1,2,5,6-tetrahydropyridine-3-carbonitrile

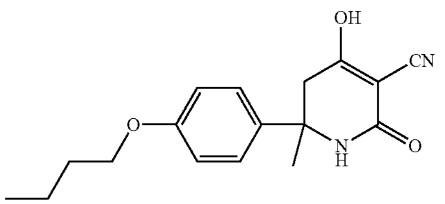 [SMILES: CCCCOc1ccc(C2(C)CC(O)=C(C#N)C(=O)N2)cc1]

To a stirred solution of Intermediate 107D (218 mg, 0.656 mmol) in MeOH (5 mL) was added 4.37 M NaOMe (0.750 mL, 3.28 mmol) in methanol solution. The reaction was heated to 55° C. for 5 h. The reaction mixture was concentrated and the residue was diluted with EtOAc. The organic layer was washed with 1 M HCl, dried over $MgSO_4$, filtered and concentrated to yield the desired product (200 mg, 102%) as a light yellow solid. LCMS Anal. Calc'd for $C_{17}H_{20}N_2O_3$ 300.15, found [M+H] 301.1.

Intermediate 107F. 6-(4-Butoxyphenyl)-4-chloro-6-methyl-2-oxo-1,2,5,6-tetrahydropyridine-3-carbonitrile

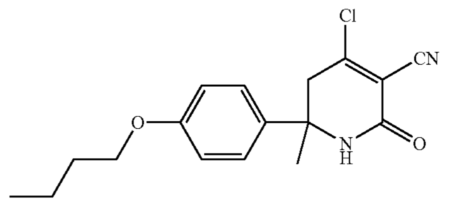 [SMILES: CCCCOc1ccc(C2(C)CC(Cl)=C(C#N)C(=O)N2)cc1]

To a stirred solution of Intermediate 107E (130 mg, 0.433 mmol) in $ClCH_2CH_2Cl$ (3 mL) was added $POCl_3$ (0.056 mL, 0.606 mmol) and Hunig's base (0.113 mL, 0.649 mmol). The reaction was stirred at rt for 30 min and then heated to 85° C. for 3 h. The reaction mixture was concentrated and the residue was diluted with EtOAc. The organic layer was washed with saturated $NH_4Cl$, dried over $MgSO_4$, filtered and concentrated. The crude product was purified by silica gel chromatography (24 g silica gel, eluted with EtOAc in hexanes) to yield the desired product (102 mg, 74%) as a white solid. LCMS Anal. Calc'd for $C_{17}H_{19}C_1N_2O_2$ 318.11, found [M+H] 319.2. $^1H$ NMR (500 MHz, $CDCl_3$) δ 7.23 (d, J=8.80 Hz, 2H), 6.90 (d, J=8.80 Hz, 2H), 3.97 (t, J=6.60 Hz, 2H), 2.05 (s, 2H), 1.74-1.82 (m, 2H), 1.69 (s, 3H), 1.46-1.55 (m, 2H), 0.99 (t, J=7.43 Hz, 3H).

Example 107

To a stirred solution of Intermediate 107F (11 mg, 0.035 mmol), p-tolylboronic acid (5.63 mg, 0.041 mmol), and 1,1'-bis(di-tert-butylphosphino)ferrocene palladium dichloride (2.270 mg, 3.45 μmol) in dioxane (1 mL) was added CsF (10.48 mg, 0.069 mmol). The reaction was degassed for 10 min and heated to 80° C. for 2 h. The reaction mixture was concentrated. The residue was diluted with EtOAc, washed with $H_2O$, brine, dried over $MgSO_4$, filtered and concentrated. The crude material was purified by preparative HPLC ($MeOH/H_2O/TFA$) to yield the desired product (5.7 mg, 44%) as a brown solid. LCMS Anal. Calc'd for $C_{24}H_{26}N_2O_2$ 374.20, found [M+H] 375.2. $^1H$ NMR (400 MHz, $CD_3OD$) δ 7.41 (d, J=8.14 Hz, 2H), 7.32 (d, J=8.80 Hz, 2H), 7.28 (d, J=8.14 Hz, 2H), 6.89 (d, J=8.80 Hz, 2H), 3.96 (t, J=6.38 Hz, 2H), 3.46 (d, J=18.05 Hz, 1H), 3.24 (d, J=17.83 Hz, 1H), 2.38 (s, 3H), 1.69-1.78 (m, 2H), 1.65 (s, 3H), 1.43-1.55 (m, 2H), 0.97 (t, J=7.48 Hz, 3H).

Example 108. 6-(5-Hexyloxazol-2-yl)-6-methyl-2-oxo-4-p-tolyl-1,2,5,6-tetrahydropyridine-3-carbonitrile

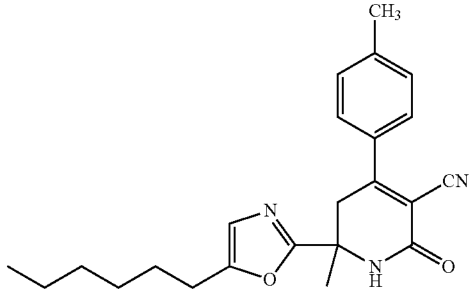 [SMILES: CCCCCCc1cnc(C2(C)CC(c3ccc(C)cc3)=C(C#N)C(=O)N2)o1]

Intermediate 108A. Ethyl 2-(2-cyanoacetamido)-2-methyl-4-oxo-4-p-tolylbutanoate

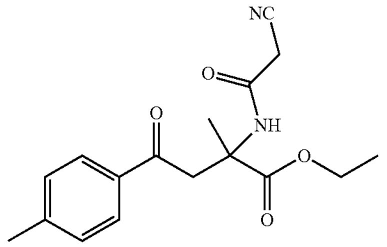 [SMILES: CCOC(=O)C(C)(CC(=O)c1ccc(C)cc1)NC(=O)CC#N]

To a solution of Intermediate 3C (2.192 g, 21.18 mmol) in DCM (30 mL) under argon was added Intermediate 102C (1.2 g, 4.81 mmol), pyridine (0.779 mL, 9.63 mmol) and DMAP (0.059 g, 0.481 mmol). The reaction mixture was stirred at rt for 1 h. The reaction mixture was loaded onto silica gel (25 g) and washed with EtOAc (4×50 mL). The filtrate was concentrated in vacuo to a dark red oil. The oil was dissolved in EtOAc (100 mL) and washed with water (2×50 mL). The organic phase was dried over $MgSO_4$ and concentrated in vacuo. The residue was purified by silica gel chromatography (80 g silica gel, eluted with EtOAc in hexanes) to afford the desired product (1.28 g, 84%) as yellow oil. LCMS Anal. Calc'd for $C_{17}H_{20}N_2O_4$ 316.1, found [M+H] 317.1. $^1H$ NMR (500 MHz, $CDCl_3$) δ 7.82 (d, J=8.0 Hz, 2H), 7.39 (s, 1H), 7.24-7.29 (m, 2H), 4.45 (d, J=18.2 Hz, 1H), 4.22-4.31 (m, 2H), 3.47 (d, J=18.2 Hz, 1H), 3.28-3.38 (m, 2H), 2.42 (s, 3H), 1.74 (s, 3H), 1.24 (t, J=7.0 Hz, 3H).

Intermediate 108B. Ethyl 5-cyano-2-methyl-6-oxo-4-p-tolyl-1,2,3,6-tetrahydropyridine-2-carboxylate

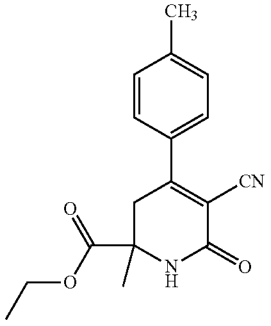 [SMILES: CCOC(=O)C1(C)CC(c2ccc(C)cc2)=C(C#N)C(=O)N1]

Intermediate 108A (1.2837 g, 4.06 mmol) was dissolved in a mixture of THF (15 mL) and water (3.00 mL) in a 25 mL 1 neck pear shaped flask that was equipped with a magnetic stirrer. Lithium hydroxide monohydrate (0.204 g, 4.87 mmol) was added and the reaction mixture was stirred at rt for 1 h. The reaction mixture was acidified to pH 4 with AcOH, diluted with EtOAc (50 mL) and the solution was washed with water (20 mL). The organic phase was dried over $MgSO_4$ and concentrated in vacuo to give the desired product (1.40 g, 115%) as yellow oil. LCMS Anal. Calc'd for $C_{17}H_{18}N_2O_3$ 298.1, found [M+H] 299.1.

Intermediate 108C. 5-Cyano-2-methyl-6-oxo-4-p-tolyl-1,2,3,6-tetrahydropyridine-2-carboxylic acid

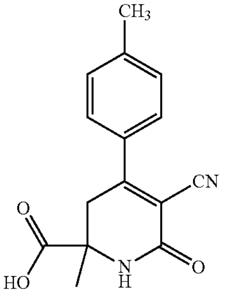 [SMILES: Cc1ccc(C2=C(C#N)C(=O)NC(C)(C(=O)O)C2)cc1]

Intermediate 108B (1.211 g, 4.06 mmol) was dissolved in acetic acid (95 mL) in a 250 mL 1 neck pear shaped flask that was equipped with a magnetic stirrer. HCl (11.67 mL, 142 mmol) was added and the reaction mixture was stirred at 60° C. overnight. The reaction mixture was concentrated in vacuo to give the desired product as a pale yellow solid. LCMS Anal. Calc'd for $C_{15}H_{14}N_2O_3$ 270.1, found [M+H] 271.0. $^1H$ NMR (500 MHz, $CDCl_3$) δ 7.48 (d, J=8.3 Hz, 2H), 7.23 (d, J=7.7 Hz, 2H), 3.39 (d, J=18.2 Hz, 1H), 2.83 (d, J=18.2 Hz, 1H), 2.35 (s, 3H), 1.54 (s, 3H).

Intermediate 108D. Ethyl 5-hexyloxazole-4-carboxylate

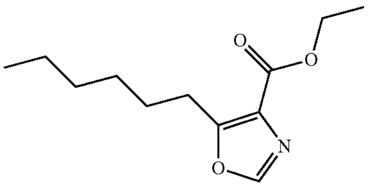 [SMILES: CCCCCCc1ocnc1C(=O)OCC]

Ethyl 2-isocyanoacetate (1.0 g, 8.84 mmol) was dissolved in DMF (5 mL) in a 25 mL 1 neck pear shaped flask that was equipped with a magnetic stirrer and an Ar inlet. DBU (1.999 mL, 13.26 mmol) and heptanoyl chloride (1.770 mL, 11.49 mmol) were added and the reaction mixture was stirred at 80° C. for 6 h. The reaction mixture was poured into water (50 mL) and extracted with EtOAc (3×30 mL). The phases were separated and the organic phase was dried over $MgSO_4$ and concentrated in vacuo to a a dark oil. The desired product was isolated by distillation at 90-95° C. at 0.3 mmHg as a clear oil (0.89 g, 45%). LCMS Anal. Calc'd for $C_{12}H_{19}NO_3$ 225.1, found [M+H] 226.1. $^1H$ NMR (500 MHz, $CDCl_3$) δ 7.76 (s, 1H), 4.37 (q, J=7.2 Hz, 2H), 3.03 (t, J=7.6 Hz, 2H), 1.71-1.64 (m, 2H), 1.38 (t, J=7.2 Hz, 3H), 1.35-1.26 (m, 6H), 0.86 (t, J=6.3 Hz, 3H).

Intermediate 108E. 1-Aminooctan-2-one, HCl salt

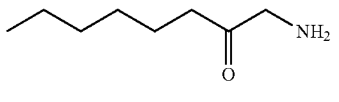

Intermediate 108D (0.8889 g, 3.95 mmol) was stirred in HCl (16.44 mL, 99 mmol) in a 100 mL 1 neck pear shaped flask that was equipped with a magnetic stirrer. The reaction mixture was heated to 100° C. and stirred for 6 h. The reaction mixture was concentrated in vacuo to a tan solid that was triturated in ether (15 mL). The slurry was filtered and was washed with ether (3 mL). The filter cake was dried under vacuum to give the desired product (0.57 g, 80%) as an off-white solid. $^1$H NMR (500 MHz, MeOD) δ 3.97 (s, 2H), 2.56 (t, J=7.4 Hz, 2H), 1.62 (quin, J=7.4 Hz, 2H), 1.26-1.40 (m, 6H), 0.88-0.93 (m, 3H).

Intermediate 108F. 5-Cyano-2-methyl-6-oxo-N-(2-oxooctyl)-4-p-tolyl-1,2,3,6-tetrahydropyridine-2-carboxamide

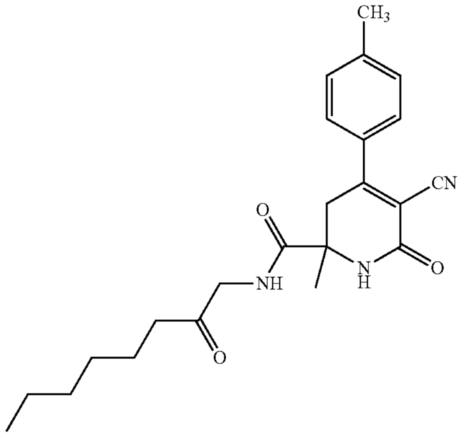 [SMILES: CCCCCCC(=O)CNC(=O)C1(C)CC(c2ccc(C)cc2)=C(C#N)C(=O)N1]

Intermediate 108C (0.1 g, 0.370 mmol) was dissolved in DCM (4 mL) in a 10 mL 1 neck pear shaped flask that was equipped with a magnetic stirrer and an Ar inlet. EDC (0.099 g, 0.518 mmol), HOBT (0.068 g, 0.444 mmol), Intermediate 108E (0.080 g, 0.444 mmol) and DIEA (0.194 mL, 1.110 mmol) were added and the reaction mixture was stirred at rt overnight. The reaction mixture was concentrated in vacuo to an orange oil that was purified by silica gel chromatography (40 g silica gel, eluted with 0-100% EtOAc in hexanes) to give the desired product (0.09 g, 61%) as yellow oil.

Example 108

Intermediate 108F (0.045 g, 0.114 mmol) was dissolved in 1,2-dichloroethane (2 mL) in a 10 mL 1 neck pear shaped flask that was equipped with a magnetic stirrer and an Ar inlet. $POCl_3$ (0.042 mL, 0.455 mmol) and DIEA (0.089 mL, 0.512 mmol) were added and the reaction mixture was stirred at 85° C. overnight. The reaction mixture was cooled in an ice/water bath and was quenched with water (3 mL). The mixture was extracted with EtOAc (2×5 mL) and the organic phases were combined, dried over $MgSO_4$ and concentrated in vacuo to a brown oil. The crude product was purified by preparative HPLC (MeOH/$H_2$O/TFA) to yield the desired product (3.5 mg, 8%) as a yellow solid. LCMS Anal. Calc'd for $C_{23}H_{27}N_3O_2$ 377.2, found [M+H] 378.2. $^1$H NMR (500 MHz, $CDCl_3$) δ 7.60 (d, J=8.0 Hz, 2H), 7.31 (d, J=8.0 Hz, 2H), 6.81 (br. s., 1H), 3.65 (d, J=17.9 Hz, 1H), 3.09 (d, J=17.9 Hz, 1H), 2.63 (t, J=7.4 Hz, 2H), 2.43 (s, 3H), 1.76 (s, 3H), 1.57-1.67 (m, 2H), 1.23-1.42 (m, 6H), 0.89 (t, J=6.7 Hz, 3H).

Example 109. 6-(1-Heptyl-1H-pyrazol-3-yl)-6-methyl-2-oxo-4-p-tolyl-1,2,5,6-tetrahydropyridine-3-carbonitrile

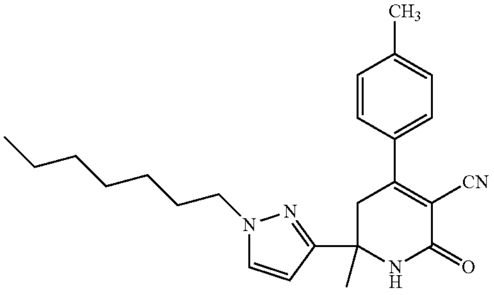 [SMILES: CCCCCCCn1ccc(C2(C)CC(c3ccc(C)cc3)=C(C#N)C(=O)N2)n1]

Intermediate 109A. 5-Cyano-N-methoxy-N,2-dimethyl-6-oxo-4-p-tolyl-1,2,3,6-tetrahydropyridine-2-carboxamide

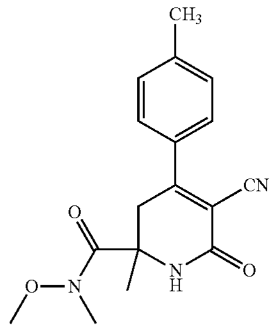 [SMILES: CON(C)C(=O)C1(C)CC(c2ccc(C)cc2)=C(C#N)C(=O)N1]

Intermediate 108C (0.25 g, 0.925 mmol) was dissolved in DCM (15 mL) in a 25 mL 1 neck rb flask that was equipped with a magnetic stirrer and an Ar inlet. N,O-Dimethylhydroxylamine (0.062 g, 1.017 mmol), EDC (0.195 g, 1.017 mmol) and N-methylmorpholine (0.112 mL, 1.017 mmol) were added and the reaction mixture was stirred at rt overnight. The reaction solvent was removed under vacuum. The residue was dissolved in EtOAc (10 mL) and washed with water (5 mL). The organic phaase was dried over $MgSO_4$ and concentrated in vacuo to a dark solid. The crude product was purified by silica gel chromatography (40 g silica gel, eluted with 0-100% EtOAc in hexanes) to give the desired product (0089 g, 31%) as a white solid. LCMS Anal. Calc'd for $C_{17}H_{19}N_3O_3$ 313.3, found [M+H] 314.1. $^1$H NMR (500 MHz, $CDCl_3$) δ 7.67 (d, J=8.3 Hz, 2H), 7.30 (d, J=8.0 Hz, 2H), 3.81 (s, 3H), 3.69-3.75 (m, 1H), 3.22 (s, 3H), 2.72 (d, J=17.6 Hz, 1H), 2.42 (s, 3H), 1.63 (s, 3H).

Intermediate 109B. 6-Methyl-2-oxo-6-propioloyl-4-p-tolyl-1,2,5,6-tetrahydropyridine-3-carbonitrile

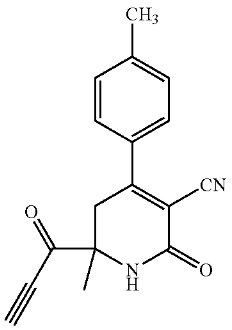 [SMILES: C#CC(=O)C1(C)CC(c2ccc(C)cc2)=C(C#N)C(=O)N1]

Intermediate 109A (0.0887 g, 0.283 mmol) was dissolved in tetrahydrofuran (1 mL) in a 25 mL 1 neck pear shaped flask that was equipped with a magnetic stirrer and an Ar inlet. Ethynylmagnesium bromide (5.66 mL, 2.83 mmol) was added dropwise and the reaction mixture was stirred at 35° C. for 4 h. The reaction mixture was cooled to rt, quenched with sat'd. aq $NH_4Cl$ (5 mL) and extracted with EtOAc (2×10 mL). The organic phases were combined and concentrated in vacuo. The residue was purified by silica gel chromatography (24 g silica gel, eluted with 0-100% EtOAc in hexanes) to give the desired product (0.06 g, 78%) as an orange solid. LCMS Anal. Calc'd for $C_{17}H_{14}N_2O_2$ 278.1, found [M+H] 279.0.

Example 109

Intermediate 109B (0.0613 g, 0.220 mmol) was dissolved in ethanol (3 mL) in a 25 mL 1 neck pear shaped flask that was equipped with a magnetic stirrer. Heptylhydrazine, HCl (0.073 g, 0.441 mmol) and TEA (0.061 mL, 0.441 mmol) were added and the reaction mixture was stirred at rt overnight. The reaction mixture was concentrated and purified by preparative HPLC (MeOH/$H_2O$/TFA) to yield the desired product (3.2 mg, 4%) as a white solid. LCMS Anal. Calc'd for $C_{24}H_{30}N_4O$ 390.2, found [M+H] 391.2. $^1H$ NMR (500 MHz, $CDCl_3$) δ 7.55 (d, J=8.3 Hz, 2H), 7.25-7.30 (m, 2H), 6.35 (s, 1H), 6.15 (d, J=1.7 Hz, 1H), 3.98-4.08 (m, 2H), 3.57 (d, J=17.9 Hz, 1H), 3.01 (d, J=17.9 Hz, 1H), 2.41 (s, 3H), 1.81 (quin, J=7.3 Hz, 2H), 1.70-1.77 (m, 2H), 1.68 (s, 3H), 1.16-1.34 (m, 6H), 0.87 (t, J=7.0 Hz, 3H).

Examples 110-273 expressed by Formula (II), unless noted in the table, may be made by one skilled in the art by appropriate application of the procedures described for Examples 1-16 and Examples 102-. $R^{11}$ to $R^{15}$ are hydrogen, unless noted in the table.

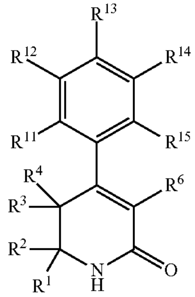
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 110 S-isomer | 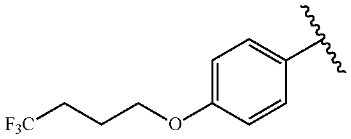 [SMILES: *c1ccc(OCCCC(F)(F)F)cc1] | $CF_3$ | H | 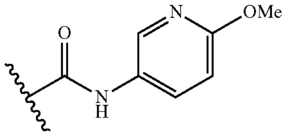 [SMILES: *C(=O)Nc1ccc(OC)nc1] | $R^{13} = CH_3$ | 608.1 | 8.13 (d, J = 2.5 Hz, 1H), 7.93 (dd, J = 9.1, 2.8 Hz, 1H), 7.46 (d, J = 9.1 Hz, 2H), 7.22 (s, 1H), 7.20-7.15 (m, 2H), 7.13-7.08 (m, 2H), 6.94 (d, J = 9.1 Hz, 2H), 6.67 (d, J = 9.1 Hz, 1H), 4.02 (t, J = 5.9 Hz, 2H), 3.90 (br. s., 3H), 3.56-3.38 (m, 2H), 2.39-2.25 (m, 5H), 2.10-2.01 (m, 2H). |
| 111 S-isomer | 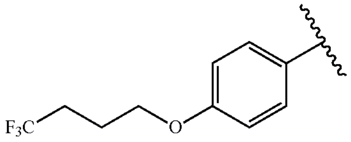 | $CF_3$ | H | 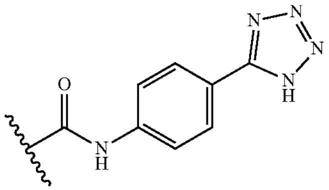 [SMILES: *C(=O)Nc1ccc(-c2nnn[nH]2)cc1] | $R^{13} = CH_3$ | 645.2 | 7.88 (d, J = 8.5 Hz, 2H), 7.60 (d, J = 8.8 Hz, 2H), 7.54 (d, J = 8.5 Hz, 2H), 7.29 (d, J = 8.0 Hz, 2H), 7.16 (d, J = 7.7 Hz, 2H), 7.00 (d, J = 8.8 Hz, 2H), 4.07 (t, J = 5.9 Hz, 2H), 3.75-3.46 (m, 2H), 2.43-2.32 (m, 2H), 2.29 (s, 3H), 2.11-1.97 (m, 2H). |
| 112 Rac | 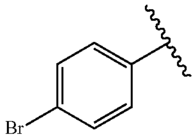 | $CF_3$ | H | 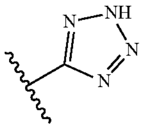 | $R^{13} = CH_3$ | 480.0 | |

-continued
(II)
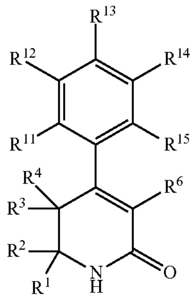
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 113 S-isomer | 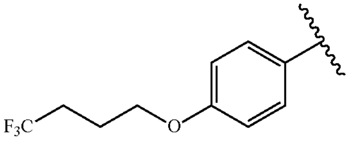 | $CF_3$ | H | 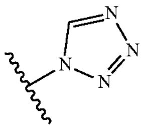 [SMILES: *n1cnnn1] | $R^{13} = CH_3$ | 526.1 | 9.07 (d, J = 1.1 Hz, 1H), 7.63 (d, J = 8.5 Hz, 2H), 7.16-7.09 (m, J = 8.0 Hz, 2H), 7.09-7.03 (m, 2H), 6.93-6.86 (d, J = 7.7 Hz, 2H), 4.12 (t, J = 6.1 Hz, 2H), 4.00 (s, 1H), 3.92 (d, J = 17.6 Hz, 1H), 3.77 (d, J = 17.6 Hz, 1H), 2.46-2.34 (m, 2H), 2.30 (s, 3H), 2.12-2.02 (m, 2H). |
| 114 S-isomer | 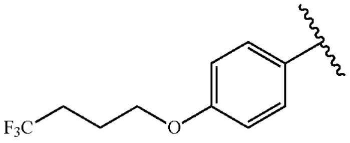 | $CF_3$ | H | 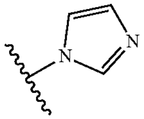 [SMILES: *n1ccnc1] | $R^{13} = CH_3$ | 524.1 | |
| 115 S-isomer | 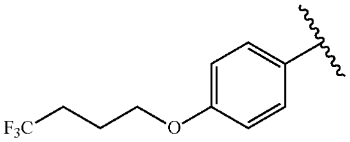 [SMILES: *c1ccc(OCCCC(F)(F)F)cc1] | $CF_3$ | H | 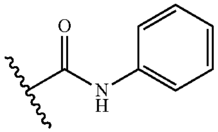 [SMILES: *C(=O)Nc1ccccc1] | $R^{13} = CH_3$ | 577.2 | |
| 116 Rac | 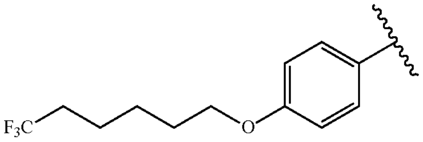 [SMILES: *c1ccc(OCCCCCC(F)(F)F)cc1] | $CF_3$ | H | 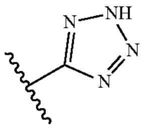 [SMILES: *c1nn[nH]n1] | $R^{13} = CH_3$ | 554.2 | 7.42 (d, J = 8.5 Hz, 2H), 7.16 (d, J = 8.0 Hz, 2H), 7.10 (br. s., 1H), 6.95 (dd, J = 15.0, 8.4 Hz, 4H), 3.97 (t, J = 6.3 Hz, 2H), 3.59 (d, J = 5.5 Hz, 2H), 2.36 (s, 3H), 2.16-2.04 (m, 2H), 1.86-1.77 (m, 2H), 1.69-1.59 (m, |

-continued
(II)
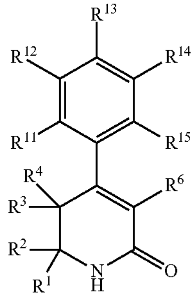
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2H), 1.59-1.50 (m, 2H), 0.93-0.79 (m, 3H) |
| 117 Rac | 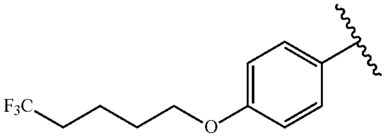 [SMILES: *c1ccc(OCCCCC(F)(F)F)cc1] | $CF_3$ | H | 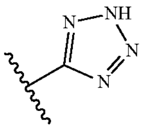 [SMILES: *c1nn[nH]n1] | $R^{13} = CH_3$ | 540.1 | 7.43 (d, J = 8.5 Hz, 2H), 7.17 (d J = 7.7 Hz, 2H), 7.03-6.91 (m, 5H), 3.99 (t, J = 5.9 Hz, 2H), 3.65-3.53 (m, 2H), 2.37 (s, 3H), 2.23-2.11 (m, 2H), 1.92-1.82 (m, 2H), 1.82-1.72 (m, 2H) |
| 118 Rac | 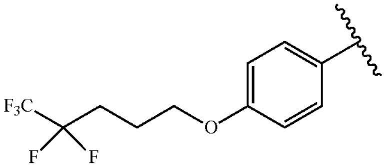 [SMILES: *c1ccc(OCCCC(F)(F)C(F)(F)F)cc1] | $CF_3$ | H | 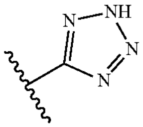 | $R^{13} = CH_3$ | 576.1 | 7.44 (d, J = 8.5 Hz, 2H), 7.17 (d, J = 8.0 Hz, 2H), 6.96 (dd, J = 11.4, 8.7 Hz, 4H), 6.80 (br. s., 1H), 4.07-4.01 (m, 2H), 3.59 (d, J = 7.4 Hz, 2H), 2.37 (s, 3H), 2.33-2.19 (m, 2H), 2.10 (dd, J = 9.5, 5.6 Hz, 2H) |
| 119 S-isomer | 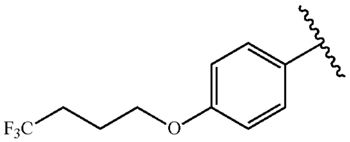 [SMILES: *c1ccc(OCCCC(F)(F)F)cc1] | $CF_3$ | H | 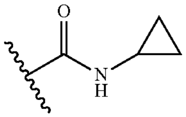 [SMILES: *C(=O)NC1CC1] | $R^{13} = CH_3$ | 541.2 | 7.44 (d, J = 8.3 Hz, 2H), 7.21-7.16 (m, 2H), 7.14-7.09 (m, 2H), 6.96 (d, J = 8.8 Hz, 2H), 4.06 (t, J = 5.9 Hz, 3H), 3.58-3.27 (m, 2H), 2.48-2.27 (m, 5H), 2.09 (dd, J = 9.5, 5.9 Hz, 2H), 0.97-0.80 (m, 2H), 0.75-0.61 (m, 2H), 0.38 (d, J = 3.6 Hz, 2H) |

-continued
(II)
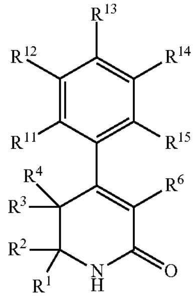
| Example | $R^1$ | $R^2$ | $R^3 = R^4$ | $R^6$ | $R^{11}$-$R^{15}$ | [M + H] | $^1$HNMR (400 MHz, $CDCl_3$) |
| --- | --- | --- | --- | --- | --- | --- | --- |
| 120 S-isomer | 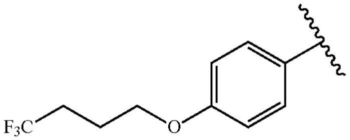 | $CF_3$ | H | 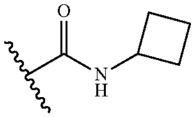 [SMILES: *C(=O)NC1CCC1] | $R^{13} = CH_3$ | 555.2 | 7.43 (d, J = 8.5 Hz, 2H), 7.20-7.03 (m, 5H), 6.97-6.88 (m, 2H), 4.36-4.22 (m, 1H), 4.08-3.98 (m, 2H), 3.53-3.27 (m, 2H), 2.44-2.16 (m, 8H), 2.12-2.02 (m, 2H), 1.78-1.51 (m, 4H) |
| 121 S-isomer | 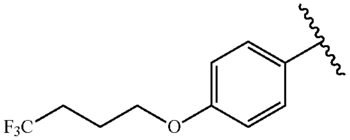 | $CF_3$ | H | 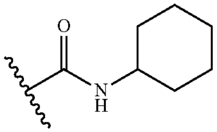 [SMILES: *C(=O)NC1CCCCC1] | $R^{13} = CH_3$ | 583.3 | 7.49-7.37 (m, 2H), 7.22-7.07 (m, 4H), 6.97-6.84 (m, 3H), 6.74 (d, J = 8.0 Hz, 1H), 4.10-3.95 (m, 3H), 3.77-3.62 (m, 1H), 3.52-3.26 (m, 2H), 2.42-2.25 (m, 6H), 2.15-1.96 (m, 3H), 1.86-1.64 (m, 2H), 1.64-1.44 (m, 4H), 1.35-1.16 (m, 3H), 1.14-0.93 (m, 4H) |
| 122 S-isomer | 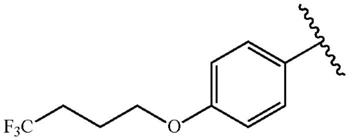 | $CF_3$ | H | 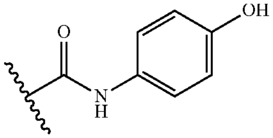 [SMILES: *C(=O)Nc1ccc(O)cc1] | $R^{13} = CH_3$ | 593.3 | 7.55 (d, J = 8.5 Hz, 2H), 7.32 (d, J = 8.3 Hz, 2H), 7.20 (d, J = 8.0 Hz, 2H), 7.14-7.09 (d, J = 8.8 Hz, 2H), 7.02-6.97 (d, J = 8.8 Hz, 2H), 6.68-6.62 (m, 2H), 4.08 (t, J = 6.1 Hz, 2H), 3.67 (d, J = 17.1 Hz, 1H), 3.51 (d, J = 17.1 Hz, 1H), 2.45-2.35 (m, 2H), 2.34 (s, 3H), 2.09-2.00 (m, 2H). |

-continued
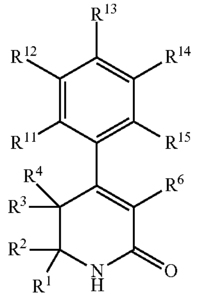
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 123 S-isomer | 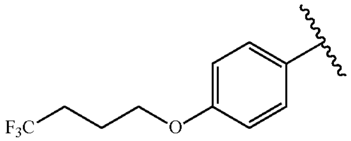 | $CF_3$ | H | 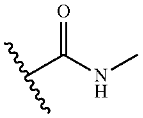 [SMILES: *C(=O)NC] | $R^{13} = CH_3$ | 515.2 | 7.57-7.50 (m, J = 8.8 Hz, 2H), 7.27-7.23 (m, J = 8.3 Hz, 2H), 7.23-7.19 (m, J = 8.3 Hz, 2H), 7.02-6.97 (m, J = 9.1 Hz, 2H), 4.08 (t, J = 6.1 Hz, 2H), 3.60 (d, J = 17.1 Hz, 1H), 3.46 (d, J = 17.1 Hz, 1H), 2.57 (s, 3H), 2.45-2.37 (m, 2H), 2.36 (s, 3H), 2.11-1.99 (m, 2H). |
| 124 Rac | 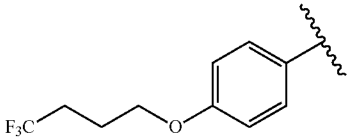 | $CF_3$ | F | 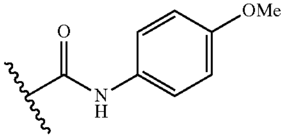 [SMILES: *C(=O)Nc1ccc(OC)cc1] | $R^{13} = CH_3$ | 643.3 | 7.90 (s, 1H), 7.62 (d, J = 8.8 Hz, 2H), 7.25-7.17 (m, 6H), 6.98 (d, J = 8.8 Hz, 2H), 6.95 (br. s., 1H), 6.78 (d, J = 9.1 Hz, 2H), 4.05 (t, J = 5.9 Hz, 2H), 3.81-3.71 (m, 3H), 2.44-2.27 (m, 5H), 2.13-2.03 (m, 2H) |
| 125 Rac | 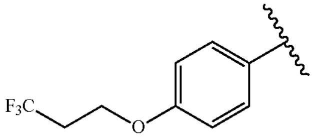 [SMILES: *c1ccc(OCCC(F)(F)F)cc1] | $CF_3$ | H | 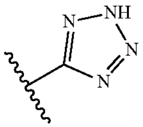 [SMILES: *c1nn[nH]n1] | $R^{13} = CH_3$ | 512.1 | 7.45 (d, J = 8.5 Hz, 3H), 7.13 (d, J = 7.7 Hz, 2H), 6.93 (d, J = 7.7 Hz, 4H), 4.18 (t, J = 6.5 Hz, 2H), 3.68-3.52 (m, 2H), 2.67-2.56 (m, 2H) |
| 126 Rac | 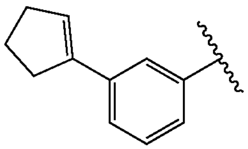 [SMILES: *c1cccc(C2=CCCC2)c1] | $CF_3$ | H | 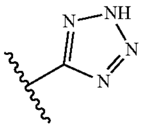 [SMILES: *c1nn[nH]n1] | $R^{13} = CH_3$ | 466.2 | |

-continued
(II)
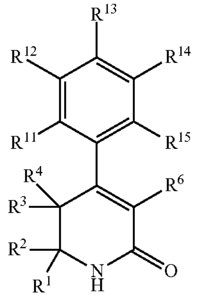
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 127 Rac | 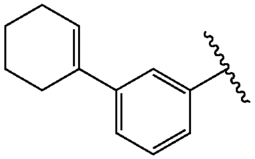 [SMILES: *c1cccc(C2=CCCCC2)c1] | $CF_3$ | H | 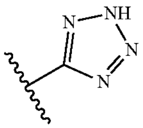 | $R^{13} = CH_3$ | 480.1 | 7.50-7.40 (m, 4H), 7.16 (d, J = 7.7 Hz, 2H), 7.09 (br. s., 1H), 6.98 (d, J = 7.7 Hz, 2H), 6.17 (br. s., 1H), 2.36 (s, 5H), 2.21 (d, J = 3.6 Hz, 2H), 1.82-1.74 (m, 2H), 1.70-1.62 (m, 2H) |
| 128 S-isomer | 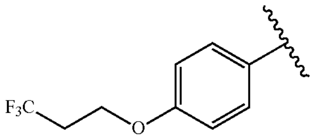 [SMILES: *c1ccc(OCCC(F)(F)F)cc1] | $CF_3$ | H | 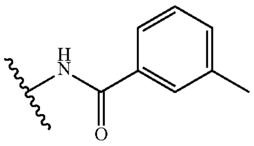 [SMILES: *NC(=O)c1cccc(C)c1] | $R^{13} = CH_3$ | 591.3 | |
| 129 S-isomer | 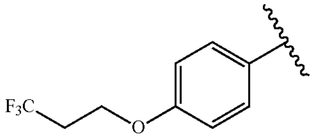 [SMILES: *c1ccc(OCCC(F)(F)F)cc1] | $CF_3$ | H | 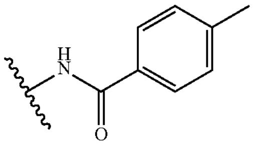 [SMILES: *NC(=O)c1ccc(C)cc1] | $R^{13} = CH_3$ | 591.3 | |
| 130 S-isomer | 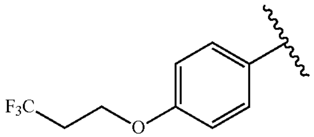 [SMILES: *c1ccc(OCCC(F)(F)F)cc1] | $CF_3$ | H | 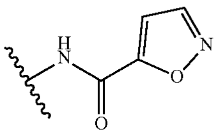 [SMILES: *NC(=O)c1ccno1] | $R^{13} = CH_3$ | 568.2 | 8.47 (d, J = 1.9 Hz, 1H), 7.61-7.54 (ab quartet, J = 8.8 Hz, 2H), 7.24-7.20 (ab quartet, J = 8.3 Hz, 2H), 7.19-7.15 (ab quartet, J = 8.3 Hz, 2H), 7.04-6.98 (m, 2H), 6.93-6.87 (m, 1H), 4.09 (t, J = 6.1 Hz, 2H), 3.75 (d, J = 17.1 Hz, 1H), 3.51 (d, J = 16.8 Hz, 1H), 2.46-2.34 |

-continued
| | | | | | | | |
|---|---|---|---|---|---|---|---|
| | 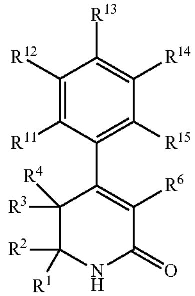 | | | | | | (II) |
| Example | $R^1$ | $R^2$ | $R^3 = R^4$ | $R^6$ | $R^{11}$-$R^{15}$ | [M + H] | $^1$HNMR (400 MHz, $CDCl_3$) |
| | | | | | | | (m, 2H), 2.32 (s, 3H), 2.12-2.01 (m, 3H). |
| 131 S-isomer | 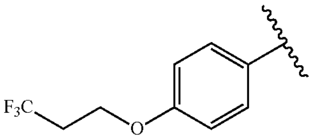 [SMILES: *c1ccc(OCCC(F)(F)F)cc1] | $CF_3$ | H | 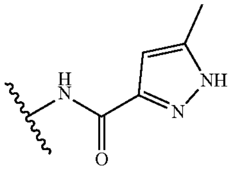 [SMILES: *NC(=O)c1cc(C)[nH]n1] | $R^{13} = CH_3$ | 581.3 | |
| 132 S-isomer | 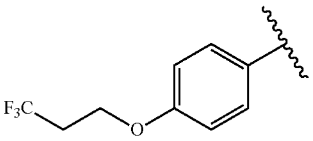 [SMILES: *c1ccc(OCCC(F)(F)F)cc1] | $CF_3$ | H | 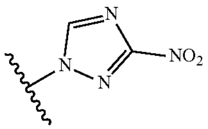 [SMILES: *n1cnc([N+](=O)[O-])n1] | $R^{13} = CH_3$ | 570.2 | |
| 133 Rac | 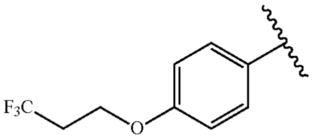 [SMILES: *c1ccc(OCCC(F)(F)F)cc1] | $CF_3$ | F | 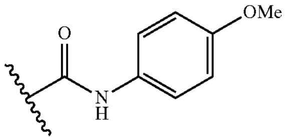 [SMILES: *C(=O)Nc1ccc(OC)cc1] | $R^{13} = CH_3$ | 643.1 | 8.07 (br. s., 1H), 7.63 (d, J = 8.8 Hz, 2H), 7.24-7.15 (m, 6H), 6.96 (d, J = 9.1 Hz, 2H), 6.76 (d, J = 8.8 Hz, 2H), 4.09-3.97 (m, 2H), 3.75 (s, 3H), 2.39-2.25 (m, 5H), 2.12-2.02 (m, 2H) |

-continued
(II)
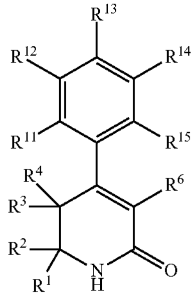
| Example | $R^1$ | $R^2$ | $R^3 = R^4$ | $R^6$ | $R^{11}$-$R^{15}$ | [M + H] $^1$HNMR (400 MHz, $CDCl_3$) |
| --- | --- | --- | --- | --- | --- | --- |
| 134 Rac | 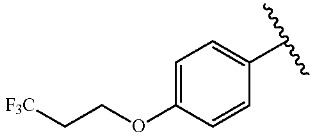 [SMILES: *c1ccc(OCCC(F)(F)F)cc1] | $CF_3$ | F | 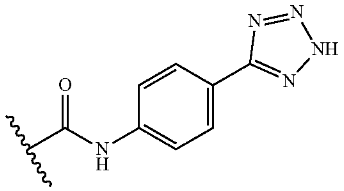 [SMILES: *C(=O)Nc1ccc(-c2nn[nH]n2)cc1] | $R^{13} = CH_3$ | 680.9 |
| 135 Rac | 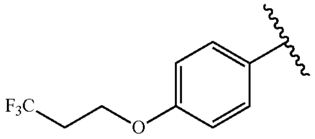 [SMILES: *c1ccc(OCCC(F)(F)F)cc1] | $CF_3$ | F | 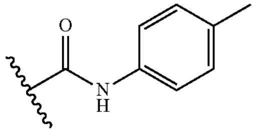 [SMILES: *C(=O)Nc1ccc(C)cc1] | $R^{13} = CH_3$ | 626.9 |
| 136 S-isomer | 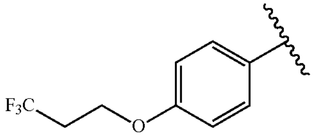 [SMILES: *c1ccc(OCCC(F)(F)F)cc1] | $CF_3$ | H | 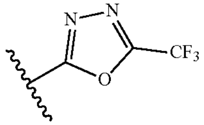 [SMILES: *c1nnc(C(F)(F)F)o1] | $R^{13} = CH_3$ | 594.1 |
| 137 S-isomer | 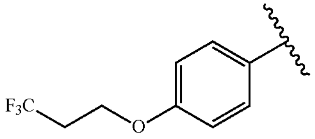 [SMILES: *c1ccc(OCCC(F)(F)F)cc1] | $CF_3$ | H | 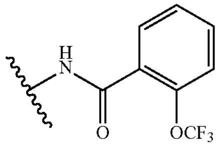 | $R^{13} = CH_3$ | 661.1 |

-continued
(II)
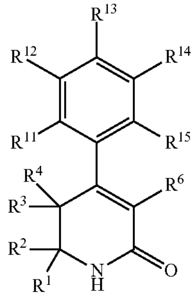
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 138 Rac | 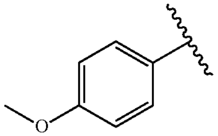 [SMILES: *c1ccc(OC)cc1] | $CF_3$ | F | CN | $R^{13} = CH_3$ | 422.8 | |
| 140 Rac | 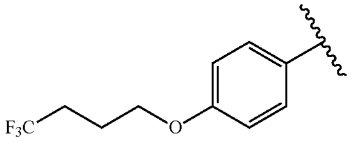 | $CF_3$ | F | 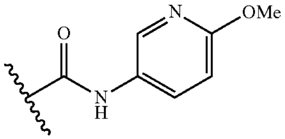 [SMILES: *C(=O)Nc1ccc(OC)nc1] | $R^{13} = CH_3$ | 643.9 | |
| 141 Rac | 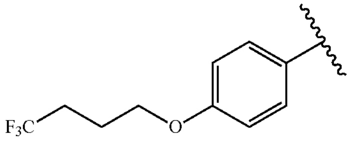 | $CF_3$ | F | 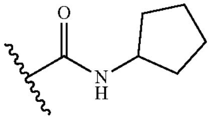 [SMILES: *C(=O)NC1CCCC1] | $R^{13} = CH_3$ | 604.9 | |
| 142 S-isomer | 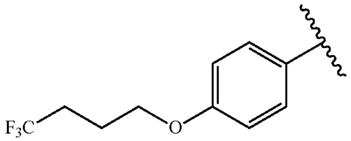 [SMILES: *c1ccc(OCCCC(F)(F)F)cc1] | $CF_3$ | H | 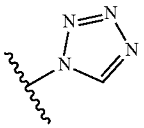 | $R^{11} = F$ $R^{13} = OCH_3$ | 560.1 | 9.17 (s, 1H), 7.59 (d, J = 8.8 Hz, 2H), 7.07-7.00 (m, 2H), 6.95 (t, J = 8.5 Hz, 1H), 6.69 (dd, J = 8.8, 2.5 Hz, 1H), 6.63 (dd, J = 12.7, 2.5 Hz, 1H), 4.09 (t, J = 6.1 Hz, 2H), 3.90-3.81 (m, 1H), 3.76 (s, 3H), 3.74-3.66 (m, 1H), 2.47-2.30 (m, 2H), 2.12-1.94 (m, 2H). |

-continued
(II)
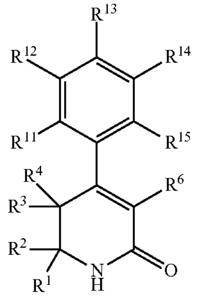
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 143 S-isomer | 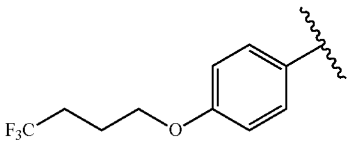 [SMILES: *c1ccc(OCCCC(F)(F)F)cc1] | $CF_3$ | H | 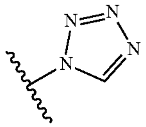 [SMILES: *n1cnnn1] | $R^{13} = OCH_3$ | 542.1 | 9.05 (s, 1H), 7.60 (d, J = 8.8 Hz, 2H), 7.04 (d, J = 9.1 Hz, 2H), 6.97-6.88 (m, 1H), 6.86-6.76 (m, 1H), 4.09 (t, J = 6.1 Hz, 2H), 3.92-3.70 (m, 2H), 3.75 (S, 3H), 2.45-2.29 (m, 2H), 2.10-1.94 (m, 2H). |
| 144 S-isomer | 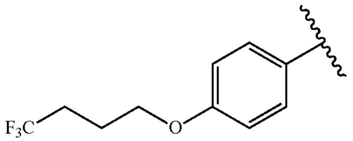 | $CF_3$ | H | CN | $R^{13} = OCHF_2$ | 535.1 | 7.65 (br. s., 2H), 7.53 (d, J = 9.1 Hz, 2H), 7.32-7.24 (m, 2H), 7.05-6.98 (m, 2H), 6.96 (t, J = 75 Hz, 1H), 4.14-3.97 (m, 2H), 3.73 (d, J = 3.3 Hz, 2H), 2.42-2.27 (m, 2H), 2.09-1.96 (m, 2H). |
| 145 S-isomer | 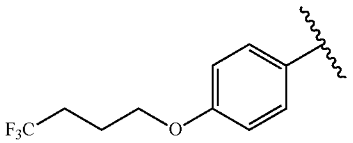 | $CF_3$ | H | CN | $R^{13} = OCH_2CH_3$ | 513.1 | 7.64 (d, J = 9.1 Hz, 2H), 7.52 (d, J = 9.1 Hz, 2H), 7.03 (d, J = 9.1 Hz, 4H), 4.12 (d, J = 6.9 Hz, 2H), 4.08-4.03 (m, 2H), 3.82-3.58 (m, 2H), 2.45-2.26 (m, 2H), 2.08-1.95 (m, 2H), 1.41 (t, J = 6.9 Hz, 3H). |
| 146 S-isomer | 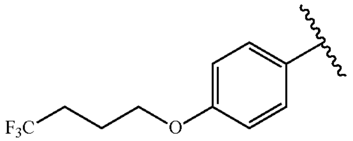 | $CF_3$ | H | CN | $R^{12}$ and $R^{13}$ 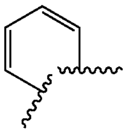 | 519.1 | 8.15 (d, J = 1.7 Hz, 1H), 8.01-7.96 (m, 2H), 7.93 (d, J = 8.0 Hz, 1H), 7.67-7.54 (m, 5H), 7.06-7.00 (m, 2H), 4.08 (s, 2H), 3.93-3.77 (m, 2H), 2.48-2.25 (m, 2H), 2.13-1.92 (m, 2H). |

-continued
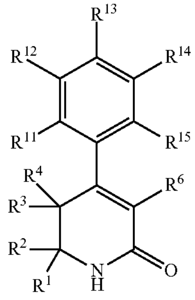
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 147<br>S-isomer | 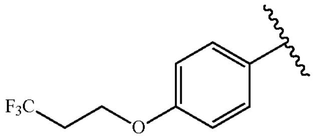 [SMILES: *c1ccc(OCCC(F)(F)F)cc1] | $CF_3$ | H | CN | $R^{13} = CH_3$ | 469.1 | 7.55 (d, J = 8.8 Hz, 2H), 7.52-7.49 (m, 2H), 7.33 (d, J = 8.0 Hz, 2H), 7.04-6.99 (m, 2H), 4.24 (t, J = 6.1 Hz, 2H), 3.77-3.66 (m, 2H), 2.75-2.63 (m, 2H), 2.41 (s, 3H). |
| 148<br>S-isomer | 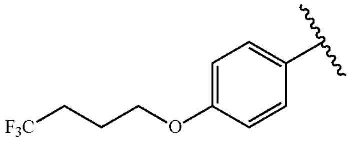 | $CF_3$ | H | 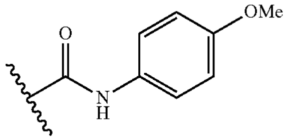 [SMILES: *C(=O)Nc1ccc(OC)cc1] | $R^{11} = CH_3$<br>$R^{13} = CH_3$ | 621.2 | 7.49-7.41 (m, 2H), 7.35 (d, J = 8.0 Hz, 2H), 7.03-6.65 (m, 7H), 4.07-3.99 (m, 2H), 3.71 (s, 3H), 3.51-3.42 (m, 1H), 3.28-3.14 (m, 1H), 2.38-2.21 (m, 8H), 2.11-1.99 (m, 2H). |
| 149<br>S-isomer | 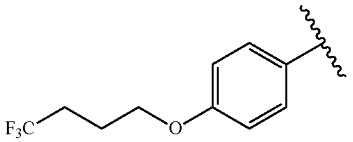 | $CF_3$ | H | 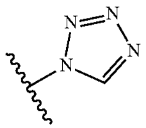 [SMILES: *n1cnnn1] | $R^{13} = OCHF_2$ | 578.1 | □□9.09 (s, 1H), 7.61 (d, J = 8.8 Hz, 2H), 7.08-7.03 (m, 6H), 6.97-6.68 (m, 1H), 4.09 (t, J = 6.1 Hz, 2H), 3.92 (d, J = 17.9 Hz, 1H), 3.77 (d, J = 17.9 Hz, 1H), 2.43-2.31 (m, 2H), 2.10-1.98 (m, 2H). |
| 150<br>S-isomer | 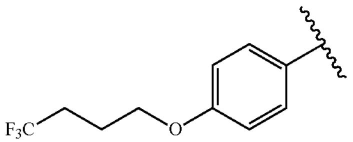 | $CF_3$ | F | 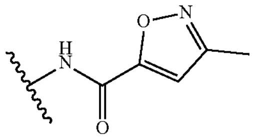 [SMILES: *NC(=O)c1cc(C)no1] | $R^{13} = CH_3$ | 582.2 | 7.54 (d, J = 8.8 Hz, 2H), 7.23-7.11 (m, 4H), 7.03-6.94 (m, 2H), 6.71 (s, 1H), 4.06 (t, J = 6.1 Hz, 2H), 3.98 (s, 1H), 3.71 (d, J = 17.1 Hz, 1H), 3.47 (d, J = 16.8 Hz, 1H), 2.45-2.31 (m, 2H), 2.29 (d, J = 6.3 Hz, 6H), 2.12-1.96 (m, 2H). |

-continued
(II)
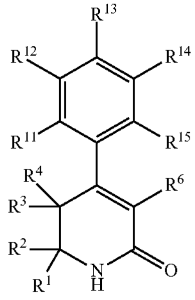
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 151 S-isomer | 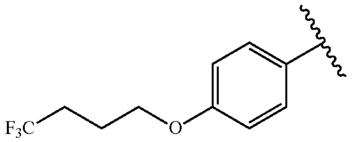 [SMILES: *c1ccc(OCCCC(F)(F)F)cc1] | $CF_3$ | H | 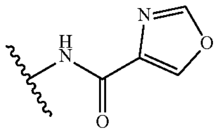 [SMILES: *NC(=O)c1cocn1] | $R^{13} = CH_3$ | 568.2 | |
| 152 S-isomer | 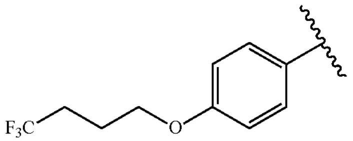 | $CF_3$ | H | 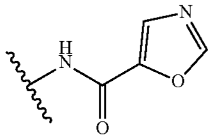 [SMILES: *NC(=O)c1cnco1] | $R^{13} = CH_3$ | 568.2 | |
| 153 S-isomer | 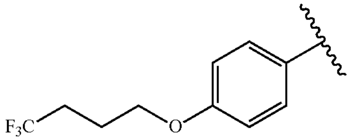 | $CF_3$ | H | 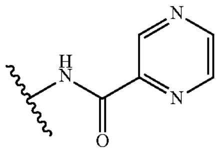 [SMILES: *NC(=O)c1cnccn1] | $R^{13} = CH_3$ | 579.2 | |
| 154 S-isomer | 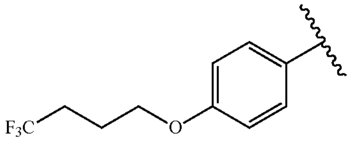 | $CF_3$ | H | 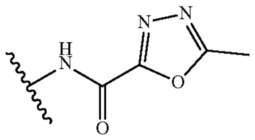 [SMILES: *NC(=O)c1nnc(C)o1] | $R^{13} = CH_3$ | 583.1 | 7.58-7.49 (ab quartet, J = 8.8 Hz, 2H), 7.20 (d, J = 8.3 Hz, 2H), 7.15 (d, J = 8.3 Hz, 2H), 7.03-6.92 (m, 2H), 4.06 (t, J = 6.1 Hz, 2H), 3.72 (d, J = 17.3 Hz, 1H), 3.49 (d, J = 17.1 Hz, 1H), 2.55 (s, 3H), 2.43-2.33 (m, 2H), 2.30 (s, 3H), 2.09-1.97 (m, 2H). |

-continued
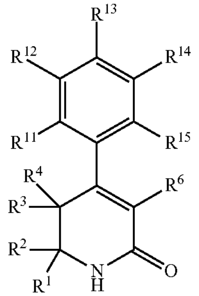
(II)
| Example | $R^1$ | $R^2$ | $R^3 = R^4$ | $R^6$ | $R^{11}$-$R^{15}$ | [M + H] $^1$HNMR (400 MHz, $CDCl_3$) |
|---|---|---|---|---|---|---|
| 155 Rac | 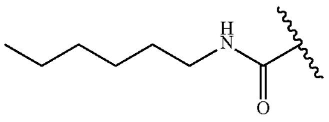 [SMILES: *C(=O)NCCCCCC] | $CH_3$ | H | 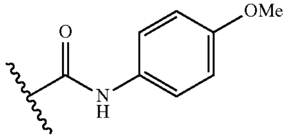 [SMILES: *C(=O)Nc1ccc(OC)cc1] | $R^{13} = CH_3$ | 478.4 |
| 156 S-isomer | 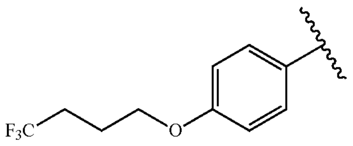 | $CF_3$ | H | 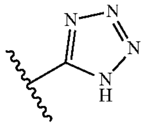 | $R^{11} = CH_3$<br>$R^{13} = CH_3$ | 540.1 |
| 157 S-isomer | 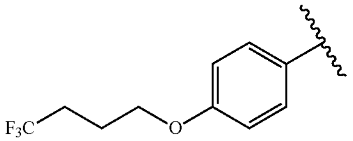 | $CF_3$ | H | 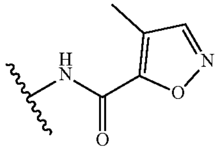 [SMILES: *NC(=O)c1oncc1C] | $R^{13} = CH_3$ | 582.2 |
| 158 S-isomer | 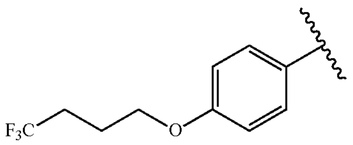 | $CF_3$ | H | 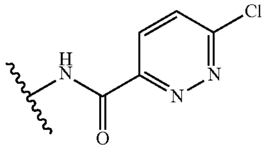 [SMILES: *NC(=O)c1ccc(Cl)nn1] | $R^{13} = CH_3$ | 613.2 |

-continued
(II)
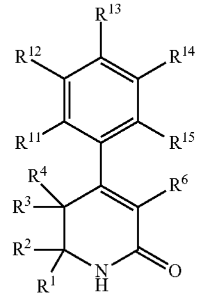
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 159 Rac | 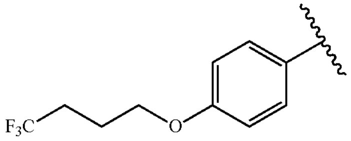 | $CF_3$ | F | 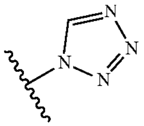 | $R^{13} = CH_3$ | 562.2 | |
| 160 Rac | 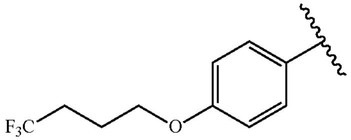 | $CF_3$ | F | CN | $R^{13} = CH_3$ | 519.2 | |
| 161 Rac | 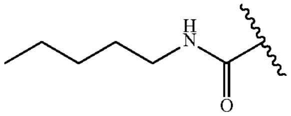 [SMILES: *C(=O)NCCCCC] | $CH_3$ | H | 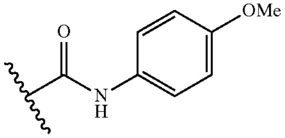 [SMILES: *C(=O)Nc1ccc(OC)cc1] | $R^{13} = CH_3$ | 464.3 | |
| 162 Rac | 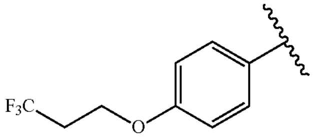 [SMILES: *c1ccc(OCCC(F)(F)F)cc1] | $CF_3$ | F | 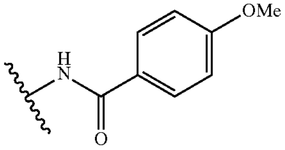 [SMILES: *NC(=O)c1ccc(OC)cc1] | $R^{13} = CH_3$ | 628.9 | |

-continued
(II)
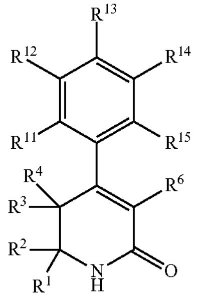
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 163 Rac | 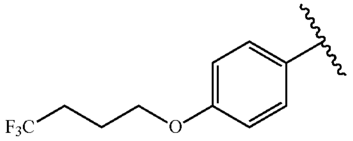 | $CF_3$ | F | 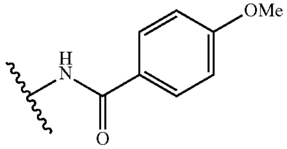 [SMILES: *NC(=O)c1ccc(OC)cc1] | $R^{13} = CH_3$ | 656.9 | 8.05 (s, 1H), 7.61 (d, J = 8.8 Hz, 2H), 7.25-7.16 (m, 6H), 7.02-6.94 (m, 2H), 6.82-6.73 (m, 2H), 6.60 (br. s., 1H), 4.01 (td, J = 6.1, 1.4 Hz, 2H), 3.75 (s, 3H), 2.35 (s, 3H), 2.24-2.10 (m, 2H), 1.93-1.85 (m, 2H), 1.83-1.74 (m, 2H), 1.67 (br. s., 3H) |
| 164 Rac | 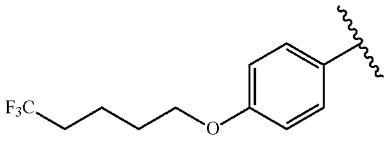 [SMILES: *c1ccc(OCCCCC(F)(F)F)cc1] | $CF_3$ | F | 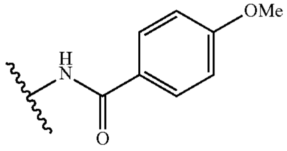 [SMILES: *NC(=O)c1ccc(OC)cc1] | $R^{13} = CH_3$ | 671.0 | |
| 165 S-isomer | 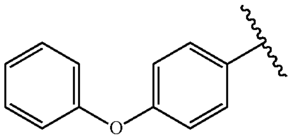 [SMILES: *c1ccc(Oc2ccccc2)cc1] | $CF_3$ | H | 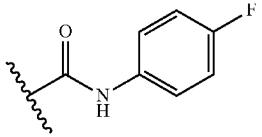 [SMILES: *C(=O)Nc1ccc(F)cc1] | $R^{13} = CH_3$ | 561.2 | 7.59 (d, J = 8.8 Hz, 2H), 7.42-7.36 (m, 2H), 7.35-0 7.28 (m, 4H), 7.20-7.16 (m, 3H), 7.06-6.99 (m, 4H), 6.98-6.93 (m, 2H), 3.66 (d, J = 17.3 Hz, 1H), 3.52 (d, J = 17.3 Hz, 1H), 2.30 (s, 3H). |
| 166 Rac | 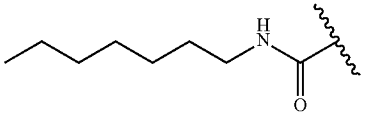 [SMILES: *C(=O)NCCCCCCC] | $CH_3$ | H | 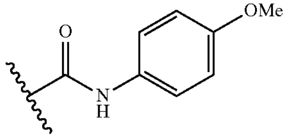 [SMILES: *C(=O)Nc1ccc(OC)cc1] | $R^{13} = CH_3$ | 492.2 | |

-continued
(II)
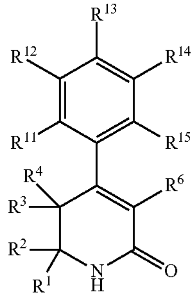
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 167 S-isomer | 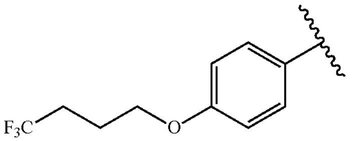 [SMILES: *c1ccc(OCCCC(F)(F)F)cc1] | $CF_3$ | H | 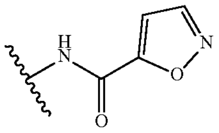 [SMILES: *NC(=O)c1ccno1] | $R^{13} = OHCF_2$ | 620.2 | 8.38 (d, J = 1.7 Hz, 1H), 7.61 (s, 1H), 7.51 (d, J = 8.8 Hz, 2H), 7.34-7.24 (m, 2H), 7.13-7.04 (ab quartet, J = 8.8 Hz, 2H), 6.99-6.92 (m, 2H), 6.86 (s, 1H), 4.26 (br. s., 1H), 4.05 (t, J = 5.9 Hz, 2H), 3.69 (d, J = 17.1 Hz, 1H), 3.42 (d, J = 17.1 Hz, 1H), 2.41-2.27 (m, 2H), 2.10-1.97 (m, 2H). |
| 168 S-isomer | 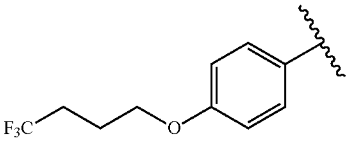 | $CF_3$ | H | 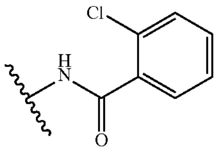 [SMILES: *NC(=O)c1ccccc1Cl] | $R^{13} = CH_3$ | 611.2 | |
| 169 S-isomer | 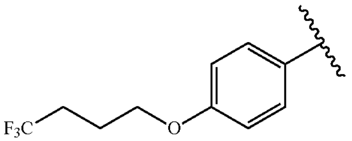 | $CF_3$ | H | 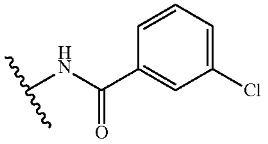 [SMILES: *NC(=O)c1cccc(Cl)c1] | $R^{13} = CH_3$ | 611.2 | |
| 170 S-isomer | 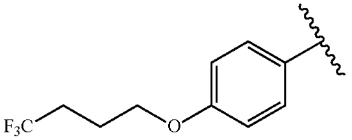 | $CF_3$ | H | 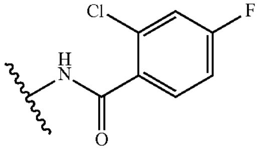 [SMILES: *NC(=O)c1ccc(F)cc1Cl] | $R^{13} = CH_3$ | 629.2 | |

-continued
(II)
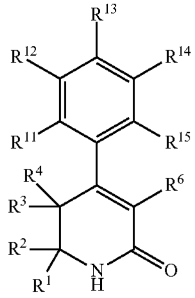
| Example | R[1] | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 171 S-isomer | 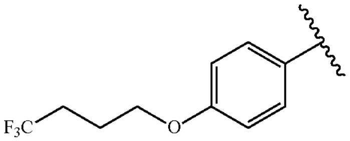 | $CF_3$ | H | 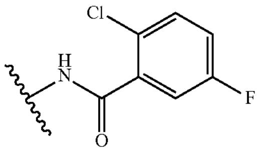 [SMILES: *NC(=O)c1cc(F)ccc1Cl] | $R^{13} = CH_3$ | 629.3 | |
| 172 S-isomer | 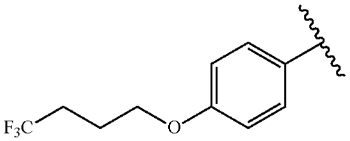 | $CF_3$ | H | 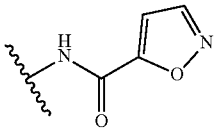 [SMILES: *NC(=O)c1ccno1] | $R^{13} = OCH_3$ | 584.2 | 8.37 (d, J = 1.7 Hz, 1H), 7.50 (d, J = 8.8 Hz, 2H), 7.28-7.17 (m, 2H), 6.99-6.91 (m, 2H), 6.89-6.82 (m, 3H), 4.05 (t, J = 6.1 Hz, 2H), 3.78 (s, 3H), 3.68 (d, J = 16.8 Hz, 1H), 3.42 (d, J = 17.1 Hz, 1H), 2.45-2.23 (m, 2H), 2.10-1.98 (m, 2H). |
| 173 Rac | 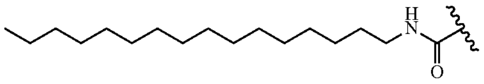 [SMILES: *C(=O)NCCCCCCCCCCCCCCCC] | $CH_3$ | H | 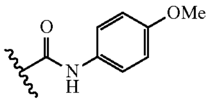 [SMILES: *C(=O)Nc1ccc(OC)cc1] | $R^{13} = CH_3$ | 618.4 | 7.34 (d, J = 8.0 Hz, 2H), 7.26 (d, J = 9.1 Hz, 2H), 7.15 (d, J = 8.0 Hz, 2H), 6.79 (d, J = 9.1 Hz, 2H), 3.76 (s, 3H), 3.43-3.37 (d, J = 17.5 Hz, 1H), 3.22 (t, J = 7.1 Hz, 2H), 2.86-2.80 (d, J = 17.2 Hz, 1H), 2.32 (s, 3H), 1.53 (s, 3H), 1.31-1.21 (m, 28H), 0.88 (t, J = 7.1 Hz, 3H) |

-continued
(II)
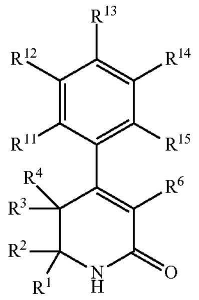
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 174 Rac | 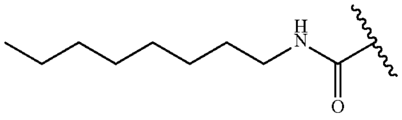 [SMILES: *C(=O)NCCCCCCCC] | $CH_3$ | H | 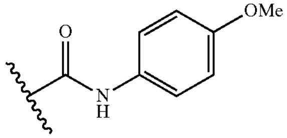 [SMILES: *C(=O)Nc1ccc(OC)cc1] | $R^{13} = CH_3$ | 506.4 | |
| 175 Rac | 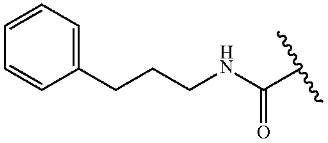 [SMILES: *C(=O)NCCCc1ccccc1] | $CH_3$ | H | 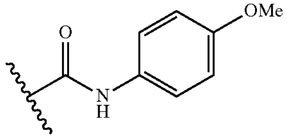 [SMILES: *C(=O)Nc1ccc(OC)cc1] | $R^{13} = CH_3$ | 512.4 | |
| 176 S-isomer | 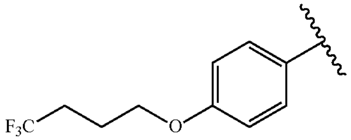 | $CF_3$ | H | 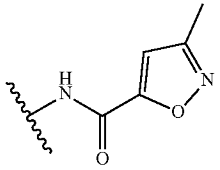 [SMILES: *NC(=O)c1cc(C)no1] | $R^{13} = OCH_3$ | 598.2 | 7.54 (d, J = 8.8 Hz, 2H), 7.32-7.23 (m, 2H), 6.97 (d, J = 8.8 Hz, 2H), 6.88 (d, J = 8.8 Hz, 2H), 6.73 (s, 1H), 4.06 (t, J = 6.1 Hz, 2H), 3.76 (s, 3H), 3.71 (d, J = 17.1 Hz, 1H), 3.49 (d, J = 17.1 Hz, 1H), 2.45-2.32 (m, 2H), 2.31-2.26 (m, 3H), 2.08-1.97 (m, 2H). |
| 177 Rac | 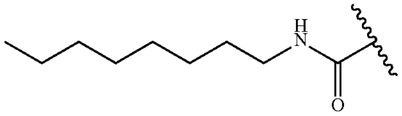 [SMILES: *C(=O)NCCCCCCCC] | $CH_3$ | H | CN | $R^{13} = CH_3$ | 382.3 | |

-continued
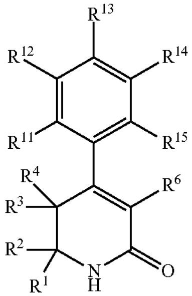
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 178 Rac | 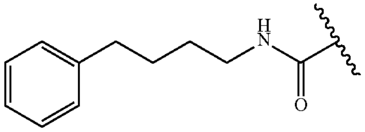 [SMILES: *C(=O)NCCCCc1ccccc1] | $CH_3$ | H | 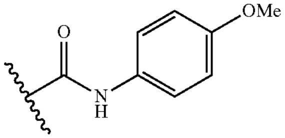 [SMILES: *C(=O)Nc1ccc(OC)cc1] | $R^{13} = CH_3$ | 526.4 | |
| 179 S-isomer | 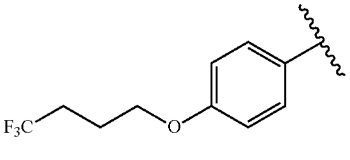 [SMILES: *c1ccc(OCCCC(F)(F)F)cc1] | $CF_3$ | H | 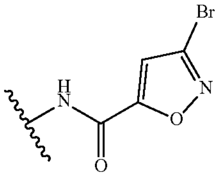 [SMILES: *NC(=O)c1cc(Br)no1] | $R^{13} = CH_3$ | 648.2 | 7.54 (d, J = 8.8 Hz, 2H), 7.23-7.11 (m, 4H), 7.03-6.93 (m, 3H), 4.06 (t, J = 6.1 Hz, 2H), 3.72 (d, J = 16.9 Hz, 1H), 3.48 (d, J = 17.2 Hz, 1H), 2.44-2.32 (m, 2H), 2.30 (s, 3H), 2.08-1.97 (m, 2H). |
| 180 S-isomer | 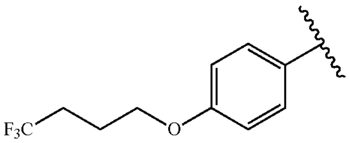 | $CF_3$ | H | 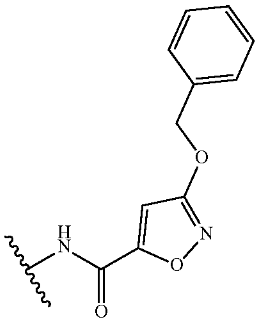 [SMILES: *NC(=O)c1cc(OCc2ccccc2)no1] | $R^{13} = CH_3$ | 674.3 | |

-continued
(II)
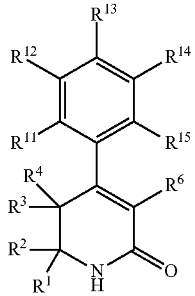
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 181 Rac | 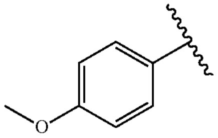 | $CF_3$ | F | 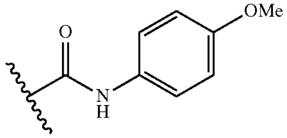 [SMILES: *C(=O)Nc1ccc(OC)cc1] | $R^{13} = CH_3$ | 547.0 | |
| 182 Rac | 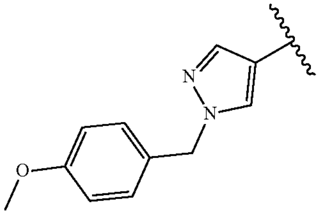 [SMILES: *c1cnn(Cc2ccc(OC)cc2)c1] | $CF_3$ | H | 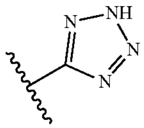 [SMILES: *c1nn[nH]n1] | $R^{13} = CH_3$ | 510.3 | |
| 183 Rac S-isomer | 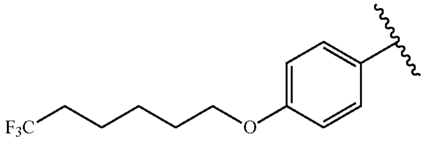 | $CF_3$ | H | 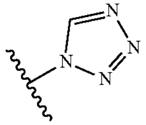 | $R^{13} = CH_3$ | 554.3 | 7.57-7.48 (m, 2H), 7.13-7.05 (m, 2H), 7.02-6.94 (m, 2H), 6.88-6.77 (m, 2H), 4.07-3.99 (m, 2H), 2.29 (s, 3H), 2.19-2.07 (m, 2H), 1.89-1.78 (m, 2H), 1.69-1.55 (m, 4H) |
| 184 S-isomer | 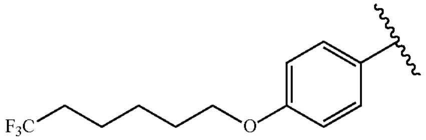 | $CF_3$ | H | CN | $R^{13} = CH_3$ | 511.1 | 7.46 (dd, J = 12.1, 8.5 Hz, 4H), 7.31 (d, J = 8.3 Hz, 2H), 6.95 (d, J = 9.1 Hz, 2H), 4.32-4.22 (m, 1H), 4.00 (s, 2H), 3.67-3.55 (m, 1H), 2.41 (s, 3H), 2.23-1.99 (m, 2H), 1.88-1.76 (m, 2H), 1.70-1.50 (m, 5H) |

-continued
(II)
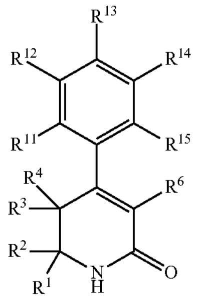
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 185 S-isomer | 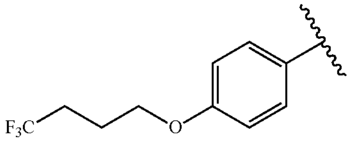 | $CF_3$ | H | 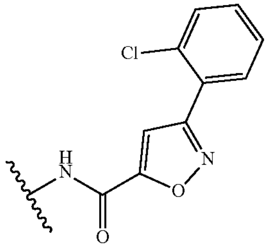 [SMILES: *NC(=O)c1cc(-c2ccccc2Cl)no1] | $R^{13} = CH_3$ | 678.3 | |
| 186 S-isomer | 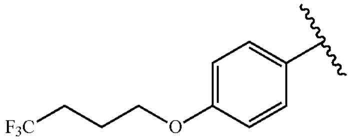 | $CF_3$ | H | 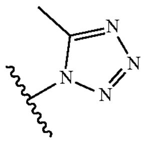 [SMILES: *n1nnnc1C] | $R^{13} = CH_3$ | 540.3 | |
| 187 S-isomer | 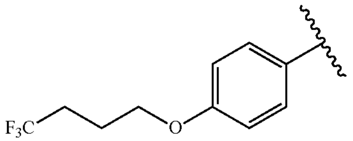 | $CF_3$ | H | 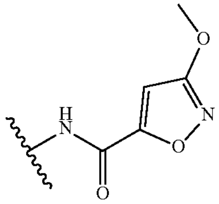 [SMILES: *NC(=O)c1cc(OC)no1] | $R^{13} = CH_3$ | 598.3 | 7.57-7.50 (m, J = 8.8 Hz, 2H), 7.21-7.12 (m, 4H), 7.01-6.94 (m, 2H), 6.48 (s, 1H), 4.06 (t, J = 6.1 Hz, 2H), 3.95 (s, 3H), 3.71 (d, J = 17.1 Hz, 1H), 3.47 (d, J = 17.1 Hz, 1H), 2.44-2.32 (m, 2H), 2.30 (s, 3H), 2.07-1.98 (m, 2H). |

-continued
(II)
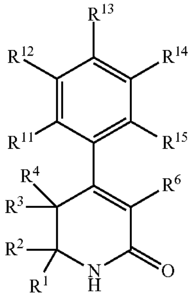
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 188 Rac | 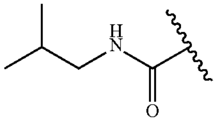 [SMILES: *C(=O)NCC(C)C] | $CH_3$ | H | 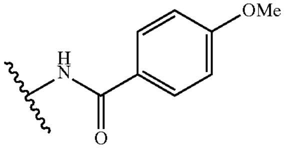 [SMILES: *NC(=O)c1ccc(OC)cc1] | $R^{13} = CH_3$ | 450.1 | |
| 189 Rac | 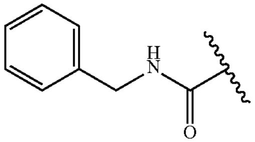 [SMILES: *C(=O)NCc1ccccc1] | $CH_3$ | H | 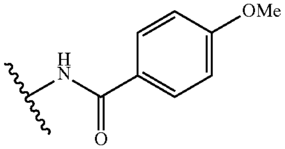 [SMILES: *NC(=O)c1ccc(OC)cc1] | $R^{13} = CH_3$ | 484.1 | |
| 190 S-isomer | 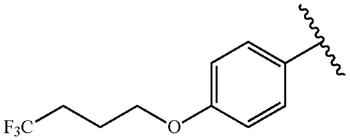 | $CF_3$ | H | 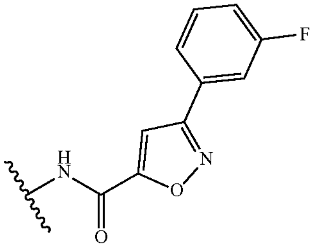 [SMILES: *NC(=O)c1cc(-c2cccc(F)c2)no1] | $R^{13} = CH_3$ | 662.3 | |

-continued
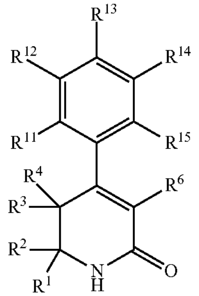
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 191 Rac | 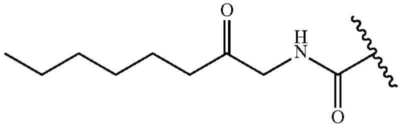 [SMILES: *C(=O)NCC(=O)CCCCCC] | $CH_3$ | H | 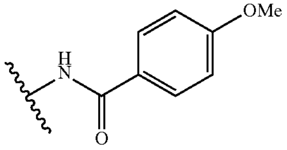 [SMILES: *NC(=O)c1ccc(OC)cc1] | $R^{13} = CH_3$ | 520.2 | |
| 192 S-isomer | 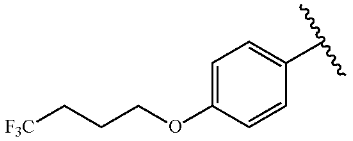 [SMILES: *c1ccc(OCCCC(F)(F)F)cc1] | $CF_3$ | H | 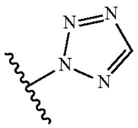 | $R^{13} = CH_3$ | 526.3 | |
| 193 S-isomer | 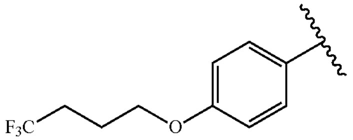 | $CF_3$ | H | 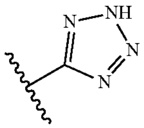 [SMILES: *c1nn[nH]n1] | $R^{13} = OCH_3$ | 542.1 | $^1$H NMR (500 MHz, $CDCl_3$: MeOD (1:1)) δ 7.65 (s, 1H), 7.54 (d, J = 8.4 Hz, 2H), 6.98 (d, J = 8.6 Hz, 2H), 6.93 (d, J = 8.4 Hz, 2H), 6.79 (d, J = 8.4 Hz, 2H), 4.07 (t, J = 6.0 Hz, 2H), 3.77 (s, 3H), 3.69 (d, J = 17.7 Hz, 1H), 3.60 (d, J = 17.7 Hz, 1H), 2.41-2.28 (m, 2H), 2.06 (dq, J = 12.1, 6.3 Hz, 2H). |
| 194 Rac | 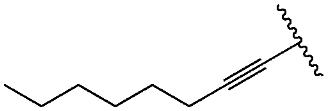 [SMILES: *C#CCCCCCC] | $CF_3$ | H | 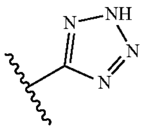 [SMILES: *c1nn[nH]n1] | $R^{13} = CH_3$ | 432.3 | 7.21 (d, J = 7.9 Hz, 2H), 7.08 (d, J = 8.1 Hz, 2H), 6.25 (s, 1H), 3.39 (d, J = 18.5 Hz, 1H), 3.34 (d, J = 18.9 Hz, 1H), 2.39 (s, 3H), 2.23 (t, J = 7.2 Hz, 2H), 1.55- |

-continued
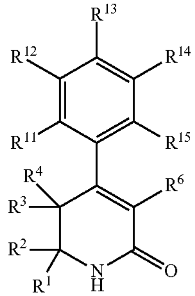
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 1.47 (m, 2H), 1.40-1.23 (m, 6H), 0.87 (t, J = 6.9 Hz, 3H). |
| 195 Rac | 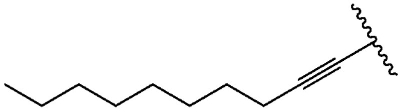 [SMILES: *C#CCCCCCCCC] | $CF_3$ | H | 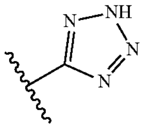 | $R^{13} = CH_3$ | 460.4 | 7.21 (d, J = 7.9 Hz, 2H), 7.08 (d, J = 8.1 Hz, 2H), 6.32 (s, 1H), 3.37 (AB quartet, J = 18.7 Hz, 2H), 2.39 (s, 3H), 2.23 (t, J = 7.0 Hz, 2H), 1.51 (quin, J = 7.2 Hz, 2H), 1.39-1.20 (m, 10H), 0.91-0.84 (m, 3H). |
| 196 R-isomer | 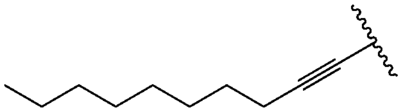 [SMILES: *C#CCCCCCCCC] | $CF_3$ | H | 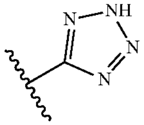 [SMILES: *c1nn[nH]n1] | $R^{13} = CH_3$ | 460.4 | 7.17 (d, J = 7.9 Hz, 2H), 7.04 (d, J = 8.1 Hz, 2H), 6.74 (s, 1H), 3.43-3.32 (m, 2H), 2.37 (s, 3H), 2.23 (t, J = 7.0 Hz, 2H), 1.55-1.47 (m, 2H), 1.37-1.22 (m, 10H). |
| 197 S-isomer | 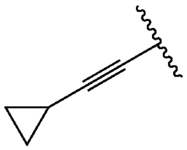 [SMILES: *C#CC1CC1] | $CF_3$ | H | 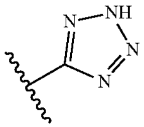 [SMILES: *c1nn[nH]n1] | $R^{13} = CH_3$ | 388.3 | 7.20 (d, J = 7.9 Hz, 2H), 7.07 (d, J = 8.1 Hz, 2H), 6.34 (s, 1H), 3.38, 3.32 (ABq, J = 18.9 Hz, 2H), 2.39 (s, 3H), 1.28 (tt, J = 8.3, 5.0 Hz, 1H), 0.89-0.83 (m, 2H), 0.76-0.71 (m, 2H). |

-continued
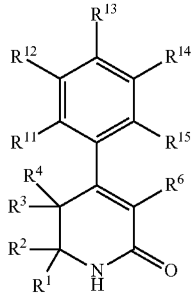
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 198 S-isomer | 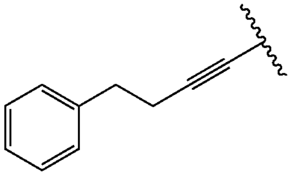 [SMILES: *C#CCCc1ccccc1] | $CF_3$ | H | 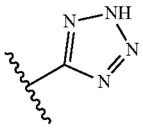 [SMILES: *c1nn[nH]n1] | $R^{13} = CH_3$ | 452.3 | 7.30-7.23 (m, 2H), 7.22-7.13 (m, 5H), 6.99 (d, J = 8.1 Hz, 2H), 6.57 (s, 1H), 3.33 (d, J = 18.9 Hz, 1H), 3.26 (d, J = 18.9 Hz, 1H), 2.85-2.80 (m, 2H), 2.57-2.53 (m, 2H), 2.38 (s, 3H) |
| 199 S-isomer | 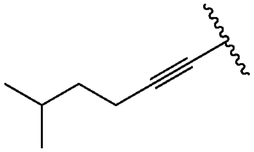 [SMILES: *C#CCCC(C)C] | $CF_3$ | H | 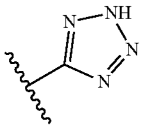 | $R^{13} = CH_3$ | 418.3 | 7.19 (d, J = 7.9 Hz, 2H), 7.06 (d, J = 8.1 Hz, 2H), 6.68 (s, 1H), 3.38, 3.35 (ABq, J = 18.9 Hz, 2H), 2.37 (s, 3H), 2.24 (t, J = 7.4 Hz, 2H), 1.63 (dquin, J = 13.4, 6.7 Hz, 1H), 1.41 (q, J = 7.3 Hz, 2H), 0.88 (d, J = 6.6 Hz, 6H) |
| 200 Rac | 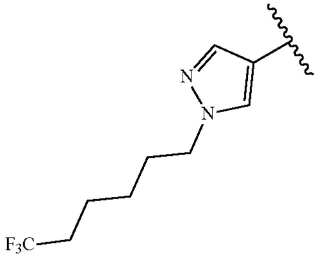 [SMILES: *c1cnn(CCCCCC(F)(F)F)c1] | $CF_3$ | H | 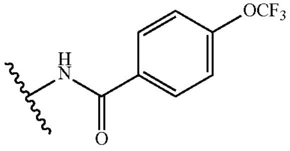 [SMILES: *NC(=O)c1ccc(OC(F)(F)F)cc1] | $R^{13} = CH_3$ | 663.2 | 9.63 (s, 1H), 7.62 (s, 1H), 7.54 (s, 1H), 7.50 (d, J = 8.9 Hz, 2H), 7.22 (d, J = 8.1 Hz, 2H), 7.18 (d, J = 8.1 Hz, 2H), 7.13 (d, J = 8.5 Hz, 2H), 6.87 (s, 1H), 4.13 (t, J = 7.2 Hz, 2H), 3.48 (d, J = 18.4 Hz, 1H), 3.25 (d, J = 18.4 Hz, 1H), 2.42-2.31 (m, 3H), 2.08-2.03 (m, 2H), 1.96-1.85 (m, 2H), 1.62-1.53 (m, 2H), 1.41-1.31 (m, 2H) |

-continued
(II)
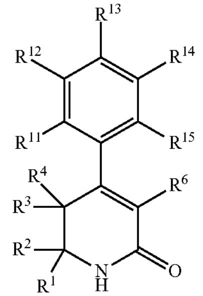
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 201 Rac | 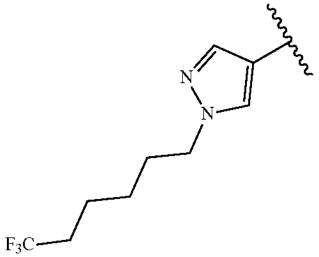 [SMILES: *c1cnn(CCCCCC(F)(F)F)c1] | $CF_3$ | H | 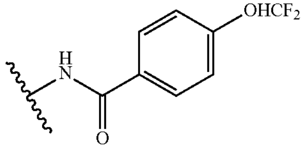 | $R^{13} = CH_3$ | 645.3 | 10.16 (s, 1H), 9.00 (s, 1H), 7.99 (s, 1H), 7.70 (s, 1H), 7.51 (d, J = 8.8 Hz, 2H), 7.39 (d, J = 8.0 Hz, 2H), 7.19 (d, J = 8.3 Hz, 2H), 7.12 (t, J = 74.3 Hz, 1H), 7.09 (d, J = 8.8 Hz, 2H), 4.11 (t, J = 6.9 Hz, 2H), 3.41-3.37 (d, J = 17.4 Hz, 1H), 3.35-3.31 (d, J = 17.4 Hz, 1H), 2.28 (s, 3H), 2.23-2.17 (m, 2H), 1.85-1.75 (m, 2H), 1.52-1.44 (m, 2H), 1.31-1.22 (m, 2H). |
| 202 S-isomer | 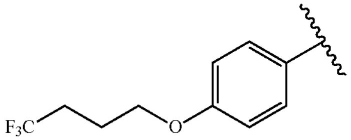 | $CF_3$ | H | 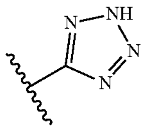 [SMILES: *c1nn[nH]n1] | $R^{13} = CH_2OCH_3$ | 556.3 | $^1$HNMR (500 MHz, DMSO-$d_6$) δ 9.57 (s, 1H), 7.64 (d, J = 8.8 Hz, 2H), 7.20 (d, J = 8.1 Hz, 2H), 7.04 (d, J = 8.8 Hz, 2H), 6.99 (d, J = 7.9 Hz, 2H), 4.36 (s, 2H), 4.09 (t, J = 6.1 Hz, 2H), 3.75 (d, J = 17.5 Hz, 1H), 3.69 (d, J = 17.5 Hz, 1H), 3.27 (s, 3H), 2.48-2.37 (m, 2H), 2.01-1.89 (m, 2H) |
| 203 S-isomer | 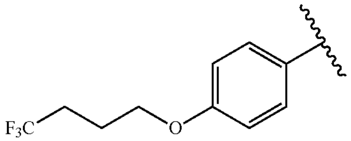 | $CF_3$ | H | 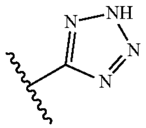 [SMILES: *c1nn[nH]n1] | $R^{12} = F$ $R^{13} = OCH_2CH_3$ | 574.3 | |

-continued (II)

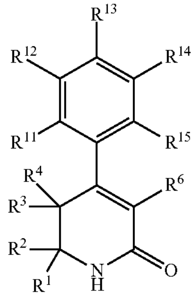

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 204 S-isomer | 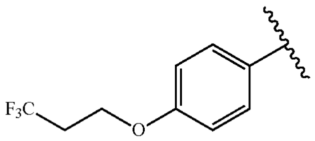 [SMILES: *c1ccc(OCCC(F)(F)F)cc1] | $CF_3$ | H | 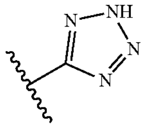 | $R^{13} = CH_3$ | 512.1 | $^1$H NMR (500 MHz, MeOD:$CDCl_3$ (1:1)) δ 7.61 (s, 2H), 7.55 (d, J = 8.6 Hz, 2H), 6.97 (dd, J = 10.4, 8.3 Hz, 4H), 6.84 (d, J = 8.1 Hz, 2H), 4.24 (t, J = 6.4 Hz, 2H), 3.71 (d, J = 17.2 Hz, 1H), 3.50 (d, J = 17.2 Hz, 1H), 3.08-3.03 (m, 4H), 2.67 (qt, J = 10.8, 6.3 Hz, 2H), 1.78 (dq, J = 11.3, 5.5 Hz, 4H), 1.69 (q, J = 5.9 Hz, 2H). |
| 205 S-isomer | 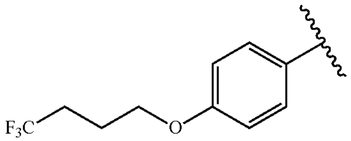 | $CF_3$ | H | 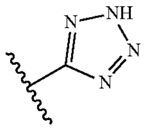 [SMILES: *c1nn[nH]n1] | $R^{13} = OCHF_2$ | 578.1 | $^1$H NMR (500 MHz, $CDCl_3$: MeOD (1:1)) δ 7.61 (s, 2H), 7.54 (d, J = 8.6 Hz, 2H), 7.05-6.96 (m, 5H), 6.66 (t, J = 73.4 Hz, 1H), 4.07 (t, J = 6.0 Hz, 2H), 3.70 (d, J = 17.9 Hz, 1H), 3.57 (d, J = 17.8 Hz, 1H), 2.41-2.28 (m, 2H), 2.11-2.02 (m, 2H). |
| 206 S-isomer | 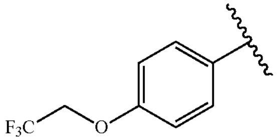 | $CF_3$ | H | 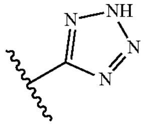 [SMILES: *c1nn[nH]n1] | $R^{13} = CH_3$ | 498.1 | $^1$H NMR (500 MHz, MeOD-$CDCl_3$ (1:1)) δ 7.60-7.57 (m, 2H), 7.07 (d, J = 8.6 Hz, 2H), 6.86 (d, J = 8.0 Hz, 1H), 4.48 (q, J = 8.2 Hz, 1H), 3.70 (d, J = 17.8 Hz, 1H), 3.58 (d, J = 17.8 Hz, 1H), 2.30 (s, 1H). |

-continued (II)

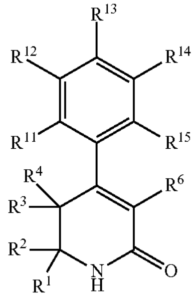

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 207 S-isomer | 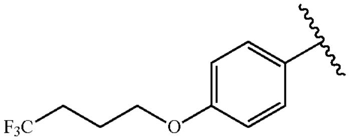 | $CF_3$ | H | 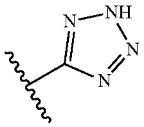 [SMILES: *c1nn[nH]n1] | $R^{12}$ $R^{13}$ = 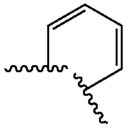 | 562.1 | $^1$H NMR (500 MHz, $CDCl_3$: MeOD (1:1)) δ 7.81-7.73 (m, 2H), 7.72 (d, J = 8.6 Hz, 1H), 7.61 (s, 1H), 7.60-7.55 (m, 3H), 7.53-7.46 (m, 2H), 7.01 (d, J = 8.8 Hz, 2H), 6.98 (dd, J = 8.5, 1.8 Hz, 1H), 4.08 (t, J = 6.0 Hz, 2H), 3.83 (d, J = 17.8 Hz, 1H), 3.70 (d, J = 17.8 Hz, 1H), 2.41-2.28 (m, 2H), 2.11-2.01 (m, 2H). |
| 208 S-isomer | 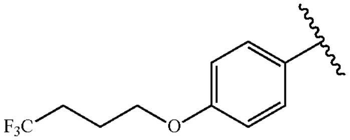 | $CF_3$ | H | 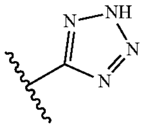 [SMILES: *c1nn[nH]n1] | $R^{13}$ = $OCH_2CH_3$ | 556.1 | $^1$H NMR (500 MHz, $CDCl_3$: MeOD (1:1)) δ 7.62 (s, 1H), 7.54 (d, J = 8.5 Hz, 2H), 6.98 (d, J = 8.9 Hz, 2H), 6.91 (d, J = 8.7 Hz, 2H), 6.77 (d, J = 8.8 Hz, 2H), 4.07 (t, J = 6.0 Hz, 2H), 4.00 (q, J = 7.0 Hz, 2H), 3.68 (d, J = 17.8 Hz, 1H), 3.59 (d, J = 17.7 Hz, 1H), 2.40-2.28 (m, 2H), 2.10-2.01 (m, 2H), 1.38 (t, J = 7.0 Hz, 3H). |
| 209 S-isomer | 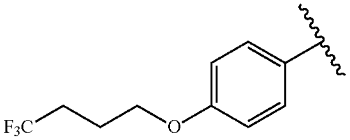 | $CF_3$ | H | 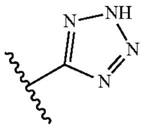 | $R^{12}$ $R^{13}$ = 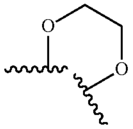 | 570.2 | $^1$H NMR (500 MHz, DMSO-$d_6$) δ 9.51 (s, 1H), 7.61 (d, J = 8.4 Hz, 2H), 7.01 (d, J = 8.8 Hz, 2H), 6.70 (d, J = 8.4 Hz, 1H), 6.57 (d, J = 2.2 Hz, 1H), 6.41 (dd, J = 8.5, 2.2 Hz, 1H), 4.25-4.14 (m, 4H), 4.06 (t, J = 6.2 Hz, 2H), 3.68 (d, J = 18.2 Hz, 1H), 3.63 (d, |

-continued
(II)
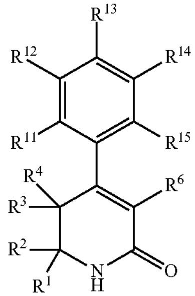
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | J = 18.5 Hz, 1H), 2.42 (ddd, J = 16.4, 8.0, 5.1 Hz, 2H), 1.93 (dq, J = 12.3, 6.4 Hz, 2H). |
| 210 S-isomer | 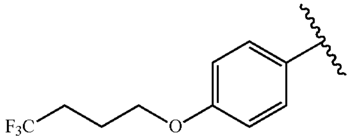 | $CF_3$ | H | 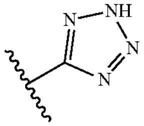 [SMILES: *c1nn[nH]n1] | $R^{12}$ $R^{13}$ = 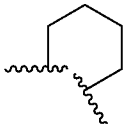 | 566.1 | $^1$H NMR (500 MHz, DMSO-$d_6$) δ 9.42 (s, 1H), 7.60 (d, J = 8.5 Hz, 2H), 7.01 (d, J = 8.6 Hz, 2H), 6.84 (d, J = 8.0 Hz, 1H), 6.80 (s, 1H), 6.56 (d, J = 7.7 Hz, 1H), 4.06 (t, J = 6.1 Hz, 2H), 3.67 (d, J = 17.8 Hz, 1H), 3.60 (d, J = 17.9 Hz, 1H), 2.61 (s, 2H), 2.56 (s, 2H), 2.42 (ddd, J = 11.4, 8.3, 5.2 Hz, 2H), 1.98-1.88 (m, 2H), 1.65 (p, J = 2.8 Hz, 4H). |
| 211 S-isomer | 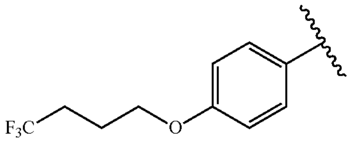 [SMILES: *c1ccc(OCCCC(F)(F)F)cc1] | $CF_3$ | H | 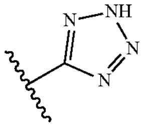 [SMILES: *c1nn[nH]n1] | $R^{12}$ $R^{13}$ = 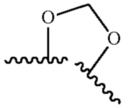 | 556.2 | $^1$H NMR (500 MHz, DMSO-$d_6$) δ 9.37 (s, 1H), 7.60 (d, J = 8.5 Hz, 2H), 7.01 (d, J = 8.6 Hz, 2H), 6.75 (d, J = 8.2 Hz, 1H), 6.57 (s, 1H), 6.48 (d, J = 8.1 Hz, 1H), 5.97 (d, J = 3.1 Hz, 2H), 4.06 (t, J = 6.1 Hz, 2H), 3.65 (d, J = 17.6 Hz, 1H), 3.58 (d, J = 17.7 Hz, 1H), 2.46-2.35 (m, 2H), 1.93 (dd, J = 9.9, 5.4 Hz, 2H). |

-continued

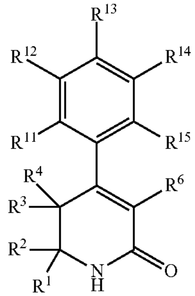

(II)

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 212 S-isomer | 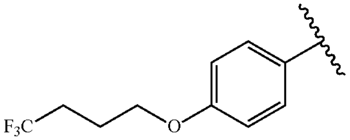 [SMILES: *c1ccc(OCCCC(F)(F)F)cc1] | $CF_3$ | H | 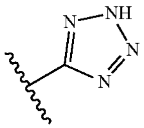 [SMILES: *c1nn[nH]n1] | $R^{11}$ $R^{12}$ = 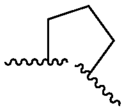 $R^{13}$ = $OCH_3$ | 582.3 | $^1$H NMR (500 MHz, DMSO-$d_6$) δ 9.30 (s, 1H), 7.56 (d, J = 8.4 Hz, 2H), 6.99 (d, J = 8.7 Hz, 2H), 6.71 (d, J = 8.2 Hz, 1H), 6.62 (d, J = 8.4 Hz, 1H), 4.12-4.01 (m, 2H), 3.70 (s, 3H), 3.67 (m, 1H), 3.60 (d, J = 17.4 Hz, 1H), 2.67-2.55 (m, 2H), 2.46-2.35 (m, 2H), 2.31-2.07 (m, 2H), 1.97-1.91 (m, 2H), 1.81-1.69 (m, 2H). |
| 213 S-isomer | 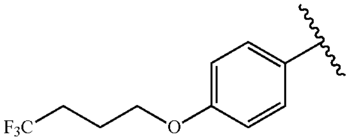 | $CHF_2$ | H | 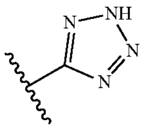 | $R^{13}$ = $CH_3$ | 508.3 | $^1$H NMR (500 MHz, DMSO-$d_6$) δ 9.10 (s, 1H), 7.52 (d, J = 8.5 Hz, 2H), 7.07 (d, J = 7.8 Hz, 2H), 7.02 (d, J = 9.0 Hz, 2H), 6.88 (d, J = 7.9 Hz, 2H), 6.33 (t, J = 55.0 Hz, 1H), 4.07 (t, J = 6.2 Hz, 2H), 3.57 (d, J = 17.9 Hz, 1H), 3.41 (d, J = 18.2 Hz, 1H), 2.44 (ddd, J = 11.4, 8.1, 5.2 Hz, 2H), 1.99-1.91 (m, 2H). |
| 214 R-isomer | 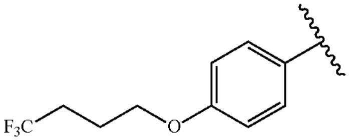 | H | H | 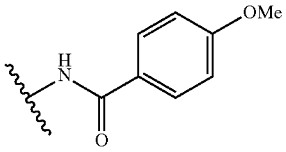 [SMILES: *NC(=O)c1ccc(OC)cc1] | $R^{13}$ = $CH_3$ | 539.4 | $^1$H NMR (500 MHz, DMSO-$d_6$) δ 9.97 (s, 1H), 8.06 (s, 1H), 7.42 (d, J = 8.6 Hz, 2H), 7.36 (dd, J = 10.3, 8.2 Hz, 4H), 7.13 (d, J = 7.9 Hz, 2H), 6.96 (d, J = 8.5 Hz, 2H), 6.85 (d, J = 9.0 Hz, 2H), 4.82-4.73 (m, 1H), 4.05 (t, J = 6.2 Hz, 2H), 3.83-3.72 (m, 1H), 3.71 (s, 3H), |

-continued
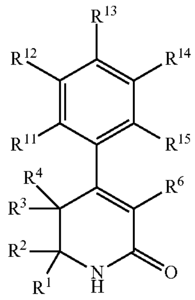
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2.88 (qd, J = 17.0, 7.6 Hz, 1H), 2.48-2.35 (m, 2H), 2.25 (s, 3H), 1.94 (dq, J = 12.5, 6.4 Hz, 2H). |
| 215 S-isomer | 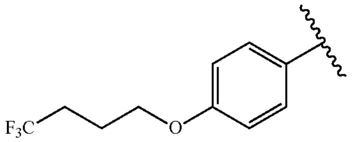 | $CF_3$ | H | CN | $R^{12} = CH_3$ $R^{13} = OCH_3$ | 513.1 | $^1$H NMR (500 MHz, MeOD) δ 7.61 (s, 1H), 7.58 (s, 1H), 7.54-7.41 (m, 1H), 7.30 (dd, J = 8.4, 2.0 Hz, 1H), 7.22 (s, 1H), 7.03 (d, J = 9.4 Hz, 1H), 6.96 (d, J = 8.9 Hz, 1H), 6.89 (d, J = 8.4 Hz, 1H), 4.32 (s, 2H), 4.10-4.03 (m, 2H), 3.86 (s, 2H), 3.67-3.55 (m, 1H), 2.40-2.27 (m, 2H), 2.27-2.23 (m, 1H), 2.22 (s, 2H), 2.10-2.00 (m, 2H) |
| 216 S-isomer | 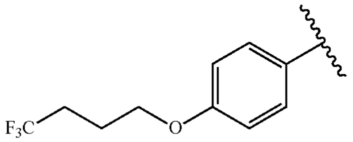 | $CF_3$ | H | CN | $R^{12} = OCH_3$ $R^{13} = OCH_3$ | 529.1 | |
| 217 S-isomer | 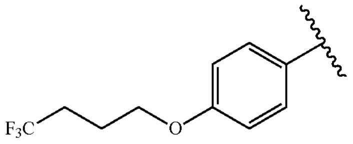 | $CF_3$ | H | CN | $R^{12} = CH_3$ $R^{13} = CH_3$ | 497.1 | $^1$H NMR (500 MHz, MeOD) δ 7.61 (s, 1H), 7.49-7.43 (m, 2H), 7.35-7.23 (m, 3H), 6.99-6.94 (m, 2H), 4.32 (s, 2H), 4.06 (t, J = 5.9 Hz, 2H), 3.61 (s, 2H), 2.38-2.33 (m, 2H), 2.31-2.28 (m, 1H), 2.09-2.01 (m, 2H) |

-continued
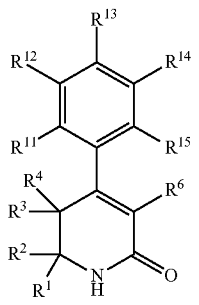
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 218 S-isomer | 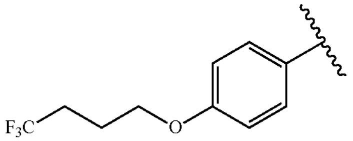 | $CF_3$ | H | CN | $R^{12}$ = F $R^{13}$ = $OCH_3$ | 517.1 | $^1$H NMR (500 MHz, MeOD) δ 7.49-7.43 (m, 3H), 7.40 (dd, J = 11.9, 2.0 Hz, 1H), 7.14 (t, J = 8.4 Hz, 1H), 7.00-6.93 (m, 2H), 4.32 (s, 2H), 4.05 (t, J = 5.9 Hz, 2H), 3.96 (s, 3H), 3.61 (d, J = 3.0 Hz, 2H), 2.39-2.27 (m, 2H), 2.09-2.01 (m, 2H) |
| 219 S-isomer | 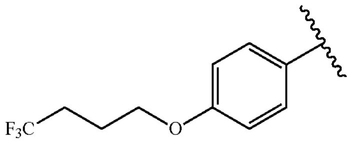 | $CF_3$ | H | CN | $R^{12}$ = F $R^{13}$ = $CH_3$ | 501.1 | $^1$H NMR (500 MHz, MeOD) δ 7.49-7.43 (m, 2H), 7.39-7.32 (m, 1H), 7.30-7.21 (m, 2H), 7.00-6.93 (m, 2H), 4.29 (s, 1H), 4.08-4.04 (m, 2H), 3.60 (d, J = 2.0 Hz, 2H), 2.35 (d, J = 5.4 Hz, 1H), 2.32-2.28 (m, 1H), 2.09-2.00 (m, 2H) |
| 220 S-isomer | 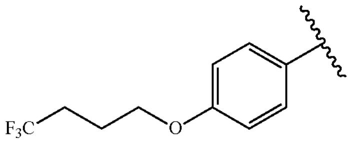 | $CF_3$ | H | CN | $R^{11}$ = F $R^{13}$ = Cl | 521.0 | $^1$H NMR (500 MHz, MeOD) δ 7.48-7.43 (m, 2H), 7.36-7.28 (m, 3H), 7.00-6.95 (m, 2H), 4.07 (t, J = 5.9 Hz, 2H), 3.59 (q, J = 1.0 Hz, 2H), 2.40-2.28 (m, 2H), 2.10-2.02 (m, 2H) |

-continued
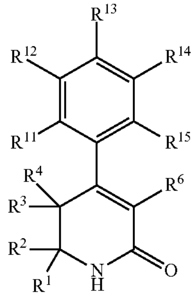
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 221 S-isomer | 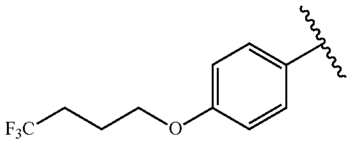 | $CF_3$ | H | CN | $R^{12} = CH_3$ $R^{13} = Cl$ | 517.1 | $^1$H NMR (500 MHz, MeOD) δ 7.61 (s, 1H), 7.58 (s, 1H), 7.54-7.41 (m, 1H), 7.30 (dd, J = 8.4, 2.0 Hz, 1H), 7.22 (s, 1H), 7.03 (d, J = 9.4 Hz, 1H), 6.96 (d, J = 8.9 Hz, 1H), 6.89 (d, J = 8.4 Hz, 1H), 4.32 (s, 2H), 4.10-4.03 (m, 2H), 3.86 (s, 2H), 3.67-3.55 (m, 1H), 2.40-2.27 (m, 2H), 2.27-2.23 (m, 1H), 2.22 (s, 2H), 2.10-2.00 (m, 2H) |
| 222 S-isomer | 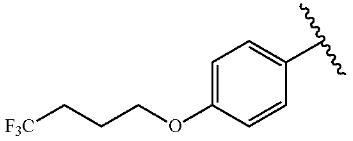 | $CF_3$ | H | CN | $R^{12} = Cl$ $R^{13} = Cl$ | 539.0 | |
| 223 S-isomer | 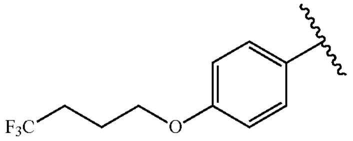 | $CF_3$ | H | CN | $R^{11} = Cl$ $R^{13} = OCH_3$ | 532.8 | |

-continued
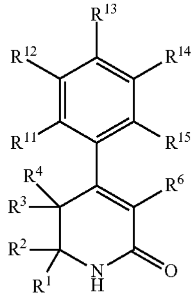
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
| --- | --- | --- | --- | --- | --- | --- | --- |
| 224 S-isomer | 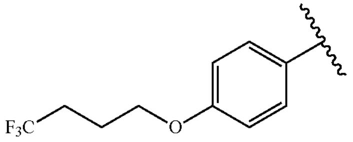 | $CF_3$ | H | CN | $R^{13}$ = CN | 493.9 | |
| 225 S-isomer | 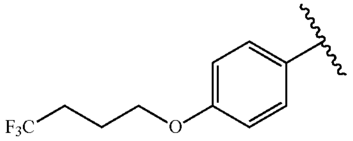 | $CF_3$ | H | CN | $R^{13}$ = $NHSO_2CH_3$ | 562.1 | |
| 226 S-isomer | 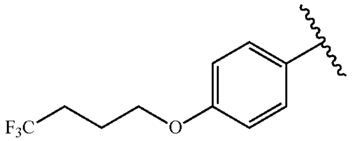 [SMILES: *c1ccc(OCCCC(F)(F)F)cc1] | $CF_3$ | H | CN | $R^{11}$ = Cl $R^{13}$ = $OCH_2CH_3$ | 547.1 | $^1$H NMR (500 MHz, MeOD) δ 7.61-7.58 (m, 1H), 7.44 (d, J = 8.4 Hz, 2H), 7.06-7.00 (m, 2H), 7.00-6.95 (m, 2H), 6.89 (dd, J = 8.4, 2.5 Hz, 1H), 4.11-4.04 (m, 4H), 3.66 (d, J = 18.3 Hz, 1H), 3.43 (d, J = 18.3 Hz, 1H), 2.40-2.28 (m, 2H), 2.10-2.02 (m, 2H), 1.45-1.39 (m, 3H) |

-continued
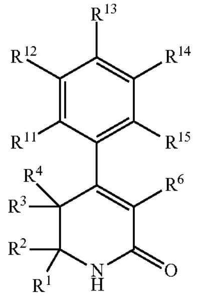
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 227 Rac | 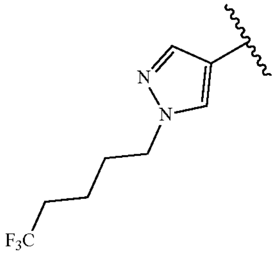 [SMILES: *c1cnn(CCCCC(F)(F)F)c1] | $CF_3$ | H | CN | $R^{13} = CH_3$ | 471.2 | |
| 228 Rac | 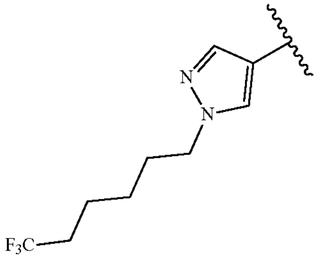 [SMILES: *c1cnn(CCCCCC(F)(F)F)c1] | $CF_3$ | H | 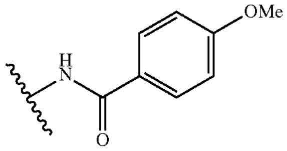 [SMILES: *NC(=O)c1ccc(OC)cc1] | $R^{13} = CH_3$ | 609.2 | 7.86 (s, 1H), 7.66 (s, 1H), 7.37 (d, J = 8.25 Hz, 2H), 7.26 (d, J = 9.08 Hz, 2H), 7.21 (d, J = 7.98 Hz, 2H), 6.82 (d, J = 9.08 Hz, 2H), 4.18 (t, J = 6.88 Hz, 2H), 3.76 (s, 3H), 3.58 (d, J = 17.33 Hz, 1H), 3.35 (d, J = 17.33 Hz, 1H), 2.34 (s, 3H), 2.13 (m, 2H), 1.89 (m, 2H), 1.57 (m, 2H), 1.35 (m, 2H). |

-continued
(II)
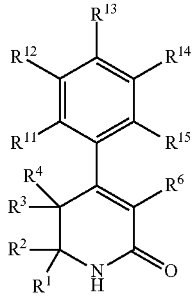
| Example | $R^1$ | $R^2$ | $R^3 = R^4$ | $R^6$ | $R^{11}$-$R^{15}$ | [M + H] | $^1$HNMR (400 MHz, $CDCl_3$) |
| --- | --- | --- | --- | --- | --- | --- | --- |
| 229<br>Rac | 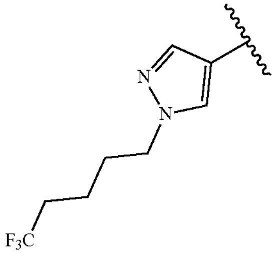 [SMILES: *c1cnn(CCCCC(F)(F)F)c1] | $CF_3$ | H | 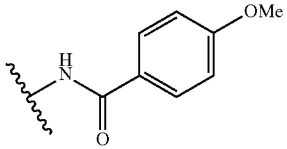 [SMILES: *NC(=O)c1ccc(OC)cc1] | $R^{13} = CH_3$ | 595.2 | |
| 230<br>Rac | 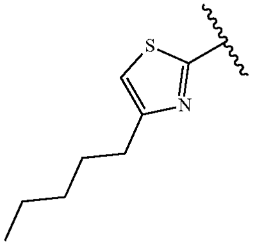 [SMILES: *c1nc(CCCCC)cs1] | $CF_3$ | H | CN | $R^{13} = CH_3$ | 434.0 | |
| 231<br>S-isomer | 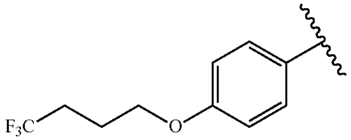 [SMILES: *c1ccc(OCCCC(F)(F)F)cc1] | $CF_3$ | H | 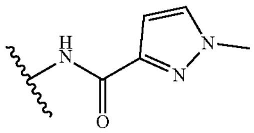 [SMILES: *NC(=O)c1ccn(C)n1] | $R^{13} = CH_3$ | 581.4 | $^1$H NMR (500 MHz, DMSO-$d_6$) δ 10.43 (s, 1H), 9.23 (s, 1H), 7.54 (d, J = 8.80 Hz, 2H), 7.48 (d, J = 1.65 Hz, 1H), 7.29 (d, J = 7.98 Hz, 2H), 7.15 (d, J = 7.98 Hz, 2H), 7.00 (d, J = 8.80 Hz, 2H), 6.34 (d, J = 1.93 Hz, 1H), 4.07 (t, J = 6.05 Hz, |

-continued
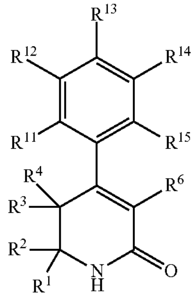
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2H), 3.67 (s, 3H), 3.48 (d, J = 17.06 Hz, 1H), 3.39 (d, J = 17.06 Hz, 1H), 2.43 (m, 2H), 2.27 (s, 3H), 1.95 (m, 2H). |
| 232 S-isomer | 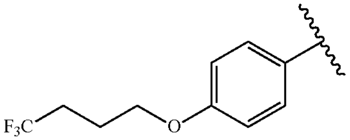 | $CF_3$ | H | 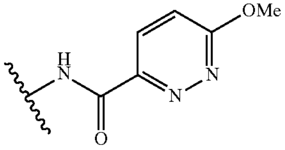 | $R^{13} = CH_3$ | 609.1 | 8.13 (d, J = 9.63 Hz, 1H), 7.54 (d, J = 8.80 Hz, 2H), 7.26 (d, J = 8.25 Hz, 2H), 7.23 (d, J = 9.63 Hz, 1H), 7.17 (d, J = 7.99 Hz, 2H), 6.99 (d, J = 9.08 Hz, 2H), 4.07 (t, J = 6.05 Hz, 2H), 4.01 (s, 3H), 3.67 (d, J = 17.33 Hz, 1H), 3.53 (d, J = 17.06 Hz, 1H), 2.37 (m, 2H), 2.29 (s, 3H), 2.03 (m, 2H). |
| 233 S-isomer | 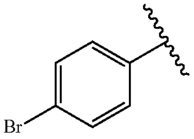 [SMILES: *c1ccc(Br)cc1] | $CF_3$ | H | 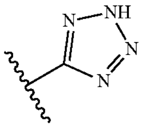 [SMILES: *c1nn[nH]n1] | $R^{13} = CH_3$ | 479.8 | |
| 234 S-isomer | 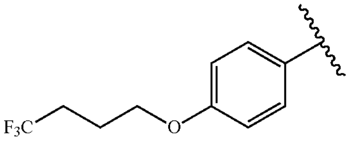 | $CF_3$ | H | 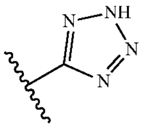 [SMILES: *c1nn[nH]n1] | $R^{13}$ = Br | 589.9 | 7.54 (d, J = 8.3 Hz, 2H), 7.43 (d, J = 8.5 Hz, 2H), 6.97 (dd, J = 8.7, 2.3 Hz, 4H), 6.85 (br. s., 1H), 4.04 (t, J = 5.8 Hz, 2H), 3.69-3.59 (m, 1H), 3.56-3.46 (m, 1H), 2.40-2.26 (m, 2H), 2.08 (dd, J = 9.4, 6.1 Hz, 2H). |

-continued (II)

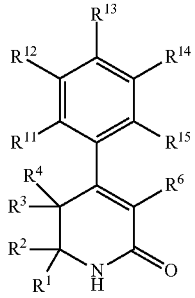

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 235 S-isomer | 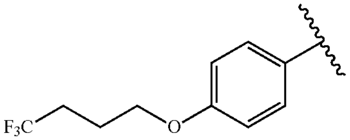 | $CF_3$ | H | 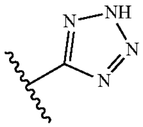 | $R^{13}$ = 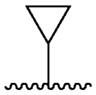 | | $^1$H NMR (500 MHz, DMSO) δ 9.55 (br. s., 1H), 7.62 (d, J = 8.8 Hz, 2H), 7.02 (d, J = 8.8 Hz, 2H), 6.98-6.92 (m, 2H), 6.87 (d, J = 8.3 Hz, 2H), 4.07 (t, J = 6.1 Hz, 2H), 3.80-3.61 (m, 2H), 2.46-2.29 (m, 2H), 2.00-1.90 (m, 2H), 1.89-1.79 (m, 1H), 1.00-0.88 (m, 2H), 0.69-0.54 (m, 2H). |
| 236 S-isomer | 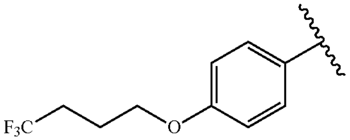 | $CF_3$ | H | 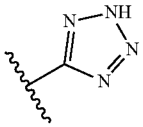 | $R^{13}$ = 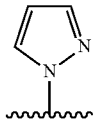 | 578.0 | $^1$H NMR (500 MHz, DMSO) δ 9.42 (br. s., 1H), 8.47 (d, J = 2.5 Hz, 1H), 7.73 (d, J = 1.1 Hz, 1H), 7.69 (d, J = 8.8 Hz, 2H), 7.64 (d, J = 8.5 Hz, 2H), 7.12 (d, J = 8.5 Hz, 2H), 7.03 (d, J = 8.8 Hz, 2H), 6.53 (d, J = 1.9 Hz, 1H), 4.08 (t, J = 6.2 Hz, 2H), 3.78-3.63 (m, 2H), 2.46-2.34 (m, 2H), 2.02-1.86 (m, 2H). |
| 237 S-isomer | 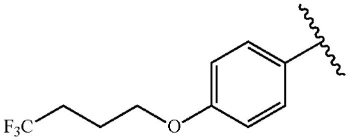 [SMILES: *c1ccc(OCCCC(F)(F)F)cc1] | $CF_3$ | H | 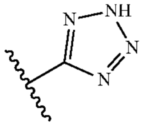 [SMILES: *c1nn[nH]n1] | $R^{12}$ $R^{13}$ = 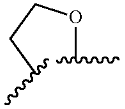 | 554.0 | $^1$H NMR (500 MHz, DMSO) δ 9.42 (br. s., 1H), 7.62 (d, J = 8.5 Hz, 2H), 7.02 (d, J = 8.8 Hz, 2H), 6.97 (s, 1H), 6.68 (d, J = 8.5 Hz, 1H), 6.59 (d, J = 8.3 Hz, 1H), 4.50 (t, J = 8.7 Hz, 2H), 4.07 (t, J = 6.2 Hz, 2H), 3.65 (br. s., 2H), |

-continued
(II)
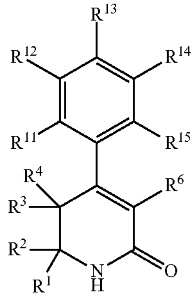
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 3.06 (t, J = 8.7 Hz, 2H), 2.47-2.34 (m, 2H), 2.00-1.89 (m, 2H). |
| 238 S-isomer | 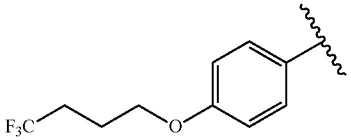 [SMILES: *c1ccc(OCCCC(F)(F)F)cc1] | $CF_3$ | H | 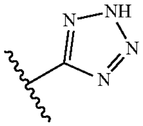 [SMILES: *c1nn[nH]n1] | $R^{13}$ = 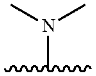 | 555.1 | $^1$H NMR (500 MHz, DMSO) δ 9.41 (br. s., 1H), 7.61 (d, J = 8.3 Hz, 2H), 7.01 (d, J = 8.5 Hz, 2H), 6.84 (d, J = 8.5 Hz, 2H), 6.52 (d, J = 8.8 Hz, 2H), 4.06 (t, J = 5.9 Hz, 2H), 3.75-3.55 (m, 2H), 2.89 (s, 6H), 2.42 (dd, J = 16.5, 11.0 Hz, 2H), 2.02-1.84 (m, 2H). |
| 239 S-isomer | 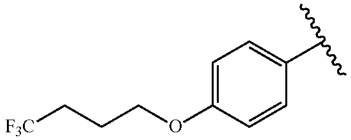 [SMILES: *c1ccc(OCCCC(F)(F)F)cc1] | $CF_3$ | H | 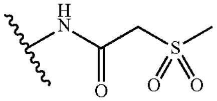 | $R^{13} = CH_3$ | 593.3 | $^1$H NMR (400 MHz, MeOD) δ 7.52 (d, J = 8.8 Hz, 2H), 7.24-7.15 (m, 4H), 6.96 (d, J = 8.8 Hz, 2H), 4.06 (t, J = 6.1 Hz, 2H), 3.97 (s, 2H), 3.67 (d, J = 16.9 Hz, 1H), 3.43 (d, J = 16.9 Hz, 1H), 2.93 (s, 3H), 2.44-2.28 (m, 5H), 2.09-1.96 (m, 2H). |
| 240 S-isomer | 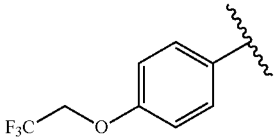 | $CF_3$ | H | 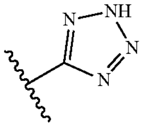 [SMILES: *c1nn[nH]n1] | $R^{13} = OCH_3$ | 514.3 | $^1$H NMR (400 MHz, MeOD) δ 7.65 (d, J = 9.0 Hz, 2H), 7.13-7.08 (m, 2H), 6.97-6.93 (m, 2H), 6.84-6.78 (m, 2H), 4.57 (q, J = 8.4 Hz, 2H), 3.75 (s, 3H), 3.72 (d, J = 2.4 Hz, 2H). |

-continued

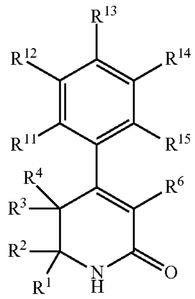

(II)

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 241 S-isomer | 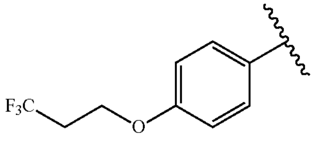 [SMILES: *c1ccc(OCCC(F)(F)F)cc1] | $CF_3$ | H | 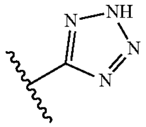 | $R^{13} = OCH_3$ | 528.3 | $^1$H NMR (400 MHz, MeOD) δ 7.61 (d, J = 8.8 Hz, 2H), 7.03 (d, J = 9.0 Hz, 2H), 6.95 (d, J = 8.8 Hz, 2H), 6.81 (d, J = 8.8 Hz, 2H), 4.25 (t, J = 6.1 Hz, 2H), 3.76 (s, 3H), 3.71 (d, J = 1.5 Hz, 2H), 2.77-2.63 (m, 2H). |
| 242 S-isomer | 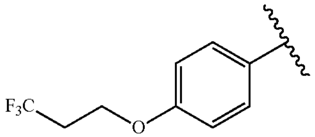 [SMILES: *c1ccc(OCCC(F)(F)F)cc1] | $CF_3$ | H | 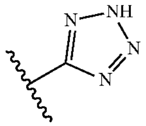 [SMILES: *c1nn[nH]n1] | $R^{13} = OCF_3$ | 582.2 | $^1$H NMR (400 MHz, MeOD) δ 7.62 (d, J = 8.8 Hz, 2H), 7.23-7.17 (m, 2H), 7.14-7.09 (m, 2H), 7.08-7.02 (m, 2H), 4.26 (t, J = 6.2 Hz, 2H), 3.83-3.66 (m, 2H), 2.77-2.63 (m, 2H). |
| 243 S-isomer | 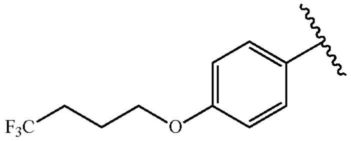 [SMILES: *c1ccc(OCCCC(F)(F)F)cc1] | $CF_3$ | H | 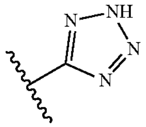 | $R^{13} = OCF_3$ | 596.3 | $^1$H NMR (400 MHz, MeOD) δ 7.61 (d, J = 8.8 Hz, 2H), 7.22-7.17 (m, 2H), 7.15-7.09 (m, 2H), 7.06-7.00 (m, 2H), 4.08 (t, J = 6.1 Hz, 2H), 3.82-3.65 (m, 2H), 2.44-2.30 (m, 2H), 2.09-1.99 (m, 2H). |
| 244 S-isomer | 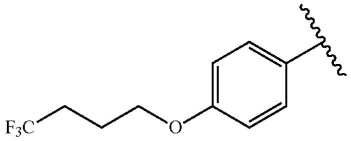 | $CF_3$ | H | 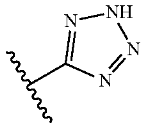 | $R^{13} = OCH_3$ | 556.3 | $^1$H NMR (400 MHz, MeOD) δ 7.58 (d, J = 8.8 Hz, 2H), 7.00 (d, J = 9.0 Hz, 2H), 6.95 (d, J = 9.0 Hz, 2H), 6.81 (d, J = 8.8 Hz, 2H), 4.04 (t, J = 6.1 Hz, 2H), 3.76 |

-continued
(II)
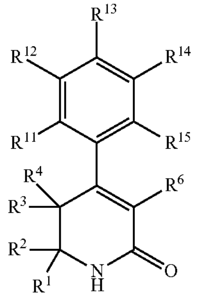
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | (s, 3H), 3.70 (d, J = 1.3 Hz, 2H), 2.31-2.17 (m, 2H), 1.92-1.83 (m, 2H), 1.80-1.70 (m, 2H). |
| 245 S-isomer | 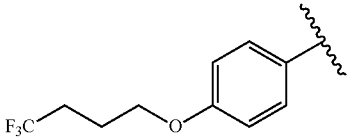 | $CF_3$ | H | 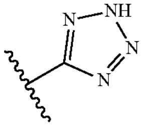 | $R^{13}$ = $OCHCF_2$ | 592.1 | $^1$H NMR (400 MHz, MeOD) δ 7.59 (d, J = 8.6 Hz, 2H), 7.05 (s, 4H), 7.02 (d, J = 9.0 Hz, 2H), 6.87 (t, J = 74.6 Hz, 1H), 4.04 (t, J = 6.1 Hz, 2H), 3.74, 3.70 (ABq, J = 18.0 Hz, 2H), 2.31-2.17 (m, 2H), 1.92-1.84 (m, 2H), 1.80-1.70 (m, 2H) |
| 246 S-isomer | 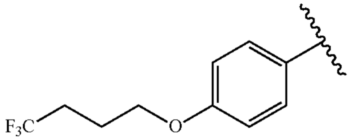 | $CF_3$ | H | 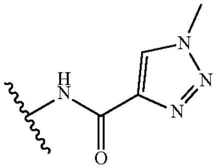 [SMILES: *NC(=O)c1cn(C)nn1] | $R^{13}$ = $CH_3$ | 582.3 | $^1$H NMR (400 MHz, MeOD) δ 8.18 (s, 1H), 7.56 (d, J = 8.8 Hz, 2H), 7.25-7.19 (m, 2H), 7.11 (d, J = 7.9 Hz, 2H), 6.98 (d, J = 9.0 Hz, 2H), 4.09 (s, 3H), 4.07-4.03 (m, 2H), 3.71 (d, J = 16.9 Hz, 1H), 3.48 (d, J = 16.9 Hz, 1H), 2.44-2.31 (m, 2H), 2.28 (s, 3H), 2.08-1.98 (m, 2H). |
| 247 S-isomer | 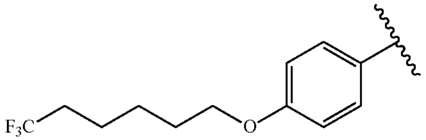 [SMILES: *c1ccc(OCCCCCC(F)(F)F)cc1] | $CF_3$ | H | 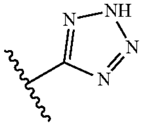 [SMILES: *c1nn[nH]n1] | $R^{13}$ = $OCH_3$ | 570.1 | $^1$H NMR (400 MHz, MeOD) δ 7.57 (d, J = 8.8 Hz, 2H), 7.03-6.92 (m, 4H), 6.84-6.79 (m, 2H), 4.02 (t, J = 6.3 Hz, 2H), 3.76 (s, 3H), 3.70 (d, J = 1.5 Hz, 2H), 2.25- |

-continued
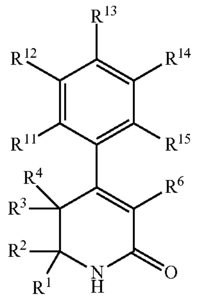
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2.11 (m, 2H), 1.87-1.77 (m, 2H), 1.69-1.53 (m, 4H). |
| 248 S-isomer | 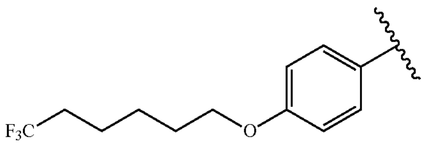 | $CF_3$ | H | 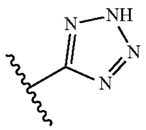 | $R^{13}$ = $OCHCF_2$ | 606.3 | $^1$H NMR (400 MHz, MeOD) δ 7.61 (d, J = 8.8 Hz, 2H), 7.08 (s, 4H), 7.05-7.01 (m, J = 9.0 Hz, 2H), 6.90 (t, J = 73.7 Hz, 1H), 4.05 (t, J = 6.2 Hz, 2H), 3.76, 3.73 (ABq, J = 18.5 Hz, 2H), 2.28-2.14 (m, 2H), 1.89-1.81 (m, 2H), 1.72-1.56 (m, 4H) |
| 249 S-isomer | 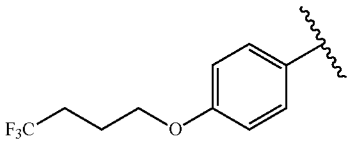 | $CF_3$ | H | 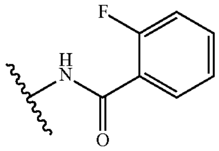 [SMILES: *NC(=O)c1ccccc1F] | $R^{13}$ = $CH_3$ | 595.3 | $^1$H NMR (400 MHz, MeOD) δ 7.62-7.53 (m, 3H), 7.51-7.45 (m, 1H), 7.27-7.09 (m, 6H), 7.01-6.95 (m, 2H), 4.07 (t, J = 6.1 Hz, 2H), 3.71 (d, J = 16.9 Hz, 1H), 3.48 (d, J = 16.9 Hz, 1H), 2.43-2.29 (m, 5H), 2.08-1.98 (m, 2H). |
| 250 S-isomer | 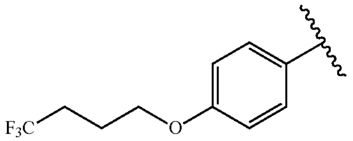 | $CF_3$ | H | 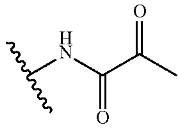 [SMILES: *NC(=O)C(C)=O] | $R^{13}$ = $CH_3$ | 543.4 | 8.35 (br. s., 1H), 7.44 (d, J = 8.8 Hz, 2H), 7.18-7.13 (m, 2H), 7.11-7.06 (m, 2H), 6.96-6.90 (m, 2H), 6.30 (s, 1H), 4.03 (t, J = 5.9 Hz, 2H), 3.61 (d, J = 17.2 Hz, 1H), 3.38 (d, J = 17.4 Hz, 1H), 2.41-2.25 (m, 8H), 2.11-2.02 (m, 2H). |

-continued (II)

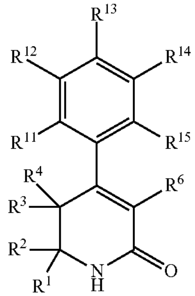

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 251 S-isomer | 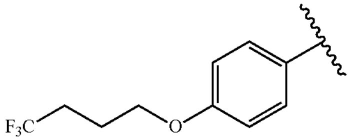 [SMILES: *c1ccc(OCCCC(F)(F)F)cc1] | $CF_3$ | H | 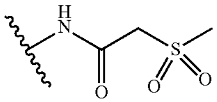 | $R^{13}$ = $OCHCF_2$ | 645.4 | $^1$H NMR (400 MHz, MeOD) δ 7.52 (d, J = 8.8 Hz, 2H), 7.35 (d, J = 8.8 Hz, 2H), 7.12 (d, J = 8.8 Hz, 2H), 6.97 (d, J = 9.0 Hz, 2H), 7.04-6.63 (m, 1H), 4.06 (t, J = 6.1 Hz, 2H), 3.98 (s, 2H), 3.69 (d, J = 16.9 Hz, 1H), 3.45 (d, J = 16.9 Hz, 1H), 2.93 (s, 3H), 2.44-2.29 (m, 2H), 2.09-1.98 (m, 2H). |
| 252 S-isomer | 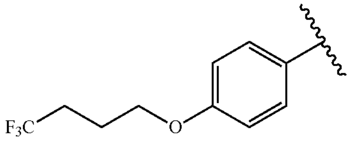 | $CF_3$ | H | 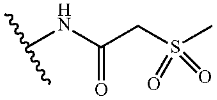 [SMILES: *NC(=O)CS(C)(=O)=O] | $R^{13}$ = $OCH_3$ | 623.3 | $^1$H NMR (400 MHz, MeOD) δ 7.51 (d, J = 8.8 Hz, 2H), 7.30 (d, J = 9.0 Hz, 2H), 6.98-6.88 (m, 4H), 4.02 (t, J = 6.1 Hz, 2H), 3.99 (s, 2H), 3.79 (s, 3H), 3.66 (d, J = 16.9 Hz, 1H), 3.44 (d, J = 16.7 Hz, 1H), 2.97 (s, 3H), 2.30-2.16 (m, 2H), 1.90-1.81 (m, 2H), 1.79-1.69 (m, 2H). |
| 253 S-isomer | 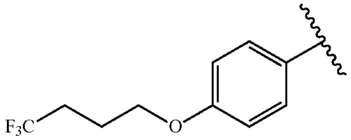 | $CF_3$ | H | 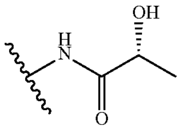 | $R^{13}$ = $CH_3$ | 545.4 | $^1$H NMR (400 MHz, MeOD) δ 7.56 (d, J = 8.8 Hz, 2H), 7.22-7.17 (m, 4H), 7.03-6.96 (m, 2H), 4.09 (t, J = 6.1 Hz, 2H), 4.02 (q, J = 6.8 Hz, 1H), 3.66 (d, J = 17.2 Hz, 1H), 3.47 (d, J = 16.9 Hz, 1H), 2.46-2.32 (m, 5H), |

-continued (II)

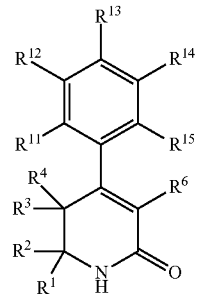

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2.10-2.00 (m, 2H), 1.19 (d, J = 6.8 Hz, 3H). |
| 254 S-isomer | 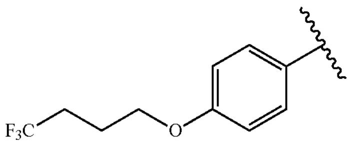 | $CF_3$ | H | 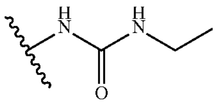 [SMILES: *NC(=O)NCC] | $R^{13}$ = $OCHCF_2$ | 596.2 | $^1$H NMR (400 MHz, MeOD) δ 7.53 (d, J = 8.8 Hz, 2H), 7.39-7.33 (m, 2H), 7.11 (d, J = 8.6 Hz, 2H), 7.00-6.95 (m, 2H), 7.02-6.63 (m, 1H), 4.06 (t, J = 6.1 Hz, 2H), 3.65 (d, J = 16.9 Hz, 1H), 3.42 (d, J = 16.7 Hz, 1H), 2.96 (q, J = 7.3 Hz, 2H), 2.43-2.28 (m, 2H), 2.07-1.97 (m, 2H), 0.92 (t, J = 7.3 Hz, 3H). |
| 255 S-isomer | 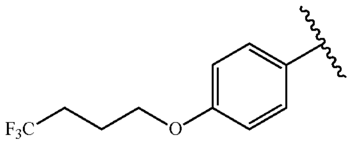 [SMILES: *c1ccc(OCCCC(F)(F)F)cc1] | $CF_3$ | H | 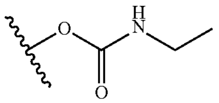 [SMILES: *OC(=O)NCC] | $R^{13}$ = $CH_3$ | 545.3 | $^1$H NMR (400 MHz, MeOD) δ 7.53 (d, J = 8.8 Hz, 2H), 7.29-7.22 (m, 2H), 7.21-7.14 (m, 2H), 6.97 (d, J = 9.0 Hz, 2H), 4.06 (t, J = 6.2 Hz, 2H), 3.66 (d, J = 16.9 Hz, 1H), 3.45 (d, J = 16.7 Hz, 1H), 3.07 (q, J = 7.2 Hz, 2H), 2.45-2.29 (m, 5H), 2.02 (dd, J = 10.2, 5.8 Hz, 2H), 1.06 (t, J = 7.2 Hz, 3H). |
| 256 S-isomer | 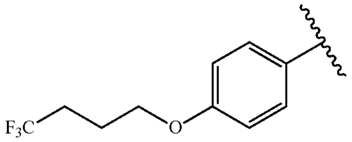 [SMILES: *c1ccc(OCCCC(F)(F)F)cc1] | $CF_3$ | H | CN | $R^{11}$ = F $R^{13}$ = $CH_3$ | 501.1 | $^1$H NMR (400 MHz, MeOD) δ 1.96-2.13 (m, 2 H) 2.24-2.39 (m, 2 H) 2.41 (s, 3 H) 3.49-3.68 (m, 2 H) 3.75 (s, 1 H) 4.06 (t, J = 5.95 Hz, 2 H) 4.33 (s, 1 H) 6.97 (d, J = |

-continued
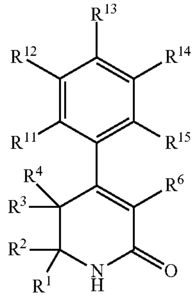
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 1.00 Hz, 2 H) 7.00-7.14 (m, 2 H) 7.24 (t, J = 7.68 Hz, 1 H) 7.45 (d, J = 1.00 Hz, 2 H) 7.61 (s, 1 H) |
| 257 S-isomer | 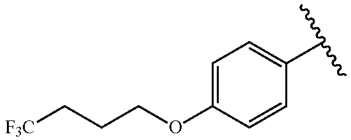 | $CF_3$ | H | CN | $R^{13}$ = $NHCO_2Me$ | 541.5 | |
| 258 S-isomer | 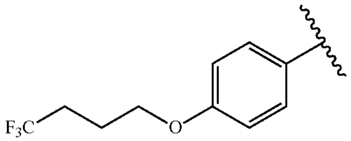 [SMILES: *c1ccc(OCCCC(F)(F)F)cc1] | $CF_3$ | H | CN | $R^{12}$ = Cl $R^{13}$ = $OCH_3$ | 533.1 | |
| 259 S-isomer | 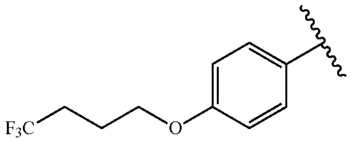 | $CF_3$ | H | CN | $R^{12}$ = Cl $R^{13}$ = $CH_3$ | [M − H] 515.0 | $^1$H NMR (500 MHz, MeOD) δ 2.05 (m, J = 9.90, 5.90 Hz, 2 H) 2.22-2.41 (m, 2 H) 2.24-2.42 (m, 2 H) 2.43 (s, 2 H) 3.62 (br. s., 1 H) 4.06 (t, J = 5.95 Hz, 2 H) 4.29-4.48 (m, 2H) 6.98 (d, J = 8.92 Hz, 1 H) 7.40 (br. s., 1 H) 7.47 (d, J = 8.42 Hz, 1 H) 7.54 (s, 1 H) 7.63 (br. s., 1 H) |

-continued
(II)
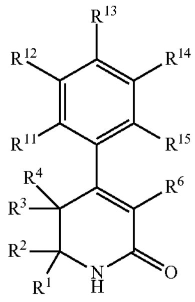
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 260 S-isomer | 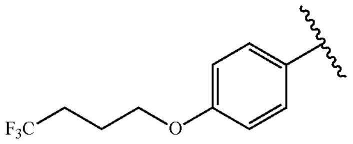 | $CF_3$ | H | CN | $R^{13}$ = $CH_2OCH_3$ | 513.1 | $^1$H NMR (500 MHz, MeOD) δ 1.97-2.11 (m, 2 H) 2.33 (m, J = 5.40 Hz, 2 H) 3.43 (s, 3 H) 3.63 (s, 2 H) 4.06 (t, J = 5.95 Hz, 2 H) 4.53 (s, 2 H) 6.97 (d, J = 1.00 Hz, 2 H) 7.47 (d, J = 8.42 Hz, 4 H) 7.55 (d, J = 7.93 Hz, 2 H) 7.60 (s, 1 H) |
| 261 S-isomer | 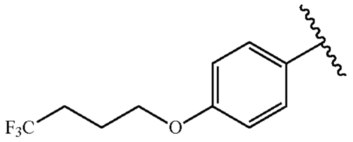 | $CF_3$ | H | CN | $R^{12}$ = F $R^{13}$ = $OCF_3$ | 571.1 | |
| 262 S-isomer | 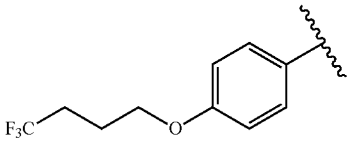 | $CF_3$ | H | CN | $R^{12}$ = $OCH_3$ $R^{13}$ = $CH_3$ | 513.1 | $^1$H NMR (500 MHz, MeOD) δ 1.95-2.12 (m, 2 H) 2.25 (s, 3 H) 2.27-2.44 (m, 2 H) 3.63 (d, J = 2.48 Hz, 2 H) 3.87 (s, 3 H) 4.05 (t, J = 5.95 Hz, 2 H) 6.97 (m, J = 8.92 Hz, 2 H) 7.08 (d, J = 1.49 Hz, 1 H) 7.24 (s, 1 H) 7.47 (m, J = 8.92 Hz, 2 H) 7.60 (s, 1 H) |

-continued (II)

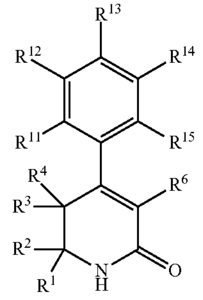

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 263 S-isomer | 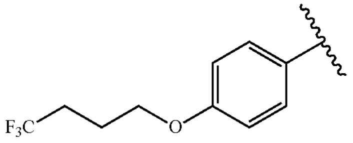 [SMILES: *c1ccc(OCCCC(F)(F)F)cc1] | $CF_3$ | H | CN | $R^{12}$ = Cl $R^{13}$ = $OCH_2CH_3$ | 547.1 | $^1$H NMR (500 MHz, MeOD) δ 1.49 (t, J = 6.94 Hz, 3 H) 1.95-2.12 (m, 2 H) 2.23-2.41 (m, 2 H) 3.60 (s, 2 H) 4.05 (t, J = 5.95 Hz, 2 H) 4.19 (q, J = 6.90 Hz, 2 H) 6.96 (d, J = 9.41 Hz, 2 H) 7.08 (d, J = 8.92 Hz, 1 H) 7.46 (d, J = 8.92 Hz, 2 H) 7.55 (dd, J = 1.00 Hz, 1 H) 7.60 (s, 1 H) 7.64 (d, J = 1.00 Hz, 1 H) |
| 264 S-isomer | 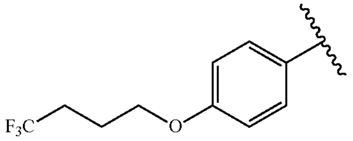 | $CF_3$ | H | CN | $R^{12}$ F $R^{13}$ = $OCH_2CH_3$ | [M − H] 529.1 | $^1$H NMR (500 MHz, MeOD) δ 1.47 (t, J = 7.18 Hz, 3 H) 1.95-2.12 (m, 2 H) 2.33 (s, 2 H) 4.06 (t, J = 5.95 Hz, 2 H) 4.19 (q, J = 6.90 Hz, 2 H) 6.97 (d, J = 8.92 Hz, 2 H) 7.12 (t, J = 1.00 Hz, 1 H) 7.37-7.53 (m, 4 H) 7.62 (s, 1H) |
| 265 S-isomer | 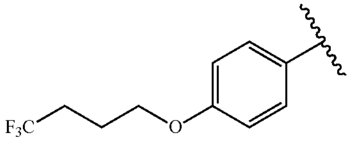 [SMILES: *c1ccc(OCCCC(F)(F)F)cc1] | $CF_3$ | H | 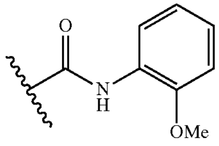 [SMILES: *C(=O)Nc1ccccc1OC] | $R^{13}$ = $CH_3$ | 607.1 | $^1$H NMR (500 MHz, MeOD) δ 7.88 (dd, J = 8.0, 1.4 Hz, 1H), 7.55 (d, J = 8.8 Hz, 2H), 7.25 (d, J = 8.0 Hz, 2H), 7.16 (d, J = 8.0 Hz, 2H), 7.05-6.97 (m, 3H), 6.89 (d, J = 7.4 Hz, 1H), 6.85-6.80 (m, 1H), 4.07 (t, J = 6.1 Hz, 2H), 3.68 (s, 3H), 3.63 (d, J = 17.3 Hz, 1H), 3.51 (d, J = 17.3 Hz, 1H), |

-continued
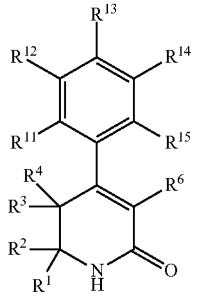
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2.43-2.32 (m, 2H), 2.31 (s, 3 H), 2.07-1.98 (m, 2H). |
| 266 S-isomer | 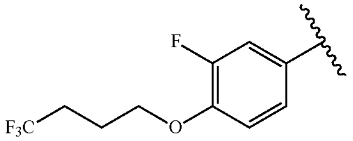 | $CF_3$ | H | 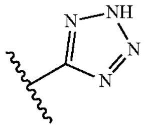 [SMILES: *c1nn[nH]n1] | $R^{13} = CH_3$ | 544.1 | $^1$H NMR (500 MHz, MeOD) δ 7.50 (dd, J = 12.7, 2.5 Hz, 1H), 7.45-7.38 (m, 1H), 7.18 (t, J = 8.7 Hz, 1H), 7.12-7.06 (m, 2H), 6.89 (d, J = 8.2 Hz, 2H), 4.16 (t, J = 6.1 Hz, 2H), 3.74 (d, J = 17.8 Hz, 1H), 3.68 (d, J = 17.8 Hz, 1H), , 2.52-2.32 (m, 2H), 2.29 (s, 3H), 2.13-1.98 (m, 2H). |
| 267 S-isomer | 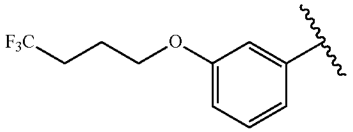 [SMILES: *c1cccc(OCCCC(F)(F)F)c1] | $CF_3$ | H | 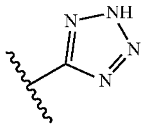 [SMILES: *c1nn[nH]n1] | $R^{13} = CH_3$ | 526.2 | |
| 268 S-isomer | 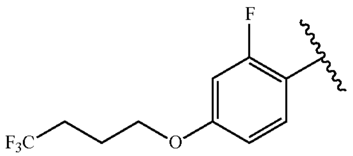 [SMILES: *c1ccc(OCCCC(F)(F)F)cc1F] | $CF_3$ | H | 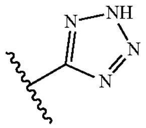 [SMILES: *c1nn[nH]n1] | $R^{13} = CH_3$ | 544.2 | $^1$HNMR (500 MHz, DMSO-$d_6$) δ 9.58 (s, 1H), 7.59 (t, J = 9.2 Hz, 1H), 7.09 (d, J = 8.0 Hz, 2H), 6.99-6.92 (m, 2H), 6.89 (d, J = 8.1 Hz, 2H), 4.11 (t, J = 6.1 Hz, 2H), 3.81 (d, J = 17.7 Hz, 1H), 3.73 (d, J = 17.8 Hz, 1H), 2.49-2.30 (m, 2H), 2.25 (s, 3H), 2.03-1.78 (m, 2H). |

-continued

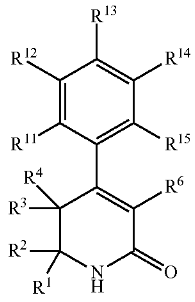

(II)

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 269<br>S-isomer | 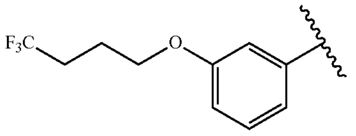 [SMILES: *c1cccc(OCCCC(F)(F)F)c1] | $CF_3$ | H | CN | $R^{13} = CH_3$ | 483.2 | $^1$HNMR (400 MHz, MeOD) δ 8.18 (s, 1H), 7.56 (d, J = 8.8 Hz, 2H), 7.25-7.19 (m, 2H), 7.11 (d, J = 7.9 Hz, 2H), 6.98 (d, J = 9.0 Hz, 2H), 4.09 (s, 3H), 4.07-4.03 (m, 2H), 3.71 (d, J = 16.9 Hz, 1H), 3.48 (d, J = 16.9 Hz, 1H), 2.44-2.31 (m, 2H), 2.28 (s, 3H), 2.08-1.98 (m, 2H). |
| 270<br>R-isomer | 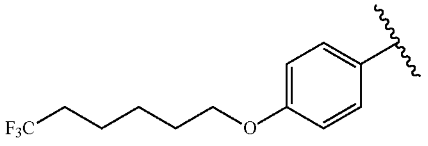 | $CF_3$ | H | 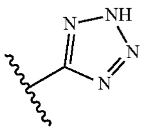 [SMILES: *c1nn[nH]n1] | $R^{13} = CH_3$ | 554.1 | $^1$H NMR (400 MHz, MeOD) δ 7.51 (d, J = 8.8 Hz, 2H), 7.30 (d, J = 9.0 Hz, 2H), 6.98-6.88 (m, 4H), 4.02 (t, J = 6.1 Hz, 2H), 3.99 (s, 2H), 3.79 (s, 3H), 3.66 (d, J = 16.9 Hz, 1H), 3.44 (d, J = 16.7 Hz, 1H), 2.97 (s, 3H), 2.30-2.16 (m, 2H), 1.90-1.81 (m, 2H), 1.79-1.69 (m, 2H). |
| 271<br>S-isomer | 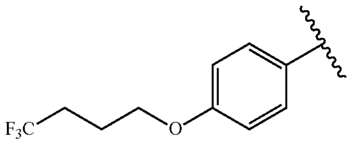 | $CF_3$ | H | 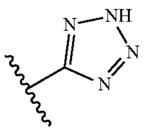 | $R^{13} = CH_2CF_3$ | 594.1 | $^1$H NMR (500 MHz, 1:1 MeOD/$CDCl_3$) δ 7.52 (d, J = 8.8 Hz, 2H), 7.20 (d, J = 8.0 Hz, 2H), 6.96 (dd, J = 8.4, 2.1 Hz, 4H), 4.04 (t, J = 6.1 Hz, 2H), 3.73-3.64 (m, 1H), 3.60-3.49 (m, 1H), 3.35 (d, J = 10.7 Hz, 2H), 2.39-2.23 (m, 2H), 2.13-1.91 (m, 2H). |

-continued
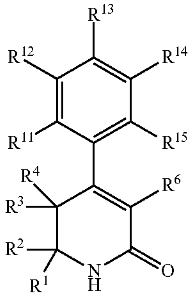
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 272 S-isomer | 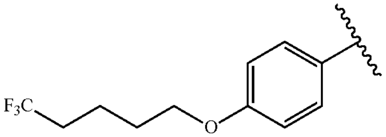 [SMILES: *c1ccc(OCCCCC(F)(F)F)cc1] | $CF_3$ | H | 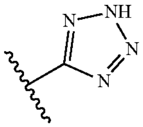 [SMILES: *c1nn[nH]n1] | $R^{13} = CH_3$ | 540.3 | |
| 273 S-isomer | 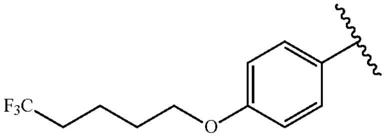 [SMILES: *c1ccc(OCCCCC(F)(F)F)cc1] | $CF_3$ | H | 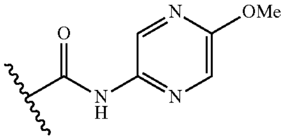 [SMILES: *C(=O)Nc1cnc(OC)cn1] | $R^{13} = CH_3$ | 608.2 | 1.98-2.11 (m, 2H), 2.29 (s, 3H), 2.33-2.49 (m, 2H), 3.71-3.47 (m, 2H), 3.91 (s, 3H), 4.20-4.02 (m, 2H), 6.95-7.03 (m, 2H), 7.15 (d, J = 8.3 Hz, 2H), 7.26 (d, J = 8.0 Hz, 2H), 7.53 (d, J = 8.8 Hz, 2H), 7.86 (d, J = 1.4 Hz, 1H), 8.76 (d, J = 1.4 Hz, 1H). |
| 274 S-isomer | 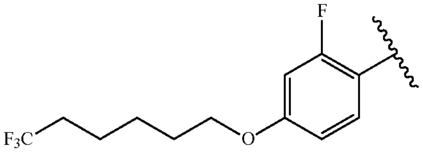 | $CF_3$ | H | 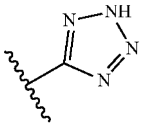 [SMILES: *c1nn[nH]n1] | $R^{13} = OCHF_2$ | 624.1 | $^1$H NMR (500 MHz, DMSO-$d_6$) δ 9.63 (s, 1H), 7.58 (t, J = 9.3 Hz, 1H), 7.43-6.98 (m, 5H), 6.92 (d, J = 12.1 Hz, 2H), 4.03 (t, J = 6.4 Hz, 2H), 3.80 (d, J = 17.8 Hz, 1H), 3.76 (d, J = 17.9 Hz, 1H), 2.37-2.14 (m, 2H), 1.83-1.66 (m, 2H), 1.63-1.32 (m, 4H). |

-continued (II)

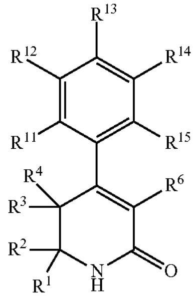

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 275 S-isomer | 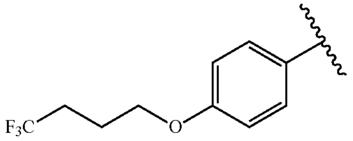 | $CF_3$ | H | 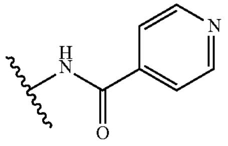 [SMILES: *NC(=O)c1ccncc1] | $R^{13} = OCHF_2$ | 630.2 | $^1$H NMR (400 MHz, MeOD) δ 8.75 (br. s., 2H), 7.87 (br. s., 2H), 7.57 (d, J = 8.6 Hz, 2H), 7.36 (d, J = 8.6 Hz, 2H), 7.12 (d, J = 8.6 Hz, 2H), 7.04-6.62 (m, 3H), 4.08 (t, J = 5.8 Hz, 2H), 3.75 (br. s., 1H), 3.52 (d, J = 16.9 Hz, 1H), 2.45-2.29 (m, 2H), 2.09-1.99 (m, 2H). |
| 276 S-isomer | 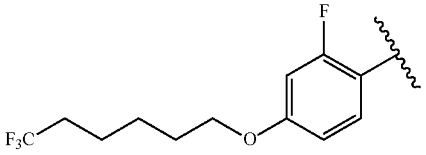 [SMILES: *c1ccc(OCCCCCC(F)(F)F)cc1F] | $CF_3$ | H | 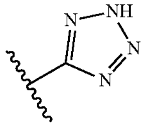 | $R^{12}$ $R^{13}$ = 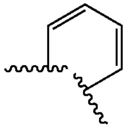 | 608.2 | $^1$H NMR (500 MHz, MeOD) δ 7.83-7.66 (m, 3H), 7.61 (s, 2H), 7.56-7.43 (m, 3H), 7.01 (d, J = 8.6 Hz, 1H), 6.85-6.67 (m, 2H), 4.05 (d, J = 18.0 Hz, 1H), 4.01 (t, J = 6.4 Hz, 2H), 3.76 (d, J = 17.9 Hz, 1H), 2.05-2.20 (m, 2H), 1.91-1.72 (m, 2H), 1.74-1.45 (m, 4H). |
| 277 S-isomer | 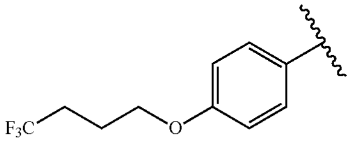 | $CF_3$ | H | 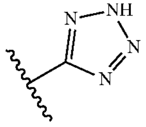 | $R^{13}$ = 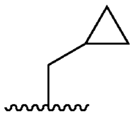 | 567.1 | $^1$H NMR (500 MHz, 1:1 $CDCl_3$:MeOD) δ 7.54 (d, J = 8.4 Hz, 2H), 7.16 (d, J = 7.9 Hz, 2H), 6.99 (d, J = 8.9 Hz, 2H), 6.90 (d, J = 8.4 Hz, 2H), 4.07 (t, J = 5.9 Hz, 2H), 3.79-3.66 (m, 1H), 3.63-3.50 (m, 1H), 2.49 (d, J = 6.9 Hz, 2H), 2.40-2.25 (m, 2H), 2.13-1.97 (m, 2H), 0.97-0.82 (m, 1H), 0.58-0.45 (m, 2H), 0.16 (q, J = 5.0 Hz, 2H). |

-continued
(II)
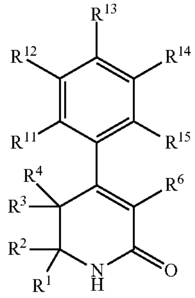
| Example | R¹ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 278 S-isomer | 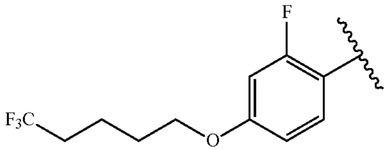 [SMILES: *c1ccc(OCCCCC(F)(F)F)cc1F] | $CF_3$ | H | 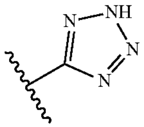 | $R^{13} = CH_3$ | 558.2 | $^1$H NMR (500 MHz, 1:1 $CDCl_3$:MeOD) δ 7.43 (t, J = 9.17 Hz, 1H), 7.02 (d, J = 7.93 Hz, 2H), 6.87 (d, J = 7.93 Hz, 2H), 6.75 (dd, J = 2.48, 8.92 Hz, 1H), 6.71 (dd, J = 2.23, 14.61 Hz, 1H), 3.99 (t, J = 5.95 Hz, 2H), 3.87 (d, J = 17.83 Hz, 1H), 3.61 (d, J = 17.83 Hz, 1H), 2.26 (s, 3H), 2.11-2.21 (m, 2H), 1.80-1.89 (m, 2H), 1.69-1.78 (m, 2H). |
| 279 S-isomer | 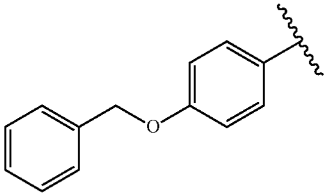 [SMILES: *c1ccc(OCc2ccccc2)cc1] | $CF_3$ | H | 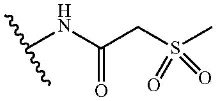 | $R^{13} = CH_3$ | 573.2 | 7.79 (br. s., 1H), 7.46-7.38 (m, 7H), 7.22-7.17 (m, 2H), 7.15-7.10 (m, 2H), 7.02 (d, J = 9.0 Hz, 2H), 6.69 (br. s., 1H), 5.07 (s, 2H), 3.82 (br. s., 2H), 3.63 (d, J = 17.2 Hz, 1H), 3.37 (d, J = 17.2 Hz, 1H), 2.95 (s, 3H), 2.36 (s, 3H). |
| 280 S-isomer | 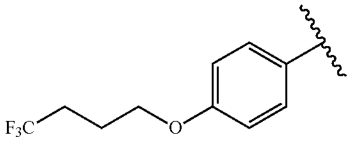 | $CF_3$ | H | 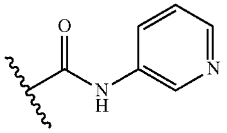 [SMILES: *C(=O)Nc1cccnc1] | $R^{13} = OCHF_2$ | 630.2 | |

-continued (II)

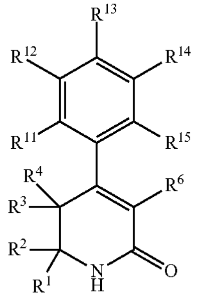

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 281 S-isomer | 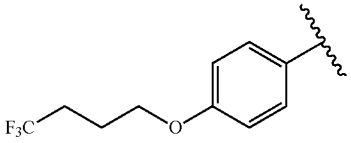 | $CF_3$ | H | 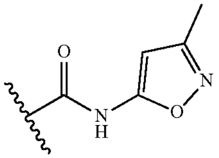 [SMILES: *C(=O)Nc1cc(C)no1] | $R^{13} = CH_3$ | 582.2 | $^1$H NMR (500 MHz, MeOD) δ 7.56 (d, J = 8.92 Hz, 2H), 7.30 (d, J = 8.42 Hz, 2H), 7.10 (d, J = 7.93 Hz, 2H), 6.97 (d, J = 8.92 Hz, 2H), 6.37 (s, 1H), 4.06 (m, 2H), 3.59 (d, J = 17.83 Hz, 1H), 3.43 (d, J = 17.34 Hz, 1H), 2.32 (m, 2H), 2.30 (s, 3H), 2.22 (s, 3H), 2.06 (m, 2H). |
| 282 S-isomer | 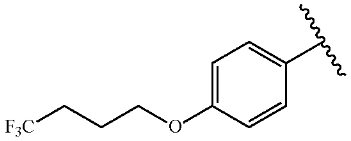 | $CF_3$ | H | 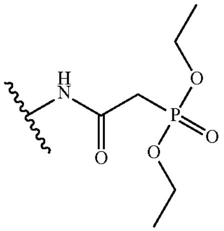 [SMILES: *NC(=O)CP(=O)(OCC)OCC] | $R^{13} = CH_3$ | 651.2 | $^1$H NMR (500 MHz, MeOD) δ 7.61 (s, 1H), 7.47 (d, J = 8.4 Hz, 2H), 7.15 (d, J = 5.9 Hz, 4H), 6.93 (d, J = 8.9 Hz, 2H), 4.33 (br. s., 1H), 4.07-4.02 (m, 2H), 4.02-3.94 (m, 4H), 3.67-3.56 (m, 1H), 3.37-3.34 (m, 1H), 2.94-2.78 (m, 2H), 2.33 (s, 5H), 2.09-2.00 (m, 2H), 1.22 (d, J = 1.5 Hz, 6H). |
| 283 S-isomer | 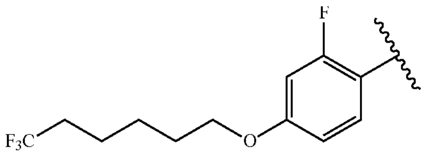 | $CF_3$ | H | 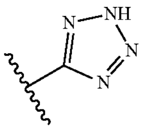 | $R^{13} = OCH_2CH_3$ | 602.2 | $^1$H NMR (500 MHz, DMSO-$d_6$) δ 9.39 (s, 1H), 7.56 (t, J = 9.3 Hz, 1H), 6.92 (t, J = 8.6 Hz, 4H), 6.81 (d, J = 8.8 Hz, 2H), 4.03 (t, J = 6.4 Hz, 2H), 3.99 (q, J = 6.9 Hz , 2H), 3.82 (d, J = 17.3 Hz, 1H), 3.69 (d, J = 17.7 Hz, 1H), 2.34-2.15 (m, 2H), 1.85-1.70 (m, 2H), 1.65-1.42 (m, 4H), 1.29 (t, J = 6.9 Hz, 3H). |

-continued

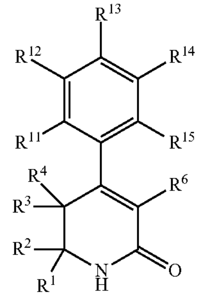

(II)

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 284 S-isomer | 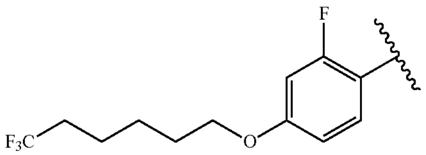 [SMILES: *c1ccc(OCCCCCC(F)(F)F)cc1F] | $CF_3$ | H | 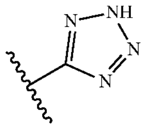 [SMILES: *c1nn[nH]n1] | $R^{13} = CH_2CF_3$ | 640.1 | $^1$H NMR (500 MHz, DMSO-$d_6$) δ 9.36 (w, 1H), 7.59 (t, J = 9.3 Hz, 1H), 7.20 (d, J = 7.9 Hz, 2H), 7.07-6.74 (m, 4H), 4.03 (t, J = 6.4 Hz, 2H), 3.76 (d, J = 17.4 Hz, 1H), 3.70 (d, J = 17.7 Hz, 1H), 3.58 (dd, J = 23.3, 11.7 Hz, 2H), 2.33-2.16 (m, 2H), 1.86-1.68 (m, 2H), 1.545-1.60 (m, 4H). |
| 285 S-isomer | 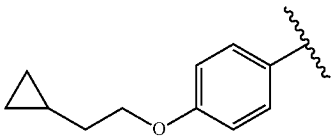 [SMILES: *c1ccc(OCCC2CC2)cc1] | $CF_3$ | H | 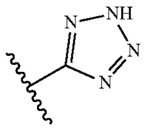 | $R^{13} = CH_3$ | 484.1 | $^1$H NMR (500 MHz, DMSO-$d_6$) δ 9.58-9.48 (m, 1H), 7.65-7.55 (m, 2H), 7.07 (d, J = 8.0 Hz, 2H), 7.04-6.97 (m, 2H), 6.94-6.85 (m, 2H), 4.06 (s, 2H), 3.69 (s, 2H), 2.24 (s, 3H), 1.63 (q, J = 6.6 Hz, 2H), 1.35-1.08 (m, 1H), 0.94-0.77 (m, 1H), 0.51-0.38 (m, 2H), 0.16-0.06 (m, 2H) |
| 286 S-isomer | 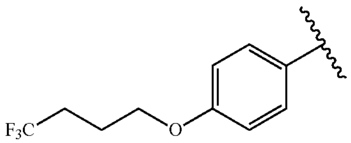 | $CF_3$ | H | 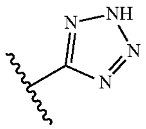 | $R^{11} = F$<br>$R^{13} = CH_3$ | 544.2 | $^1$H NMR (500 MHz, DMSO-$d_6$) δ 7.62 (d, J = 8.80 Hz, 2H), 7.02 (d, J = 8.80 Hz, 2H), 7.01 (m, 1H), 6.98 (t, J = 7.98 Hz, 1H), 6.93 (d, J = 11.55 Hz, 1H), 4.08 (t, J = 6.93 Hz, 2H), 3.68 (d, J = 18.16 Hz, 1H), 3.62 (d, J = 17.88 Hz, 1H), 2.42 (m, 2H), 2.28 (s, 3H), 1.95 (m, 2H). |

-continued
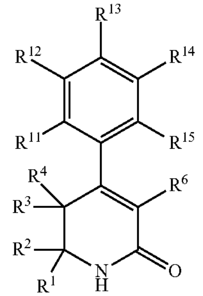
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 287 S-isomer | 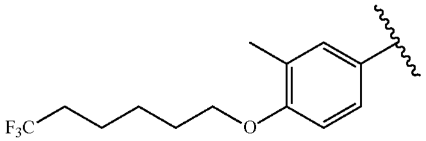 | $CF_3$ | H | 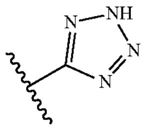 [SMILES: *c1nn[nH]n1] | $R^{13} = CH_3$ | 568.2 | $^1$H NMR (500 MHz, DMSO-$d_6$) δ 9.47 (s, 1H), 7.49 (s, 1H), 7.45 (d, J = 8.80 Hz, 1H), 7.07 (d, J = 7.98 Hz, 2H), 6.98 (d, J = 8.80 Hz, 1H), 6.89 (d, J = 8.25 Hz, 2H), 4.00 (t, J = 6.19 Hz, 2H), 3.66 (s, 2H), 2.24 (s, 3H), 2.20-2.32 (m, 2H), 2.17 (s, 3H), 1.71-1.80 (m, 2H), 1.47-1.61 (m, 4H). |
| 288 S-isomer | 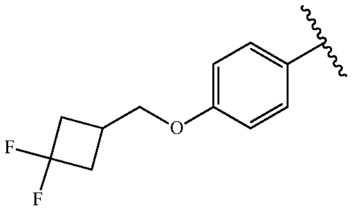 [SMILES: *c1ccc(OCC2CC(F)(F)C2)cc1] | $CF_3$ | H | 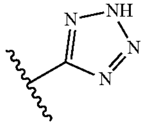 | $R^{13} = CH_3$ | 520.0 | $^1$H NMR (500 MHz, DMSO-$d_6$) δ 9.67 (s, 1H), 8.15 (d, J = 4.1 Hz, 1H), 7.55 (d, J = 8.8 Hz, 2H), 7.05 (d, J = 4.1 Hz, 1H), 6.98 (d, J = 8.8 Hz, 2H), 4.03 (t, J = 6.2 Hz, 2H), 3.98 (d, J = 17.6 Hz, 1H), 3.62 (d, J = 17.3 Hz, 1H), 2.45-2.33 (m, 2H), 2.31-2.23 (m, 1H), 1.94-1.79 (m, 2H), 1.23-1.11 (m, 2H), 0.87-0.77 (m, 2H). |
| 289 S-isomer | 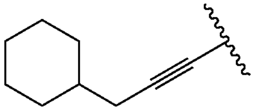 [SMILES: *C#CCC1CCCCC1] | $CF_3$ | H | 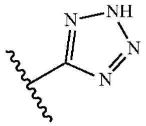 | $R^{13} = CH_3$ | 444.1 | 7.17 (d, J = 7.9 Hz, 2H), 7.05 (d, J = 8.4 Hz, 2H), 6.84 (s, 1H), 3.39 (AB quartet, J = 18.7 Hz, 2H), 2.36 (s, 3H), 2.13 (d, J = 6.6 Hz, 2H), 1.77-1.60 (m, 5H), 1.55-1.42 (m, 1H), 1.29-0.88 (m, 5H). |

-continued
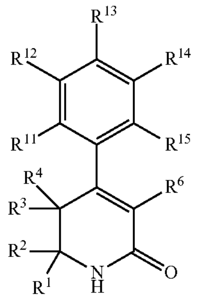
(II)
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 290 S-isomer | 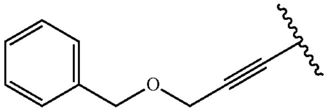 [SMILES: *C#CCOCc1ccccc1] | $CF_3$ | H | 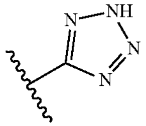 [SMILES: *c1nn[nH]n1] | $R^{13} = CH_3$ | 468.1 | 7.36-7.27 (m, 5H), 7.18 (s, 1H), 7.13 (d, J = 7.9 Hz, 2H), 7.01 (d, J = 8.1 Hz, 2H), 4.57 (AB quartet, J = 11.7 Hz, 2H), 4.22 (s, 2H), 3.39 (AB quartet, J = 18.9 Hz, 2H), 2.34 (s, 3H). |
| 291 S-isomer | 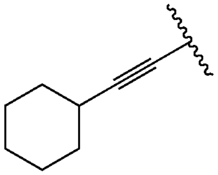 [SMILES: *C#CC1CCCCC1] | $CF_3$ | H | 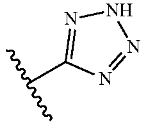 [SMILES: *c1nn[nH]n1] | $R^{13} = CH_3$ | 430.1 | 7.19 (d, J = 7.9 Hz, 2H), 7.06 (d, J = 8.1 Hz, 2H), 6.59 (s, 1H), 3.38 (AB quartet, J = 18.9 Hz, 2H), 2.49-2.41 (m, 1H), 2.38 (s, 3H), 1.81-1.72 (m, 2H), 1.65 (dd, J = 5.9, 2.4 Hz, 2H), 1.54-1.40 (m, J = 12.5, 8.9, 8.9, 8.9 Hz, 3H), 1.38-1.28 (m, 3H). |
| 292 Rac | 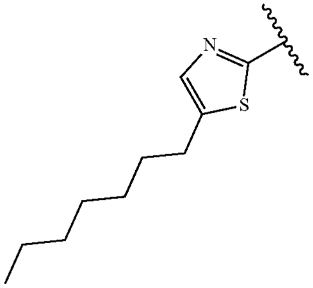 [SMILES: *c1ncc(CCCCCCC)s1] | $CF_3$ | H | 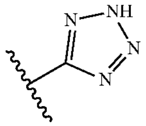 [SMILES: *c1nn[nH]n1] | $R^{13} = CH_3$ | 394.5 | |

-continued (II)

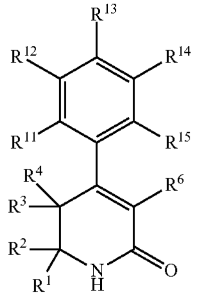

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 293 S-isomer | 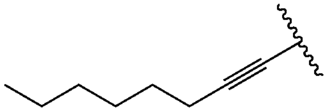 [SMILES: *C#CCCCCCC] | $CF_3$ | H | 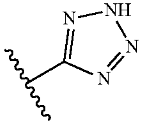 | $R^{13} = CH_3$ | 432.1 | 7.19 (d, J = 7.9 Hz, 2H), 7.06 (d, J = 8.1 Hz, 2H), 6.67 (s, 1H), 3.38 (AB quartet, J = 18.9 Hz, 2H), 2.37 (s, 3H), 2.23 (t, J = 7.0 Hz, 2H), 1.51 (quin, J = 7.3 Hz, 2H), 1.40-1.22 (m, 6H), 0.87 (t, J = 6.8 Hz, 3H). |
| 294 S-isomer | 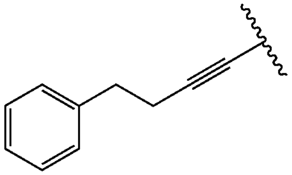 [SMILES: *C#CCCc1ccccc1] | $CF_3$ | H | 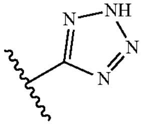 [SMILES: *c1nn[nH]n1] | $R^{13} = OCH_3$ | 468.1 | 1H NMR (500 MHz, MeOD) δ 7.31-7.15 (m, 5H), 6.96 (d, J = 8.9 Hz, 2H), 6.81 (d, J = 8.9 Hz, 2H), 3.79 (s, 3H), 3.34 (AB quartet, J = 18.3 Hz, 2H, partially overlapping with solvent), 2.85 (t, J = 7.2 Hz, 2H), 2.58 (t, J = 7.4 Hz, 2H). |
| 295 S-isomer | 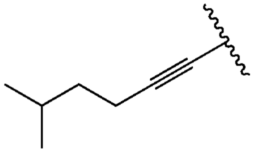 | $CF_3$ | H | 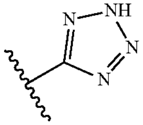 | $R^{13} = OCH_3$ | 434.1 | 1H NMR (500 MHz, MeOD) δ 7.01 (d, J = 8.9 Hz, 2H), 6.78 (d, J = 8.9 Hz, 2H), 3.77 (s, 3H), 3.40 (s, 2H), 2.29 (t, J = 7.4 Hz, 2H), 1.69 (dt, J = 13.5, 6.9 Hz, 1H), 1.45 (q, J = 7.4 Hz, 2H), 0.91 (dd, J = 6.9, 2.0 Hz, 6H). |
| 296 S-isomer | 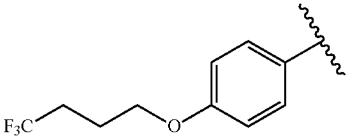 | $CF_3$ | H | 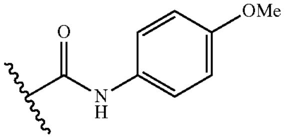 [SMILES: *C(=O)Nc1ccc(OC)cc1] | $R^{11} = F$<br>$R^{13} = CH_3$ | 625.2 | $^1$H NMR (500 MHz, DMSO-$d_6$) δ 7.55 (d, J = 8.80 Hz, 2H), 7.31 (d, J = 9.08 Hz, 2H), 7.13 (m, 1H), 7.06 (d, J = 11.83 Hz, 1H), 7.00 (d, J = 8.8 Hz, 2H), 6.94 (d, J = 7.70 |

-continued
(II)
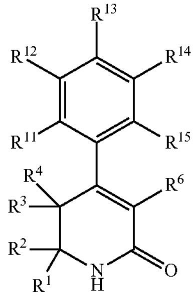
| Example | R[1] | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | Hz, 1H), 6.80 (d, J = 9.08 Hz, 2H), 4.08 (m, 2H), 3.70 (m, 2H), 3.68 (s, 3H), 2.43 (m, 2H), 2.27 (s, 3H), 1.95 (m, 2H). |
| 297 S-isomer | 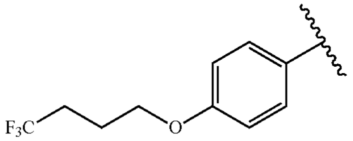 | $CF_3$ | H | 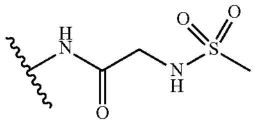 [SMILES: *NC(=O)CNS(C)(=O)=O] | $R^{13} = CH_3$ | 608.1 | 7.43 (d, J = 8.6 Hz, 2H), 7.20-7.16 (m, 2H), 7.15-7.10 (m, 2H), 6.93 (d, J = 8.8 Hz, 2H), 6.57 (s, 1H), 5.10 (br. s., 1H), 4.03 (t, J = 5.9 Hz, 2H), 3.72 (br. s., 2H), 3.62 (d, J = 17.6 Hz, 1H), 3.38 (d, J = 17.8 Hz, 1H), 2.80-2.74 (m, 3H), 2.40-2.24 (m, 5H), 2.12-2.02 (m, 2H) |
| 298 S-isomer | 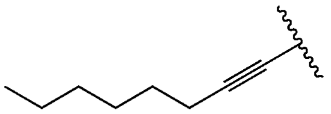 [SMILES: *C#CCCCCCC] | $CF_3$ | H | 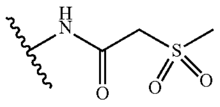 | $R^{13} = CH_3$ | 499.1 | 7.74 (br. s., 1H), 7.26-7.20 (m, 4H), 5.88 (s, 1H), 3.84 (s, 2H), 3.29 (ABq, J = 17.6 Hz, 2H), 2.95 (s, 3H), 2.37 (s, 3H), 2.23 (t, J = 7.0 Hz, 2H), 1.57-1.48 (m, 2H), 1.41-1.25 (m, 6H), 0.89 (t, J = 6.8 Hz, 3H) |
| 299 S-isomer | 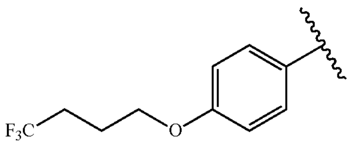 [SMILES: *c1ccc(OCCCC(F)(F)F)cc1] | $CF_3$ | H | 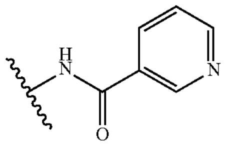 [SMILES: *NC(=O)c1cccnc1] | $R^{13} = CH_3$ | 578.1 | 9.08 (br. s., 1H), 8.77 (d, J = 4.2 Hz, 1H), 8.37 (br. s., 1H), 8.25 (br. s., 1H), 7.65 (br. s., 1H), 7.46 (d, J = 8.8 Hz, 2H), 7.19-7.11 (m, 4H), 6.95 (d, J = 9.0 Hz, 2H), 6.88 (s, 1H), 4.04 (t, J = 5.9 |

-continued (II)

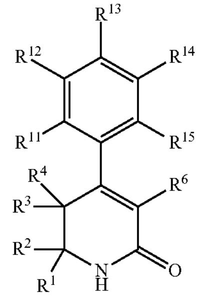

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | Hz, 2H), 3.66 (d, J = 17.6 Hz, 1H), 3.43 (d, J = 17.4 Hz, 1H), 2.40-2.25 (m, 5H), 2.12-2.03 (m, 2H). |
| 300 S-isomer | 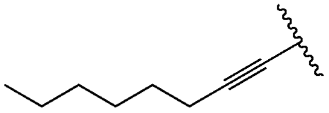 [SMILES: *C#CCCCCCC] | $CF_3$ | H | 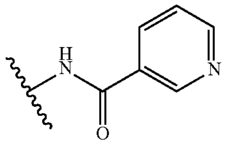 [SMILES: *NC(=O)c1cccnc1] | $R^{13} = CH_3$ | 484.2 | $^1$H NMR (400 MHz, MeOD) δ 9.00 (br. s., 1H), 8.79 (dd, J = 5.3, 1.3 Hz, 1H), 8.46 (d, J = 7.3 Hz, 1H), 7.78 (dd, J = 8.0, 5.4 Hz, 1H), 7.33 (d, J = 8.1 Hz, 2H), 7.21 (d, J = 7.9 Hz, 2H), 3.38 (s, 2H), 2.35-2.27 (m, 5H), 1.60-1.50 (m, 2H), 1.48-1.38 (m, 2H), 1.35-1.27 (m, 4H), 0.93-0.87 (m, 3H). |
| 301 S-isomer | 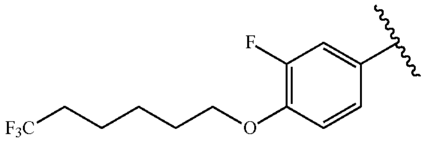 [SMILES: *c1ccc(OCCCCCC(F)(F)F)c(F)c1] | $CF_3$ | H | 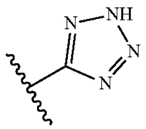 [SMILES: *c1nn[nH]n1] | $R^{13} = OCHF_2$ | 624.2 | $^1$H NMR (500 MHz, DMSO-$d_6$) δ 9.53 (s, 1H), 7.65 (dd, J = 13.0, 2.0 Hz, 1H), 7.49 (d, J = 7.4 Hz, 1H), 7.46-6.88 (m, 6H), 4.11 (t, J = 6.3 Hz, 2H), 3.77 (d, J = 17.9 Hz, 1H), 3.72 (d, J = 17.9 Hz, 1H), 2.36-2.08 (m, 2H), 1.88-1.71 (m, 2H), 1.67-1.34 (m, 4H). |
| 302 S-isomer | 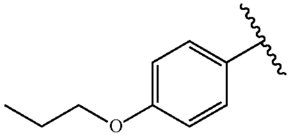 [SMILES: *c1ccc(OCCC)cc1] | $CF_3$ | H | 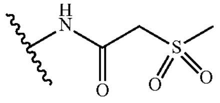 | $R^{13} = CH_3$ | 525.0 | $^1$HNMR (400 MHz, MeOD) δ 7.50 (d, J = 8.8 Hz, 2H), 7.23-7.15 (m, 4H), 6.93 (d, J = 9.0 Hz, 2H), 4.00-3.92 (m, 4H), 3.66 (d, J = 17.2 Hz, 1H), 3.43 (d, J = 16.9 |

-continued
(II)
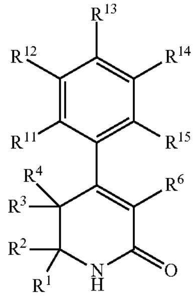
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | Hz, 1H), 2.93 (s, 3H), 2.32 (s, 3H), 1.79 (sxt, J = 7.0 Hz, 2H), 1.04 (t, J = 7.4 Hz, 3H). |
| 303 S-isomer | 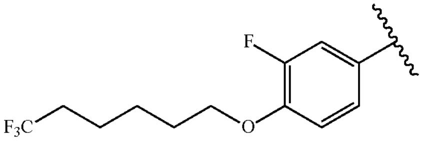 | $CF_3$ | H | 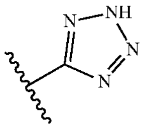 [SMILES: *c1nn[nH]n1] | $R^{13} = CH_3$ | 572.3 | |
| 304 S-isomer | 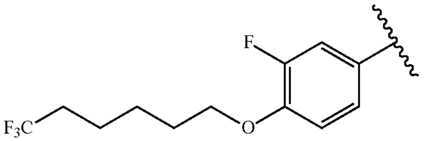 [SMILES: *c1ccc(OCCCCCC(F)(F)F)c(F)c1] | $CF_3$ | H | 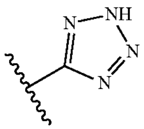 [SMILES: *c1nn[nH]n1] | $R^{12}$ R13 = 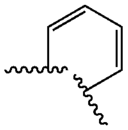 | 608.3 | $^1$HNMR (500 MHz, DMSO-$d_6$) δ 9.57 (br. s., 1H), 7.84 (dd, J = 7.84, 13.34 Hz, 2H), 7.71-7.77 (m, 2H), 7.67 (d, J = 12.93 Hz, 1H), 7.47-7.57 (m, 3H), 7.26 (t, J = 8.94 Hz, 1H), 6.93 (d, J = 8.80 Hz, 1H), 5.56 (d, J = 7.70 Hz, 1H), 4.10 (t, J = 6.19 Hz, 2H), 3.79-3.92 (m, 2H), 2.20-2.33 (m, 2H), 1.68-1.83 (m, 2H), 1.45-1.65 (m, 4H). |
| 305 S-isomer | 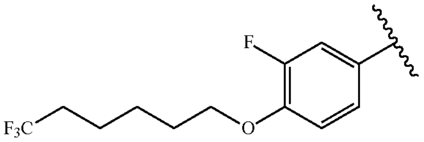 | $CF_3$ | H | 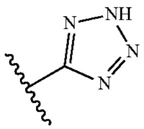 | $R^{13}$ = $OCH_2CH_3$ | 602.3 | $^1$HNMR (500 MHz, DMSO-$d_6$) δ 9.38-9.54 (m, 1H), 7.63 (d, J = 13.20 Hz, 1H), 7.46 (d, J = 8.80 Hz, 1H), 7.24 (t, J = 8.80 Hz, 1H), 6.96 (d, J = 8.53 Hz, 2H), 6.79 (d, J = 8.53 Hz, 2H), 4.09 (t, J = 6.33 Hz, 2H), 3.98 (q, J = 6.88 Hz, 2H), 2.20-2.34 (m, 2H), 1.77 (quin, J = 6.81 Hz, |

-continued

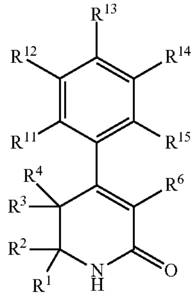

(II)

| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| | | | | | | | 2H), 1.46-1.61 (m, 4H), 1.28 (t, J = 7.02 Hz, 3H). |
| 306 S-isomer | 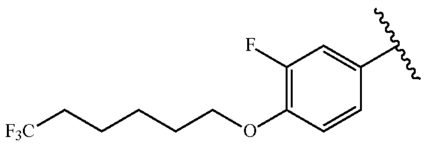 [SMILES: *c1ccc(OCCCCCC(F)(F)F)c(F)c1] | $CF_3$ | H | 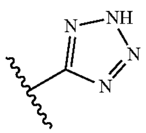 | $R^{13} = CH_2CF_3$ | 640.2 | $^1$HNMR (500 MHz, DMSO-$d_6$) δ 9.56 (br. s., 1H), 7.65 (d, J = 12.93 Hz, 1H), 7.49 (d, J = 8.80 Hz, 1H), 7.20-7.28 (m, 3H), 7.03 (d, J = 7.98 Hz, 2H), 4.10 (t, J = 6.33 Hz, 2H), 3.71-3.81 (m, 2H), 3.61 (q, J = 11.55 Hz, 2H), 2.20-2.33 (m, 2H), 1.78 (quin, J = 6.74 Hz, 2H), 1.44-1.61 (m, 4H) |
| 307 S-isomer | 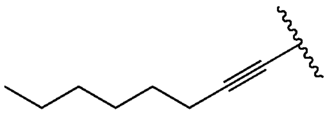 | $CF_3$ | H | 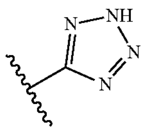 [SMILES: *c1nn[nH]n1] | $R^{13} = OCHF_2$ | 484.1 | 7.19 (d, J = 8.8 Hz, 2H), 7.12 (d, J = 8.6 Hz, 2H), 6.78 (br. s., 1H), 6.56 (t, J = 73.1 Hz, 1H), 3.37 (AB quartet, J = 18.9 Hz, 2H), 2.24 (t, J = 7.0 Hz, 2H), 1.52 (quin, J = 7.3 Hz, 2H), 1.41-1.21 (m, 6H), 0.87 (t, J = 6.8 Hz, 3H). |
| 308 S-isomer | 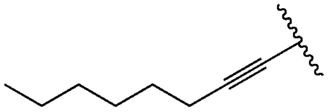 [SMILES: *C#CCCCCCC] | $CF_3$ | H | 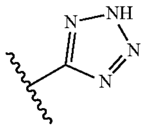 [SMILES: *c1nn[nH]n1] | $R^{13} = OCH_2CH_3$ | 462.1 | 7.10 (d, J = 9.0 Hz, 2H), 6.85 (d, J = 8.8 Hz, 2H), 6.72 (s, 1H), 4.04 (q, J = 7.0 Hz, 2H), 3.37 (AB quartet, J = 18.9 Hz, 2H), 2.22 (t, J = 7.2 Hz, 2H), 1.51 (quin, J = 7.3 Hz, 2H), 1.42 (t, J = 7.0 Hz, 3H), 1.39-1.22 (m, 6H), 0.87 (t, J = 6.6 Hz, 3H). |

-continued
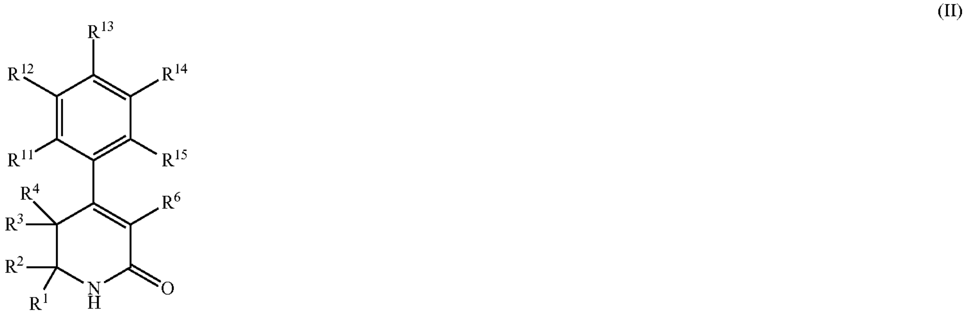
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 309 S-isomer | 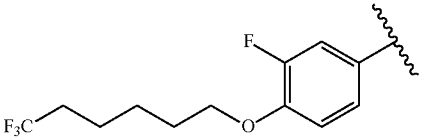 | $CF_3$ | H | 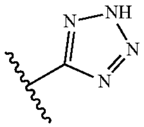 [SMILES: *c1nn[nH]n1] | $R^{12}$ R13 = 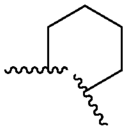 | 612.1 | $^1$HNMR (500 MHz, DMSO-$d_6$) δ 9.52 (br. s., 1H), 7.63 (d, J = 13.20 Hz, 1H), 7.46 (d, J = 8.53 Hz, 1H), 7.25 (t, J = 8.94 Hz, 1H), 6.88 (d, J = 7.98 Hz, 1H), 6.83 (s, 1H), 6.58 (d, J = 7.98 Hz, 1H), 4.09 (t, J = 6.19 Hz, 2H), 3.64-3.75 (m, 2H), 2.54-2.67 (m, 4H), 2.20-2.34 (m, 2H), 1.77 (quin, J = 6.74 Hz, 2H), 1.67 (br. s., 4H), 1.44-1.61 (m, 4H). |
| 310 S-isomer | 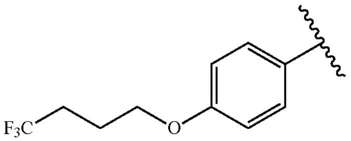 | $CF_3$ | H | 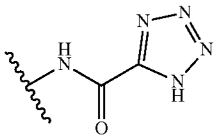 [SMILES: *NC(=O)c1nnn[nH]1] | $R^{13} = CH_3$ | 569.0 | $^1$HNMR (400 MHz, MeOD) δ 7.56 (d, J = 8.8 Hz, 2H), 7.26-7.21 (m, 2H), 7.18-7.12 (m, 2H), 6.99 (d, J = 9.0 Hz, 2H), 4.07 (t, J = 6.2 Hz, 2H), 3.73 (d, J = 17.2 Hz, 1H), 3.51 (d, J = 16.9 Hz, 1H), 2.43-2.32 (m, 2H), 2.29 (s, 3H), 2.08-1.98 (m, 2H). |
| 311 S-isomer | 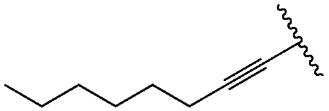 [SMILES: *C#CCCCCCC] | $CF_3$ | H | 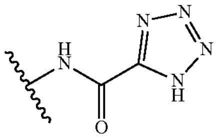 | $R^{13} = CH_3$ | 475.1 | $^1$HNMR (400 MHz, MeOD) δ 7.34 (d, J = 8.1 Hz, 2H), 7.19 (d, J = 7.9 Hz, 2H), 3.37 (s, 2H), 2.34-2.26 (m, 5H), 1.53 (d, J = 7.3 Hz, 2H), 1.42 (br. s., 2H), 1.34-1.25 (m, 4H), 0.92-0.86 (m, 3H). |

-continued
(II)
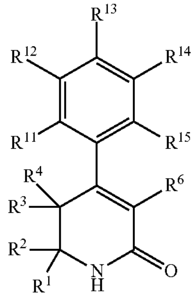
| Example | $R^1$ | $R^2$ | $R^3 = R^4$ | $R^6$ | $R^{11}$-$R^{15}$ | [M + H] | $^1$HNMR (400 MHz, $CDCl_3$) |
|---|---|---|---|---|---|---|---|
| 312 S-isomer | 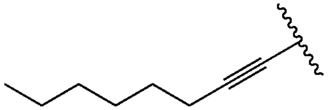 [SMILES: *C#CCCCCCC] | $CF_3$ | H | 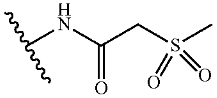 [SMILES: *NC(=O)CS(C)(=O)=O] | $R^{13}$ = $OCH_2CH_3$ | 529.4 | 7.73 (br. s., 1H), 7.31 (d, J = 8.6 Hz, 2H), 6.92 (d, J = 8.8 Hz, 2H), 5.91 (s, 1H), 4.06 (q, J = 7.0 Hz, 2H), 3.86 (s, 2H), 3.30, 3.28 (ABq, J = 18.3 Hz, 2H), 2.99 (s, 3H), 2.23 (t, J = 7.0 Hz, 2H), 1.52 (quin, J = 7.3 Hz, 2H), 1.43 (t, J = 6.9 Hz, 3H), 1.41-1.22 (m, 7H), 0.89 (t, J = 6.9 Hz, 2H). |
| 313 S-isomer | 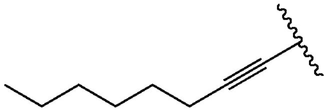 [SMILES: *C#CCCCCCC] | $CF_3$ | H | 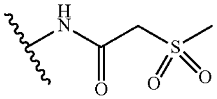 [SMILES: *NC(=O)CS(C)(=O)=O] | $R^{13}$ = $OCHF_2$ | 551.0 | 7.85 (br. s., 1H), 7.38 (d, J = 8.6 Hz, 2H), 7.17 (d, J = 8.6 Hz, 2H), 6.55 (t, J = 72.4 Hz, 1H), 5.97 (s, 1H), 3.84 (s, 2H), 3.30, 3.28 (ABq, J = 17.8 Hz, 2H), 2.89 (s, 3H), 2.24 (t, J = 7.0 Hz, 2H), 1.52 (dt, J = 14.6, 7.2 Hz, 2H), 1.43-1.23 (m, 6H), 0.89 (t, J = 6.8 Hz, 3H). |
| 314 S-isomer | 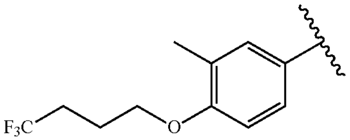 | $CF_3$ | H | 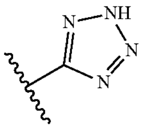 [SMILES: *c1nn[nH]n1] | $R^{13}$ = $CH_3$ | 540.3 | |

What is claimed is:

1. A compound of Formula (II):

(II)

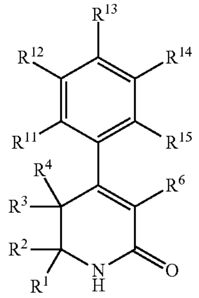

or a stereoisomer, a tautomer, or a pharmaceutically acceptable salt thereof, wherein:

$R^1$ is independently selected from the group consisting of: $C_{1-6}$ alkyl, $C_{3-6}$ cycloalkyl, —$CONHC_{4-18}$ alkyl, —$CONHC_{2-8}$ haloalkyl, —$CONH(CH_2)_{1-8}$ Ph, —$(CH_2)_m$-(phenyl substituted with 1 $R^b$ and 0-2 $R^g$), and a 5- to 6-membered heteroaryl substituted with 0-1 $R^b$ and 0-2 $R^g$, wherein said heteroaryl is selected from: pyridyl, oxazolyl, thiazolyl and

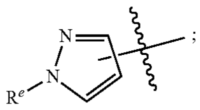

;

$R^2$ is independently selected from the group consisting of: $C_{1-4}$ alkyl and $C_{1-4}$ haloalkyl;

$R^3$ is independently selected from the group consisting of: H and F;

$R^4$ is independently selected from the group consisting of: H and F;

$R^6$ is independently $R^c$ or —$(CH_2)_n$—$(X)_t$—$(CH_2)_m R^c$;

$R^{11}$ and $R^{15}$ are independently selected from the group consisting of: H, $C_{1-4}$ alkyl and halo;

$R^{12}$ and $R^{14}$ are independently selected from the group consisting of: H, halo, $C_{1-4}$ alkyl and $C_{1-4}$ alkoxy;

$R^{13}$ is independently selected from the group consisting of: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, —$(CH_2)_m$—$C_{3-4}$ cycloalkyl, CN, $N(C_{1-4}$ alkyl$)_2$, $NHCO_2(C_{1-4}$ alkyl), $NHSO_2(C_{1-4}$ alkyl), pyrazolyl, and morpholinyl;

alternatively, $R^{12}$ and $R^{13}$, together with the carbon atoms to which they are attached, combine to form a 5- to 6-membered carbocyclic ring or a 5- to 6-membered heterocyclic ring comprising: carbon atoms and 1-3 heteroatoms selected from N, $NR^e$, O, and S;

$R^b$ is, at each occurrence, independently selected from the group consisting of: halo, OH, $C_{1-8}$ alkyl, $C_{1-8}$ alkoxy, $C_{1-8}$ haloalkyl, $C_{1-10}$ haloalkoxy, —$O(CH_2)_sO(C_{1-6}$ alkyl), $N(C_{1-4}$ alkyl$)_2$, —$CONH(CH_2)_{6-20}H$, —$(CH_2)_m(C_{3-6}$ cycloalkyl), —$(CH_2)_m(C_{4-6}$ cycloalkenyl), —$O(CH_2)_m(C_{3-6}$ cycloalkyl), 4-$C_{1-4}$ alkoxy-Ph, —$O(CH_2)_m$Ph, morpholinyl, pyridyl, 2-$C_{1-4}$ alkoxy-pyridin-5-yl, pyrimidinyl, pyrazinyl, and —O-pyrimidinyl;

$R^c$ is, at each occurrence, independently selected from the group consisting of: $C_{3-6}$ cycloalkyl substituted with 0-2 $R^d$, $C_{3-6}$ cycloalkenyl substituted with 0-2 $R^d$, —$(CH_2)_m$-(phenyl substituted with 0-3 $R^d$), and a 5- to 6-membered heterocycle comprising: carbon atoms and 1-4 heteroatoms selected from N, $NR^e$, O, and S; wherein said heterocycle is substituted with 0-2 $R^d$;

$R^d$ is, at each occurrence, independently selected from the group consisting of: halo, OH, CN, $NO_2$, $C_{1-4}$ alkyl, $C_{1-4}$ alkoxy, $C_{1-4}$ haloalkyl, $C_{1-4}$ haloalkoxy, tetrazolyl, OBn and phenyl substituted with 0-2 Rh;

$R^e$ is, at each occurrence, independently selected from the group consisting of: H, $C_{1-8}$ alkyl, $C_{1-8}$ haloalkyl, benzyl optionally substituted with $C_{1-4}$ alkoxy, $CO(C_{1-4}$ alkyl) and COBn;

$R^f$ is, at each occurrence, independently selected from the group consisting of: H and $C_{1-4}$ alkyl;

$R^g$ and $R^h$ are, at each occurrence, independently selected from the group consisting of: halo, $C_{1-4}$ alkyl, $C_{1-4}$ alkoxy, $C_{1-4}$ haloalkyl, and $C_{1-4}$ haloalkoxy;

n, at each occurrence, is independently 0 or 1;

m, at each occurrence, is independently 0, 1, 2 or 3;

s, at each occurrence, is independently 1, 2, or 3; and t, at each occurrence, is independently 0 or 1.

2. A compound according to claim 1, wherein:

$R^1$ is independently selected from the group consisting of: $C_{1-6}$ alkyl, —$CONHC_{4-18}$ alkyl, —$CONH(CH_2)_{1-8}$Ph, and

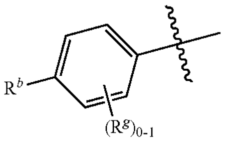

;

$R^6$ is independently $R^c$, $OR^c$, —$CONHR^c$, or —$NHCOR^c$;

$R^{12}$ is independently selected from the group consisting of: H, halo, $C_{14}$ alkyl and $C_{14}$ alkoxy;

$R^{13}$ is independently selected from the group consisting of: H, halo, $C_{14}$ alkyl substituted with 0-1 $C_{1-4}$ alkoxy, $C_{14}$ alkoxy, $C_{1-4}$ haloalkyl, $C_{14}$ haloalkoxy, —$(CH_2)_m$—$C_{3-4}$ cycloalkyl, CN, $N(C_{1-4}$ alkyl$)_2$, $NHCO_2(C_{14}$ alkyl), $NHSO_2(C_{1-4}$ alkyl), pyrazolyl, and morpholinyl;

alternatively, $R^{12}$ and $R^{13}$, together with the carbon atoms to which they are attached, combine to form a 5- to 6-membered carbocyclic ring or a 5- to 6-membered saturated heterocyclic ring comprising: carbon atoms and 1-2 oxygen atoms;

$R^{14}$ is independently selected from the group consisting of: H and $C_{14}$ alkoxy;

$R^b$ is, at each occurrence, independently selected from the group consisting of: halo, $C_{1-6}$ alkyl, $C_{1-6}$ alkoxy, $C_{1-6}$ haloalkyl, $C_{1-10}$ haloalkoxy, —$O(CH_2)_sO(C_{1-6}$ alkyl), —$CONH(CH_2)_{6-20}H$, —$(CH_2)_m(C_{3-6}$ cycloalkyl), —$(CH_2)_m(C_{4-6}$ cycloalkenyl), —$O(CH_2)_m(C_{3-6}$ cycloalkyl), phenoxy, benzoxy, morpholinyl, 2-$C_{1-4}$ alkoxy-pyridin-5-yl, pyrimidin-5-yl, pyrazin-2-yl and —O-pyrimidinyl; and $R^c$ is, at each occurrence, independently selected from the group consisting of: $C_{3-6}$ cycloalkyl substituted with 0-2 $R^d$, —$(CH_2)_m$-(phenyl substituted with 0-3 $R^d$), and a heteroaryl selected from: oxazolyl, isoxazolyl, thiazolyl, pyrazolyl, imidazolyl, oxadiazolyl, triazolyl, tetrazolyl, pyridyl, and pyrazinyl; wherein said heteroaryl is substituted with 0-2 $R^d$.

3. A compound according to claim 2, wherein:

$R^1$ is

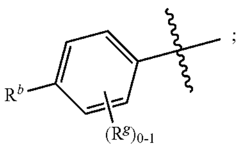

$R^6$ is independently selected from the group consisting of: OPh, —CONH($C_{3-6}$ cycloalkyl), —CONHPh, —CONH-(2-halo-Ph), —CONH-(3-halo-Ph), —CONH-(4-halo-Ph), —CONH-(4-$C_{1-4}$ alkyl-Ph), —CONH(4-OH-Ph), —CONH-(3-$C_{1-4}$ alkoxy-Ph), —CONH-(4-$C_{1-4}$ alkoxy-Ph), —CONH-(4-$C_{1-4}$ haloalkyl-Ph), —CONH-(4-$C_{1-4}$ haloalkoxy-Ph), —CONH-(4-CN-Ph), —CONH-(4-tetrazolyl-Ph), —CONH-(3-halo-4-$C_{1-4}$ alkyl-Ph), —CONH-(3-halo-4-$C_{1-4}$ alkoxy-Ph), —CONH($CH_2$)$_2$Ph, —CONH(4-(4-$C_{1-4}$ alkoxy-Ph)-thiazol-2-yl), —CONH(1-$C_{1-4}$ alkyl-pyrazol-3-yl), —CONH(5-$C_{1-4}$ alkoxy-pyrid-2-yl), —CONH(6-$C_{1-4}$ alkoxy-pyrid-3-yl), —CONH(5-$C_{1-4}$ alkoxy-pyrazin-2-yl), —CONH(6-$C_{1-4}$ alkoxy-pyridazin-3-yl), —NHCO($CH_2$)$SO_2$($C_{1-4}$ alkyl), —NHCOPh, —NHCO(2-$C_{1-4}$ alkyl-Ph), —NHCO(3-$C_{1-4}$ alkyl-Ph), —NHCO(4-$C_{1-4}$ alkyl-Ph), —NHCO (2-halo-Ph), —NHCO(3-halo-Ph), —NHCO(2-$C_{1-4}$ haloalkyl-Ph), —NHCO(2-$C_{1-4}$ haloalkoxy-Ph), —NHCO(2-halo-4-halo-Ph), —NHCO(2-halo-5-halo-Ph), —NHCO(oxazolyl), —NHCO(isoxazolyl), —NHCO(3-$C_{1-4}$ alkyl-isoxazol-5-yl), —NHCO(4-$C_{1-4}$ alkyl-isoxazol-5-yl), —NHCO(3-$C_{1-4}$ alkoxy-isoxazol-5-yl), —NHCO(4-$C_{1-4}$ alkoxy-isoxazol-5-yl), —NHCO(3-halo-isoxazol-5-yl), —NHCO(3-OBn-isoxazol-5-yl), —NHCO(3-(2-halo-Ph)-isoxazol-5-yl), —NHCO(3-(3-halo-Ph)-isoxazol-5-yl), —NHCO(5-$C_{1-4}$ alkyl-1H-pyrazol-3-yl), imidazolyl, —NHCO(5-$C_{1-4}$ alkyl-1,3,4-oxadiazol-2-yl), —NHCO(1-$C_{1-4}$ alkyl-1,2,3-triazol-4-yl), —NHCO(6-$C_{1-4}$ alkoxy-pyrid-3-yl), —NHCO(pyrazinyl), —NHCO(6-halo-pyridazin-3-yl), 5-$C_{1-4}$ haloalkyl-1,3,4-oxadiazol-2-yl, 3-$NO_2$-1H-1,2,4-triazol-1-yl, tetrazolyl and 5-$C_{1-4}$ alkyl-tetrazol-1-yl;

$R^b$ is independently selected from the group consisting of: halo, $C_{1-6}$ alkyl, $C_{1-6}$ alkoxy, $C_{1-6}$ haloalkyl, $C_{1-8}$ haloalkoxy, —CONH($CH_2$)$_{6-20}$H, $C_{3-6}$ cycloalkyl, $C_{4-6}$ cycloalkenyl, —O($CH_2$)$_m$($C_{3-6}$ cycloalkyl), phenoxy, benzoxy, pyrimidinyl, pyrazinyl and —O-pyrimidinyl; and $R^g$ is independently selected from the group consisting of: halo and $C_{1-4}$ alkyl.

4. A compound according to claim 3, wherein:

$R^2$ is independently selected from the group consisting of: $CF_3$ and Me;

$R^3$ is independently selected from the group consisting of: H and F;

$R^4$ is independently selected from the group consisting of: H and F;

$R^6$ is independently selected from the group consisting of: OPh, —CONH(cyclopropyl), —CONH(cyclobutyl), —CONH(cyclopentyl), —CONH(cyclohexyl), —CONHPh, —CONH(4-F-Ph), —CONH(2-Cl-Ph), —CONH(4-Cl-Ph), —CONH(4-Me-Ph), —CONH(4-OH-Ph), —CONH(3-OMe-Ph), —CONH(4-OMe-Ph), —CONH(4-$CF_3$-Ph), —CONH(4-$OCF_3$-Ph), —CONH(1-Me-pyrazol-3-yl), —CONH(4-(1H-tetrazol-2-yl)-Ph), —CONH(4-(2H-tetrazol-5-yl)-Ph), —CONH(3-F-4-Me-Ph), —CONH(3-F-4-OMe-Ph), —CONH($CH_2$)$_2$Ph, —CONH(5-OMe-pyrid-2-yl), —CONH(6-OMe-pyrid-3-yl), —CONH(5-OMe-pyrazin-2-yl), —CONH(6-OMe-pyridazin-3-yl), —NHCO($CH_2$)$SO_2$Me, —NHCOPh, —NHCO(2-Me-Ph), —NHCO(3-Me-Ph), —NHCO(4-Me-Ph), —NHCO(2-Cl-Ph), —NHCO(3-Cl-Ph), —NHCO(2-$C_{1-4}$—F-Ph), —NHCO(2-$C_{1-5}$-F-Ph), —NHCO(isoxazol-5-yl), —NHCO(3-Me-isoxazol-5-yl), —NHCO (4-Me-isoxazol-5-yl), —NHCO(3-OMe-isoxazol-5-yl), —NHCO(3-Br-isoxazol-5-yl), —NHCO(3-(2-Cl-Ph)-isoxazol-5-yl), —NHCO(3-(3-F-Ph)-isoxazol-5-yl), —NHCO(3-OBn-isoxazol-5-yl), 1H-imidazol-1-yl, —NHCO(5-Me-1,3,4-oxadiazol-2-yl), —NHCO(1-Me-1,2,3-triazol-4-yl), —NHCO(6-OMe-pyrid-3-yl), —NHCO(6-Cl-pyridazin-3-yl), 5-$CF_3$-1,3,4-oxadiazol-2-yl, 1H-tetrazol-1-yl, 1H-tetrazol-3-yl, and 2H-tetrazol-5-yl;

$R^{11}$ and $R^{15}$ are independently selected from the group consisting of: H, Me, F, and Cl;

$R^{12}$ is independently selected from the group consisting of: H, F, Cl, Me and OMe;

$R^{13}$ is independently selected from the group consisting of: H, F, Cl, Br, Me, OMe, OEt, $CH_2OMe$, $CF_3$, $CH_2CF_3$, $OCHF_2$, $OCF_3$, CN, $N(Me)_2$, cyclopropyl and cyclopropylmethyl;

alternatively, $R^{12}$ and $R^{13}$, together with the carbon atoms to which they are attached, combine to form a 5- to 6-membered carbocyclic ring or a 5- to 6-membered saturated heterocyclic ring comprising: carbon atoms and 1-2 oxygen atoms;

$R^{14}$ is H;

$R^b$ is, at each occurrence, independently selected from the group consisting of:

n-pentyl, methoxy, n-butoxy, i-butoxy, i-pentoxy, —O($CH_2$)$_{1-6}$$CF_3$, —O($CH_2$)$_{1-4}$$CF_2CF_3$, —CONH ($CH_2$)$_{6-20}$H, cyclopropyl, cyclopent-1-en-1-yl, cyclohex-1-en-1-yl, —O($CH_2$)$_2$(cyclopentyl), phenoxy, benzoxy, pyrimidin-5-yl, pyrazin-2-yl and —O-pyrimidin-2-yl; and $R^g$ is F.

5. A compound according to claim 2, wherein:

$R^{13}$ is independently selected from the group consisting of: H, halo, $C_{1-4}$ alkyl substituted with 0-1 $C_{1-4}$ alkoxy, $C_{1-4}$ alkoxy, $C_{1-4}$ haloalkyl, $C_{1-4}$ haloalkoxy, CN or $C_{3-4}$ cycloalkyl.

6. A compound according to claim 5, wherein:

$R^1$ is independently

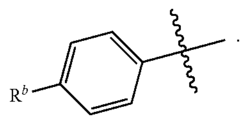

7. A compound according to claim 6, wherein:

$R^b$ is independently selected from: —O($CH_2$)$_{1-6}$$CF_3$, and —O($CH_2$)$_{1-4}$$CF_2CF_3$.

8. A compound according to claim 7, wherein:

$R^6$ is independently 5-membered nitrogen heteroaryl.

9. A compound according to claim 8, wherein:

$R^6$ is independently 1H-imidazol-1-yl, 1H-tetrazol-1-yl, 1H-tetrazol-3-yl, or 2H-tetrazol-5-yl.

10. A compound selected from:
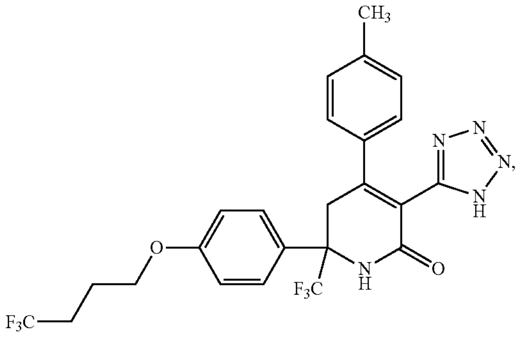
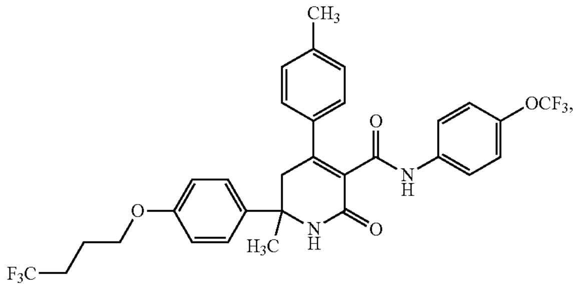
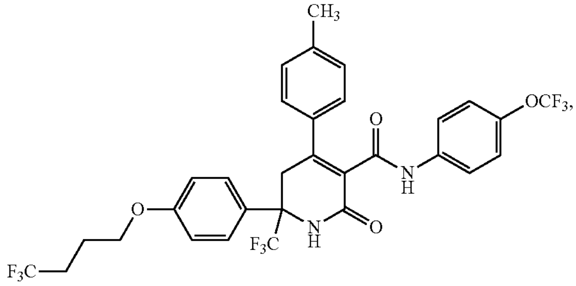
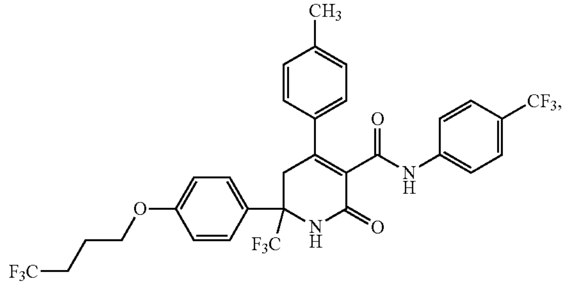
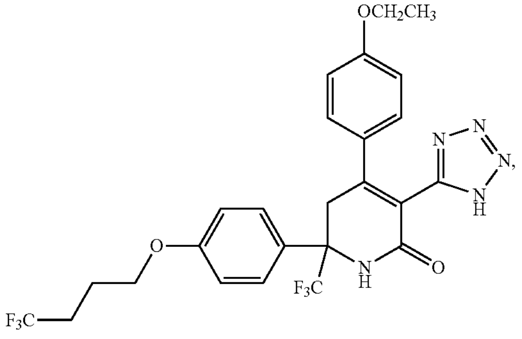
-continued
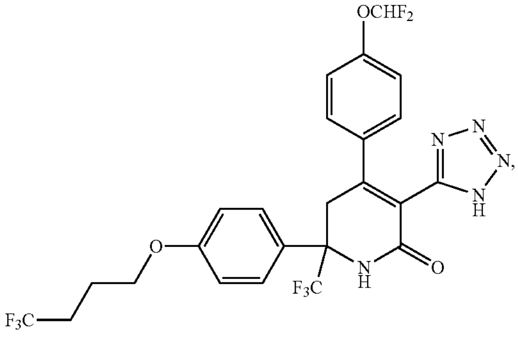
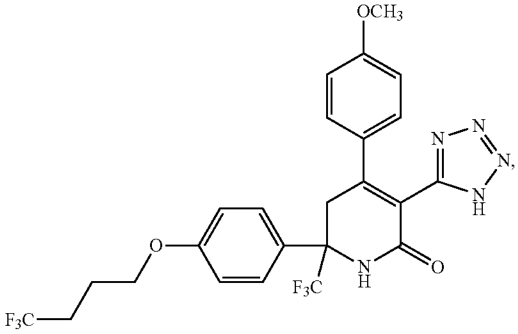
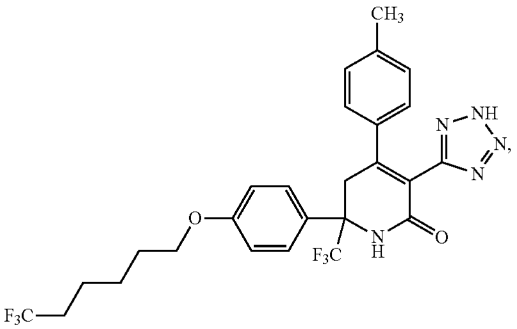
and
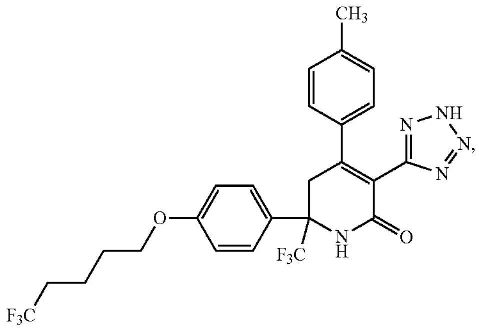
or a stereoisomer, a tautomer, or a pharmaceutically acceptable salt thereof.

11. A compound having the following formula:

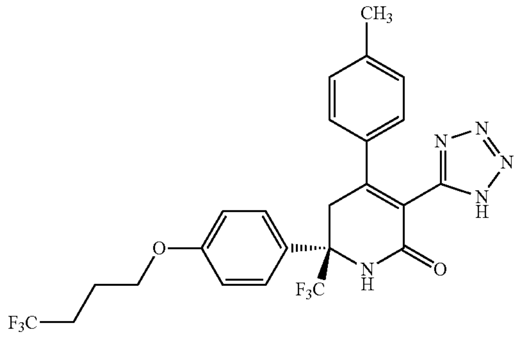 [SMILES: Cc1ccc(C2=C(c3nnn[nH]3)C(=O)N[C@@](c3ccc(OCCCC(F)(F)F)cc3)(C(F)(F)F)C2)cc1]

or a tautomer, or a pharmaceutically acceptable salt thereof.

12. A compound according to claim 11, wherein the compound has the following formula:

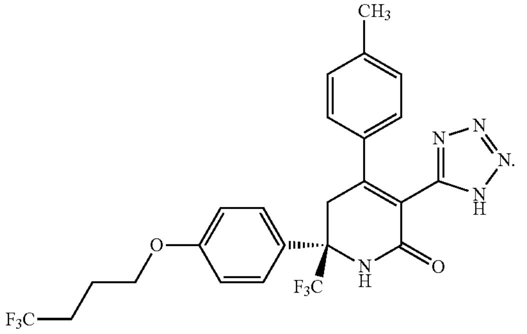 [SMILES: Cc1ccc(C2=C(c3nnn[nH]3)C(=O)N[C@@](c3ccc(OCCCC(F)(F)F)cc3)(C(F)(F)F)C2)cc1]

13. A compound having the following formula:

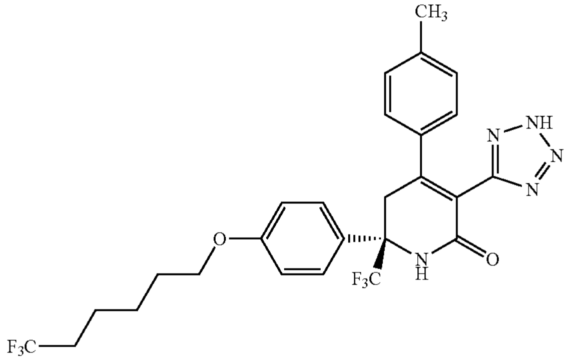 [SMILES: Cc1ccc(C2=C(c3nn[nH]n3)C(=O)N[C@@](c3ccc(OCCCCCC(F)(F)F)cc3)(C(F)(F)F)C2)cc1]

or a tautomer, or a pharmaceutically acceptable salt thereof.

14. A compound according to claim 13, wherein the compound has the following formula:

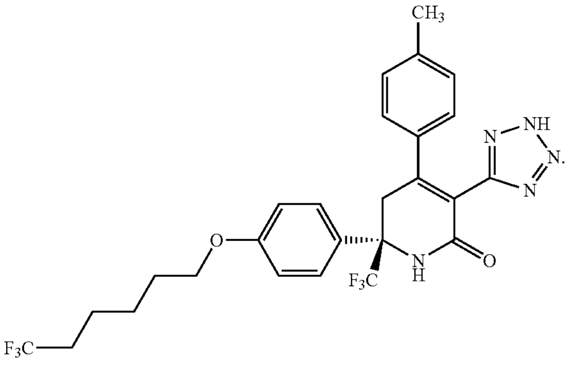 [SMILES: Cc1ccc(C2=C(c3nn[nH]n3)C(=O)N[C@@](c3ccc(OCCCCCC(F)(F)F)cc3)(C(F)(F)F)C2)cc1]

15. A compound having the following formula:

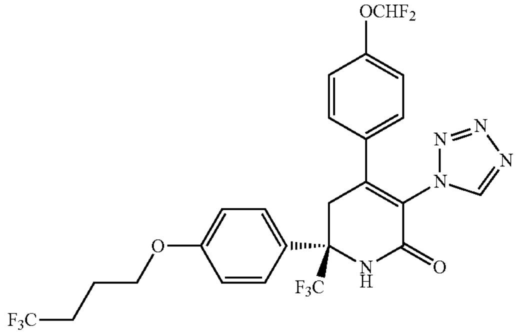 [SMILES: O=C1N[C@@](c2ccc(OCCCC(F)(F)F)cc2)(C(F)(F)F)CC(c2ccc(OC(F)F)cc2)=C1n1cnnn1]

or a tautomer, or a pharmaceutically acceptable salt thereof.

16. A compound according to claim 15, wherein the compound has the following formula:

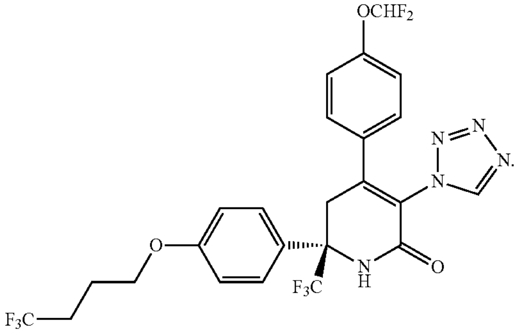 [SMILES: O=C1N[C@@](c2ccc(OCCCC(F)(F)F)cc2)(C(F)(F)F)CC(c2ccc(OC(F)F)cc2)=C1n1cnnn1]

17. A pharmaceutical composition, comprising: a pharmaceutically acceptable carrier and a compound of claim 1, or a stereoisomer, a tautomer, or a pharmaceutically acceptable salt thereof.

18. The pharmaceutical composition according to claim 17, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

19. A pharmaceutical composition, comprising: a pharmaceutically acceptable carrier and a compound of claim 10, or a stereoisomer, a tautomer, or a pharmaceutically acceptable salt thereof.

20. The pharmaceutical composition according to claim 19, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

21. A pharmaceutical composition, comprising: a pharmaceutically acceptable carrier and a compound of claim 11, or a stereoisomer, a tautomer, or a pharmaceutically acceptable salt thereof.

22. The pharmaceutical composition according to claim 21, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

23. A pharmaceutical composition, comprising: a pharmaceutically acceptable carrier and a compound of claim 12, or a stereoisomer, a tautomer, or a pharmaceutically acceptable salt thereof.

24. The pharmaceutical composition according to claim 23, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

25. A pharmaceutical composition, comprising: a pharmaceutically acceptable carrier and a compound of claim 13, or a stereoisomer, a tautomer, or a pharmaceutically acceptable salt thereof.

26. The pharmaceutical composition according to claim 25, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

27. A pharmaceutical composition, comprising: a pharmaceutically acceptable carrier and a compound of claim 14, or a stereoisomer, a tautomer, or a pharmaceutically acceptable salt thereof.

28. The pharmaceutical composition according to claim 27, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

29. A pharmaceutical composition, comprising: a pharmaceutically acceptable carrier and a compound of claim 15, or a stereoisomer, a tautomer, or a pharmaceutically acceptable salt thereof.

30. The pharmaceutical composition according to claim 29, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

31. A pharmaceutical composition, comprising: a pharmaceutically acceptable carrier and a compound of claim 16, or a stereoisomer, a tautomer, or a pharmaceutically acceptable salt thereof.

32. The pharmaceutical composition according to claim 31, further comprising one or more other suitable therapeutic agents selected from: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, lipid lowering agents, anorectic agents, and appetite suppressants.

33. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 1.

34. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 10.

35. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 11.

36. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 12.

37. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 13.

38. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 14.

39. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 15.

40. A method for the treatment of diabetes, hyperglycemia, impaired glucose tolerance, gestational diabetes, insulin resistance, hyperinsulinemia, nonalcoholic fatty liver disease, nonalcoholic steatohepatitis, retinopathy, neuropathy, nephropathy, delayed wound healing, Metabolic Syndrome, obesity, dyslipidemia, and glaucoma, comprising administering to a patient in need of such treatment a therapeutically effective amount of at least a compound of claim 16.

* * * * *

UNITED STATES PATENT AND TRADEMARK OFFICE

CERTIFICATE OF CORRECTION

PATENT NO. : 10,695,328 B2
APPLICATION NO. : 16/445913
DATED : June 30, 2020
INVENTOR(S) : Turdi et al.

It is certified that error appears in the above-identified patent and that said Letters Patent is hereby corrected as shown below:

In the Claims

Claim 2, Column 292

Line 39, "$C_{14}$ alkyl" should read -- $C_{1-4}$ alkyl -- and
Line 39, "$C_{14}$ alkoxy" should read -- $C_{1-4}$ alkoxy --.

Line 41, "$C_{14}$ alkyl" should read -- $C_{1-4}$ alkyl --.

Line 42, "$C_{14}$ alkoxy" should read -- $C_{1-4}$ alkoxy -- and
Line 42, "$C_{14}$ haloalkoxy" should read -- $C_{1-4}$ haloalkoxy --.

Line 43, "$NHCO_2(C_{14}$" should read -- $NHCO_2(C_{1-4}$ --.

Line 52, "$C_{14}$ alkoxy" should read -- $C_{1-4}$ alkoxy --.

Signed and Sealed this
Thirteenth Day of October, 2020

Andrei Iancu
*Director of the United States Patent and Trademark Office*